US012624396B2

(12) United States Patent
van der Maarel et al.

(10) Patent No.: US 12,624,396 B2
(45) Date of Patent: *May 12, 2026

(54) METHODS FOR ALLEVIATING FACIOSCAPULOHUMERAL DYSTROPHY (FSHD) BY AN ANTISENSE NUCLEIC ACID MOLECULE INHIBITING THE EXPRESSION OF DOUBLE HOMEOBOX 4 (DUX4)

(71) Applicants: Fred Hutchinson Cancer Center, Seattle, WA (US); University of Rochester, Rochester, NY (US); Leiden University Medical Center, Leiden (NL)

(72) Inventors: Silvere M. van der Maarel, Leiden (NL); Stephen J. Tapscott, Seattle, WA (US); Rabi Tawil, Rochester, NY (US); Richard J.L.F. Lemmers, Leiden (NL); Linda Geng, Seattle, WA (US); Lauren Snider, Seattle, WA (US)

(73) Assignees: Fred Hutchinson Cancer Center, Seattle, WA (US); University of Rochester, Rochester, NY (US); Leiden University Medical Center, Leiden (NL)

( * ) Notice: Subject to any disclaimer, the term of this patent is extended or adjusted under 35 U.S.C. 154(b) by 232 days.

This patent is subject to a terminal disclaimer.

(21) Appl. No.: 17/113,778

(22) Filed: Dec. 7, 2020

(65) Prior Publication Data

US 2021/0198739 A1 Jul. 1, 2021

Related U.S. Application Data

(63) Continuation of application No. 13/817,531, filed as application No. PCT/US2011/048318 on Aug. 18, 2011, now Pat. No. 10,865,445.

(Continued)

(51) Int. Cl.
| | |
|---|---|
| *C12N 15/11* | (2006.01) |
| *A61K 48/00* | (2006.01) |

(Continued)

(52) U.S. Cl.
CPC ......... *C12Q 1/6883* (2013.01); *C12Q 1/6809* (2013.01); *C12Q 1/6897* (2013.01); *G01N 33/6896* (2013.01); *A61K 9/0019* (2013.01); *A61K 31/7105* (2013.01); *A61K 31/713* (2013.01); *A61K 48/00* (2013.01); *A61N 1/326* (2013.01); *A61N 1/36003* (2013.01); *A61P 21/00* (2018.01); *C07K 2319/71* (2013.01); *C07K 2319/81* (2013.01); *C12N 7/00* (2013.01); *C12N 15/102* (2013.01); *C12N 15/11* (2013.01); *C12N 15/111* (2013.01); *C12N 15/113* (2013.01); *C12N 15/86* (2013.01); *C12N 2310/11* (2013.01); *C12N 2310/14* (2013.01); *C12N 2310/141* (2013.01);

*C12N 2310/321* (2013.01); *C12N 2310/322* (2013.01); *C12N 2320/11* (2013.01); *C12N 2320/30* (2013.01); *C12N 2320/33* (2013.01); *C12N 2330/51* (2013.01); *C12N 2501/60* (2013.01); *C12N 2710/10043* (2013.01); *C12N 2750/00032* (2013.01); *C12N 2750/14132* (2013.01); *C12N 2750/14143* (2013.01); *C12N 2800/80* (2013.01); *C12Q 2600/156* (2013.01); *C12Q 2600/172* (2013.01); *C12Q 2600/178* (2013.01); *G01N 33/6887* (2013.01); *G01N 2800/2878* (2013.01)

(58) Field of Classification Search
CPC ...... C12Q 1/6883; C07K 16/18; C07K 14/00; C07K 14/4723; C12N 15/113; C12N 2310/14; C12N 2310/11; C12N 2320/33; A61K 38/00; A61K 38/1709; A61K 38/1729; G01N 33/5008
See application file for complete search history.

(56) References Cited

U.S. PATENT DOCUMENTS

| | | | |
|---|---|---|---|
| 4,683,202 | A | 7/1987 | Mullis |
| 5,091,513 | A | 2/1992 | Huston et al. |

(Continued)

FOREIGN PATENT DOCUMENTS

| | | | |
|---|---|---|---|
| EP | 10175125 | | 9/2010 |
| EP | 2426203 | * | 9/2011 |

(Continued)

OTHER PUBLICATIONS

Cohen et al., Trends Mol. Med. Feb. 2021; 22:123-137. doi:10.1016/j.molmed.2020.09.08.*
Lemmers et al., Science 2010; 329:1650-1653.*
Arnett et al. Curr. Opin. Genet. Dev. 2009; 19:290-297.*
Bennett et al. Ann. Rev. Pharmacol. Toxicol. 2010; 50:259-93.*
Vanderplank et al. PLoS ONE, 2011; 6:e26820. doi:10.1371/journal.pone.0026820.*
Sahenk et al. Curr. Rheumatol. Rept, 2011; 13:199-207.*
Tillman et al.,J. Pharmaceu. Sci. 2008; 97:225-236.*
Carrin et al., Eur. J. Lipid Sci. Technol., 2010; 112:697-707.*
Borchani et al. J. Agr. Sci. Tech., 2010; 12:585-596.*

(Continued)

*Primary Examiner* — Chang-Yu Wang
(74) *Attorney, Agent, or Firm* — Norton Rose Fulbright LLP

(57) ABSTRACT

In one aspect, the invention provides a method of screening a human subject to determine if said subject has a genetic predisposition to develop, or is suffering from Facioscapulohumeral Dystrophy (FSHD), said method comprising: (a) providing a biological sample comprising genomic DNA from the subject; and (b) analyzing the portion of the genomic DNA in the sample corresponding to the distal D4Z4-pLAM region on chromosome 4 and determining the presence or absence of a polymorphism resulting in a functional polyadenylation sequence operationally linked to exon 3 of the DUX4 gene.

16 Claims, 44 Drawing Sheets

Specification includes a Sequence Listing.

Related U.S. Application Data

(60) Provisional application No. 61/513,467, filed on Jul. 29, 2011, provisional application No. 61/513,456, filed on Jul. 29, 2011, provisional application No. 61/384,609, filed on Sep. 20, 2010, provisional application No. 61/374,967, filed on Aug. 18, 2010.

(51) Int. Cl.

| | |
|---|---|
| *C07H 19/00* | (2006.01) |
| *C07H 21/04* | (2006.01) |
| *C12N 15/00* | (2006.01) |
| *C12N 15/09* | (2006.01) |
| *C12N 15/10* | (2006.01) |
| *C12N 15/113* | (2010.01) |
| *C12Q 1/6809* | (2018.01) |
| *C12Q 1/6883* | (2018.01) |
| *C12Q 1/6897* | (2018.01) |
| *G01N 33/68* | (2006.01) |
| *A61K 9/00* | (2006.01) |
| *A61K 31/7105* | (2006.01) |
| *A61K 31/713* | (2006.01) |
| *A61N 1/32* | (2006.01) |
| *A61N 1/36* | (2006.01) |
| *A61P 21/00* | (2006.01) |
| *C12N 7/00* | (2006.01) |
| *C12N 15/86* | (2006.01) |

(56) References Cited

U.S. PATENT DOCUMENTS

| | | | |
|---|---|---|---|
| 5,288,644 A | 2/1994 | Beavis et al. | |
| 5,399,363 A | 3/1995 | Liversidge et al. | |
| 5,466,468 A | 11/1995 | Schneider et al. | |
| 5,543,158 A | 8/1996 | Gref et al. | |
| 5,580,579 A | 12/1996 | Ruddy et al. | |
| 5,629,001 A | 5/1997 | Michael et al. | |
| 5,641,515 A | 6/1997 | Ramtoola | |
| 5,725,871 A | 3/1998 | Illum | |
| 5,756,353 A | 5/1998 | Debs | |
| 5,780,045 A | 7/1998 | McQuinn et al. | |
| 5,792,451 A | 8/1998 | Sarubbi et al. | |
| 5,804,212 A | 9/1998 | Illum | |
| 6,506,559 B1 | 1/2003 | Fire et al. | |
| 6,573,099 B2 | 6/2003 | Graham | |
| 6,613,308 B2 | 9/2003 | Bartus et al. | |
| 6,753,514 B2 | 6/2004 | Harashima | |
| 6,881,557 B2 | 4/2005 | Foote | |
| 8,487,008 B2 | 7/2013 | Bonaldo et al. | |
| 9,469,851 B2 * | 10/2016 | Harper | C12N 15/86 |
| 9,988,628 B2 * | 6/2018 | Belayew | A61P 35/00 |
| 10,865,445 B2 * | 12/2020 | Van Der Maarel | C12Q 1/6897 |
| 10,907,157 B2 * | 2/2021 | Belayew | A61P 35/00 |
| 2002/0168707 A1 | 11/2002 | Graham | |
| 2003/0051263 A1 | 3/2003 | Fire et al. | |
| 2003/0055020 A1 | 3/2003 | Fire et al. | |
| 2003/0159161 A1 | 8/2003 | Graham et al. | |
| 2004/0014099 A1 | 1/2004 | Gretarsdottier et al. | |
| 2004/0064842 A1 | 4/2004 | Graham et al. | |
| 2004/0265833 A1 | 12/2004 | Lofton-Day et al. | |
| 2004/0265839 A1 | 12/2004 | Mello et al. | |
| 2005/0214860 A1 | 9/2005 | Zhu et al. | |
| 2009/0280517 A1 | 11/2009 | Bloch et al. | |
| 2012/0225034 A1 * | 9/2012 | Belayew | C12N 15/113 800/298 |
| 2012/0329800 A1 | 12/2012 | Bonaldo et al. | |
| 2014/0242093 A1 | 8/2014 | Tapscott et al. | |
| 2014/0322169 A1 | 10/2014 | Harper et al. | |
| 2018/0265870 A1 * | 9/2018 | Belayew | A61P 35/00 |
| 2020/0231966 A1 * | 7/2020 | Belayew | A61P 35/00 |
| 2021/0163941 A1 * | 6/2021 | Belayew | C12N 15/113 |
| 2021/0163942 A1 * | 6/2021 | Belayew | C12N 15/113 |

FOREIGN PATENT DOCUMENTS

| | | |
|---|---|---|
| EP | 2426203 B1 | 7/2016 |
| EP | 2736539 | 8/2017 |
| FR | 2919616 | 2/2009 |
| JP | 2006-129807 | 5/2006 |
| WO | WO 97/40832 | 11/1997 |
| WO | WO 01/19776 | 3/2001 |
| WO | WO 2001/75067 | 10/2001 |
| WO | WO 2004/097005 | 11/2004 |
| WO | WO 2005/037231 | 4/2005 |
| WO | WO 2009/016206 | 2/2009 |
| WO | WO 2010/035140 | 4/2010 |
| WO | WO 2011/130624 | 10/2011 |
| WO | WO 2012/024535 | 2/2012 |
| WO | WO 2013/016352 | 1/2013 |
| WO | WO 2013/019623 | 2/2013 |
| WO | WO 2017/201585 | 11/2017 |

OTHER PUBLICATIONS

Dubois et al., Eur. J. Lipid Sci. Technol.2007; 109:710-732.*

Bennett and Swayze, "RNA Targeting Therapeutics: Molecular Mechanisms of Antisense Oligonucleotides as a Therapeutic Platform" *Annu. Rev. Pharmacol. Toxicol.* 2010, 50, 259-93.

Consolidated List of EPO Citations (updated) from Notices of Opposition to a European Patent issued in European Application No. EPI 16191567.3, in 2 pages, Nov. 27, 2020.

Geng et al., "DUX4 Activates Germline Genes, Retroelements, and Immune Mediators: Implications for Facioscapulohumeral Dystrophy" *Developmental Cell* 2012, 22, 38-51.

Kim and Rossi, "Strategies for silencing human disease using RNA interference" *Nature Reviews Genetics* 2007, 8, 173-184.

Yao et al., "DUX4-induced gene expression is the major molecular signature in FSHD skeletal muscle" *Human Molecular Genetics* 2014, 23(20), 5342-5352.

Aartsma-Rus, "Overview on AON design", Mol. Bio., 867 :117-129, 2012.

Ahmed et al., "Prediction of polyadenylation signals in human DNA sequences using nucleotide frequencies", In Silico Biol, 9(3):135-148, 2009.

Allo et al., "Control of alternative splicing through siRNA-mediated transcriptional gene silencing", Nat. Struct Mol. Biol., 16:717-724, 2009.

Anan et al., "LSD1 mediates metabolic reprogramming by glucocorticoids during myogenic differentiation" Nucleic Acids Research 2018, 46(11), 5441-5454.

Ansseau et al., "DUX4c Is Up-Regulated in FSHD. It Induces the MYF5 Protein and Human Myoblast Proliferation", PloS One, 4(10):e7482, 11 pages, 2009.

Balog et al., "Correlation analysis of clinical parameters with epigenetic modifications in the DUX4 promoter in FSHD", Epigenetics, 7(6):579-584, 2012.

Balog et al., "Increased DUX4 expression during muscle differentiation correlates with decreased SMCHD1 protein levels at D4Z4" Epigenetics 2015, 10(12), 1133-1142.

Bamshad et al., "Exome sequencing as a tool for Mendelian disease gene discovery", Nat. Rev. Genet., 12:745-755, 2011.

Belancio et al., "All y'all need to know 'bout retroelements in cancer", Semin. Cancer Biol., 20(4):200-210, 2010.

Belayew et al., "Suppression of DUX4 or DUX4c protein expression by antisense strategies in a therapeutic approach for FSHD" MOA National Scientific Conference—Neuromuscular Therapeutic Strategies: Overcoming the Barriers from Microscope to Marketplace 2011, 1 page.

Bennett, C. Frank and Swayze, Eric E., "RNA Targeting Therapeutics: Molecular Mechanisms of Antisense Oligonucleotides as a Therapeutic Platform" Annu. Rev. Pharmacol. Toxicol. 2010, 50, 259-293.

Bhalla et al., "Mutation of YCS4, a Budding Yeast Condensin Subunit, Affects Mitotic and Nonmitotic Chromosome Behavior", Mol. Biol. Cell, 13:632-645, 2002.

(56)          References Cited

OTHER PUBLICATIONS

Blewitt et al., "An N-ethyl-N-nirtosourea screen for genes involved in variegation in the mouse", Proc. Natl. Acad. Sci. USA, 102(21):7629-7634, 2005.

Blewitt et al., "SmcHD1, containing a structural-maintenance-of-chromosomes hinge domain, has a critical role in X inactivation", Nat. Genet., 40:663-669, 2008.

Bodega et al., "Remodeling of the chromatin structure of the facioscapulohumeral muscular dystrophy (FSHD) locus and upregulation of FSHD-related gene I (FRGI) expression during human myogenic differentiation", BMC. Biol. , 7:41, 15 pages, 2009.

Bonnefont, "Evolutionary Forces Shape the Human RFPLI,2,3 Genes toward a Role in Neocortex Development", Am. J Hum. Genet, 83:208-218, 2008.

Booth and Holland, "Annotation, nomenclature and evolution of four novel homeobox genes expressed in the human germ line", Gene 387(1-2):7-14, 2007.

Bortolanza et al., "AAV6-mediated Systemic shRNA Delivery Reverses Disease in a Mouse Model of Facioscapulohumeral Muscular Dystrophy" Molecular Therapy 2011, 19(11 ), 2055-2064.

Bosch et al., "Characterization and evolution of the novel gene family FAM90A in primates originated by multiple duplication and rearrangement events", Hum. Mol. Genet., 16(21):2572-2582, 2007.

Bosnakovski et al., "An isogenetic myoblast expression screen identified DUX4-mediated FSHD-associated molecular pathologies", EMBO J, 27 :2766-2779, 2008.

Bosnakovski et al., "Biphasic Myopathic Phenotype of Mouse DUX, an ORF within conserved FSHD-Related Repeats", PloS One, 4(9):e7003, 10 pages, 2009.

Bosnakovski et al., "DUX4c, an FSHD candidate gene, interferes with myogenic regulators and abolishes myoblast differentiation", Exp Neural, 214(1) :87-96, 2008.

Boussif et al., "A versatile vector for gene and oligonucleotide transfer into cells in culture and in vivo: Polyethylenimine", Proc. Natl. Acad. Sci. USA, 92(16) :7297-7301, 1995.

Bowie et al., "Deciphering the Message in Protein Sequences: Tolerance to Amino Acid Substitutions" Science 1990, 247, 1306-1310.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" J of Cell Bio. 1990, 111, 2129-2138.

Cabianca et al., "A Long ncRNA links Copy Number Variation to a Polycomb/Trithorax Epigenetic Switch in FSHD muscular Dystrophy", Cell, 149(4):819-831, 2012.

Candille et al., "A beta-Defensin Mutation Causes Black Coat Color in Domestic Dogs", Science, 318 :1418-1423, 2007.

Cao et al., "Genome-wide MyoD binding in skeletal muscle cells: a potential for broad cellular reprogramming", Dev. Cell, 18(4):662-674, 2010.

Cassano et al., "Magic Factor-1 , a Partial Agonist of Met, Induces Muscle Hypertrophy by Protecting Myogenic Progenitors from Apoptosis" Molecular Therapy 2009, 17, S151.

Celegato, et al., "Parallel protein and transcript profiles of FSHD patient rnuscles correlate to the D4Z4 arrangement and reveal a common impairment of slow to fast fibre differentiation and a general deregulation of MyoD-dependent genes," Proteomics. (2006), 6:5303-5321.

Chamberlain et al., "Validity of RNAi-based therapeutics as a treatment for FSHD as demonstrated in a mouse model of muscular dystrophy" MOA National Scientific Conference—Neuromuscular Therapeutic Strategies: Overcoming the Barriers from Microscope to Marketplace 2011, 1 page.

Chang et al., "The Expansion of the PRAME Gene Family in Eutheria", PloS One, 6(2):e16867, 11 pages, 2011.

Chen and Okayama, "High-Efficiency Transformation of Mammalian Cells by Plasmid DNA", Mol. Cell Biol., 7(8) :2745-2752, 1987.

Choi et al., "Histone demethylase LSD1 is required to induce skeletal muscle differentiation by regulating myogenic factors" Biochemical and Biophysical Research Communications 2010, 401, 327-332.

Chuang et al., "DPY-27:a chromosome condensation protein homolog that regulates C. elegans dosage compensation through association with the X chromosome", Cell, 79(3):459-474, 1994.

Church and Gilbert, "Genomic sequencing", Proc. Natl. Acad. Sci. USA, 81 : 1991-1995, 1984.

Clapp et al., "Evolutionary conservation of Coding Function for D4Z4, the Tandem DNA Repeat Mutated in Facioscapulohumeral Muscular Dystrophy", Am. J Hum. Genet., 81:264-279, 2007.

Clark et al., "High sensitivity mapping of methylated cytosines", Nucleic Acids Res., 22(15):2990-2997, 1994.

Consolidated List of EPO Citations from Notices of Opposition to a European Patent issued in European Application No. EPI 16191567.3, Jul. 7, 2020 in 2 pages.

Cotton et al., "Reactivity of cytosine and thymine in single-base-pair mismatches with hydroxylamine and osmium tetroxide and its application to the study of mutations", Proc. Natl. Acad. Sci. USA, 85 :4397-4401, 1985.

Culhane et al., "Comparative Analysis of Small Molecules and Histone Substrate Analogs as LSD1 Lysine Demethylase Inhibitors" J Am Chem Soc. 2010, 132(9), 3164-3176.

Database Geneseq [online] Apr. 12, 2012, "Human double homeobox 4 (DUX4) mRNA SEQ ID No. 46," Retrieved from EBI accession No. GSN:AZT86869, Database accession No. AZT86869.

Database Geneseq [online] Apr. 12, 2012, "Human double homeobox 4 Polyadenylation Signal Containing DNA SEQ IS:67," retrieved from EBI accession No. GSN:AZT86890, Database accession No. AZT86890.

Database Geneseq [online] Jan. 27, 2005, "Retroelement consensus sequence identifier oligonucleotide #102," retrieved from EBI accession No. GSN:ADU24632, Database accession No. ADU24632.

Database Geneseq [online] Feb. 4, 2010, "Human Chromosome 4q35 D4Z4 repeat region PCR reverse primer, SEQ ID 2," retrieved from EBI accession No. GSN:AXT24501, Database accession No. AXT24501.

De Greef et al., "Clinical Features of facioscapulohumeral muscular dystrophy 2", Neurology, 75(17) :1548-1554, 2010.

De Greef et al., "Common epigenetic changes of D4Z4 in contraction-dependent and contraction-independent FSHD", Hum Mutat, 30 1449-1459, 2009.

De Greef et al., "Epigenetic Mechanisms of Facioscapulohumeral Muscular Dystrophy", Mutat Res., 647 :94-102, 2008.

De Jager et al., "Current status of cancer immunodetection with radiolabeled human monoclonal antibodies", Semin. Nucl. Med., 23(2) :165-179, 1993.

Dej et al., "Mutations in the *Drosophila* Condensin Subunit dCAP-G: Defining the Role fo Condensin for Chromosome Condensation in Mitosis and Gene Expression ni Interphase", Genetics, 168 :895-906, 2004.

Dixit et al., "DUX4, a candidate gene of facioscapulohumeral muscular dystrophy, encodes a transcriptional activator of PITXI", PNAS, 104(46):18157-18162, 2007.

Doolittle and Ben-Zeev, "Immunodetection of lipoprotein lipase: antibody production, immunoprecipation, and western blotting techniques", Methods Mol. Biol., 109:215-237, 1999.

Duhl et al., "Neomorphic agouti mutations in obese yellow mice", Nat. Genet., 8 :59-65, 1994.

DUX4 is RNA in the catalogue of Santa Cruz Biotechnology, Inc. (p. 33, published on May 16, 2008).

Eckert and Kunkel, "DNA polymerase fidelity and the polymerase chain reaction", PCR Methods and Applications, 1(1) :17-24, 1991.

Eckstein, Fritz. "The versatility of oligonucleotides as potential therapeutics" Exp. Opin. Biol. Ther. 2007, 7(7), 1021-1034.

Ehrlich et al., "Primary Muscle myoblasts and myotubes" Duke/UNC/UT/EBI Encode group, Dec. 7, 2009, 9 pages.

El Mansouri et al., "Lysine-specific demethylase 1-mediated demethylation of histone H3 lysine 9 contributes to interleukin 1 ß-induced microsomal prostaglandin E synthase 1 expression in human osteoarthritic chondrocytes" Arthritis Research & Therapy 2014, 16:R113, 15 pages.

(56) References Cited

OTHER PUBLICATIONS

Evidence of the date of publication of the abstracts of the 7th Australasian Gene Therapy Society Meeting, May 4-6, 2011, Melbourne, Australia (Jun. 27, 2011) of Chamberlain et al., "Validity of RNAi-based therapeutics as a treatment for FSHD as demonstrated in a mouse model of muscular dystrophy" MOA National Scientific Conference—Neuromuscular Therapeutic Strategies: Overcoming the Barriers from Microscope to Marketplace 2011, 1 page.

Extended Search Report issued in European Patent Application No. 16191567 issued Jun. 6, 2017.

Fechheimer et al., "Transfection of mammalian cells with plasmid DNA by scrape loading and sonication loading", Proc. Natl. Acad. Sci. USA, 84 :8463-8467, 1987.

Feng et al., "Cutting Edge: Human beta Defensin 3-A Novel Antagonist of the HIV-1 Coreceptor CXCR4", J mmunol., 177 :782-786, 2006.

Flavell et al., "Analysis of the beta-delta-globin gene loci in normal and Hb Lepore DNA: direct determination of gene linkage and intergene distance", Cell, 15(1):25-41, 1978.

Fraley et al., "Entrapment of a bacterial plasmid in phospholipid vesicles: Potential for gene transfer", Proc. Natl. Acad. Sci. USA, 76(7):3348-3352, 1979.

Frisullo et al., "CD8(+) T cells in facioscapulohumeral muscular dystrophy patients with inflammatory features at muscle MRI", J Clin. Immunol., 31 : 155-166, 2011.

Frommer et al., "A genomic sequencing protocol that yields a positive display of 5-methylcytosine residues in individual DNA strands", Proc. Natl. Acad. Sci. USA, 89 :1837-1831, 1992.

Gabellini et al., "Facioscapulohumeral muscular dystrophy in mice overexpressing FRG1", Nature, 439 :973-977, 2006.

Gabellini et al., "Inappropriate gene activation if FSHD: a repressor complex binds a chromosomal repeat deleted in dystrophic muscle", Cell, 110 :339-348, 2002.

Gabriels et al., "Nucleotide sequence of the partially deleted D4Z4 locus in a patient with FSHD identifies a putative gene within each 3.3 kb element", Gene, 236:25-32, 1999.

Geever et al., "Direct identification of sickle cell anemia by blot hybridization", Proc. Natl. Acad. Sci. USA, 78:5081, 1981.

Geier and Modrich, "Recognition sequence of the dam methylase of *Escherichia coli* K23 and mode of cleavage of Dpn I endonuclease", J Biol. Chem., 254:1408-1413, 1979.

GenBank No. HQ266762, "*Homo sapiens* clone 38-1 double homeodomain protein DUX4-s(DUX4) mRNA, complete cds, alternatively spliced", 4 pages, 2010.

GenBank ref. FJ439133, "*Homo sapiens* clone lambda42 DUX4 (DUX4) genes, complete cds", 8 pages, 2009.

Geng et al., "DUX4 activates germline genes, retroelements and immune-mediators: Implications for facioscapulohumeral dystrophy", Dev. Cell., 22:38-51, 2012.

Geng et al., "Immunodetection of Human Double Homeobox 4", Hybridoma Larchmt, 30(2):125-130, 2011.

Gopal, "Gene Transfer Method for Transient Gene Expression, Stable Transformation, and cotransformation of Suspension Cell Cultures", Imol. Cell Biol., 5 : 1188-1190, 1985.

Graham and van der Eb, "A new technique for the assay of infectivity of human adenovirus 5 DNA", Virology, 52:456-467, 1973.

Griffin et al., "Chemokine expression and control of muscle cell migration during myogenesis", J Cell Sci., 123(18):3052-3060, 2010.

Guatelli et al, "Isothermal, in vitro amplification of nucleic acids by a multienzyme reaction modeled after retroviral replication", Proc. Nat. Acad. Sci. USA, 87: 1874-1878, 1990.

Gulbis and Galand, "Immunodetection of the p21-ras products in human normal and preneoplastic tissues and solid tumors: a review", Hum. Pathol., 24(12):1271-1285, 1993.

Harland and Weintraub, "Translation of mRNA Injected into Xenopus Oocytes Is Specifically Inhibited by Antisense RNA", J Cell Biol., 101(3):1094-1099, 1985.

Hayward et al., "LSD1 Histone Demethylase Assays and Inhibition" Methods Enzymol. 2016, 573, 261-278.

Hewitt et al., "Analysis of the tandem repeat locus D4Z4 associated with facioscapulohumeral muscular dystrophy", Hum. Mol. Genet., 3:1287-1295, 1994.

Himeda et al., "Myogenic Enhancers Regulate Expression of the Facioscapulohumeral Muscular Dystrophy-Associated DUX4 Gene" Molecular and Cellular Biology 2014, 34(11), 1942-1955.

Holland et al., "Classification and nomenclature of all human homeobox genes", BMC Biol., 5:47, 2007.

Hu et al., "Minibody : A Novel Engineered Anti-Carcinoembryonic Antigen Anitbody Fragment (Single-Chain Fv-C H3) Which Exhibits Rapid, High-Level Targeting of Xenografts", Cancer Res., 56 :3055-3061, 1996.

Hwang et al., "Gastric retentive drug-delivery systems", Crit. Rev. Ther. Drug Carrier Syst., 15(3):243-284, 1998.

International Preliminary report on Patentability issued in PCT Application No. PCT/US2011/048318, mailed Feb. 19, 2013.

International Search Report and Written Opinion issued in PCT Application No. PCT/US2012/048557, mailed Feb. 28, 2013.

International Search Report issued in PCT Application No. PCT/US2011/048318, mailed Mar. 26, 2012.

Jagasia et al., "Chromosome 9 related aberrations and deletions of the CDKN2 and MTS2 putative tumor suppressor genes in human chondrosarcomas", Cancer Letters, 105 :91-103, 1996.

Ji and Tian, "Reprogramming of 3' Untranslated Regions of mRNAs by Alternative Polyadenylation in Generation of Pluripotent Stern Cells from Different Cell Types", PloS One, 4(12):e8419, 13 pages, 2009.

Jiang et al., "MBD3L1 and MBD3L2, two new proteins homologous to the methyl-CpG-binding proteins MBD2 and MBD3: characterization of MBD3L1 as a testis-specific transcriptional repressor", Genomics, 80(6):621-629, 2002.

Jiang et al., "Testing the position-effect variegation hypothesis for facioscapulohumeral muscular dystrophy by analysis of histone modification and gene expression in subtelomeric 4q", Hum. Mol. Genet., 12(22):2909-2921, 2003.

Jin et al., "An Antimicrobial Peptide Regulates Tumor-Associated Macrophage Trafficking via the Chemokine Receptor CCR2, a Model for Tumorigenesis", PloS One, 5 :e10993, 2010.

Jin et al., "The haploid male germ cell- and oocyte-specific Mdb3l1 and Mbd3l2 genes are dispensable for early development, fertility, and zygotic DNA demethylation in the mouse", Dev. Dyn., 237 :3435-3443, 2008.

Kaessmann et al., "RNA-based Gene duplication: mechanistic and evolutionary insights", Nat. Rev. Genet, 10:19-31, 2009.

Kanno et al., "A structural-maintenance-of-chromosomes hinge domain-containing protein is required for RNA-directed DNA methylation", Nat. Genet., 40:670-675, 2008.

Klooster et al., "Comprehensive expression analysis of FSHD candidate genes at the mRNA and protein level", Eur. J Hum. Genet., 17 :1615-1624, 2009.

Kowaljow et al., "The DUX4 gene at the FSHD1A locus encodes a pro-apoptotic protein", Neuromuscul. Disord., 17(8):611-623, 2007.

Krauss et al., "Keep Your Friends Close: Cell-Cell Contact and Skeletal Myogenesis" Cold Spring Harb Perspect Biol. 2017, 9:a029298, 1-16.

Kwoh et al., "Transcription-based amplification system and detection of amplified human immunodeficiency virus type 1 with a bead-based sandwich hybridization format", Proc. Natl Acad. Sci. USA, 86 :1173, 1989.

Lai and Gallo, "AMPed Up immunity: how antimicrobial peptides have multiple roles in immune defense", Trends Immunol., 30(3):131-141, 2009.

Lam et al., "siRNA Versus miRNA as Therapeutics for Gene Silencing" Molecular Therapy Nucleic Acids 2015, 4(9), 20 pages.

Landegren et al., "A ligase-mediated gene detection technique", Science, 241(4869):1077-1080, 1988.

Laoudj-Chenivesse et al., "Increased levels of adenine nucleotide translocator 1 protein and response to oxidative stress are early events in facioscapulohumeral muscular dystrophy muscle", J Mol. Med., 82 :216-224, 2005.

(56) References Cited

OTHER PUBLICATIONS

S. Lamande et al. "Reduced Collagen VI causes Bethlem myopathy: a heterozygous COL6A1 nonsense mutation results in mRNA decay and functional haploinsufficiency", Human Molecular Genetics, vol. 7, No. 6, pp. 981-989, Jun. 1, 1998.

Laskowski et al., "The Pharmacology of Experimental Myopathies" Ann. Rev. Pharmacol. Toxicol. 1977; 17, 387-409.

Lassar et al., "Regulatory mechanisms that coordinate skeletal muscle differentiation and cell cycle withdrawal" Current Opinion in Cell Biology 1994, 6:788-794.

Lee et al., "Histone H3 Lysine 4 Demethylation Is a Target of Nonselective Antidepressive Medications" Chemistry & Biology 2006, 13, 563-567.

Lemmers et al. "Worldwide Population Analysis of the 4q and 10q Subtelomeres Identifies Only four Kiscrete Interchromosomal Sequence Transfers in Human Evolution", Am. J Hum. Genet., 86(3):364-377, 2010.

Lemmers et al., "A unifying genetic model for facioscapulohumeral muscular dystrophy", Science, 329(5999) :1650-1653, 2010.

Lemmers et al., "Complete allele information in the diagnosis of facioscapulohumeral muscular dystrophy by triple DNA analysis", Am. J Hum. Genet., 50(6):816-819, 2001.

Lemmers et al., "Contractions of D4Z4 on 4qB Subtelomeres Do Not Cause Facioscapulohumeral Muscular Dystrophy", Am. J Hum. Genet., 75 :1124-1130, 2004.

Lemmers et al., "Digenic inheritance of an SMCHD1 mutation and an FSHD-permissive D4Z4 allele causes facioscapulohumeral muscular dystrophy type 2", Nat. Genet., 44(12):1370-1374, 2012.

Lemmers et al., "Facioscapulohumeral muscular dystrophy is uniquely associated with one of the two variants of the 4q subtelomere", Nat. Genet., 32 :235-236, 2002.

Lemmers et al., "Inter- and intrachromosomal sub-telomeric rearrangements on 4q35: implications for facioscapulohumeral muscular dystrophy (FSHD) aetiology and diagnosis", Hum. Mol. Genet., 7 :1207-1214, 1998.

Lemmers et al., "Specific Sequence Variations within the 4q35 Region Are Associated with Facioscapulohumeral Muscular Dystrophy", Am. J Hum. Genet., 81 :884-894, 2007.

Lieb et al., "DPY-26, a link between dosage compensation and meiotic chromosome segregation in the nematode", Science, 274 :1732-1736, 1996.

Liu et al., "DNAFSMiner: a web-based software toolbox to recognize two types of functional sites in DNA sequences", Bioinformatics, 21(5):671-673, 2005.

Luco et al., "Regulation of Alternative Splicing by Histone Modifications", Science, 327(5968) :996-1000,2010.

Lyle et al., "The FSHD-associated repeat, D4Z4, is a member of a dispersed family of homeobox-containing repeats, subsets of which are clustered on the short arms of the acrocentric chromosomes", Genomics, 28:389-397, 1995.

Marinus and Morris, "Isolation of Deoxyribonucleic Acid Methylase Mutants of *Escherichia coli* K-12", J Bacteriol, 114(3): 1143-1150, 1973.

Masny et al., "Analysis of the allele-specific RNA transcription in FSHD by RNA-DNA Fish in single myonuclei", Eur. J Hum. Genet., 18, 448-456, 2010.

Mathiowitz et al., "Biologically erodible microspheres as potential oral drug delivery systems", Nature, 386(6623) :410-414, 1997.

Mattila et al., "Fidelity of DNA synthesis by the Thermococcus litoralis DNA polymerase—an extremely heat stable enzyme with proofreading activity", Nucleic Acids Res., 19(13):4967, 1991.

May and Hattman, "Analysis of bacteriophage deoxyribonucleic acid sequences methylated by host- and R-factor-controlled enzymes", J Bacteriol, 123(2):768-770, 1975.

MDA National Scientific Conference, "Neuromuscular Therapeutic Strategies: Overcoming the Barriers from Microscope to Marketplace," Muscular Dystrophy Association Inc., 2011.

Melchionna et al., "Induction of myogenic differentiation by SDF-1 via CXCR4 and CXCR7 receptors", Muscle Nerve, 41 :828-835, 2010.

Menazza, et al., "Oxidative stress by rnonoamine oxidases is casually involved in myofiber damage in muscular dystrophy," Human Molecular Genetics, (2010), 19(21): 4207-4215.

Metzger, et al, "LSD1 demethylates repressive histone marks to promote androgen-receptor-dependent transcription," Nature, (2005), 437(15): 436-439.

Midorikawa et al., "*Staphylococcus aureus* Susceptibility to Innate Antimicrobial Peptides, Beta-Defensins and CAP18, Expressed by Human Keratinocytes", Infect. Immun., 71(7):3730-3739, 2003.

Molnar et al., "Inflammatory changes in facioscapulohumeral muscular dystrophy", Eur. Arch. Psychiatry Clin. Neuroscie., 241 :105-108, 1991.

Mousumi, Debnath. "Chapter 5 Reporter Gene." Molecular Diagnostics: Promises and Possibilities, Dordrech Heidelberg London, Springer, 2010 pp. 71-84.

Myers et al., "Detection of single base substitutions by ribonuclease cleavage at mismatches in RNA:DNA duplexes", Science, 230(4731):1242, 1985.

Neguembor, Maria V. and Gabellini, Davide, "In Junk we Trust: Repetitive DNA, Epigenetics and FacioScapulohumeral Muscular Dystrophy," Epigenomics, vol. 2 No. 2. Apr. 1, 2010, pp. 271-287.

Nelson et al., "Protocol for the fast chromatin immunoprecipitation (ChIP) method", Nat. Protoc, 1(1):179-185, 2006.

Nguyen et al., "The Nrf2-Antioxidant Response Element Signaling Pathway and Its Activation by Oxidative Stress" Journal of Biological Chemistry 2009, 284(20), 13291-13295.

Nicolau and Sene, "Liposome-mediated DNA transfer in eukaryotic cells. Dependence of the transfer efficiency upon the type of liposomes used and the host cell cycle stage", Biochim. Biophys. Acta, 721(2):185-190, 1982.

Notice of Opposition Letter to a European Patent issued in European Application No. EPI 16191567.3 issued Jul. 8, 2020.

Notice of Opposition Letter to a European Patent issued in European Application No. EPI 16191567.3 issued Jul. 7, 2020.

Notice of Opposition to a European Patent issued in European Application No. EPI 16191567.3 issued Jul. 8, 2020.

Notice of Opposition to a European Patent issued in European Application No. EPI 16191567.3 issued Jul. 7, 2020.

Notice of Opposition to a European Patent issued in European Application No. EPI 1818806.9 issued Jul. 4, 2017.

Orita et al., "Rapid and sensitive detection of point mutations and DNA polymorphisms using the polymerase chain reaction", Genomics, 5(4):874-879, 1989.

Parker et al., "An Expressed Fgf4 Retrogene Is Associated with Breed-Defining Chondrodysplasia in Domestic Dogs", Science, 325(5943):995-998, 2009.

Pawson et al., "Assembly of Cell Regulatory Systems Through Protein Interaction Domains" Science 2003, 300, 445-452.

Pfaffl, "A new mathematical model for relative quantification in real-time RT-PCR", Nucleic Acids Res., 29(9) :e45, 6 pages 2001.

Pierre et al., "Atypical structure and phylogenomic evolution of the new eutherian oocyte- and embryo-expressed KHDC1/DPPA5/ECAT1/OOEP gene family", Genomics, 90(5):583-594, 2007.

Potter et al., "Enhancer-dependent expression of human K immunoglobulin genes introduced into mouse pre-B lymphocytes by electroporation", Proc. Natl. Acad. Sci. USA, 81 :7161-7165, 1984.

Prevalence of rare diseases: Bibliographic data, www.orpha.net, Nov. 2008, No. 1, Orphanet Report Series.

Raca et al., "Deletion analysis of the imprinting center region in patients with Angelman syndrome and Prader-Willi syndrome by real-time quantitative PCR", Genet. Test, 8(4):387-94, 2004.

Rakyan et al., "Metastable epialleles in mammals", Trends Genet, 18:348-351, 2002.

Redon et al., "Global variation in copy number in the human genome", Nature, 444(7118):444-454, 2006.

Reed et al., "Abnormal expression of mu-cyrstallin in facioscapulohumeral muscular dystrophy", Exp. Neural., 205(2):583-586, 2007.

Sacconi et al., "Patients with a phenotype consistent with facioscapulohumeral muscular dystrophy display genetic and epigenetic heterogeneity", J Med. Genet., 49(1) :41-46, 2012.

US 12,624,396 B2

Page 6

(56)        References Cited

OTHER PUBLICATIONS

Saiki et al., "Analysis of enzymatically amplified beta-globin and HLA-DQ alpha DNA with allele-specific oligonucleotide probes", Nature, 324 :163-166, 1986.
Sandling et al., "A candidate gene study of the type I interferon pathway implicates IKBKE and IL8 as risk loci for SLE", Eur. J Hum. Genet., 19(4):479-484, 2011.
Sass et al., "Human Beta-Defensin 3 Inhibits Cell Wall Biosynthesis in Staphylococci", Infec. Immun., 78(6):2793-2800, 2010.
Schulz et al., "L1 Retrotransposons in Human Cancers", J Biomed. Biotecnol., 83672, 2006, p. 1-12.
Scionti et al., "LSD1 Controls Timely MyoD Expression via MyoD Core Enhancer Transcription" Cell Reports 2017, 18, 1996-2006.
Semple et al., "Human B-defensin 3 affects the activity of pro-inflammatory pathways associated with MyD88 and TRIF", Eur. J Immunol., 41(11) :3291-3300, 2011.
Semple et al., "Human B-defensin 3 has immunosuppressive activity in vitro and in vivo", Eur. J Immunol., 40:1073-1078, 2010.
Seroussi et al., "Duplications on Human Chromosome 22 Reveal a Novel Ret finger Protein- Like Gene Family with Sense and Endogenous Antisense Transcripts", Genome Research, 9:803-814, 1999.
Sheffield et al., "Attachment of a 40-base-pair G+C-rich sequence (GC-clamp) to genomic DNA fragments by the polymerase chain reaction results in improved detection fo single-base changes", Proc. Natl. Acad. Sci. USA, 86:232-236, 1989.
Siegfried and Cedar, "DNA methylation: a molecular lock", Curr. Biol., 7:r305-307, 1997.
Simpson et al., "Cancer/testis antigens, gametogenesis and cancer", Nat. Rev. Cancer, 5(8):615-625, 2005.
Smit, "Identification of a new, abundant superfamily of mammalian LTR-transposons", Nucleic Acids Res., 21(8):1863-1872, 1993.
Snider et al., "Facioscapulohumeral Dystrophy: Incomplete Suppression of a Retrotransposed Gene", PloS Genet, 6:e1001181, 2010.
Snider et al., "RNA transcripts, miRNA-sized fragments and proteins produced from D4Z4 units: new candidates for the pathophysiology of facioscapulohumeral dystrophy", Hum. Mol. Genet, 18(13):2414-2430, 2009.
Spurlock et al., "Confirmation that the specific SSLP microsatellite allele 4qA161 segregates with fascioscapulohumeral muscular dystrophy (FSHD) in a cohort of multiplex and simplex FSHD families", Muscle Nerve, 42 :820-821, 2010.
Stanghellini et al., "Trim43a, Trim43b, and Trim43c: novel mouse genes expressed specifically in mouse preimplantation embryos", Gene Expr. Patterns, 9(8):595-602, 2009.
Statland and Tawil, "Facioscapulohumeral muscular dystrophy: molecular pathological advances and future directions", Curr. Opin. Neural., 24(5):423-428, 2011.
Sun et al., "A mutated human homologue to yeast Upf1 protein has a dominant-negative effect on the decay of nonsense-containing mRNAs in mammalian cells", Proc. Natl. Acad. Sci. USA, 95 :10009-10014, 1998.
Sun et al., "Histone Demethylase LSDI Regulates Neural Stern Cell Proliferation" Molecular and Cellular Biology 2010, 1997-2005.
Takenaga et al., "Microparticle resins as a potential nasal drug delivery system for insulin", J Control Release, 52(1-2):81-87, 1998.
Tarn et al., "Pseudogene-derived small interfering RNAs regulate gene expression in mouse oocytes", Nature, 453(7194) :534-538, 2008.
Tawil and van der Maarel, "Facioscapulohumeral muscular dystrophy", Muscle Nerve, 3491):1-15, 2006.
Thomas et al., "A large patient study confirming that facioscapulohumeral muscular dystrophy (FSHD) disease expression is almost exclusively associated with an FSHD locus located on a 4qA-defined 4qter subtelomer", J. Med. Genet., 44 :215-218, 2007.

Trompteter et al., "Rapid and highly efficient gene transfer into natural killer cells by nucleofection", J Immunol. Methods, 274(1-2) :245-256, 2003.
Tsumagari et al., "FSH dystrophy and a subtelomeric 4q hapoltype : a new assay and associations with disease", Journal of Medical Genetics, 47(11):745-751, 2010.
Tupler et al., "Monosomy of distal 4q does not cause facioscapulohumeral muscular dystrophy", J Med. Genet., 33 :366-370, 1996.
Tur-Kaspa et al., "Use of Electroporation to Introduce Biologically Active Foreign Genes into Primary Rat Hepatocytes", Mol. Cell Biol., 6(2):716-718, 1986.
Underhill et al., "Detection of Numerous Y Chromosome Biallelic Polymorphisms by Denaturing High-Performance Liquid Chromatography", Genome Research, 7(10) :996-1005, 1997.
U.S. Appl. No. 61/511,319, filed Jul. 25, 2011 by Harper, et al.
Van Der Maarel et al., "The D4Z4 Repeat-Mediated Pathogenesis of Facioscapulohumeral Muscular Dystrophy" Am. J. Hum. Genet. 2005; 76, 375-386.
Van Der Maarel, et al. "Facioscapulohurneral Muscular Dystrophy and DUX4: Breaking the Silence," Trends Mol Med., (2011), 17(5): 252-258.
Van Deutekom et al., "FSHD associated DNA rearrangements are due to deletions of integral copies of a 3.2 kb tandemly repeated unit", Hum. Mol. Genet., 2(12):2037-2042, 1993.
Van Overveld et al., "Hypomethylation of D4Z4 in 4q-linked and non-4q-linked facioscapulohumeral muscular dystrophy", Nat. Genet., 35(4):315-317, 2003.
Van Overveld et al., "Variable hypomethylation of D4Z4 in facioscapulohumeral muscular dystrophy", Ann. Neural., 58(4):569-576, 2005.
Vanderplanck C. et al. "Keynote 5: Suppression of DUX4 or DUX4C expression by antisense strategies in a therapeutic approach for FSHD," Journal of Gene Medicine, vol. 13(7-8), p. 414 (2011).
Wallace et al., "Developing RNAi Therapy for FSHD" Molecular Therapy 2009, vol. 17, supp. 1, S151, abstract 387.
Wallace et al., "DUX4, a candidate gene for facioscapulohumeral muscular dystrophy, causes p53-dependent myopathy in vivo", Ann. Neural, 69 :540-552, 2011.
Wallace et al., "Chapter 7: RNAi Therapy for Dominant Muscular Dystrophies and Other Myopathies" Muscle Gene Therapy, edited by Dongsheng Duan, Springer New York, 2010, 99-115.
Wantanabe et al., "Endogenous siRNAs from naturally formed dsRNAs regulated transcripts in mouse oocytes", Nature, 453:539-543, 2008.
Wijmenga et al., "Chromosome 4q DNA rearrangements associated with facioscapulohumeral muscular dystrophy", Nat. Genet., 2(1):26-30, 1992.
Wu and Wallace, "The ligation amplification reaction (LAR)-amplification of specific DNA sequences using sequential rounds of template-dependent ligation", Genomics, 4(4):560-569, 1989.
Wu and Wu, "Evidence for targeted gene delivery to Hep G2 hepatoma cells in vitro", Biochemistry, 27(3):887-892, 1988.
Wu and Wu, "Receptor-mediated in Vitro Gene Transformation by a Soluble DNA Carrier System", J Biol. Chem., 262(10):4429-4432, 1987.
Wu et al., "Characterization of Genomic Structures and Expression Profiles of Three Tandem Repeats of a Mouse Double Homeobox Gene: Duxbl", Duxbl Dev. Dyn, 239 :927-940, 2010.
Wuebbles et al., "Testing the effects of FSHD candidate gene expression in vertebrate muscle development", Int. J Clin. Exp. Pathol., 3(4):386-400, 2010.
Xu, X., et al., "DNaseI Hypersensitivity at gene-poor, FSH Dystrophy-linked 4q35.2," Nucleic Acids Research, vol. 37, No. 22. Dec. 1, 2009, pp. 7381-7393.
Yang and Russell, "Maize sucrose synthase-1 promoter directs phloem cell-specific expression of Gus gene in transgenic tobacco plants", Proc. Natl. Acad. Sei. USA, 87:4144-4148, 1990.
Yang et al., "Beta-defensins: linking innate adaptive immunity through dendritic and T cell CCR6", Science, 286(5439):525-528, 1999.
Zalzman et al., "Zscan4 regulates telomere elongation and genomic stability in ES cells", Nature, 464(7290):858-863, 2010.

(56) References Cited

OTHER PUBLICATIONS

Zeng et al., "Specific Loss of Histon H3 Lysine 9 Trimethylation and HP1γ/Cohesin Binding at D4Z4 Repeats Is associated with Facioscapulohumeral Dystrophy (FSHD)", PloS Genet, 5(7):e1000559, 14 pages, 2009.

Zeschnigk et al., "Imprinted segments in the human genome: different DNA methylation patterns in the Prader-Willi/Angelman syndrome region as determined by the genomic sequencing method", Hum. Mol. Genet., 6(3):387-395, 1997.

European Search Report in corresponding European Application No. 22150754.4-118, dated Jul. 26, 2022.

Fougerolles et al., "Interfering with disease: a progress report on siRNA-based therapeutics", *Nat Rev Drug Discov.*, pp. 443-453, 2007.

Kurreck, Jens; "siRNA Efficiency: Structure or Sequence—That is the Question", *Journal of Biomedicine and Biotechnology*, pp. 1-7, 2006.

Mansoor, M. and Melendez, AJ., "Advances in antisense oligo-nucleotide development for target identification, validation, and as novel therapeutics", *Gene Regul Syst Bio.*, 2:275-295; 2008.

"*Homo sapiens* clone lambda42 DUX4 (DUX4) genes, complete cds", *GenBank*: FJ439133.1.

Bouwman et al., "Systemic delivery of a DUX4-targeting antisense oligonucleotide to treat facioscapulohumeral muscular dystrophy", *Mol Ther Nucleic Acids*, 26:813-827, 2021.

* cited by examiner

Fig.3A

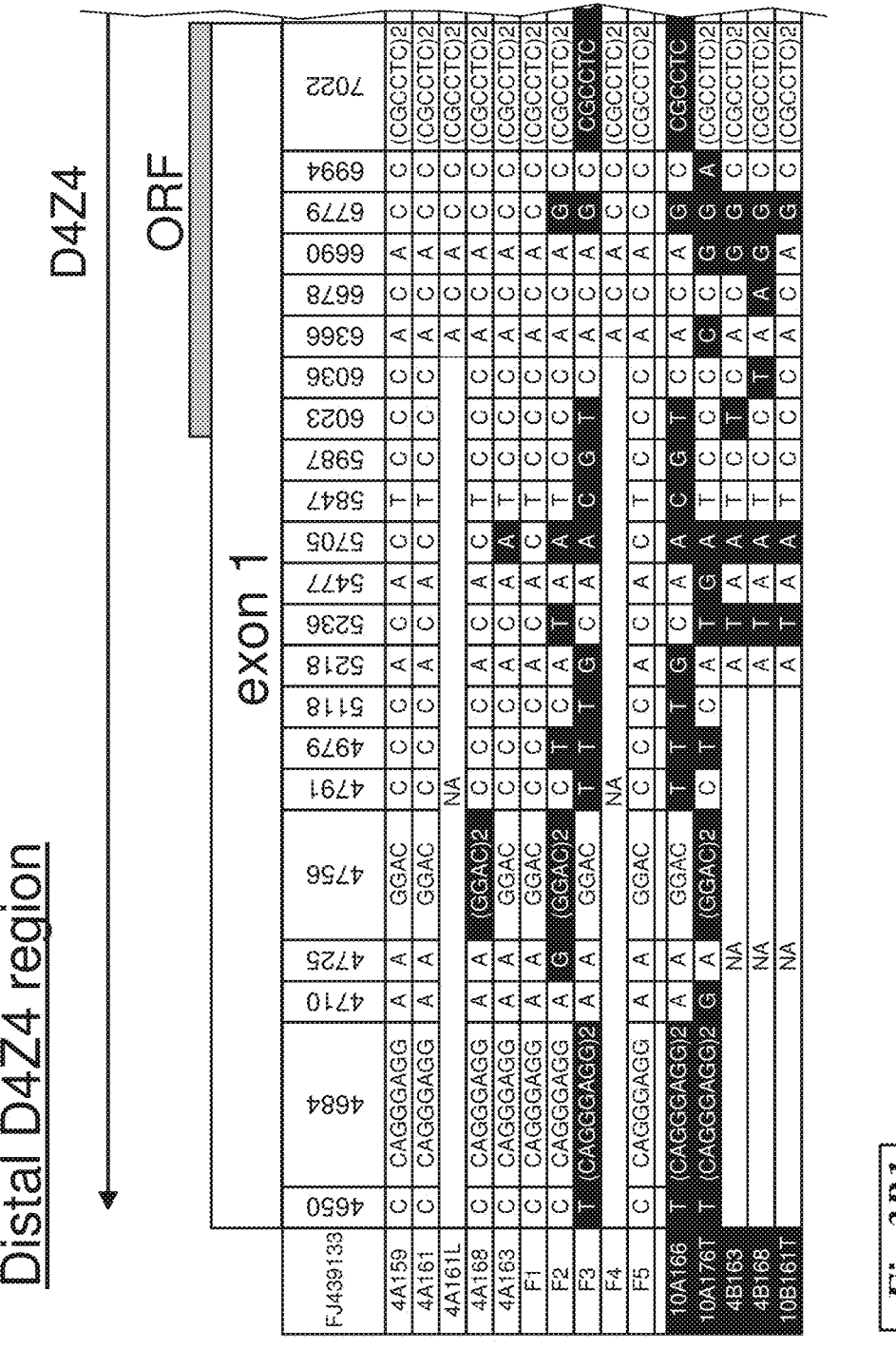
*Fig.3B1*
| | Fig.3B1 |
|---|---|
| | Fig.3B2 |

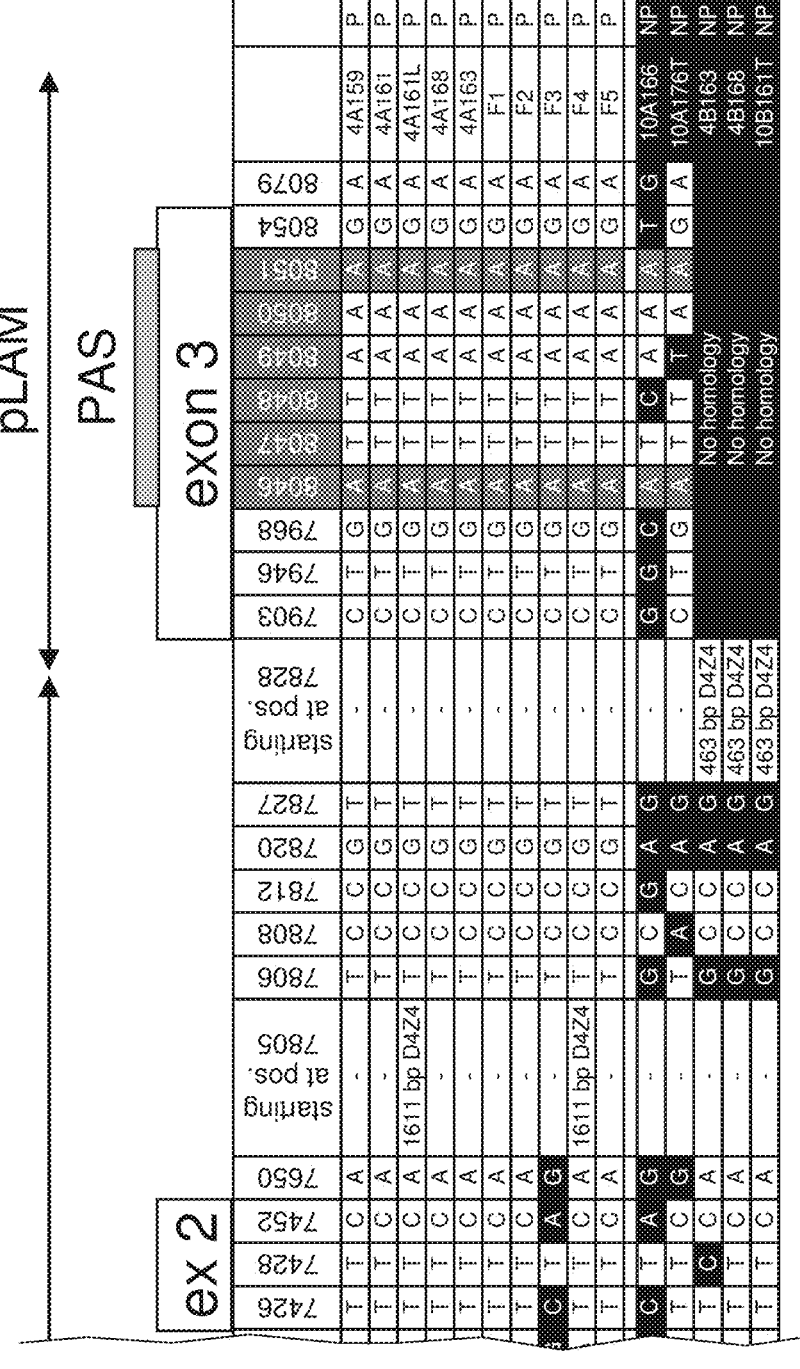
*Fig.3B2*
| | | Fig.3B1 |
|---|---|---|
| | | Fig.3B2 |

Fig. 4D

DUX4 SNPs comparing 4qa161 with 10 sequences

Red = SNP

<u>Underline</u> = Poly-A addition sites in 4qA161

Alignment of chromosome 4A161 with 10

```
04-AGCCTCCCAGCTGCCAGCGCGGAGCTCCTGGCGGTCAAAAGCATACCTCTGTCTGTCTTTAGCCCGGCTAGACCTGGCGCGCCAGTGCGCACCCCG
10-AGCCTCCCAGCTGCCAGCGCGGAGCGCGGAGCTCCTGGCGGTCAAAAGCATACCTCTGTCTGTCTTTAGCCCGGCTAGACCTGGCGCGCCAGTGCGCACCCCG

04-GCTCGACGTGCAAGGAGCTCCGCTCTCTGTCCCTCTCTGTCTGTCTTCCGTGAAAATTCGGCTGAAATTCTCCCCCACTTCCGACCGCTGTCTAGGCAAA
10-GCTCGACGTGCAAGGAGCTCCGCTCTCTGTCCCTCTCTGTCTGTCTTCCGTGAAAATTCTCGCTGAAATTCTCCCCCACTTCCGACCGCTGTCTAGGCAAA

04-CCTGGATTAGAGTTACATCTCCTGGATGATTAGTTCAGAGATAAAGATTTGCATCTTTGTGTGGAT
10-CCTGGATTAGAGTTACATCTCCTGGATGATTAGTTCAGAGATAAAGATTTGCATCTTTGTGTGGATC
```

Fig. 4E

DUX4 Intron 2 and Exon 3 Sequence

Red = SNP

<u>Underline</u> = Poly-A addition site

Transcript-Intron2

```
GTGGGCCGCTACTGCCACGGCGGCGGTTTGCGGCAGCCGCCGGGGCTGTGGGAGCAGCCCGGCAGAGCTCTCTCCTCTCCACCA
GCCACCCGCGCCTGACCGCCCCTCCCCACCCCGGAAAACGCGTGTCCCTGGGCTGGGTGGGAGACCCCG
GTCCCGGGAAACACCGGGCCCGGTCCGGCTGACTCCTGGGCCCGCCGCCACCGTCGCC
CGCCCGCCGGGCCCCGGGGCTCCAGCGCGGAGCTCCTGGCGGTCAAAAGCATACCTCGTCTGTCTGTTGCCCGGCTTCC
TGGCTAG
```

Transcript-Exon3-pA sites underlined

```
ACCTGCCGCCAGCTGCCGCACCCCGCCTGACCTGCCAAGGGGAGCTCGGCTGCCCCTTGTTCTTCCGTGAAATTCTGGCTGAAT
GTCTCCCCCCACCTTCCGACCGCTGTCTAGGCAAACCTGGATTAGAGTTACATCTCCTGGATGATTAGTTCAGAGATATATTAAAATGCC
CCCTCCCTGTGGATCCTATAGAAGATTTGCATCTTTGTGTGATGAGTGAGTAGCAGTATCCCCTGTAGAAAAAGCCTGAA
ATTGGTTTACATAACTTCGGTGATCAGTGCAGATGTGTTTCAGAACCTAGAACCTAGAGAAATGGTTACATCACTTAGGT
GATCAGTGTAGAGATATGTTAAAATTCTCGTGTAGACAGAGCCTAGAACCTAGTGATCAGTGCAGGATAAGTCAT
AAAGCCTCCTGTAGGCAGAGTGTAGGCAAGTGTTCCCTCCCTGGGCTGATCAGTGCAGAGATATCTCACAAAGCCCCTATAAGCCAAAC
CTTGACAAGGGTTACATCACCTGTTTGAGCAGTGGAAATATATATCACAAAGCCCCAGACAATTTTTACATCTC
CTGAGTGAGCATTGGAGAGATCTGTCACAATGCCCCTGTAGGCAGAGCTTAGCATCACCTGGTGATCAGTGCAGAGAT
ATGTCAAAAACGCTCCTGTAGTCTGAACCTAGACAGAGTTACATCACCTTGGGGATCAGTCAGTCAGTGCAGAGAATTCC
```

*Fig.5A*

F4
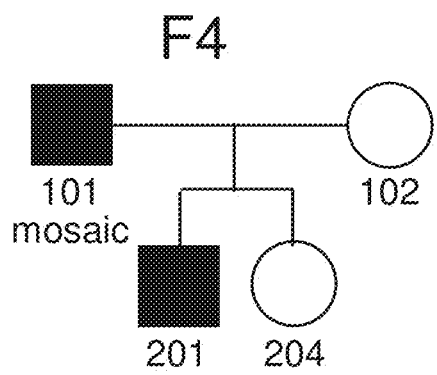
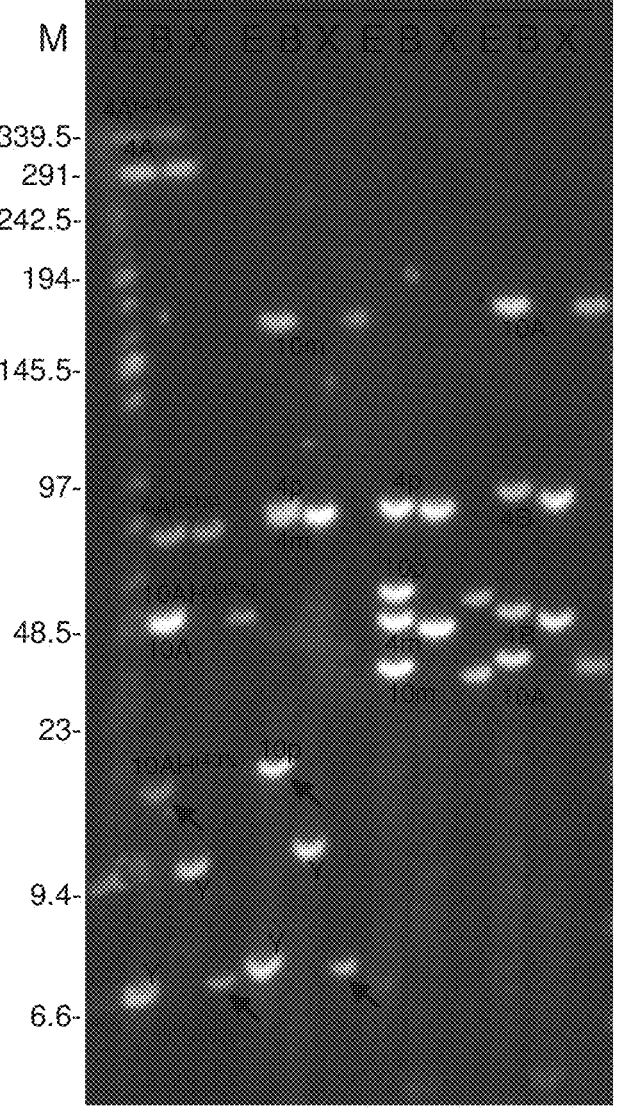
p13E-11
*Fig.5B*

F6 (4A161L, 6 D4Z4 units)
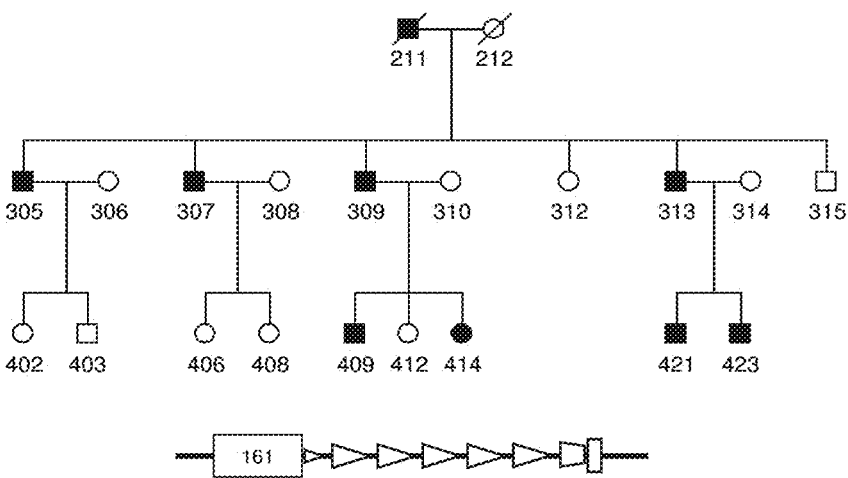
F7 (4A159, 5.5 D4Z4 units)
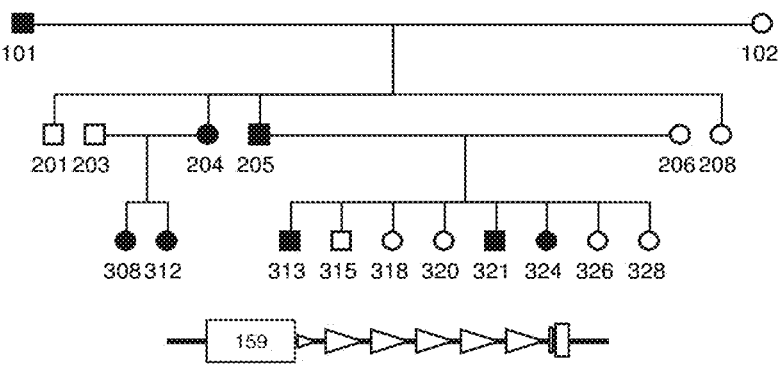
F8 (4A168, 5.5 D4Z4 units)
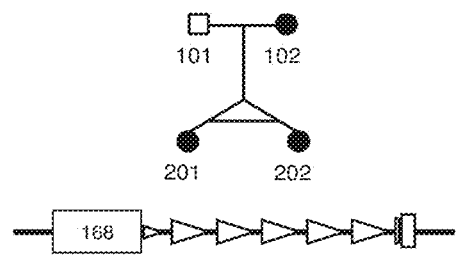
*Fig.6*

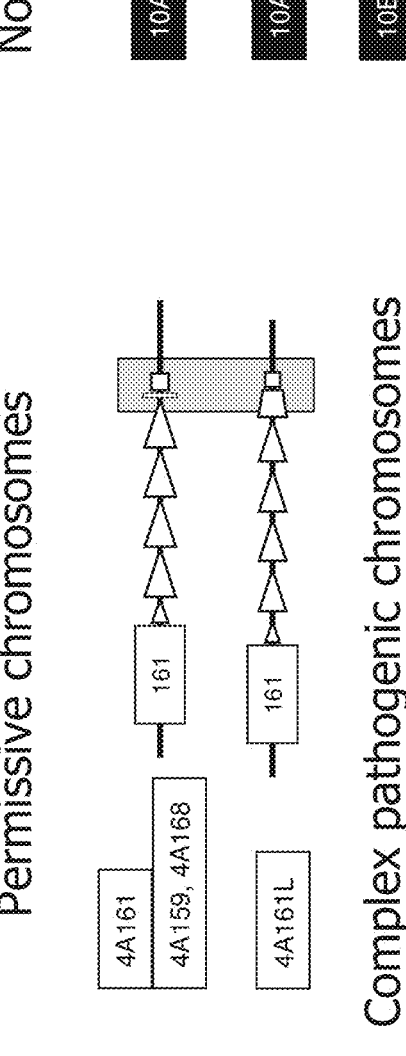
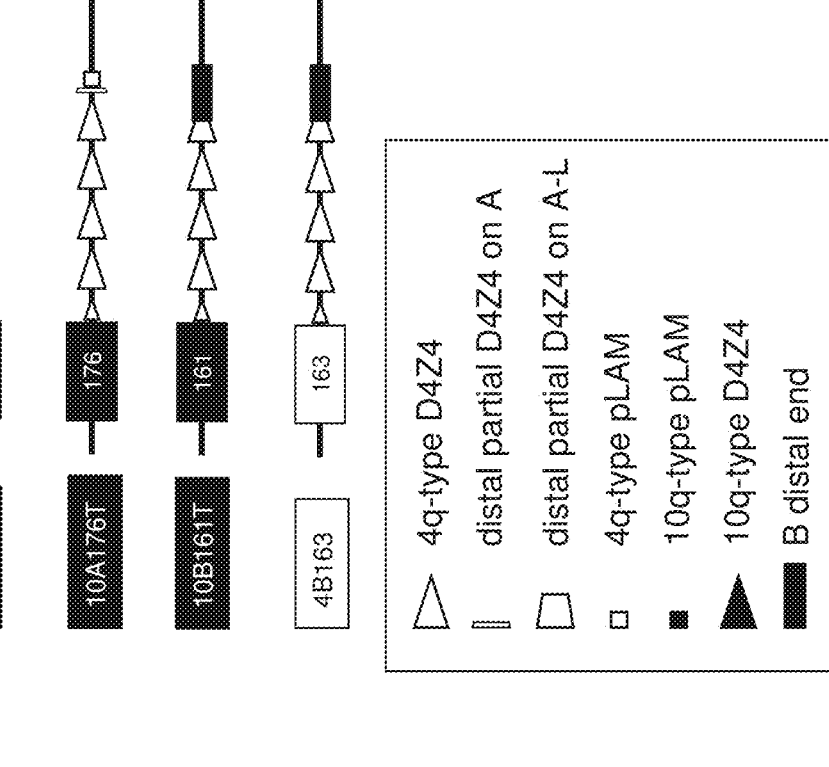
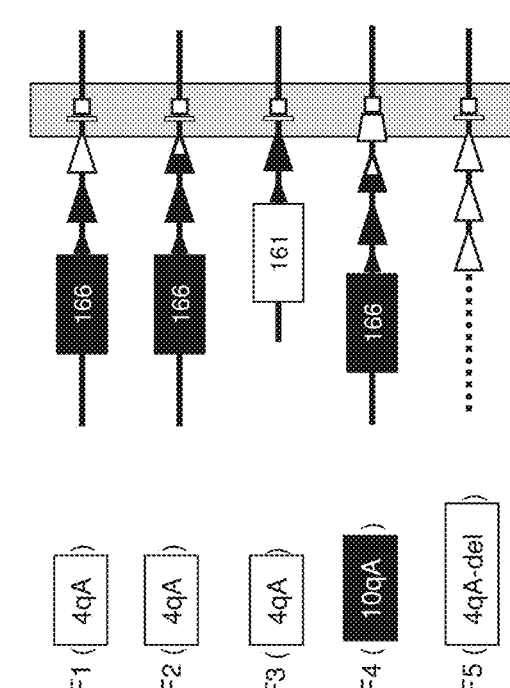
*Fig. 7*

*Fig. 9D*

TRIM43 relative to RPL13a control          FSHD

KHDC1 relative to RPL13a control          FSHD

ZSCAN4 relative to RPL13a control          FSHD

*Fig.21A-C*

SEQUENCE LISTING

```
<160> NUMBER OF SEQ ID NOS: 125

<210> SEQ ID NO 1
<211> LENGTH: 8100
<212> TYPE: DNA
<213> ORGANISM: Homo sapiens

<400> SEQUENCE: 1
gaattctatc tggtacccag agggaagggg gttcccagtg agggcaggac caggcttcat      60
gcacctcttc aggaatgttc tcctcatagt ccagcctcaa ggtgtgcatc ctctgtgtgc     120
atggagtcca tggcaggctc tgcctgggga gccgtccagc tgcacacctg caatgtggtg     180
gtgaccctca tgaatgggtg gttctgggcc ccatggctgg cagcagagag ggagatgttc     240
agccaccaag cccagagccc tgccacaggc ttctgtgagg cctccatctg ctctgggttc     300
ttgccctgag aggctgccct gaagtcaaac agaagcaggt gggcctctct tccagggctg     360
ctctctcccc cactgacagc tccctagagg gagactcaga cagcggggac agattcctca     420
ggcataagca ctggagttta ggctggccag ttcattccat acgcccacat gacatgacac     480
aaggcagagg ctgtgggaca aaggtattgc cttttcttct ggcatgagga atggcttagg     540
aagcagggga tggtgggggct ggggttgagt gatgggctgt gggccacaag gagtgggtgg     600
gcgctgagaa agtgtcctgg ttgtctgtcc atagacgcag aatgagtggc atcccaggag     660
cctgtgaggg gctggcagag acttactggt tccagtaaaa gccccatgtg gatgcagtaa     720
tgctgcctgc tggtccttgg ctgtaattac aaacaggtac atgaggtacc catgcatctt     780
gaagctctca gggagtgggt tccagctgct catggtaggc acttttagtc actgaacatg     840
cttcaggcat gtccaagctt gattaagcca ggcatcttgc tgtgaggccc tccacttcac     900
taagaacact cttccttgct tcccctggaa gttggacctt ccagttctgg ttctggagac     960
acgatggccc ctcctggacc cctgggagaa tgtgctcagg tgacacacag ttgatggggc    1020
ccatttccaa gccattcttc catttcccac tgtttgaggg acccgaggcc ggtgacaagc    1080
acagagccac ccaaggccag ctgtctgcac ctaaatgtga tgcttgtctg gatgtctcag    1140
ggccagaacc ctccaggtga gatggcctgg tcctcaccac ctggcgtccg tgctcccttt    1200
tcctctgttc aatcctggcg ccaatgcctc cctcaactct caggtcacca ttggagaaga    1260
tgctcaggaa gaacaagcag ctgcagttaa ccctgctgaa agtggcagat gggtccaggc    1320
tcttgagctc gtcttggaca tggaacatgt ggatacaggc tttgagcagt gtgtgtagct    1380
ctttcaggaa ggaagggaaa agggtgttac ccgggtccta caccctggaa cgaccttct     1440 cagacagtaa atagttggca gggtgcggtc atgtgtgatt ttagtttca  actttaggct    1500 ttcattttca aattccacaa taaacacata aggtggagtt ctggtttcag cacacacaca    1560
cacacacaca aacacacaca cacacacaca cacagtctct ctctctgtat gtctctttct    1620
gtctctctct ctctccttcc tgcaaggatc cttgttaaca agaaaccttc tgccaaatgc    1680
ctctgaagca caggcaggtc ttggggagcc acaaggccac ttcctctttg tgcactagtg    1740
tcttgggtag gcatagcttt cagagctctg gggcctccac aaccttgccc tgctgtccag    1800
```

```
gggcagccct catgcagggg tgtcctaaga acttttcagg atgcacaagt tcagcactgt   1860
cttccaatgt gtgtttcacg atattttaat ggtggttctt ttgggaaaaa ggaaaggttc   1920
tgtgatcaat tatgggacac attgagctac agatcttttt cacaattgct cttaacaagc   1980
aggtagaccc tgagaacatg agtagcttcc ccgcaggtaa cttgagtgca tgagaacttt   2040
tgctttacaa ccatgccaat ctcacctcag cagttggcag tgctgcacgg ggcagacttc   2100
cctactcaaa ggctgtgaag cttttctttc tttttttta aacattattt ttctttatag   2160
aattttgttg ggctgatatc aagcctggct tggtactgcc tcattttttt tggaatcaga   2220
acgctgttct ttaactcacg ggttgtgaag ttagaaggtg ctggtgtgac agcctgacaa   2280
gcagagcgca gctccaatcc caccttcatg ctctcatctg acgcagagcc ctcagagaag   2340
tggggaagtg cttcctggcc ctgcttctgg gggccgtccc caaggcagtc caccgaactt   2400
ccaaaacagc cttccctcac acacagccct gagccctcct gccgctcctc aatgttgcac   2460
atctctgaga agtggtccag catgttgctg tccaggggca gtgagaagca ggtgcggtga   2520
cacatgtctt cacggaccat gagcaccggg taaatctcct gcacaatctc cttgggggac   2580
accttgaggg agaaagcccc aacaactgat ggcatgccac atggcagaaa gcaaagactt   2640
acccttcccc cagcccaaag tcctgagaat catgccaaaa atccttggtt tcccactttt   2700
taaaaatttt aaaattaaaa tcccaggttc cgcgtataca tgccatgccc acctgcacct   2760
gtgtgtgtgt gtgtgtttgt gcacgcagga cagagcctgg cccattgact attcctgcag   2820
accaagaaaa atccctatgc agagtaaggg gagatggaag aaacgaggga gagaaatgg   2880 cagccttgcc tcctcccttg cccagtgcta aggtccccag ggcaaatggc ttttgccttc   2940
aacttcacct taacaacata caaaatatat tcatttttac ttccgtcact ttcttaacat   3000
tacaaattgt atctttatat atgatttgta ttttcacaga gatttaagaa tttaatgcac   3060
cattatagta gaaaattgta tatctgtgta tatatttaca ttgaacagag agctttatat   3120
tttcatgtgg ttttatgatg ctgtccagca tcatttaatt tttcaacata attaactctc   3180
tttagcattt tttttcctag ggttattcta gtagttaaca acctcagctt ttttatttta   3240
atctttgaaa gtctttattt ttttctaatt tttgaaatac agtatttccc agatcaatta   3300
ttattggttg ctagtatttt ttctttcatc gctttgaaat ctggaaagtt cttagcatcc   3360
ccgctttttc tctgaaataa tgtttatgcc attttctccc tctattcttt ttaaaagact   3420
ctatctctga atgtattggt ctacttgatg gtgtccagta agtcttatat ttcacccgta   3480
attttcccat tctttaaaat attagtttcc aggactcaat atttgtgaat aatatatgtt   3540
caattttctt ttttctgctc cattgtttgc tgttgtgtct ctgtagtgaa tttataaaac   3600
tcagttatta tattcttcaa ctctatgatt tctgttgggt ttttaaaaat agtttttatc   3660
tctttgttga tattttgctc attcgttatt tttaaatttc actcagttgt ctctttctgt   3720
tatagttttg ctcactgaga atgcataaga tgattatttt aagttctcca tcagatatgc   3780
aaaaatcttt atttgttaaa attcagtttc tgaatattta tgtttttctt ccaatgggga   3840
atattttctg ccttctctgt gtgccttgtg attttttttt ttaaagagat ctggggatct   3900
atacagcact catcaaatct agcatttaaa gactggctca gtaaaggggg ataccgacag   3960
caatagtcca ggctatagat tctaggtgct tcacaaacac attcccaaat atattttctc   4020
tggacttcgc tgtgtttcca agttaaagag aattttttct caatgtattt tagattctat   4080
tgtatatttt cttccccagt tggctgtctg tggtattgca gtttcactag tgctgtagca   4140
aacactcatc tttcttctca gcagacacaa actgtcatct atatgactcc atcatgtcct   4200
```

-continued

```
tcagcactcc acatcaggag agaaagaatc tagtcattag acaatttatc aaaaagccaa   4260
acatttcaac acatattcta ctgttttaat tctctcctga aggagatact gggagttggg   4320
cattttctca ttagcccagt tactgttctg ggtgaaaaaa taaactgcag tggacaggct   4380
gtaagccaga cttcatcaaa tttctgcacc aatgaaaaaa aaatttacaa gagaaaaaca   4440 aaaaaccccta ttaaacgtca cggacaaggc cagagtttga atatactgtg gtcatctctg   4500
ctccagtgca aactgtttcc agaaagccta cttctatttt ccttgctgta acagaggaac   4560
atttcctgtc ttatgtttat tctactctgc aatcccctaa ggctttttct ctccctccca   4620
gaatcttaaa gtgcattcga actcacaggc aaaatcctcc cagaatcttg tgagaacata   4680
aatgatctga ctagtttggc attgcttttg gggatctggg aaaatctgtg cacacttctg   4740
gagacccttg tcatgccatt ttttataaat ctattgtgcc tcaagtcaga agtgtgtgag   4800
gggagatggg gagacattgg gatgcgcgcg cctggggctc tcccacaggg ggctttcgtg   4860
agccaggcag cgagggccgc ccccgcgctg cagcccagcc aggccgcgac ggcagagggg   4920
gtctcccaac ctgccccggc gcgcggggat ttcgcctacg ccgccccggc tcctccggac   4980
ggggcgctct cccaccctca ggctcctcgg tggcctccgc acccgggcaa aagccgggag   5040
gaccgggacc cgcagcgcga cggcctgccg ggccctgcg cggtggcaca gcctgggccc   5100
gctcaagcgg ggccgcaggg ccaaggggtg cttgcgccac ccacgtccca ggggagtccg   5160
tggtggggct ggggccgggt ccccaggtcg ccggggcggc gtgggaaccc caagccgggg   5220
caagcttcca cctccccagc ccgcgccccc ggacgcctcc gcctccgcgc ggcaggggca   5280
gatgcaaggc atcccggcgc cctcccaggc gctccaggag ccggcgccct ggtctgcact   5340
cccctgcggc ctgctgctgg atgagctcct ggcgagcccg gagtttctgc agcaggcgca   5400
acctctccta gaaacggagg ccccgggga gctggaggcc tcggaagagg ccgcctcgct   5460
ggaagcaccc ctcagcgagg aagaataccg ggctctgctg gaggagcttt aggacgcggg   5520
gttgggacgg ggtcgggtgg ttcggggcag ggcggtggcc tctctttcgc ggggaacacc   5580
tggctggcta cggaggggcg tgtctccgcc ccgcccctc caccgggctg accggcctgg   5640
gattcctgcc ttctaggtct aggcccggtg agagactcca caccgcggag aactgccatt   5700
ctttcctggg catcccgggg atcccagagc cggcccaggt accagcaggt gggccgccta   5760
ctgcgcacgc gcgggtttgc gggcagccgc ctgggctgtg ggagcagccc gggcagagct   5820
ctcctgcctc tccaccagcc cacccgccg cctgaccgcc ccctccccac cccccacccc   5880 ccaccccgg aaaacgcgtc gtccctggg ctgggtggag accccgtcc cgcgaaacac   5940 cgggccccgc gcagcgtccg ggcctgacac cgctccggcg gctcgcctcc tatgcgcccc   6000
cgcgccaccg tcgcccgccc gcccgggccc ctgcagccgc ccaggtgcca gcacggagcg   6060
cctggcggcg gaacgcagac cccaggcccg cgcacaccg gggacgctga gcgttccagg   6120
cgggagggaa ggcgggcaga gatggagaga ggaacgggag acctagaggg gcggaaggac   6180
gggcggaggg acgttaggag ggagggaggg aggcagggag gcaggagga acggagggaa   6240 agacagagcg acgcagggac tggggcgggg cgggagggag ccggggaacg gggggaggaa   6300
ggcagggagg aaaagcggtc ctcggcctcc gggagtagcg ggaccccgc cctccgggaa   6360 aacggtcagc gtccggcgcg ggctgagggc tgggcccaca gccgccgcgc cggccggcgg   6420
ggcaccaccc attcgccccg gttccgtggc ccagggagtg ggcggtttcc tccgggacaa   6480
aagaccggga ctcgggttgc cgtcgggtct tcacccgcgc ggttcacaga ccgcacatcc   6540
```

-continued

```
ccaggctgag ccctgcaacg cggcgcgagg ccgacagccc cggccacgga ggagccacac    6600
gcaggacgac ggaggcgtga tttttggtttc cgcgtggctt tgccctccgc aaggcggcct    6660
gttgctcacg tctctccggc ccccgaaagg ctggccatgc cgactgtttg ctcccggagc    6720
tctgcgggca cccggaaaca tgcagggaag ggtgcaagcc cggcacggtg ccttcgctct    6780
ccttgccagg ttccaaaccg gccacactgc agactcccca cgttgccgca cgcgggaatc    6840
catcgtcagg ccatcacgcc ggggaggcat ctcctctctg gggtctcgct ctggtcttct    6900
acgtggaaat gaacgagagc cacacgcctg cgtgtgcgag accgtcccgg caacggcgac    6960
gcccacaggc attgcctcct tcacggagag agggcctggc acactcaaga ctcccacgga    7020
ggttcagttc cacactcccc tccaccctcc caggctggtt tctccctgct gccgacgcgt    7080
gggagcccag agagcggctt cccgttcccg cgggatccct ggagaggtcc ggagagccgg    7140
cccccgaaac gcgccccct cccccctccc ccctctcccc cttcctcttc gtctctccgg    7200
ccccaccacc accaccgcca ccacgccctc cccccccacc ccccccccc accaccacca    7260 ccaccacccc gccggccggc cccaggcctc gacgccctgg ggtccttcc ggggtggggc    7320 gggctgtccc agggggggctc accgccattc atgaaggggt ggagcctgcc tgcctgtggg    7380
cctttacaag ggcggctggc tggctggccg gctgtccggg caggcctcct ggctgcacct    7440
gccgcagtgc acagtccggc tgaggtgcac gggagcccgc cggcctctct ctgcccgcgt    7500
ccgtccgtga aattccggcc ggggctcacc gcgatggccc tcccgacacc ctcggacagc    7560
accctccccg cggaagcccg gggacgagga cggcgacgga gactcgtttg gaccccgagc    7620
caaagcgagg ccctgcgagc ctgctttgag cggaacccgt acccgggcat cgccaccaga    7680
gaacggctgg cccaggccat cggcattccg gagcccaggg tccagatttg gtttcagaat    7740
gagaggtcac gccagctgag gcagcaccgg cgggaatctc ggccctggcc cgggagacgc    7800
ggcccgccag aaggccggcg aaagcggacc gccgtcaccg gatcccagac cgccctgctc    7860
ctccgagcct ttgagaagga tcgctttcca ggcatcgccg cccgggagga gctggccaga    7920
gagacgggcc tcccggagtc caggattcag atctggtttc agaatcgaag ggccaggcac    7980
ccgggacagg gtggcagggc gcccgcgcag gcaggcggcc tgtgcagcgc ggcccccggc    8040
gggggtcacc ctgctccctc gtgggtcgcc ttcgcccaca ccggcgcgtg gggaacgggg    8100
```

```
<210> SEQ ID NO 2
<211> LENGTH: 27
<212> TYPE: DNA
<213> ORGANISM: Artificial sequence
<220> FEATURE:
<223> OTHER INFORMATION: Synthetic

<400> SEQUENCE: 2
ctgggagttg ggcattttct cattagc                                             27

<210> SEQ ID NO 3
<211> LENGTH: 27
<212> TYPE: DNA
<213> ORGANISM: Artificial sequence
<220> FEATURE:
<223> OTHER INFORMATION: Synthetic

<400> SEQUENCE: 3
ctgggagttg ggcattttct gattagc                                             27

<210> SEQ ID NO 4
<211> LENGTH: 20
```

```
<212> TYPE: DNA
<213> ORGANISM: Artificial sequence
<220> FEATURE:
<223> OTHER INFORMATION: Synthetic

<400> SEQUENCE: 4
ggcggtctgg gatccggtga                                          20

<210> SEQ ID NO 5
<211> LENGTH: 8671
<212> TYPE: DNA
<213> ORGANISM: Homo sapiens

<400> SEQUENCE: 5
gggatgcgcg cgcctggggc tctcccacag ggggctttcg tgagccaggc agcgagggcc        60
gcccccgcgc tgcagcccag ccaggccgcg acggcagagg gggtctccca acctgccccg       120
gcgcgcgggg atttcgccta cgccgccccg gctcctccgg acggggcgct ctcccaccct       180
caggctcctc ggtggcctcc gcacccgggc aaaagccggg aggaccggga cccgcagcgc       240
gacggcctgc cgggcccctg cgcggtggca cagcctgggc ccgctcaagc ggggccgcag       300
ggccaagggg tgcttgcgcc acccacgtcc caggggagtc cgtggtgggg ctggggccgg       360
ggtccccagg tcgccggggc ggcgtgggaa ccccaagccg gggcagctcc acctccccag       420
cccgcgcccc cggacgcctc cgcgcggcag gggcagatgc aaggcatccc ggcgccctcc       480
caggcgctcc aggagccggc gccctggtct gcactcccct gcggcctgct gctggatgag       540
ctcctggcga gcccggagtt tctgcagcag gcgcaacctc tcctagaaac ggaggccccg       600
ggggagctgg aggcctcgga agaggccgcc tcgctggaag caccccctcag cgaggaagaa       660 taccgggctc tgctggagga gctttaggac gcggggttgg gacggggtcg ggtggttcgg       720
ggcagggcgg tggcctctct ttcgcgggga acgcctggct ggctacggag gggcgtgtct       780
ccgccccgcc ccctccaccg ggctgaccgg cctgggattc ctgccttcta ggtctaggcc       840
cggtgagaga ctccacaccg cggagaactg ccattctttc ctgggcatcc cggggatccc       900
agagccggcc caggtaccag caggtgggc gcctactgcg cacgcgcggg tttgcgggca       960
gccgcctggg ctgtgggagc agcccgggca gagctctcct gcctctccac cagcccaccc      1020
cgccgcctga ccgcccctc cccaccccca cccccaccc ccggaaaacg cgtcgtcccc      1080
tgggctgggt ggagaccccc gtcccgcgaa acaccgggcc ccgcgcagcg tccgggcctg      1140
acaccgctcc ggcggctcgc ctcctctgcg ccccgcgcc accgtcgccc gcccgcccgg      1200 gccctgcag ccgcccaggt gccagcacg agcgcctggc ggcggaacgc agaccccagg      1260
cccggcgcac accggggacg ctgagcgttc caggcgggag ggaaggcggg cagagatgga      1320
gagaggaacg ggagacctag aggggcggaa ggacgggcgg agggacgtta ggagggaggg      1380
agggaggcag ggaggcaggg aggaacggag ggaaagacag agcgacgcag ggactggggg      1440
cgggcgggag ggagccgggg acggacgggg ggaggaaggc agggaggaaa agcggtcctc      1500
ggcctccggg agtagcggga cccccgccct ccgggaaaac ggtcagcgtc cggcgcgggc      1560
tgagggctgg gcccacagcc gccgcgccgg ccggcgcggc acccattcgc cccggttccg      1620
tggcccaggg agtgggcggt ttcctccggg acaaaagacc gggactcggg ttgccgtcgg      1680
gttttcaccc gcgcggttca cagaccgcac atccccaggc tgagccctgc aacgcggcgc      1740
gaggccgaca gccccggcca cggaggagcc acacgcagga cgacggaggc gtgattttgg      1800
tttccgcgtg gctttgccct ccgcaaggcg gcctgttgct cacgtctctc cggcccccga      1860
```

-continued

```
aaggctggcc atgccgactg tttgctcccg gagctctgcg ggcacccgga aacatgcagg      1920
gaagggtgca agcccggcat ggtgccttcg ctctccttgc caggttccaa accggccaca      1980
ctgcagactc cccacgttgc cgcacgcggg aatccatcgt caggccatca cgccgggggag     2040 gcatctcctc tctggggtct cgctctggtc ttctacgtgg aaatgaacga gagccacacg      2100
cctgcgtgtg cgagaccgtc ccggcaacgg cgacgcccac aggcattgcc tccttcacgg      2160 agagagggc tggcacactc aagactccca cggaggttca gttccacact cccctccacc       2220
ctcccaggct ggtttctccc tgctgccgac gcgtgggagc ccagagagcg gcttcccgtt      2280
cccgcgggat ccctggagag gtccggagag ccggccccg aaacgcgccc ccctccccc        2340 tcccccctct ccccgttcct cttcgtctct ccggccccac caccaccacc gccaccacgc      2400
cctcccccac cacccccccc ccccccacca ccaccaccac caccccgccg gccggcccca      2460
ggcctcgacg ccctgggtcc cttccggggt ggggcgggct gtcccagggg ggctcaccgc      2520
cattcatgaa ggggtggagc ctgcctgcct gtgggccttt acaagggcgg ctggctgggt      2580
ggctggctgt ccgggcaggc cccctggctg cacctgccgc agtgcacagt ccggctgagg      2640
tgcacgggag cccgccggcc tctctctgcc cgcgtccgtc cgtgaaattc cggccggggc      2700
tcaccgcgat ggccctcccg acaccctcgg acagcaccct ccccgcggaa gcccggggac      2760
gaggacggcg acggagactc gtttggaccc cgagccaaag cgaggccctg cgagcctgct      2820
ttgagcggaa cccgtacccg ggcatcgcca ccagagaacg gctggcccag gccatcggca      2880
ttccggagcc cagggtccag atttggtttc agaatgagag gtcacgccag ctgaggcagc      2940
accggcggga atctcggccc tggcccggga gacgcggccc gccagaaggc cggcgaaagc      3000
ggaccgccgt caccggatcc cagaccgccc tgctcctccg agcctttgag aaggatcgct      3060
ttccaggcat cgccgcccgg gaggagctgg ccagagagac gggcctcccg gagtccagga      3120
ttcagatctg gtttcagaat cgaagggcca ggcacccggg acagggtggc agggcgcccg      3180
cgcaggcagg cggcctgtgc agcgcggccc ccggcggggg tcaccctgct ccctcgtggg      3240
tcgccttcgc ccacaccggc gcgtggggaa cggggcttcc cgcaccccac gtgccctgcg      3300
cgcctggggc tctcccacag ggggctttcg tgagccaggc agcgagggcc gccccgcgc       3360 tgcagcccag ccaggccgcg ccggcagagg ggatctccca acctgccccg gcgcgcgggg      3420
atttggccta cgccgccccg gctcctccgg acggggcgct ctcccaccct caggctcctc      3480
ggtggcctcc gcacccgggc aaaagccggg aggaccggga cccgcagcgc gacggcctgc      3540
cgggcccctg cgcggtggca cagcctgggc ccgctcaagc ggggccgcag ggccaagggg      3600
tgcttgcgcc acccacgtcc caggggagtc cgtggtgggg ctgggccggg ggtccccagg      3660
tcgccggggc ggcgtgggaa ccccaagccg gggcagctcc acctccccag cccgcgcccc      3720
cggacgcctc cgcctccgcg cggcaggggc agatgcaagg catcccggcg ccctcccagg      3780
cgctccagga gccggcgccc tggtctgcac tccctgcgg cctgctgctg gatgagctcc       3840
tggcgagccc ggagtttctg cagcaggcgc aacctctcct agaaacggag gccccggggg      3900
agctggaggc ctcggaagag gccgcctcgc tggaagcacc cctcagcgag gaagaatacc      3960
gggctctgct ggaggagctt taggacgcgg ggttgggacg gggtcgggtg gttcggggca      4020
gggcggtggc ctctctttcg cggggaacac ctggctggct acggaggggc gtgtctccgc      4080
cccgccccct ccaccgggct gaccggcctg ggattcctgc cttctaggtc taggcccggt      4140
gagagactcc acaccgcgga gaactgccat tctttcctgg gcatcccggg gatcccagag      4200
ccggcccagg taccagcagg tgggccgcct actgcgcacg cgcgggtttg cgggcagccg      4260
```

-continued

```
cctgggctgt gggagcagcc cgggcagagc tctcctgcct ctccaccagc ccaccccgcc    4320
gcctgaccgc cccctcccca cccccacccc ccacccccgg aaaacgcgtc gtccctggg      4380 ctgggtggag accccgtcc cgcgaaacac cgggccccgc gcagcgtccg ggcctgacac      4440
cgctccggcg gctcgcctcc tctgcgcccc cgcgccaccg tcgcccgccc gcccgggccc     4500
ctgcagccgc ccaggtgcca gcacggagcg cctggcggcg gaacgcagac cccaggcccg     4560
gcgcacaccg gggacgctga gcgttccagg cgggagggaa ggcgggcaga gatggagaga     4620
ggaacgggag acctagaggg gcggaaggac gggcggaggg acgttaggag ggagggaggg     4680
aggcaggggg gcagggagga acggagggaa agacagagcg acgcagggac tggggggcggg    4740 cgggagggag ccggggggacg gggggaggaa ggcagggagg aaaagcggtc ctcggcctcc    4800
gggagtagcg ggacccccgc cctccgggaa aacggtcagc gtccggcgcg ggctgagggc     4860
tgggcccaca gccgccgcgc cggccggcgg ggcaccaccc attcgccccg gttccggggc     4920
ccagggagtg ggcggtttcc tccgggacaa aagaccggga ctcgggttgc cgtcgggtct     4980
tcacccgcgc ggttcacaga ccgcacatcc ccaggctcag ccctgcaacg cggcgcgagg     5040
ccgacagccc cggccacgga ggagccacac gcaggacgac ggaggcgtga ttttggtttc     5100
cgcgtggctt tgccctccgc aaggcggcct gttgctcacg tctctccggc ccccgaaagg     5160
ctggccatgc cgactgtttg ctcccggagc tctgcgggca cccggaaaca tgcagggaag     5220
ggtgcaagcc cggcacggtg ccttcgctct ccttgccagg ttccaaaccg gccacactgc     5280
agactcccca cgttgccgca cgcgggaatc catcgtcagg ccatcacgcc ggggaggcat     5340
ctcctctctg gggtctcgct ctggtcttct acgtggaaat gaacgagagc cacacgcctg     5400
cgtgtgcgag accgtcccgg caacggcgac gcccacaggc attgcctcct tcacggagag     5460
agggcctggc acactcaaga ctcccacgga ggttcagttc cacactcccc tccaccctcc     5520
caggctggtt tctccctgct gccgacgcgt gggagcccag agagcggctt cccgttcccg     5580
cgggatccct ggagaggtcc ggagagccgg cccccgaaac gcgcccccct ccccccctccc    5640 ccctctcccc cttcctcttc gtctctccgg ccccaccacc accaccgcca ccacgccctc     5700
cccccccacc ccccccccc accaccacca ccaccaccac cccgccggcc ggccccaggc      5760
ctcgacgccc tgggtccctt ccggggtggg gcgggctgtc ccaggggggc tcaccgccat     5820
tcatgaaggg gtggagcctg cctgcctgtg ggcctttaca aggcggctg gctggctggc      5880 tggctgtccg ggcaggcctc ctggctgcac ctgccgcagt gcacagtccg gctgaggtgc     5940
acgggagccc gccggcctct ctctgcccgc gtccgtccgt gaaattccgg ccggggctca     6000
ccgcgatggc cctcccgaca ccctcggaca gcaccctccc cgcggaagcc cggggacgag     6060
gacggcgacg gagactcgtt tggaccccga gccaaagcga ggcctgcga gcctgctttg      6120 agcggaaccc gtaccggggc atcgccacca gagaacggct ggcccaggcc atcggcattc     6180
cggagcccag ggtccagatt tggtttcaga atgagaggtc acgccagctg aggcagcacc     6240
ggcgggaatc tcggccctgg cccgggagac gcggcccgcc agaaggccgg cgaaagcgga     6300
ccgccgtcac cggatcccag accgccctgc tcctccgagc ctttgagaag gatcgctttc     6360
caggcatcgc cgcccgggag gagctggcca gagagacggc cctccggag tccaggattc      6420 agatctggtt tcagaatcga agggccaggc acccgggaca gggtggcagg gcgcccgcgc     6480
aggcaggcgg cctgtgcagc gcggccccg gcgggggtca ccctgctccc tcgtgggtcg      6540
ccttcgccca caccggcgcg tggggaacgg ggcttcccgc accccacgtg ccctgcgcgc     6600
```

-continued

```
ctggggctct cccacagggg gctttcgtga gccaggcagc gagggccgcc cccgcgctgc    6660
agcccagcca ggccgcgccg gcagagggga tctcccaacc tgccccggcg cgcggggatt    6720
tcgcctacgc cgccccggct cctccggacg gggcgctctc ccaccctcag gctcctcgct    6780
ggcctccgca cccgggcaaa agccgggagg accgggaccc gcagcgcgac ggcctgccgg    6840
gcccctgcgc ggtggcacag cctgggcccg ctcaagcggg gccgcagggc caaggggtgc    6900
ttgcgccacc cacgtcccag gggagtccgt ggtggggctg gggccggggt ccccaggtcg    6960
ccggggcggc gtgggaaccc caagccgggg cagctccacc tccccagccc gcgccccgg     7020 acgcctccgc ctccgcgcgg caggggcaga tgcaaggcat cccggcgccc tcccaggcgc    7080
tccaggagcc ggcgccctgg tctgcactcc cctgcggcct gctgctggat gagctcctgg    7140
cgagcccgga gtttctgcag caggcgcaac ctctcctaga aacggaggcc ccggggggagc   7200 tggaggcctc ggaagaggcc gcctcgctgg aagcacccct cagcgaggaa gaataccggg    7260
ctctgctgga ggagctttag gacgcggggt tgggacgggg tcgggtggtt cggggcaggg    7320
ccgtggcctc tctttcgcgg ggaacacctg gctggctacg gagggggcgtg tctccgcccc    7380 gcccctcca ccgggctgac cggcctggga ttcctgcctt ctaggtctag gcccggtgag     7440
agactccaca ccgcggagaa ctgccattct ttcctgggca tcccgggat cccagagccg      7500 gcccaggtac cagcaggtgg gccgcctact gcgcacgcgc gggtttgcgg gcagccgcct    7560
gggctgtggg agcagcccgg gcagagctct cctgcctctc caccagccca ccccgccgcc    7620
tgaccgcccc ctccccaccc ccaccccca cccccggaaa acgcgtcgtc ccctgggctg       7680
ggtggagacc cccgtcccgc gaaacaccgg gccccgcgca gcgtccgggc ctgacaccgc     7740
tccggcggct cgcctcctct gcgcccccgc gccaccgtcg cccgcccgcc cgggcccctg     7800
cagcctccca gctgccagcg cggagctcct ggcggtcaaa agcatacctc tgtctgtctt     7860
tgcccgcttc ctggctagac ctgcgcgcag tgcgcacccc ggctgacgtg caagggagct    7920
cgctggcctc tctgtgccct tgttcttccg tgaaattctg gctgaatgtc tcccccacc     7980 ttccgacgct gtctaggcaa acctggatta gagttacatc tcctggatga ttagttcaga    8040
gatatattaa aatgcccct ccctgtggat cctatagaag atttgcatct tttgtgtgat    8100
gagtgcagag atatgtcaca atatcccctg tagaaaaagc ctgaaattgg tttacataac    8160
ttcggtgatc agtgcagatg tgtttcagaa ctccatagta gactgaacct agagaatggt    8220
tacatcactt aggtgatcag tgtagagata tgttaaaatt ctcgtgtaga cagagcctag    8280
acaattgtta catcacctag tgatcagtgc agggataagt cataaagcct cctgtaggca    8340
gagtgtaggc aagtgttccc tccctgggct gatcagtgca gagatatctc acaaagcccc    8400
tataagccaa accttgacaa gggttacatc acctgtttga gcagtggaaa tatatatcac    8460
aaagccccct gtagacaaag cccagacaat ttttacatct cctgagtgag cattggagag    8520
atctgtcaca atgcccctgt aggcagagct tagacaagtg ttacatcacc tgggtgatca    8580
gtgcagagat atgtcaaaac gctcctgtag tctgaaccta gacaggagtt acatcacctt    8640
ggggatcagt gcagagatac gtgagaattc c                                  8671
```

<210> SEQ ID NO 6
<211> LENGTH: 22
<212> TYPE: DNA
<213> ORGANISM: Artificial sequence
<220> FEATURE:
<223> OTHER INFORMATION: Synthetic

<400> SEQUENCE: 6
agcgttccag gcgggaggga ag                                                                        22

<210> SEQ ID NO 7
<211> LENGTH: 33
<212> TYPE: DNA
<213> ORGANISM: Artificial sequence
<220> FEATURE:
<223> OTHER INFORMATION: Synthetic

<400> SEQUENCE: 7 cagggggatat tgtgacatat ctctgcactc atc                                                           33

<210> SEQ ID NO 8
<211> LENGTH: 27
<212> TYPE: DNA
<213> ORGANISM: Artificial sequence
<220> FEATURE:
<223> OTHER INFORMATION: Synthetic

<400> SEQUENCE: 8
tggagttctg aaacacatct gcactga                                                                   27

<210> SEQ ID NO 9
<211> LENGTH: 3080
<212> TYPE: DNA
<213> ORGANISM: Homo sapiens

<400> SEQUENCE: 9
cccgcgaaac accgggcccc gcgcagcgtc cgggcctgac ctccgctccg gcggctcgcc          60
tcctctgcgc ccccgcgcca ccgtcgcccg cccgcccggg cccctgcagc cgcccagctg          120
ccagcacgga gcgcctggcg gcggaacgca gaccccaggc ccggcgcaca ccggggacgc          180
tgagcgttcc aggcgggagg gaaggcgggc agagatggag agaggaacgg gagacctaga          240
ggggcggaag gacgggcgga gggacgttag gagggaggca gggaggcagg gaggcaggga          300
ggaacggagg gagagacaga gcgacgcagg gactgggggc gggcgggagg gagccgggga          360
cggacggggg gaggaaggca gggaggaaaa gcggtcctcg gcctccggga gtagcgggac          420
ccccgccctc cgggaaaacg gtcagcgtcc ggcgcgggct gagggctggg cccacagccg          480
ccgcgccggc cggcgggggca ccacccattc gccccggttc cggggcccag ggagtgggcg          540
gtttcctccg ggacaaaaga ccgggactcg agactccgtt caataaatgg tgctgggata          600
actggctagc cacatgctga agattgaact gggccccttt cttacaccat acacaaaaat          660
gaactcagga tggattaaag acttaagtgt aaaacccaaa aatataaaaa ccctggaaga          720
caacctaggc aataccatcc tggacataag gacaggcaaa gatttcatga caaagacaac          780
aaaagcaata gcaatgaaag caaaaattga cgtgggatct agttaaacta aagagcttct          840
acacagcaaa agaaactatc aacaaagtaa acaggcaact tgcagattgg gagaaagtat          900
ttacaaacta tgcatctgac aaaggtctaa tatccagcat ctataaggaa cttaaacaaa          960
tttacaagag aaaaacaacc ccattaaaaa gtgggccaag gacataaaga gacacttctc          1020
caaaggagac aaacatgtgt gccgggcgtg gtggctcacg cctgtaattc ctgcattttg          1080
ggaggccaag gagggtggat cacaacgtca ggagattgag accatcctga ctaacatggt          1140
gaaaccccgt ctctactaaa aatacaaaaa attagccggg tgtggtggca ggcacctgta          1200
gtcccagcta cttgggaggc tgaggcagga gaatggcgtg aaccaggag gcagagcttg          1260

-continued

```
cagttagctg agatcgcacc actgcactct ggcctgggtg acagagcgag actcgggcta      1320
agaaaaaaaa aaaaaaaaaa ggcaaacgtg gcaaacaaac atatggaaaa aagctctaga      1380
tcactgatca ctagagaaat gctcatcaaa accacagtga ggcaccatct cacaccagtc      1440
agaatggcta ttactaaaaa ctaaaaaact aacagaagtt ggcaagattg cagggaaaag      1500
tgaacatgta tacaccattg gtgggagtgt aagttaattc aactgtggtg gaaagcagta      1560
tggtgattcc tcaaagagct aaaagcagaa ctacaacatt tgacctagca atcccattac      1620
tggttatata cccagatgaa tataaatcat tctaccatga agttacatgc atgcaaatgt      1680
tcattgcagc actattcaca atagcaaaga catagaatca acccaaatac tcatcagtca      1740
cggattggat aaagaaaatg tgctacatat acaccatgga ataatatgca gccataaaaa      1800
agaatgagat tatgtctttt gcattagtat ggatgaagct gaagggtatt atccttagca      1860
aactaacgca ggaacagaaa accaaataca gcatgttcta acttataagt gggagctaaa      1920
tgataagaac ttgtgaacac aaagaaggaa acaaaagaca ctggggtcta cttgatgggg      1980
ggagggtggg aggagggaga ggagcagaaa agataactat tggatactgg gcctaatacc      2040
tggatgatga ataacaggt acaacaaacc cctgtgacac gtatttaact gtataacaaa      2100
ccctcccgtg tacccctaa cctaaataa aagttaaaaa aaaagaaaca cagctttta       2160 tttttttct ttttaatccc ataaaggtca tgggccattt gccacctgaa cagtcagtaa       2220
cacatgagtg gaaagaaact gaacacccag ggacaccaga gaccgttcac tgtagaggaa      2280
ggaggcaggt ataactcata aggtgatctt cctccagtcc cagagttgtt cccctctcct      2340
taaatgtggg tcccatggaa ttcagactag gaagtaaagc aaatgagaaa ggcctacagg      2400
ggagcagttc aaatgtgtgg aaaaggatag agcagcccca atgaggaagg aaggctggac      2460
aagcaatgga tttgtaggga agacaatgtg cacccatcgg agctctgatt ccttcatttt      2520
cactaccctc ccctgcccac taacataaaa aaagtattga tggcaagtgt tgggccataa      2580
gacatttcct tgctttataa tctggatttg ggggttaca tttcagagat aatgaaaatc       2640
tcctccttta gttaactttt aatttcataa ttgtaacttt gtttttacag atttgtgaac      2700
atgtaaaaca aagaaaacag catgggagta atttataatc aacaaatatg tgttcactga      2760
gtgacactca catggcatat ggcatatggg catcctgaga gtaggatcgt ggggcatccg      2820
atggtgattc tccttagagt tggtcggagc ccagccttcc acggtctgcg cactgctgtg      2880
tgtacaatcg gtgccttctt taagttcaca gcaatgccac aaggcaaata gcactgtctt      2940
cactttctgt gtgagagaac taaggctggg tgagagtatg cagagctgga tcatggattt      3000
gtttggctcc ttctagtttc aaaacctgta aatattttgt tgtctctggt gctaatctta      3060
gcactatatt tggaataagc                                                 3080
```

<210> SEQ ID NO 10
<211> LENGTH: 22
<212> TYPE: DNA
<213> ORGANISM: Artificial sequence
<220> FEATURE:
<223> OTHER INFORMATION: Synthetic

<400> SEQUENCE: 10

```
cgcggttcac agaccgcaca tc                                                22
```

<210> SEQ ID NO 11
<211> LENGTH: 25
<212> TYPE: DNA
<213> ORGANISM: Artificial sequence -continued

```
<220> FEATURE:
<223> OTHER INFORMATION: Synthetic

<400> SEQUENCE: 11
gcccggcaca catgtttgtc tcctt                                          25

<210> SEQ ID NO 12
<211> LENGTH: 3664
<212> TYPE: DNA
<213> ORGANISM: Homo sapiens

<400> SEQUENCE: 12
ggtacctgcg cacgcgcggg tttgcgggca gccgcctggg ctgtgggagc agcccgggca      60
gagctctcct gcctctccac cagcccaccc cgccgcctga ccgccccctc cccacccccc     120 acccccacc cccggaaaac gcgtcgtccc ctgggctggg tggagacccc cgtcccgcga      180
aacaccgggc cccgcgcagc gtccgggcct gacaccgctc cggcggctcg cctcctctgc     240 gccccgcgg cgcaccgtcg cccgcccgcc cgggcccctg cagccgccca ggtgccagca      300
cggagcgcct ggcggcggaa cgcagacccc aggcccggcg cacaccgggg acgctgagcg     360
ttccaggcgg gagggaaggc gggcagagat ggagagagga acgggagacc tagaggggcg     420
gaaggacggg cggagggacg ttaggaggga gggagggagg cagggaggca gggaggaacg     480
gagggaaaga cagagcgacg cagggactgg gggcgggcgg gagggaaccg gggacggggg     540
gaggaaggca gggaggaaaa gcggtcctcg gcctccggga gtagcgggac cccccgcctc     600
cgggaaaacg gtcagcgtcc ggcgcgggct gagggctggg cccacagccg ccgcgccggc     660
cggcggggca ccacccattc gccccggttc cggggcccag ggagtgggcg gtttcctccg     720
ggacaaaaga ccgggactcg ggttgccgtc gggtcttcac ccgcgcggtt cacagaccgc     780
acatccccag gctgagccct gcaacgcggc gcgaggccga cagccccggc cacggaggag     840
ccacacgcag gacgacggag gcgtgatttt ggtttccgcg tggctttgcc ctccgcaagg     900
cggcctgttg ctcacgtctc tccggccccc gaaaggctgg ccatgccgac tgtttgctcc     960
cggagctctg cggcacccgg aaacatgcag ggaagggtgc aagcccggca cggtgccttc    1020
gctctccttg ccaggttcca aaccggccac actgcagact ccccacgttg ccgcacgcgg    1080
gaatccatcg tcaggccatc acgccgggga ggcatctcct ctctggggtc tcgctctggt    1140
cttctacgtg gaaatgaacg agagccacac gcctgcgtgt gcgagaccgt cccggcaacg    1200
gcgacgccca caggcattgc ctccttcacg gagagagggc ctggcacact caagactccc    1260
acggaggttc agttccacac tcccctccac cctcccaggc tggtttctcc ctgctgccga    1320
cgcgtgggag cccagagagc ggcttcccgt tcccgcggga tccctggaga ggtccggaga    1380
gccgcccccc gaaacgcgcc cccctccccc ctcccccctc tccccgttcc tcttcgtctc    1440
tccggcccca ccaccaccac cgccaccacg cctcccccc aacccccccc ccccaccacc     1500
accaccacca ccaccccgcc ggccggcccc aggcctcgac gccctgggtc ccttccgggg    1560
tggggcgggc tgtcccaggg gggctcaccg ccattcatga aggggtggag cctgcctgcc    1620
tgtgggcctt tacaagggcg gctggctggc tggctggctg tccgggcagg ccccctggct    1680
gcacctgccg cagtgcacag tccggctgag gtgcacggga gcccgccggc ctctctctgc    1740
ccgcgtccgt ccgtgaaatt ccggccgggg ctcaccgcga tggccctccc gacaccctcg    1800
gacagcaccc tccccgcgga agcccgggga cgaggacggc gacggagact cgtttggacc    1860
ccgagccaaa gcgaggccct gcgagcctgc agcctcccag ctgccagcgc ggagctctgg    1920
```

```
cggtcaaaag catacctctg tctgtctttg cccgcttcct ggctagacct gcgcgcagtg      1980
cgcaccccgg ctgacgtgca agggagctcg ctggcctctc tgtgcccttg ttcttccgtg      2040
aaattctggc tgaatgtctc cccccacctt ccgacgctgt ctaggcaaac ctggattaga      2100
gttacatctc ctggatgatt agttcagaga tatattaaaa tgcccctcc ctgtggatcc       2160 tatagaagat ttgcatcttt tgtgtgatga gtgcagagat atgtcacaat atccctgta      2220 gaaaaagcct gaaattggtt tacataactt cggtgatcag tgcagatgtg tttcagaact      2280
ccatagtaga ctgaacctag agaatggtta catcacttag gtgatcagtg tagagatatg      2340
ttaaaattct cgtgtagaca gagcctagac aattgttaca tcacctagtg atcagtgcag      2400
ggataagtca taaagcctcc tgtaggcaga gtgtaggcaa gtgttccctc cctgggctga      2460
tcagtgcaga gatatctcac aaagccccta taagccaaac cttgacaagg gttacatcac      2520
ctgtttgagc agtggaaata tatatcacaa agcccctgt agacaaagcc cagacaattt       2580
ttacatctcc tgagtgagca ttggagagat ctgtcacaat gccctgtag gcagagctta       2640 gacaagtgtt acatcacctg ggtgatcagt gcagagatat gtcaaacgc tcctgtagtc       2700 tgaacctaga caggagttac atcaccttgg ggatcagtgc agagatacgt gagaattccc       2760
gtgtaggcag agcctagaca agtgttacat cacctagttt atcagtgtaa ttattagtca      2820
taaagcctcc tgtaggcaga gcgtagacaa gagttccctc ctcagggtga tcagtgcaga      2880
gatgtgtcac aaagcccctg taggcagagc ctagacaaga gtttcatcac ttggttgatc      2940
agttcagaga tgtgtcagaa tgcccatgta ggcagatcta agacaagcgt ccatcacctg      3000
ggtgatcagt gcagagatat gtaccagtgt cccctgtagg cagtgcctag acaagagttg      3060
aatcacctca gagatcagtg catagatatg tcacaaagcc ttctgtaggc aaagcccata      3120
caaggtttag atcacctagg tgatcagtgc agtgatatgt cacaaaaatc cctgtagaca      3180
gagcctagac aagagttact tcacctgggt gatcagtgca gatatttgac acaatgcccc      3240
catagacaga gcctaggcaa gacttccatc acctgggtga tcagtgcaga gatatgtcac      3300
aaatccccct ctaggcagag tatagagaag agtcccatca cctgggtgat cagtgcagag      3360
atatttcaca atgcccctg taggcagaga gtggacaaga gttacatcac ctagatgatc       3420
tgtgcagagc tatgtcaaaa cgcccctgta ggcagagcct agatgagtgt tacatcacct      3480
gggtgatcat tgcagagata cgtcacaata ccccctgtag gtggggccta gacaagagtt      3540
acattcacct gggtgatcag tacagaagta tgtcacaaag cccctgtagg cagagcctag      3600
acaagagtta catcacctgg gttatcagtg cagaaatatg tcacaaagcc cctgtaggtc      3660
taga                                                                   3664
```

<210> SEQ ID NO 13
<211> LENGTH: 26
<212> TYPE: DNA
<213> ORGANISM: Artificial sequence
<220> FEATURE:
<223> OTHER INFORMATION: Synthetic
<400> SEQUENCE: 13
agcccagggt ccagatttgg tttcag                                           26

<210> SEQ ID NO 14
<211> LENGTH: 25
<212> TYPE: DNA
<213> ORGANISM: Artificial sequence
<220> FEATURE:
<223> OTHER INFORMATION: Synthetic

```
<400> SEQUENCE: 14
gctggaagca cccctcagcg aggaa                                        25

<210> SEQ ID NO 15
<211> LENGTH: 44
<212> TYPE: DNA
<213> ORGANISM: Artificial sequence
<220> FEATURE:
<223> OTHER INFORMATION: Synthetic

<400> SEQUENCE: 15
ggatccacag ggagggggaa ttttgatata tctctgaact aatc                   44

<210> SEQ ID NO 16
<211> LENGTH: 44
<212> TYPE: DNA
<213> ORGANISM: Artificial sequence
<220> FEATURE:
<223> OTHER INFORMATION: Synthetic

<400> SEQUENCE: 16
gattagttca gagatatatc aaaattcccc ctccctgtgg atcc                   44

<210> SEQ ID NO 17
<211> LENGTH: 44
<212> TYPE: DNA
<213> ORGANISM: Artificial sequence
<220> FEATURE:
<223> OTHER INFORMATION: Synthetic

<400> SEQUENCE: 17
ggatccacag ggaggggggca ttttaatata tctctgaact aatc                  44

<210> SEQ ID NO 18
<211> LENGTH: 44
<212> TYPE: DNA
<213> ORGANISM: Artificial sequence
<220> FEATURE:
<223> OTHER INFORMATION: Synthetic

<400> SEQUENCE: 18
gattagttca gagatatatt aaaatgcccc ctccctgtgg atcc                   44

<210> SEQ ID NO 19
<211> LENGTH: 18
<212> TYPE: DNA
<213> ORGANISM: Artificial sequence
<220> FEATURE:
<223> OTHER INFORMATION: Synthetic

<400> SEQUENCE: 19
cccaggtacc agcagacc                                                18

<210> SEQ ID NO 20
<211> LENGTH: 24
<212> TYPE: DNA
<213> ORGANISM: Artificial sequence
<220> FEATURE:
<223> OTHER INFORMATION: Synthetic

<400> SEQUENCE: 20
tccaggagat gtaactctaa tcca                                         24

<210> SEQ ID NO 21
```

-continued

```
<211> LENGTH: 23
<212> TYPE: DNA
<213> ORGANISM: Artificial sequence
<220> FEATURE:
<223> OTHER INFORMATION: Synthetic

<400> SEQUENCE: 21
tgatcacaca aaagatgcaa atc                                              23

<210> SEQ ID NO 22
<211> LENGTH: 18
<212> TYPE: DNA
<213> ORGANISM: Artificial sequence
<220> FEATURE:
<223> OTHER INFORMATION: Synthetic

<400> SEQUENCE: 22
agcacatcgc tcagacac                                                    18

<210> SEQ ID NO 23
<211> LENGTH: 19
<212> TYPE: DNA
<213> ORGANISM: Artificial sequence
<220> FEATURE:
<223> OTHER INFORMATION: Synthetic

<400> SEQUENCE: 23
gcccaatacg accaaatcc                                                   19

<210> SEQ ID NO 24
<211> LENGTH: 28
<212> TYPE: DNA
<213> ORGANISM: Artificial sequence
<220> FEATURE:
<223> OTHER INFORMATION: Synthetic

<400> SEQUENCE: 24
cactcccctg cggcctgctg ctggatga                                        28

<210> SEQ ID NO 25
<211> LENGTH: 27
<212> TYPE: DNA
<213> ORGANISM: Artificial sequence
<220> FEATURE:
<223> OTHER INFORMATION: Synthetic

<400> SEQUENCE: 25
gagctcctgg cgagcccgga gtttctg                                         27

<210> SEQ ID NO 26
<211> LENGTH: 6
<212> TYPE: DNA
<213> ORGANISM: Artificial sequence
<220> FEATURE:
<223> OTHER INFORMATION: Synthetic

<400> SEQUENCE: 26 attaaa                                                                 6

<210> SEQ ID NO 27
<211> LENGTH: 6
<212> TYPE: DNA
<213> ORGANISM: Artificial sequence
<220> FEATURE:
<223> OTHER INFORMATION: Synthetic
```

-continued

<400> SEQUENCE: 27 atcaaa                                                                          6

<210> SEQ ID NO 28
<211> LENGTH: 6
<212> TYPE: DNA
<213> ORGANISM: Artificial sequence
<220> FEATURE:
<223> OTHER INFORMATION: Synthetic

<400> SEQUENCE: 28 atttaa                                                                          6

<210> SEQ ID NO 29
<211> LENGTH: 30
<212> TYPE: DNA
<213> ORGANISM: Artificial sequence
<220> FEATURE:
<223> OTHER INFORMATION: Synthetic

<400> SEQUENCE: 29
ccccgagcca aagcgaggcc ctgcgagcct                                               30

<210> SEQ ID NO 30
<211> LENGTH: 26
<212> TYPE: DNA
<213> ORGANISM: Artificial sequence
<220> FEATURE:
<223> OTHER INFORMATION: Synthetic

<400> SEQUENCE: 30
gtaactctaa tccaggtttg cctaga                                                   26

<210> SEQ ID NO 31
<211> LENGTH: 28
<212> TYPE: DNA
<213> ORGANISM: Artificial sequence
<220> FEATURE:
<223> OTHER INFORMATION: Synthetic

<400> SEQUENCE: 31
cggccctggc ccgggagacg cggcccgc                                                 28

<210> SEQ ID NO 32
<211> LENGTH: 29
<212> TYPE: DNA
<213> ORGANISM: Artificial sequence
<220> FEATURE:
<223> OTHER INFORMATION: Synthetic

<400> SEQUENCE: 32
ggattcagat ctggtttcag aatcgaagg                                                29

<210> SEQ ID NO 33
<211> LENGTH: 25
<212> TYPE: DNA
<213> ORGANISM: Artificial sequence
<220> FEATURE:
<223> OTHER INFORMATION: Synthetic

<400> SEQUENCE: 33
tctaatccag gtttgcctag acagc                                                    25

<210> SEQ ID NO 34

-continued

```
<211> LENGTH: 30
<212> TYPE: DNA
<213> ORGANISM: Artificial sequence
<220> FEATURE:
<223> OTHER INFORMATION: Synthetic

<400> SEQUENCE: 34
ccaggagatg taactctaat ccaggtttgc                                    30

<210> SEQ ID NO 35
<211> LENGTH: 30
<212> TYPE: DNA
<213> ORGANISM: Artificial sequence
<220> FEATURE:
<223> OTHER INFORMATION: Synthetic

<400> SEQUENCE: 35
gtaactctaa tccaggtttg cctagacagc                                    30

<210> SEQ ID NO 36
<211> LENGTH: 31
<212> TYPE: DNA
<213> ORGANISM: Artificial sequence
<220> FEATURE:
<223> OTHER INFORMATION: Synthetic

<400> SEQUENCE: 36
gtctaggccc ggtgagagac tccacaccgc g                                  31

<210> SEQ ID NO 37
<211> LENGTH: 31
<212> TYPE: DNA
<213> ORGANISM: Artificial sequence
<220> FEATURE:
<223> OTHER INFORMATION: Synthetic

<400> SEQUENCE: 37
gtctaggccc ggtgagagac tccacacagc g                                  31

<210> SEQ ID NO 38
<211> LENGTH: 31
<212> TYPE: DNA
<213> ORGANISM: Artificial sequence
<220> FEATURE:
<223> OTHER INFORMATION: Synthetic

<400> SEQUENCE: 38
gcctaggccc ggtgagagac tccacacagc g                                  31

<210> SEQ ID NO 39
<211> LENGTH: 31
<212> TYPE: DNA
<213> ORGANISM: Artificial sequence
<220> FEATURE:
<223> OTHER INFORMATION: Synthetic

<400> SEQUENCE: 39
gtccaggccc ggtgagagac tccacaccgc g                                  31

<210> SEQ ID NO 40
<211> LENGTH: 31
<212> TYPE: DNA
<213> ORGANISM: Artificial sequence
<220> FEATURE:
<223> OTHER INFORMATION: Synthetic
```

-continued

<400> SEQUENCE: 40
cggagtttct gcagcaggcg caacctctcc t                                        31

<210> SEQ ID NO 41
<211> LENGTH: 31
<212> TYPE: DNA
<213> ORGANISM: Artificial sequence
<220> FEATURE:
<223> OTHER INFORMATION: Synthetic

<400> SEQUENCE: 41
ctgctggtac ctgggccggc tctgggatcc c                                        31

<210> SEQ ID NO 42
<211> LENGTH: 31
<212> TYPE: DNA
<213> ORGANISM: Artificial sequence
<220> FEATURE:
<223> OTHER INFORMATION: Synthetic

<400> SEQUENCE: 42
gtacctgggc cggctctggg atccccggga t                                        31

<210> SEQ ID NO 43
<211> LENGTH: 25
<212> TYPE: DNA
<213> ORGANISM: Artificial sequence
<220> FEATURE:
<223> OTHER INFORMATION: Synthetic

<400> SEQUENCE: 43
caaggggtgc ttgcgccacc cacgt                                               25

<210> SEQ ID NO 44
<211> LENGTH: 22
<212> TYPE: DNA
<213> ORGANISM: Artificial sequence
<220> FEATURE:
<223> OTHER INFORMATION: Synthetic

<400> SEQUENCE: 44
ggggtgcgca ctgcgcgcag gt                                                  22

<210> SEQ ID NO 45
<211> LENGTH: 30
<212> TYPE: DNA
<213> ORGANISM: Artificial sequence
<220> FEATURE:
<223> OTHER INFORMATION: Synthetic

<400> SEQUENCE: 45
atggccctcc cgacaccctc ggacagcacc                                          30

<210> SEQ ID NO 46
<211> LENGTH: 30
<212> TYPE: DNA
<213> ORGANISM: Artificial sequence
<220> FEATURE:
<223> OTHER INFORMATION: Synthetic

<400> SEQUENCE: 46
ctcggacagc accctccccg cggaagcccg                                          30

<210> SEQ ID NO 47

-continued

```
<211> LENGTH: 30
<212> TYPE: DNA
<213> ORGANISM: Artificial sequence
<220> FEATURE:
<223> OTHER INFORMATION: Synthetic

<400> SEQUENCE: 47
ggaagcccgg ggacgaggac ggcgacggag                                        30

<210> SEQ ID NO 48
<211> LENGTH: 36
<212> TYPE: DNA
<213> ORGANISM: Artificial sequence
<220> FEATURE:
<223> OTHER INFORMATION: Synthetic

<400> SEQUENCE: 48
ctaaagctcc tccagcagag cccggtattc ttcctc                                 36

<210> SEQ ID NO 49
<211> LENGTH: 34
<212> TYPE: DNA
<213> ORGANISM: Artificial sequence
<220> FEATURE:
<223> OTHER INFORMATION: Synthetic

<400> SEQUENCE: 49
cccggtattc ttcctcgctg aggggtgctt ccag                                   34

<210> SEQ ID NO 50
<211> LENGTH: 30
<212> TYPE: DNA
<213> ORGANISM: Artificial sequence
<220> FEATURE:
<223> OTHER INFORMATION: Synthetic

<400> SEQUENCE: 50
ggggtgcttc cagcgaggcg gcctcttccg                                        30

<210> SEQ ID NO 51
<211> LENGTH: 24
<212> TYPE: DNA
<213> ORGANISM: Artificial sequence
<220> FEATURE:
<223> OTHER INFORMATION: Synthetic

<400> SEQUENCE: 51
gacaggggca ggggaggagc tagg                                              24

<210> SEQ ID NO 52
<211> LENGTH: 26
<212> TYPE: DNA
<213> ORGANISM: Artificial sequence
<220> FEATURE:
<223> OTHER INFORMATION: Synthetic

<400> SEQUENCE: 52
cttccctcca accagttgcc ccaaac                                            26

<210> SEQ ID NO 53
<211> LENGTH: 20
<212> TYPE: DNA
<213> ORGANISM: Artificial sequence
<220> FEATURE:
<223> OTHER INFORMATION: Synthetic
```

-continued

```
<400> SEQUENCE: 53
gctagtctcc aagcgacgaa                                                20

<210> SEQ ID NO 54
<211> LENGTH: 20
<212> TYPE: DNA
<213> ORGANISM: Artificial sequence
<220> FEATURE:
<223> OTHER INFORMATION: Synthetic

<400> SEQUENCE: 54
gcaagaagcc tctccttgaa                                                20

<210> SEQ ID NO 55
<211> LENGTH: 26
<212> TYPE: DNA
<213> ORGANISM: Artificial sequence
<220> FEATURE:
<223> OTHER INFORMATION: Synthetic

<400> SEQUENCE: 55
cctgctcaag ctgactcgac accgtg                                         26

<210> SEQ ID NO 56
<211> LENGTH: 25
<212> TYPE: DNA
<213> ORGANISM: Artificial sequence
<220> FEATURE:
<223> OTHER INFORMATION: Synthetic

<400> SEQUENCE: 56
ggaaaagctg gccctggggt ggagc                                          25

<210> SEQ ID NO 57
<211> LENGTH: 20
<212> TYPE: DNA
<213> ORGANISM: Artificial sequence
<220> FEATURE:
<223> OTHER INFORMATION: Synthetic

<400> SEQUENCE: 57
cagtctggac actggctgaa                                                20

<210> SEQ ID NO 58
<211> LENGTH: 20
<212> TYPE: DNA
<213> ORGANISM: Artificial sequence
<220> FEATURE:
<223> OTHER INFORMATION: Synthetic

<400> SEQUENCE: 58
ctcgctgatt aggctccaac                                                20

<210> SEQ ID NO 59
<211> LENGTH: 20
<212> TYPE: DNA
<213> ORGANISM: Artificial sequence
<220> FEATURE:
<223> OTHER INFORMATION: Synthetic

<400> SEQUENCE: 59
tatgacccac actgccagaa                                                20

<210> SEQ ID NO 60
```

```
<211> LENGTH: 20
<212> TYPE: DNA
<213> ORGANISM: Artificial sequence
<220> FEATURE:
<223> OTHER INFORMATION: Synthetic

<400> SEQUENCE: 60
tgggaacttg accatgattg                                                 20

<210> SEQ ID NO 61
<211> LENGTH: 20
<212> TYPE: DNA
<213> ORGANISM: Artificial sequence
<220> FEATURE:
<223> OTHER INFORMATION: Synthetic

<400> SEQUENCE: 61
cggaactctt gtgcgtaagg                                                 20

<210> SEQ ID NO 62
<211> LENGTH: 20
<212> TYPE: DNA
<213> ORGANISM: Artificial sequence
<220> FEATURE:
<223> OTHER INFORMATION: Synthetic

<400> SEQUENCE: 62
ctcagccaag gttgtgaggt                                                 20

<210> SEQ ID NO 63
<211> LENGTH: 21
<212> TYPE: DNA
<213> ORGANISM: Artificial sequence
<220> FEATURE:
<223> OTHER INFORMATION: Synthetic

<400> SEQUENCE: 63
tgttgccatc aatgacccct t                                               21

<210> SEQ ID NO 64
<211> LENGTH: 19
<212> TYPE: DNA
<213> ORGANISM: Artificial sequence
<220> FEATURE:
<223> OTHER INFORMATION: Synthetic

<400> SEQUENCE: 64
ctccacgacg tactcagcg                                                  19

<210> SEQ ID NO 65
<211> LENGTH: 424
<212> TYPE: PRT
<213> ORGANISM: Homo sapiens

<400> SEQUENCE: 65

Met Ala Leu Pro Thr Pro Ser Asp Ser Thr Leu Pro Ala Glu Ala Arg
1               5                   10                  15

Gly Arg Gly Arg Arg Arg Arg Leu Val Trp Thr Pro Ser Gln Ser Glu
            20                  25                  30

Ala Leu Arg Ala Cys Phe Glu Arg Asn Pro Tyr Pro Gly Ile Ala Thr
        35                  40                  45

Arg Glu Arg Leu Ala Gln Ala Ile Gly Ile Pro Glu Pro Arg Val Gln
    50                  55                  60
```

```
Ile Trp Phe Gln Asn Glu Arg Ser Arg Gln Leu Arg Gln His Arg Arg
65                  70                  75                  80

Glu Ser Arg Pro Trp Pro Gly Arg Arg Gly Pro Pro Glu Gly Arg Arg
                85                  90                  95

Lys Arg Thr Ala Val Thr Gly Ser Gln Thr Ala Leu Leu Leu Arg Ala
            100                 105                 110

Phe Glu Lys Asp Arg Phe Pro Gly Ile Ala Ala Arg Glu Glu Leu Ala
            115                 120                 125

Arg Glu Thr Gly Leu Pro Glu Ser Arg Ile Gln Ile Trp Phe Gln Asn
        130                 135                 140

Arg Arg Ala Arg His Pro Gly Gln Gly Gly Arg Ala Pro Ala Gln Ala
145                 150                 155                 160

Gly Gly Leu Cys Ser Ala Ala Pro Gly Gly Gly His Pro Ala Pro Ser
                165                 170                 175

Trp Val Ala Phe Ala His Thr Gly Ala Trp Gly Thr Gly Leu Pro Ala
                180                 185                 190

Pro His Val Pro Cys Ala Pro Gly Ala Leu Pro Gln Gly Ala Phe Val
                195                 200                 205

Ser Gln Ala Ala Arg Ala Ala Pro Ala Leu Gln Pro Ser Gln Ala Ala
        210                 215                 220

Pro Ala Glu Gly Ile Ser Gln Pro Ala Pro Ala Arg Gly Asp Phe Ala
225                 230                 235                 240

Tyr Ala Ala Pro Ala Pro Pro Asp Gly Ala Leu Ser His Pro Gln Ala
                245                 250                 255

Pro Arg Trp Pro Pro His Pro Gly Lys Ser Arg Glu Asp Arg Asp Pro
                260                 265                 270

Gln Arg Asp Gly Leu Pro Gly Pro Cys Ala Val Ala Gln Pro Gly Pro
        275                 280                 285

Ala Gln Ala Gly Pro Gln Gly Gln Gly Val Leu Ala Pro Pro Thr Ser
        290                 295                 300

Gln Gly Ser Pro Trp Trp Gly Trp Gly Arg Gly Pro Gln Val Ala Gly
305                 310                 315                 320

Ala Ala Trp Glu Pro Gln Ala Gly Ala Ala Pro Pro Pro Gln Pro Ala
                325                 330                 335

Pro Pro Asp Ala Ser Ala Ser Ala Arg Gln Gly Gln Met Gln Gly Ile
                340                 345                 350

Pro Ala Pro Ser Gln Ala Leu Gln Glu Pro Ala Pro Trp Ser Ala Leu
                355                 360                 365

Pro Cys Gly Leu Leu Leu Asp Glu Leu Leu Ala Ser Pro Glu Phe Leu
        370                 375                 380

Gln Gln Ala Gln Pro Leu Leu Glu Thr Glu Ala Pro Gly Glu Leu Glu
385                 390                 395                 400

Ala Ser Glu Glu Ala Ala Ser Leu Glu Ala Pro Leu Ser Glu Glu Glu
                405                 410                 415

Tyr Arg Ala Leu Leu Glu Glu Leu
                420
```

<210> SEQ ID NO 66
<211> LENGTH: 1574
<212> TYPE: DNA
<213> ORGANISM: Homo sapiens

<400> SEQUENCE: 66
atggccctcc cgacaccctc ggacagcacc ctccccgcgg aagcccgggg acgaggacgg          60
cgacggagac tcgtttggac cccgagccaa agcgaggccc tgcgagcctg ctttgagcgg         120
aacccgtacc cgggcatcgc caccagagaa cggctggccc aggccatcgg cattccggag         180
cccagggtcc agatttggtt tcagaatgag aggtcacgcc agctgaggca gcaccggcgg         240
gaatctcggc cctggcccgg gagacgcggc ccgccagaag gccggcgaaa gcggaccgcc         300
gtcaccggat cccagaccgc cctgctcctc cgagcctttg agaaggatcg ctttccaggc         360
atcgccgccc gggaggagct ggccagagag acgggcctcc cggagtccag gattcagatc         420
tggtttcaga atcgaagggc caggcacccg ggacagggtg gcagggcgcc cgcgcaggca         480
ggcggcctgt gcagcgcggc ccccggcggg ggtcaccctg ctccctcgtg ggtcgccttc         540
gcccacaccg gcgcgtgggg aacggggctt cccgcacccc acgtgccctg cgcgcctggg         600
gctctcccac aggggctttt cgtgagccag gcagcgaggg ccgcccccgc gctgcagccc         660
agccaggccg cgccggcaga ggggatctcc caacctgccc cggcgcgcgg ggatttcgcc         720
tacgccgccc cggctcctcc ggacggggcg ctctcccacc ctcaggctcc tcgctggcct         780
ccgcacccgg gcaaaagccg ggaggaccgg gacccgcagc gcgacggcct gccgggcccc         840
tgcgcggtgg cacagcctgg gcccgctcaa gcggggccgc agggccaagg ggtgcttgcg         900
ccacccacgt cccaggggag tccgtggtgg ggctggggcc ggggtcccca ggtcgccggg         960
gcggcgtggg aaccccaagc cggggcagct ccacctcccc agcccgcgcc cccggacgcc        1020
tccgcctccg cgcggcaggg gcagatgcaa ggcatcccgg cgccctccca ggcgctccag        1080
gagccggcgc cctggtctgc actcccctgc ggcctgctgc tggatgagct cctggcgagc        1140
ccggagtttc tgcagcaggc gcaacctctc ctagaaacgg aggccccggg ggagctggag        1200
gcctcggaag aggccgcctc gctggaagca cccctcagcg aggaagaata ccgggctctg        1260
ctggaggagc tttaggacgc ggggtctagg cccggtgaga gactccacac cgcggagaac        1320
tgccattctt tcctgggcat cccggggatc ccagagccgg cccaggtacc agcagacctg        1380
cgcgcagtgc gcaccccggc tgacgtgcaa gggagctcgc tggcctctct gtgcccttgt        1440
tcttccgtga aattctggct gaatgtctcc ccccaccttc cgacgctgtc taggcaaacc        1500
tggattagag ttacatctcc tggatgatta gttcagagat atattaaaat gccccctccc        1560
tgtggatcct atag                                                         1574

<210> SEQ ID NO 67
<211> LENGTH: 1710
<212> TYPE: DNA
<213> ORGANISM: Homo sapiens

<400> SEQUENCE: 67
atggccctcc cgacaccctc ggacagcacc ctccccgcgg aagcccgggg acgaggacgg          60
cgacggagac tcgtttggac cccgagccaa agcgaggccc tgcgagcctg ctttgagcgg         120
aacccgtacc cgggcatcgc caccagagaa cggctggccc aggccatcgg cattccggag         180
cccagggtcc agatttggtt tcagaatgag aggtcacgcc agctgaggca gcaccggcgg         240
gaatctcggc cctggcccgg gagacgcggc ccgccagaag gccggcgaaa gcggaccgcc         300
gtcaccggat cccagaccgc cctgctcctc cgagcctttg agaaggatcg ctttccaggc         360
atcgccgccc gggaggagct ggccagagag acgggcctcc cggagtccag gattcagatc         420

-continued

```
tggtttcaga atcgaagggc caggcacccg ggacagggtg gcaggcgccc cgcgcaggca   480
ggcggcctgt gcagcgcggc ccccggcggg ggtcaccctg ctccctcgtg ggtcgccttc   540
gcccacaccg gcgcgtgggg aacggggctt cccgcacccc acgtgccctg cgcgcctggg   600
gctctcccac aggggggcttt cgtgagccag gcagcgaggg ccgcccccgc gctgcagccc  660
agccaggccg cgccggcaga ggggatctcc caacctgccc cggcgcgcgg ggatttcgcc   720
tacgccgccc cggctcctcc ggacggggcg ctctcccacc ctcaggctcc tcgctggcct   780
ccgcacccgg gcaaaagccg ggaggaccgg gacccgcagc gcgacggcct gccgggcccc   840
tgcgcggtgg cacagcctgg gcccgctcaa gcggggccgc agggccaagg ggtgcttgcg   900
ccacccacgt cccagggggag tccgtggtgg ggctggggcc ggggtcccca ggtcgccggg   960
gcggcgtggg aaccccaagc cggggcagct ccacctcccc agcccgcgcc cccggacgcc  1020
tccgcctccg cgcggcaggg gcagatgcaa ggcatcccgg cgccctccca ggcgctccag  1080
gagccggcgc cctggtctgc actcccctgc ggcctgctgc tggatgagct cctggcgagc  1140
ccggagtttc tgcagcaggc gcaacctctc ctagaaacgg aggccccggg ggagctggag  1200
gcctcggaag aggccgcctc gctggaagca cccctcagcg aggaagaata ccgggctctg  1260
ctggaggagc tttaggacgc ggggttggga cggggtcggg tggttcgggg cagggccgtg  1320
gcctctcttt cgcggggaac acctggctgg ctacggaggg gcgtgtctcc gccccgcccc  1380
ctccaccggg ctgaccggcc tgggattcct gccttctagg tctaggcccg gtgagagact  1440
ccacaccgcg gagaactgcc attctttcct gggcatcccg gggatcccag agccggccca  1500
ggtaccagca gacctgcgcg cagtgcgcac cccggctgac gtgcaaggga gctcgctggc  1560
ctctctgtgc ccttgttctt ccgtgaaatt ctggctgaat gtctccccc accttccgac   1620 gctgtctagg caaacctgga ttagagttac atctcctgga tgattagttc agagatatat  1680
taaaatgccc cctccctgtg gatcctatag                                   1710
```

<210> SEQ ID NO 68
<211> LENGTH: 160
<212> TYPE: PRT
<213> ORGANISM: Homo sapiens

<400> SEQUENCE: 68

```
Met Ala Leu Pro Thr Pro Ser Asp Ser Thr Leu Pro Ala Glu Ala Arg
1               5                   10                  15

Gly Arg Gly Arg Arg Arg Leu Val Trp Thr Pro Ser Gln Ser Glu
            20                  25                  30

Ala Leu Arg Ala Cys Phe Glu Arg Asn Pro Tyr Pro Gly Ile Ala Thr
            35                  40                  45

Arg Glu Arg Leu Ala Gln Ala Ile Gly Ile Pro Glu Pro Arg Val Gln
        50                  55                  60

Ile Trp Phe Gln Asn Glu Arg Ser Arg Gln Leu Arg Gln His Arg Arg
65                  70                  75                  80

Glu Ser Arg Pro Trp Pro Gly Arg Arg Gly Pro Pro Glu Gly Arg Arg
                85                  90                  95

Lys Arg Thr Ala Val Thr Gly Ser Gln Thr Ala Leu Leu Leu Arg Ala
            100                 105                 110

Phe Glu Lys Asp Arg Phe Pro Gly Ile Ala Ala Arg Glu Glu Leu Ala
            115                 120                 125

Arg Glu Thr Gly Leu Pro Glu Ser Arg Ile Gln Ile Trp Phe Gln Asn
        130                 135                 140
```

-continued

```
Arg Arg Ala Arg His Pro Gly Gln Gly Gly Arg Ala Pro Ala Gln Val
145                 150                 155                 160
```

<210> SEQ ID NO 69
<211> LENGTH: 768
<212> TYPE: DNA
<213> ORGANISM: Homo sapiens

<400> SEQUENCE: 69

```
atggccctcc cgacaccctc ggacagcacc ctccccgcgg aagcccgggg acgaggacgg      60
cgacggagac tcgtttggac cccgagccaa agcgaggccc tgcgagcctg ctttgagcgg     120
aacccgtacc cgggcatcgc caccagagaa cggctggccc aggccatcgg cattccggag     180
cccagggtcc agatttggtt tcagaatgag aggtcacgcc agctgaggca gcaccggcgg     240
gaatctcggc cctggcccgg gagacgcggc ccgccagaag gccggcgaaa gcggaccgcc     300
gtcaccggat cccagaccgc cctgctcctc cgagcctttg agaaggatcg ctttccaggc     360
atcgccgccc gggaggagct ggccagagag acgggcctcc cggagtccag gattcagatc     420
tggtttcaga atcgaagggc caggcacccg ggacagggtg gcagggcgcc cgcgcaggtc     480
taggcccggt gagagactcc acaccgcgga gaactgccat tctttcctgg gcatcccggg     540
gatcccagag ccggcccagg taccagcaga cctgcgcgca gtgcgcaccc cggctgacgt     600
gcaagggagc tcgctggcct ctctgtgccc ttgttcttcc gtgaaattct ggctgaatgt     660 ctcccccac cttccgacgc tgtctaggca aacctggatt agagttacat ctcctggatg     720
attagttcag agatatatta aaatgccccc tccctgtgga tcctatag                 768
```

<210> SEQ ID NO 70
<211> LENGTH: 1437
<212> TYPE: DNA
<213> ORGANISM: Homo sapiens

<400> SEQUENCE: 70

```
gcctttacaa gggcggctgg ctggctggct ggctgtccgg gcaggcctcc tggctgcacc      60
tgccgcagtg cacagtccgg ctgaggtgca cgggagcccg ccggcctctc tctgcccgcg     120
tccgtccgtg aaattccggc cggggctcac cgcgatggcc ctcccgacac cctcggacag     180
caccctcccc gcggaagccc ggggacgagg acggcgacgg agactcgttt ggaccccgag     240
ccaaagcgag gccctgcgag cctgctttga gcggaacccg tacccgggca tcgccaccag     300
agaacggctg gcccaggcca tcggcattcc ggagcccagg gtccagattt ggtttcagaa     360
tgagaggtca cgccagctga ggcagcaccg gcgggaatct cggccctggc ccgggagacg     420
cggcccgcca gaaggccggc gaaagcggac cgccgtcacc ggatcccaga ccgccctgct     480
cctccgagcc tttgagaagg atcgcttttcc aggcatcgcc gcccgggagg agctggccag     540
agagacgggc ctcccggagt ccaggattca gatctggttt cagaatcgaa gggccaggca     600
cccgggacag ggtggcaggg cgcccgcgca ggcaggcggc ctgtgcagcg cggccccgg      660 cgggggtcac cctgctccct cgtgggtcgc cttcgcccac accggcgcgt ggggaacggg     720 gcttccgca ccccacgtgc cctgcgcgcc tggggctctc ccacaggggg ctttcgtgag     780
ccaggcagcg agggccgccc ccgcgctgca gcccagccag gccgcgccgg cagaggggat     840
ctcccaacct gccccggcgc gcggggattt cgcctacgcc gccccggctc ctccggacgg     900
ggcgctctcc caccctcagg ctcctcgctg gcctccgcac ccgggcaaaa gccgggagga     960
ccgggacccg cagcgcgacg gcctgccggg ccctgcgcg gtggcacagc ctgggcccgc    1020
```

-continued

```
tcaagcgggg ccgcagggcc aaggggtgct tgcgccaccc acgtcccagg ggagtccgtg   1080
gtggggctgg ggccggggtc cccaggtcgc cggggcggcg tgggaacccc aagccggggc   1140
agctccacct ccccagcccg cgcccccgga cgcctccgcc tccgcgcggc aggggcagat   1200
gcaaggcatc ccggcgccct cccaggcgct ccaggagccg cgcgccctggt ctgcactccc   1260 ctgcggcctg ctgctggatg agctcctggc gagcccggag tttctgcagc aggcgcaacc   1320
tctcctagaa acggaggccc cgggggagct ggaggcctcg gaagaggccg cctcgctgga   1380
agcacccctc agcgaggaag aataccgggc tctgctggag gagctttagg acgcggg       1437

<210> SEQ ID NO 71
<211> LENGTH: 92
<212> TYPE: DNA
<213> ORGANISM: Homo sapiens

<400> SEQUENCE: 71
gtctaggccc ggtgagagac tccacaccgc ggagaactgc cattctttcc tgggcatccc     60
ggggatccca gagccggccc aggtaccagc ag                                   92

<210> SEQ ID NO 72
<211> LENGTH: 201
<212> TYPE: DNA
<213> ORGANISM: Homo sapiens

<400> SEQUENCE: 72
acctgcgcgc agtgcgcacc ccggctgacg tgcaagggag ctcgctggcc tctctgtgcc     60
cttgttcttc cgtgaaattc tggctgaatg tctcccccca ccttccgacg ctgtctaggc    120
aaacctggat tagagttaca tctcctggat gattagttca gagatatatt aaaatgcccc    180
ctccctgtgg atcctataga a                                              201

<210> SEQ ID NO 73
<211> LENGTH: 65
<212> TYPE: DNA
<213> ORGANISM: Homo sapiens

<400> SEQUENCE: 73
gcagaggcta acaagagtt acatcacctg gattttgttt cctgcaatat gtcacaatgg      60
cgagg                                                                 65

<210> SEQ ID NO 74
<211> LENGTH: 68
<212> TYPE: DNA
<213> ORGANISM: Homo sapiens

<400> SEQUENCE: 74
gctattaaga catgtttgtc ttcaaagaat ggccttggtt tctgtggaca gtttctcctc     60
atggaaag                                                              68

<210> SEQ ID NO 75
<211> LENGTH: 99
<212> TYPE: DNA
<213> ORGANISM: Homo sapiens

<400> SEQUENCE: 75
cagcctttgt cgcttcaaac accgcaagtg ttcttttaaa agaattatat caacctttca     60
agtgaaatgc aacatgtctg aaacgtggta tctggagag                           99
```

<210> SEQ ID NO 76
<211> LENGTH: 94
<212> TYPE: DNA
<213> ORGANISM: Homo sapiens

<400> SEQUENCE: 76
gaacagtaag aggaccttgt gagtgaataa tttgtttcca cattacagag tgggtaataa        60
gcagattagt aaaaacaatt ctgcttcact tcaa                                   94

<210> SEQ ID NO 77
<211> LENGTH: 31
<212> TYPE: DNA
<213> ORGANISM: Artificial sequence
<220> FEATURE:
<223> OTHER INFORMATION: Synthetic

<400> SEQUENCE: 77
aggagtgatg ataatttaat cagccgtgca a                                      31

<210> SEQ ID NO 78
<211> LENGTH: 31
<212> TYPE: DNA
<213> ORGANISM: Artificial sequence
<220> FEATURE:
<223> OTHER INFORMATION: Synthetic

<400> SEQUENCE: 78
aggagtgatg atacttttat gagccgtgca a                                      31

<210> SEQ ID NO 79
<211> LENGTH: 31
<212> TYPE: DNA
<213> ORGANISM: Artificial sequence
<220> FEATURE:
<223> OTHER INFORMATION: Synthetic

<400> SEQUENCE: 79
cctgtgggag gtaatccaat catggaggca g                                      31

<210> SEQ ID NO 80
<211> LENGTH: 31
<212> TYPE: DNA
<213> ORGANISM: Artificial sequence
<220> FEATURE:
<223> OTHER INFORMATION: Synthetic

<400> SEQUENCE: 80
cctgtgggag gtactcctat gatggaggca g                                      31

<210> SEQ ID NO 81
<211> LENGTH: 31
<212> TYPE: DNA
<213> ORGANISM: Artificial sequence
<220> FEATURE:
<223> OTHER INFORMATION: Synthetic

<400> SEQUENCE: 81
ccaggtggag ataattgaat catgggggca g                                      31

<210> SEQ ID NO 82
<211> LENGTH: 31
<212> TYPE: DNA
<213> ORGANISM: Artificial sequence
<220> FEATURE:
<223> OTHER INFORMATION: Synthetic

<400> SEQUENCE: 82
ccaggtggag atacttgtat gatgggggca g                                      31

<210> SEQ ID NO 83
<211> LENGTH: 20
<212> TYPE: DNA
<213> ORGANISM: Artificial sequence
<220> FEATURE:
<223> OTHER INFORMATION: Synthetic

<400> SEQUENCE: 83
acccctcatg gagaacctct                                                   20

<210> SEQ ID NO 84
<211> LENGTH: 20
<212> TYPE: DNA
<213> ORGANISM: Artificial sequence
<220> FEATURE:
<223> OTHER INFORMATION: Synthetic

<400> SEQUENCE: 84
accctcttct cacagctcca                                                   20

<210> SEQ ID NO 85
<211> LENGTH: 21
<212> TYPE: DNA
<213> ORGANISM: Artificial sequence
<220> FEATURE:
<223> OTHER INFORMATION: Synthetic

<400> SEQUENCE: 85
ttctcaggct tcaagatttg g                                                 21

<210> SEQ ID NO 86
<211> LENGTH: 20
<212> TYPE: DNA
<213> ORGANISM: Artificial sequence
<220> FEATURE:
<223> OTHER INFORMATION: Synthetic

<400> SEQUENCE: 86
ctggagcttg cggaatttag                                                   20

<210> SEQ ID NO 87
<211> LENGTH: 20
<212> TYPE: DNA
<213> ORGANISM: Artificial sequence
<220> FEATURE:
<223> OTHER INFORMATION: Synthetic

<400> SEQUENCE: 87
caccccaagt tcgaggagat                                                   20

<210> SEQ ID NO 88
<211> LENGTH: 20
<212> TYPE: DNA
<213> ORGANISM: Artificial sequence
<220> FEATURE:
<223> OTHER INFORMATION: Synthetic

<400> SEQUENCE: 88
agcgttggac acgtcaaata                                                   20

<210> SEQ ID NO 89
<211> LENGTH: 11

-continued

```
<212> TYPE: DNA
<213> ORGANISM: Artificial sequence
<220> FEATURE:
<223> OTHER INFORMATION: Synthetic

<400> SEQUENCE: 89
taaybbaatc a                                                    11

<210> SEQ ID NO 90
<211> LENGTH: 11
<212> TYPE: DNA
<213> ORGANISM: Artificial sequence
<220> FEATURE:
<223> OTHER INFORMATION: Synthetic

<400> SEQUENCE: 90
taatttaatc a                                                    11

<210> SEQ ID NO 91
<211> LENGTH: 11
<212> TYPE: DNA
<213> ORGANISM: Artificial sequence
<220> FEATURE:
<223> OTHER INFORMATION: Synthetic

<400> SEQUENCE: 91
tacttttatg a                                                    11

<210> SEQ ID NO 92
<211> LENGTH: 11
<212> TYPE: DNA
<213> ORGANISM: Artificial sequence
<220> FEATURE:
<223> OTHER INFORMATION: Synthetic

<400> SEQUENCE: 92
taattgaatc a                                                    11

<210> SEQ ID NO 93
<211> LENGTH: 11
<212> TYPE: DNA
<213> ORGANISM: Artificial sequence
<220> FEATURE:
<223> OTHER INFORMATION: Synthetic

<400> SEQUENCE: 93
taatccaatc a                                                    11

<210> SEQ ID NO 94
<211> LENGTH: 10
<212> TYPE: DNA
<213> ORGANISM: Artificial sequence
<220> FEATURE:
<223> OTHER INFORMATION: Synthetic

<400> SEQUENCE: 94
tacttctatg                                                      10

<210> SEQ ID NO 95
<211> LENGTH: 11
<212> TYPE: DNA
<213> ORGANISM: Artificial sequence
<220> FEATURE:
<223> OTHER INFORMATION: Synthetic
```

<400> SEQUENCE: 95
tactcctatg a                                                                          11

<210> SEQ ID NO 96
<211> LENGTH: 31
<212> TYPE: DNA
<213> ORGANISM: Artificial sequence
<220> FEATURE:
<223> OTHER INFORMATION: Synthetic

<400> SEQUENCE: 96
aggagtgatg ataatttaat cagccgtgca a                                                    31

<210> SEQ ID NO 97
<211> LENGTH: 31
<212> TYPE: DNA
<213> ORGANISM: Artificial sequence
<220> FEATURE:
<223> OTHER INFORMATION: Synthetic

<400> SEQUENCE: 97
aatcacgtct ttaaatcaat cactgacatg g                                                    31

<210> SEQ ID NO 98
<211> LENGTH: 141
<212> TYPE: DNA
<213> ORGANISM: Artificial sequence
<220> FEATURE:
<223> OTHER INFORMATION: Synthetic

<400> SEQUENCE: 98
agtaattcaa tcaacagaca agtgttatcc aatcacgtct ttaaatcaat cactgacatg      60
gagctggggc tggatgaaga ttccatcagt aattcaatca acagacaagt gttatccaat     120
cacgtcttta aatcaatcac t                                                              141

<210> SEQ ID NO 99
<211> LENGTH: 300
<212> TYPE: DNA
<213> ORGANISM: Homo sapiens

<400> SEQUENCE: 99
agccgcccag gtgccagcac ggagcgcctg gcggtcaaaa gcatacctct gtctgtcttt      60
gcccgcttcc tggctagacc tgcgcgcagt gcgcaccccg ggtgacgtgc aagggagctc     120
gctggcctct ctgtgccctt gttcgtccgt gaaattctgg ctgaatctct ccccccacct     180
tccgaggctg tctaggcaaa cctggattag agttacatct cctggatgat tagttcagag     240
atatatcaaa attcccctc cctgtggatc ctatagagga tttgcatctt ttgtgtgatc     300

<210> SEQ ID NO 100
<211> LENGTH: 12
<212> TYPE: DNA
<213> ORGANISM: Homo sapiens

<400> SEQUENCE: 100
tctcactatt gt                                                                        12

<210> SEQ ID NO 101
<211> LENGTH: 12
<212> TYPE: DNA
<213> ORGANISM: Homo sapiens -continued

```
<400> SEQUENCE: 101
ggctgtcgga ag                                                  12

<210> SEQ ID NO 102
<211> LENGTH: 12
<212> TYPE: DNA
<213> ORGANISM: Homo sapiens

<400> SEQUENCE: 102
ggctgtcgga ag                                                  12

<210> SEQ ID NO 103
<211> LENGTH: 12
<212> TYPE: DNA
<213> ORGANISM: Homo sapiens

<400> SEQUENCE: 103
tcttaccatt gt                                                  12

<210> SEQ ID NO 104
<211> LENGTH: 12
<212> TYPE: DNA
<213> ORGANISM: Homo sapiens

<400> SEQUENCE: 104
ggctgtcgga ag                                                  12

<210> SEQ ID NO 105
<211> LENGTH: 54
<212> TYPE: DNA
<213> ORGANISM: Homo sapiens

<400> SEQUENCE: 105
tagcaggttt tccaggccag ggaggcaggg aggggaccct atccatgact gccc        54

<210> SEQ ID NO 106
<211> LENGTH: 54
<212> TYPE: DNA
<213> ORGANISM: Homo Sapiens

<400> SEQUENCE: 106
tagccagttt tccaggccag ggaggcaggg aggggacccg atccacgact cccc        54

<210> SEQ ID NO 107
<211> LENGTH: 53
<212> TYPE: DNA
<213> ORGANISM: Homo sapiens

<400> SEQUENCE: 107
tactcaacct tacatctcag ggaggcaggg aggcgcacgc ggcatcactc tct         53

<210> SEQ ID NO 108
<211> LENGTH: 61
<212> TYPE: DNA
<213> ORGANISM: Homo sapiens

<400> SEQUENCE: 108
tagccagttc tacgggtcag ggaggcaggg aggcagggag gtgcacgatg tgccaccctg    60
t                                                             61

<210> SEQ ID NO 109
<211> LENGTH: 61
```

-continued

```
<212> TYPE: DNA
<213> ORGANISM: Homo sapiens

<400> SEQUENCE: 109
tcgccagttc tacgggtcag ggaggcaggg aggcagggag gtgcacgatg tgccaccctg    60
t                                                                    61

<210> SEQ ID NO 110
<211> LENGTH: 60
<212> TYPE: DNA
<213> ORGANISM: Homo sapiens

<400> SEQUENCE: 110
aagccacgcc tcatttccga tgtcagggag gcagggaggg gactgtatgc atccgtctcc    60

<210> SEQ ID NO 111
<211> LENGTH: 43
<212> TYPE: DNA
<213> ORGANISM: Homo sapiens

<400> SEQUENCE: 111
ccagggagga aggaccccac actcccacac ccgcctccgc ctc                      43

<210> SEQ ID NO 112
<211> LENGTH: 17
<212> TYPE: DNA
<213> ORGANISM: Homo sapiens

<400> SEQUENCE: 112
acacccgcct ccgcctc                                                   17

<210> SEQ ID NO 113
<211> LENGTH: 47
<212> TYPE: DNA
<213> ORGANISM: Homo sapiens

<400> SEQUENCE: 113
ccagggagga aggacggacc ccacactccc acacccgcct ccgcctc                  47

<210> SEQ ID NO 114
<211> LENGTH: 43
<212> TYPE: DNA
<213> ORGANISM: Homo sapiens

<400> SEQUENCE: 114
ccagggagga aggaccccac aatcccacac ccgcctccgc ctc                      43

<210> SEQ ID NO 115
<211> LENGTH: 47
<212> TYPE: DNA
<213> ORGANISM: Homo sapiens

<400> SEQUENCE: 115
ccagggagga gggacggacc tcataatccc acagccgcct ccgcctc                  47

<210> SEQ ID NO 116
<211> LENGTH: 45
<212> TYPE: DNA
<213> ORGANISM: Homo sapiens

<400> SEQUENCE: 116
tcagggaggc agggaggaag gactttgcaa cgtcacagcc gcctc                     45
```

-continued

```
<210> SEQ ID NO 117
<211> LENGTH: 55
<212> TYPE: DNA
<213> ORGANISM: Homo sapiens

<400> SEQUENCE: 117
tcagggaggc agggagggag gacggacctc atgatccccc ggacgcctcc gcctc                55

<210> SEQ ID NO 118
<211> LENGTH: 25
<212> TYPE: DNA
<213> ORGANISM: Homo sapiens

<400> SEQUENCE: 118
ataatctcac ggccgcctcc gcctc                                                  25

<210> SEQ ID NO 119
<211> LENGTH: 25
<212> TYPE: DNA
<213> ORGANISM: Homo sapiens

<400> SEQUENCE: 119
ataatcctaa ggccgcctcc gcctc                                                  25

<210> SEQ ID NO 120
<211> LENGTH: 25
<212> TYPE: DNA
<213> ORGANISM: Homo sapiens

<400> SEQUENCE: 120
ataatcccac agccgcctcc gcctc                                                  25

<210> SEQ ID NO 121
<211> LENGTH: 20
<212> TYPE: DNA
<213> ORGANISM: Homo sapiens

<400> SEQUENCE: 121
ttcatccgtc tgattaaaga                                                        20

<210> SEQ ID NO 122
<211> LENGTH: 20
<212> TYPE: DNA
<213> ORGANISM: Homo sapiens

<400> SEQUENCE: 122
ctagtccgtc tgattaaaga                                                        20

<210> SEQ ID NO 123
<211> LENGTH: 20
<212> TYPE: DNA
<213> ORGANISM: Homo sapiens

<400> SEQUENCE: 123
ctaggcgagg gcatcaaatg                                                        20

<210> SEQ ID NO 124
<211> LENGTH: 20
<212> TYPE: DNA
<213> ORGANISM: Homo sapiens

<400> SEQUENCE: 124
ttcgtacagc tgatttaaga                                                        20
```

-continued

```
<210> SEQ ID NO 125
<211> LENGTH: 300
<212> TYPE: DNA
<213> ORGANISM: Homo sapiens

<400> SEQUENCE: 125
agcctcccag ctgccagcgc ggagctcctg gcggtcaaaa gcatacctct gtctgtcttt          60
gcccgcttcc tggctagacc tgcgcgcagt gcgcaccccg gctgacgtgc aagggagctc         120
gctggcctct ctgtgccctt gttcttccgt gaaattctgg ctgaatgtct cccccacct         180 tccgacgctg tctaggcaaa cctggattag agttacatct cctggatgat tagttcagag         240
atatattaaa atgcccctc cctgtggatc ctatagaaga tttgcatctt ttgtgtgatg         300
```

METHODS FOR ALLEVIATING FACIOSCAPULOHUMERAL DYSTROPHY (FSHD) BY AN ANTISENSE NUCLEIC ACID MOLECULE INHIBITING THE EXPRESSION OF DOUBLE HOMEOBOX 4 (DUX4)

CROSS-REFERENCE(S) TO RELATED APPLICATIONS

This application is a continuation of U.S. application Ser. No. 13/817,531, filed May 23, 2013, now U.S. Pat. No. 10,865,445, which is a national phase application under 35 U.S.C. § 371 of International Application No. PCT/US2011/048318 filed Aug. 18, 2011, which claims priority to U.S. Provisional Application No. 61/374,967, filed Aug. 18, 2010; U.S. Provisional Application No. 61/384,609, filed Sep. 20, 2010; U.S. Provisional Application No. 61/513,456, filed Jul. 29, 2011; and U.S. Provisional Application No. 61/513,467, filed Jul. 29, 2011, the disclosures of which are incorporated herein by reference.

STATEMENT OF GOVERNMENT LICENSE RIGHTS

This invention was made with Government support under grant NS069539, AR045203, and AR045113, awarded by National Institutes of Health. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is: FHCCP0039USC1_ST25.txt. The text file is 65866 bytes and was created on Jan. 18, 2023.

BACKGROUND

Facioscapulohumeral dystrophy (FSHD) is the third most common muscular dystrophy. The mutation that causes FSHD was identified nearly 20 years ago (Wijmenga et al., *Nat. Genet.* 2:26-30 (1992)), yet the molecular mechanism(s) of the disease remains elusive. The most prevalent form of FSHD (FSHD1) is caused by the deletion of a subset of D4Z4 macrosatellite repeats in the subtelomeric region of chromosome 4q. Unaffected individuals have 11-100 of the 3.3 kb D4Z4 repeat units, whereas FSHD1 individuals have 10 or fewer repeats. At least one repeat unit appears necessary for FSHD because no case has been identified with a complete deletion of D4Z4 repeats (Tuplet et al., *J. Med. Genet.* 33:366-370 (1996)). Each repeat unit contains a copy of the double homeobox retrogene DUX4 (Clapp et al., *Am. J. Hum. Genet.* 81:264-279 (2007); Gabriels et al., *Gene* 236:25-32 (1999); Lyle et al., *Genomics* 28:389-397 (1995)), and inappropriate expression of DUX4 was initially proposed as a possible cause of FSHD. This was supported by the observations that repeat contraction is associated with decreased repressive epigenetic marks in the remaining D4Z4 units (van Overveld et al., *Nat. Genet.* 35:315-317 (2003); Zeng et al., *PloS Genet* 5, e1000559 (2009)), and that overexpression of the DUX4 protein in a variety of cells, including skeletal muscle, causes apoptotic cell death (Kowaljow et al., *Neuromuscul. Disord.* 17:611-623 (2007); Wallace et al., *Ann. Neurol.* 69:540-552 (2011); Wuebbles et al., *Int. J. Clin. Exp. Pathol.* 3:386-400 (2010)). However, initial attempts to identify DUX4 mRNA transcripts in FSHD muscle were unsuccessful, leading to the suggestion that other genes in the region were causative for FSHD (Gabellini et al., *Cell* 110:339-348 (2002); Klooster et al., *Eur. J. Hum. Genet.* 17:1615-1624 (2009); Laoudj-Chenivesse et al., *J. Mol. Med.* 83:216-224 (2005); Reed et al., *Exp. Neurol.* 205: 583-586 (2007)).

Currently, the diagnostic test for FSHD1 requires pulse-field gel electrophoresis and Southern blotting to detect the contraction of the D4Z4 repeats, and there are no commercially available diagnostic tests for FSHD2. FSHD1 can be genetically diagnosed by the contraction of the number of D4Z4 repeats to 10 or fewer repeats on a specific 4qA haplotype. FSHD2 is associated with decreased DNA methylation of the D4Z4 repeats on the same 4qA haplotype. The methods described herein provide an improved method for screening for the presence or risk of developing FSHD and for the treatment of FSHD, and apply both to FSHD1 and FSHD2.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the invention provides a method of screening a human subject to determine if said subject has a genetic predisposition to develop, or is suffering from Facioscapulohumeral Dystrophy (FSHD). The method according to this aspect of the invention comprises: (a) providing a biological sample comprising genomic DNA from the subject; and (b) analyzing the portion of the genomic DNA in the sample corresponding to the distal D4Z4-pLAM region on chromosome 4 and determining the presence or absence of a polymorphism resulting in a functional polyadenylation sequence operationally linked to exon 3 of the DUX4 gene, wherein a determination of the absence of a functional polyadenylation sequence operationally linked to exon 3 of the DUX4 gene indicates that the subject does not have a genetic predisposition to develop, and is not suffering from FSHD, and/or wherein a determination of the presence of a functional polyadenylation sequence operationally linked to exon 3 of the DUX4 gene indicates that the subject has a genetic predisposition to develop, or is suffering from Facioscapulohumeral Dystrophy (FSHD).

In another aspect, the invention provides a method of screening a human subject to determine if said subject is at risk for developing, or is suffering from Facioscapulohumeral Dystrophy (FSHD). The method according to this aspect of the invention comprises: (a) providing a biological sample from the subject; (b) determining, in the biological sample, the presence or amount of at least one of: (i) DUX4-fl polypeptide, set forth as SEQ ID NO:65, or a naturally occurring variant thereof, or (ii) polyadenylated mRNA encoding DUX4-fl, or nucleic acid molecules derived therefrom; and (c) comparing the presence or amount of DUX4-fl polypeptide or nucleic acid sequence encoding DUX4-fl determined in step (b) with a reference standard or control sample; wherein an increase in the presence or amount of at least one of DUX-fl polypeptide, or nucleic acid sequence encoding DUX4-fl in comparison to the reference standard or control sample is indicative of the presence of FSHD, or increased risk of developing FSHD in the mammalian subject.

In another aspect, the invention provides an isolated polynucleotide probe or primer for use in a screening assay for the presence or risk of FSHD, wherein the polynucleotide probe or primer has a length of from at least 10 nucleotides to 200 nucleotides and specifically hybridizes to a nucleic acid molecule having a sequence at least 95% identical to the sequence set forth in nucleotides 7903 to 8671 of SEQ ID NO:5, or the complement thereof, which encompasses the DUX4 exon 3 to the end of the pLAM sequence in FJ439133.

In another aspect, the invention provides a kit for determining susceptibility or presence of FSHD in a mammalian subject based on the detection of a polymorphism in the polyA signal adjacent Exon 3 of Dux 4 in chromosome 4, said kit comprising one or more isolated polynucleotide probe or primer molecules having a length of from at least 10 nucleotides to 200 nucleotides and capable of specifically hybridizing to a nucleic acid molecule having a sequence at least 95% identical to the sequence set forth in nucleotides 7903 to 8671 of SEQ ID NO:5, or the complement thereof, which encompasses the DUX4 exon 3 to the end of the pLAM sequence in FJ439133.

In another aspect, the invention provides a method of treating a mammalian subject suffering from, or at risk for developing Facioscapulohumeral Dystrophy (FSHD, the method comprising administering to the mammalian subject an agent capable of inhibiting or suppressing the level of DUX4-fl expression, or an agent capable of inhibiting DUX4-fl mediated transcription activation in a population of cells in the mammalian subject.

The invention thus provides methods, reagents and kits for assessing the risk or presence of FSHD in a mammalian subject, and further provides methods for treating a subject suffering from or at risk for developing FSHD.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3A shows a comparison of the sequence variants identified at the proximal end of the D4Z4 repeat on permissive and non-permissive haplotypes, wherein the sequence is compared to nucleotides 4361-7551 of the sequence of GenBank Ref. AF117653, set forth as SEQ ID NO:1, as described in Example 1; the sequences shown in FIG. 3A correspond to SEQ ID NOS:100, 100, 101, 101, 102, 103, 104, and 104, respectively (top), and SEQ ID NOS: 105, 106, 107, 108, 109, 110, 107, and 107, respectively (bottom);

FIG. 3B1 shows a comparison of the sequence variants identified at the distal end of the D4Z4 repeat on permissive and non-permissive haplotypes, wherein the sequence shown is with reference to nucleotides 4650-8079 of the sequence of GenBank Ref FJ439133, set forth as SEQ ID NO:5, as described in Example 1; the sequences shown in FIG. 3B1 correspond to SEQ ID NOS:111, 111, 112, 113, 114, 111, 115, 116, 113, 111, 116, 117, 118, 119, and 120, respectively;

FIG. 3B2 shows a comparison of the sequence variants identified at the distal end of the D4Z4 repeat on permissive and non-permissive haplotypes, wherein the sequence shown is with reference to nucleotides 4650-8079 of the sequence of GenBank Ref FJ439133, set forth as SEQ ID NO:5, as described in Example 1; the sequences shown in FIG. 3B2 correspond to SEQ ID NOS: 121, 121, 121, 121, 121, 121, 121, 122, 121, 121, 123, and 124, respectively;

FIG. 4D shows an alignment between nt 7802 to nt 8101 of SEQ ID NO:5 (set forth as SEQ ID NO:125) (pLAM region of Chromosome 4qA161) and the corresponding region from chromosome 10, set forth as SEQ ID NO:99, wherein the consensus polyA site is in the boxed region, the poly-A addition sites are underlined, and the SNPs are shown in red (greyscale in black and white), as described in Example 1;

FIG. 4E shows the sequence of intron 2 of 4qa161 (corresponding to nt 7516 to nt 7878 of SEQ ID NO:5) and the sequence of exon 3 of 4qa161 and adjacent pLAM region (corresponding to nt 7879 to nt 8671 of SEQ ID NO:5), wherein the SNP locations are shown in red (greyscale in black and white), which are the same as those described in connection with FIG. 4D, as described in Example 1;

FIG. 5A shows the pedigrees of five FSHD families with complex pathogenic chromosomes, wherein Families F1-F4 all carry a hybrid D4Z4 repeat that commences with chromosome 10-type repeat units (closed triangles), but end with 4-type repeat units (open triangles). In family F3, a meiotic rearrangement between chromosomes 4 and 10 generated a short hybrid repeat structure on 4A161. In family F4, this pathogenic repeat is located on chromosome 10 and originates from a mitotic D4Z4 contraction in the mildly affected father which is transmitted to his affected son. Family F5 represents a disease chromosome in which in addition to partial deletion of the D4Z4 repeat, the region proximal to the D4Z4 repeat is also deleted, as described in Example 1;

FIG. 5B shows the results of a PFGE Southern blot of genomic DNA digested with EcoRI (E), EcoRI and BlnI (B) or with XapI (X) and hybridized with p13E-11. The chromosomal origin of the different D4Z4 repeat arrays as well as the percentage mosaicism is indicated. The pathogenic allele is marked with an arrow. The cross-hybridizing Y fragment is labeled with Y. Marker lane on the left, as described in Example 1;

FIG. 6 illustrates the pedigrees of three FSHD families F6, F7 and F8 with D4Z4 repeat contractions on rare permissive haplotypes 4A161L, 4A159 and 4A168. In all families, the contracted D4Z4 repeat cosegregated with the disease. The composition of the disease repeat is shown below each pedigree, as described in Example 1;

FIG. 7 illustrates the structure of chromosomes that are permissive or non-permissive for FSHD. As shown in FIG. 7, all permissive chromosomes, including those with unusual disease associated repeat structures (complex pathogenic chromosomes that have been identified in FSHD families F1-F5) share the distal end of the D4Z4 repeat and flanking pLAM sequences indicated by the open grey box. This region is absent in the non-permissive chromosomes in the right panel, as described in Example 1;

FIG. 9D graphically illustrates the results of quantitative RT-PCR analysis of DUX4-fl3' showing relative abundance in muscle cells, muscle biopsies, human testis and other indicated cells, as described in Example 2;

FIG. 15A shows that in vitro translated DUX4-fl binds to radiolabeled oligos containing the TAATTAATCA (SEQ ID NO:90) core sequence found near the TRIM48 gene. Competition with cold TRIM48 oligos reduces binding whereas competition with cold TRIM48mut oligos, containing the mutated core sequence TACTTTTATGA (SEQ ID NO:91), does not. Supershift with DUX4 antibody E14-3 confirmed the specificity of binding. FIG. 15B shows that in vitro translated DUX4-fl binds to radiolabeled oligos containing the TAATTGAATCA (SEQ ID NO:92) core sequence found within the LTR of a THE1B retroelement near the CSF1R gene; FIG. 15C shows that in vitro translated DUX4-fl binds to radiolabeled oligos containing the TAATCCAATCA (SEQ ID NO:93) core sequence found within the LTR of the THE1D retroelement; Competition with the cold CSF1R and THE1D probes to their respective radioactive oligos inhibited binding, whereas competition with cold mutant CSF1Rmut and THE1Dmut oligos, containing sites TACTTCTATG (SEQ ID NO:94) and TACTCCTATGA (SEQ ID NO:95), respectively, do not; FIG. 15D shows that DUX4-s also binds the same core motifs; left, CSF1R; right, TRIM48. Supershift with anti-DUX4 N-terminus antibody E14-3 confirmed specificity of binding, as described in Example 4;

FIG. 16A shows the reporter construct structure; FIG. 16B and FIG. 16C shows that genomic fragments near the TRIM48 (FIG. 16B) and ZSCAN4 genes (FIG. 16C) containing DUX4 binding sites were cloned into pGL3-promoter reporter vector (schematic, top) and transfected into human rhabdomyoscaroma cell line RD. Cells were co-transfected with DUX4-fl or DUX4-s. pCS2-P galactosidase (beta gal) was used to balance DNA amount in control condition. TRIM48mut and ZSCAN4mut, mutated binding sites. Luciferase activity was set relative to control, as described in Example 4;

FIG. 17B shows that DUX4-fl highly activates the luciferase expression, whereas mutation of the binding sites (ZSCAN4mut) drastically reduces this induction. FIG. 17C: Co-transfection of equal amounts of DUX4-fl and DUX4-s diminishes luciferase activity. Luciferase activity from DUX4-fl co-transfected with equal amount of beta gal is set at 100%. FIG. 17D: Genomic fragment from the LTR of THE1D MaLR element containing the DUX4 binding site were cloned into pGL3-promoter vector and tested for response to DUX4-fl as in (b). FIG. 17E: Transcripts from endogenous retroelement MaLRs are upregulated by lentiviral transduction of DUX4-fl into primary human myoblasts. No upregulation is seen with lentiviral transduction of GFP or DUX4-s. Real-time RT-PCR quantitation is reported relative to internal standard RPL13a. All data represent mean+/−SD from at least triplicates, as described in Example 4;

(FIG. 19A) PRAMEF1; (FIG. 19B) RFPL2; (FIG. 19C) MBD3L2; (FIG. 19D) TRIM43; (FIG. 19E) KHDC1; and (FIG. 19F) ZSCAN4. It is noted that the DUX4-fl mRNA is at extremely low abundance in FSHD muscle and it is notable that some biopsy samples in which the DUX4-fl mRNA was not detected showed elevation of DUX4 regulated targets (Table 9), indicating that the target mRNA is of significantly higher abundance and perhaps more stable than the DUX4 mRNA, as described in Example 5;

DETAILED DESCRIPTION

Figure 1A:
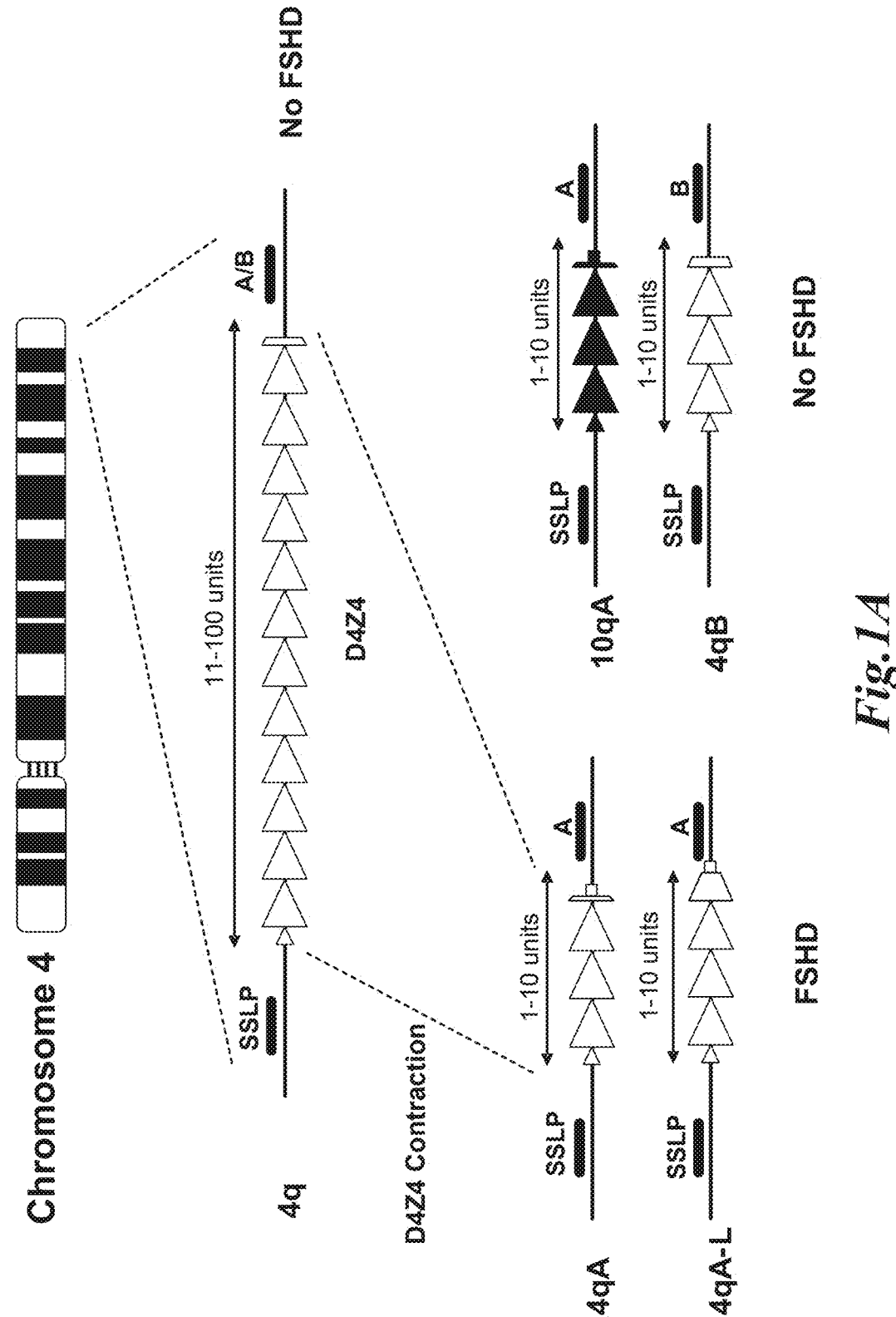
FIG. 1A is a schematic diagram of the minimal genetic requirement for FSHD illustrating the D4Z4 repeat array on chromosome 4 (open triangles) and its homologue on chromosome 10 (closed, filled-in triangles), showing the localization of the simple sequence length polymorphism ("SSLP") and 4qA/4qB polymorphisms that define the genetic background of the D4Z4 repeat, wherein patients with FSHD1 have a D4Z4 repeat array size of 1-10 units on 4qA but not on 4qB or 10q chromosomes, as described in Example 1.

Unless specifically defined herein, all terms used herein have the same meaning as they would to one skilled in the art of the present invention.

The terms "percent identity" or "percent identical," as applied to polypeptide sequences, such as the DUX4-fl polypeptide, set forth as SEQ ID NO:65 (encoded by the DUX4-fl cDNA set forth as SEQ ID NO:66 or SEQ ID NO:67), or a portion thereof, is defined as the percentage of amino acid residues in a candidate protein sequence that are identical with the subject protein sequence (such as the amino acid sequence encoded by SEQ ID NO:65, or a portion thereof comprising at least 10 consecutive amino acid residues) after aligning the candidate and subject sequences to achieve the maximum percent identity. For example, percentage identity between two protein sequences can be determined by pairwise comparison of the two sequences using the bl2seq interface at the Web site of the National Center for Biotechnology Information (NCBI), U.S. National Library of Medicine, 8600 Rockville Pike, Bethesda, Maryland 20894, USA. The bl2seq interface permits sequence alignment using the BLAST tool described by Tatiana, A., et al., "Blast 2 Sequences-A New Tool for Comparing Protein and Nucleotide Sequences," *FEMS Microbiol. Lett.* 174:247-250 (1999). The following alignment parameters are used: Matrix=BLOSUM62; Gap open penalty=11; Gap extension penalty=1; Gap x_dropff=50; Expect=10.0; Word size=3; and Filter=off. In some embodiments, the DUX4-fl variants or DUX4-s variants are naturally occurring variants and comprise at least 90%, or at least 95%, or at least 96%, or at least 97%, or at least 98%, or at least 99% identity to the DUX4-fl polypeptide (SEQ ID NO:65) or to the DUX4-s polypeptide (SEQ ID NO:68).

The terms "percent identity" or "percent identical," as applied to nucleic acid molecules, is the percentage of nucleotides in a candidate nucleic acid sequence that are identical with a subject nucleic acid molecule sequence (such as the nucleic acid molecule sequence set forth in SEQ ID NO:5, SEQ ID NO:66, SEQ ID NO:67 or SEQ ID NO:69, or a portion thereof comprising at least 20 consecutive nucleotides) after aligning the sequences to achieve the maximum percent identity, and not considering any nucleic acid residue substitutions as part of the sequence identity. No gaps are introduced into the candidate nucleic acid sequence in order to achieve the best alignment. Nucleic acid sequence identity can be determined in the following manner. The subject polynucleotide molecule sequence is used to search a nucleic acid sequence database, such as the Gen-Bank database, using the program BLASTN version 2.1 (based on Altschul, et al., *Nucleic Acids Research* 25:3389-3402 (1997)). The program is used in the ungapped mode. Default filtering is used to remove sequence homologies due to regions of low complexity as defined in Wootton, J. C., and S. Federhen, *Methods in Enzymology* 266:554-571 (1996). The default parameters of BLASTN are utilized. In some embodiments, the invention encompasses nucleic acid sequences comprising at least 90%, or at least 95%, or at least 96%, or at least 97%, or at least 98%, or at least 99% identity to the nucleic acid sequences set forth as SEQ ID NO:5, SEQ ID NO:66, SEQ ID NO:67 or SEQ ID NO:69, or a portion thereof comprising at least 20 consecutive nucleotides, including naturally occurring variants thereof.

As used herein, the term "specifically hybridizes" refers to the ability of a nucleic acid probe/primer of the invention to hybridize to at least 10, 12, 15, 20, 25, 30, 35, 40, 45, 50 or 100 consecutive nucleotides of a target gene sequence, or a sequence complementary thereto, or naturally occurring mutants thereof, such that it has less than 15%, preferably less than 10%, and more preferably less than 5% background hybridization to a cellular nucleic acid (e.g., mRNA or genomic DNA) other than the target gene. A variety of hybridization conditions may be used to detect specific hybridization, and the stringency is determined primarily by the wash stage of the hybridization assay. Generally high temperatures and low salt concentrations give high stringency, while low temperatures and high salt concentrations give low stringency. Low stringency hybridization is achieved by washing in, for example, about 2.0×SSC at 50° C., and high stringency is achieved with about 0.2×SSC at 50° C.

As used herein, the term "healthy human subject" refers to an individual who is known not to suffer from FSHD, such knowledge being derived from clinical data on the individual.

As used herein, the term "DUX4-fl induced gene product" refers to a gene product (mRNA or polypeptide) expressed from a gene that is induced at least 2-fold (i.e., at least 3-fold, at least 5-fold, at least 8-fold, at least 10-fold, at least 16-fold or greater) in the presence of DUX4-fl, including genes driven by a promoter that is directly bound by DUX4-fl as well as genes that are induced indirectly by DUX4-fl. In some embodiments, the DUX4-fl induced genes contain one or more DUX4-fl responsive element(s) which are directly bound by DUX4-fl.

As used herein, the term "DUX4-fl" encompasses naturally occurring DUX4-fl protein that is isolated from a human subject (i.e. SEQ ID NO:65, or a naturally occurring variant thereof (i.e., comprising Exons 1-3 of DUX4), encoded by at least one of SEQ ID NO:66 or SEQ ID NO:67, or a naturally occurring variant thereof), as well as cultured cells making DUX4-fl, or made by recombinant DNA technology (e.g., in eukaryotic expression systems (e.g., COS cells), in yeast, mammalian, or in bacterial expression systems). The term "variant of DUX4-fl" refers to a polypeptide comprising at least 90%, or at least 95%, or at least 96%, or at least 97%, or at least 98%, or at least 99% identity to DUX4-fl polypeptide, set forth as SEQ ID NO:65, including naturally occurring variants thereof.

As used herein, the term "DUX-s" encompasses naturally occurring DUX4-s protein that is isolated from a human subject (i.e., SEQ ID NO:68, or a naturally occurring variant thereof, encoded by DUX4-s cDNA (GenBank No. HQ266762) (SEQ ID NO:69). The term "variant of DUX4-s" refers to a polypeptide comprising at least 90%, or at least 95%, or at least 96%, or at least 97%, or at least 98%, or at least 99% identity to DUX4-s polypeptide, set forth as SEQ ID NO:68, including naturally occurring variants thereof.

As used herein, the term "DUX4-fl-derived polynucleotides" refers to the RNA transcribed from DUX4-fl, any cDNA or cRNA produced therefrom, and any nucleic acid derived therefrom, such as synthetic nucleic acid having a sequence derived from the gene corresponding to the DUX4-fl gene.

As used herein, the term "DUX-s-derived polynucleotides" refers to the RNA transcribed from DUX4-s, any cDNA or cRNA produced therefrom, and any nucleic acid derived therefrom, such as synthetic nucleic acid having a sequence derived from the gene corresponding to the DUX4-s gene.

As used herein, the term "biological sample" refers to any type of material of biological origin isolated from a subject, including, for example, DNA, RNA, protein, such as, for example, blood, plasma, serum, fecal matter, urine, semen, bone marrow, bile, spinal fluid, tears, saliva, muscle biopsy, organ tissue or other material of biological origin known by those of ordinary skill in the art.

As used herein, the term "antibody" encompasses antibodies and antibody fragments thereof, derived from any antibody-producing mammal (e.g., mouse, rat, rabbit, and primate including human), that specifically bind to DUX4 polypeptides or portions thereof. Exemplary antibodies include polyclonal, monoclonal and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof.

As used herein, "a mammalian subject" includes all mammals, including without limitation, humans, non-human primates, dogs, cats, horses, sheep, goats, cows, rabbits, pigs and rodents.

As used herein, the term "operatively linked" refers to a juxtaposition wherein the components so described are in a relationship permitting them to function in their intended manner. For example, a promoter sequence is operatively linked to a coding sequence if the promoter sequence promotes transcription of the coding sequence. In another example, a polyadenylation signal sequence is operatively linked to a coding sequence if the polyadenylation signal sequence promotes polyadenylation of the transcribed sequence.

As used herein, the term "vector" is a nucleic acid molecule, preferably self-replicating, which transfers and/or replicates an inserted nucleic acid molecule into and/or between host cells.

As used herein, the term "nucleic acid sequences allowing for autonomous replication" refers to a polynucleotide comprising an origin of replication (generally referred to as an on sequence) which allows for replication of the polynucleotide in the appropriate host cell.

As used herein, the term "nucleic acid sequences allowing for selection" refers to polynucleotides encoding any protein that provides a phenotypic marker, for example, a protein that is necessary for cell growth, or resistance to a toxin, or a protein providing a surface antigen for which specific antibodies/ligands are available.

As used herein, the term "therapeutically effective amount" is an amount of an agent of the invention that alleviates, totally or partially, the pathophysiological effects of FSHD. The amount will depend on, for example, the subject size, gender, magnitude of the associated condition or injury, and the like. For a given subject in need thereof, a therapeutically effective amount can be determined by those of ordinary skill in the art by methods known to those of ordinary skill in the art.

As used herein, the term "treat" and all its forms and tenses refer to both therapeutic treatment and prophylactic or preventative treatment.

As used herein, the amino acid residues are abbreviated as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His; H), isoleucine (Ile;j), leucine (Leu;L), lysine (Lys;K), methionine (Met;M), phenylalanine (Phe;F), proline (Pro; P), serine (Ser;S), threonine (Thr;T), tryptophan (Trp;W), tyrosine (Tyr;Y), and valine (Val;V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further subclassed as follows. By "uncharged hydrophilic" amino acid is meant either Ser, Thr, Asn or Gln. By "acidic" amino acid is meant either Glu or Asp. By "basic" amino acid is meant either Lys, Arg or His.

As used herein the term "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

As used herein, the term "primer" means a polynucleotide which can serve to initiate a nucleic acid chain extension reaction. Typically, primers have a length of 5 to about 50 nucleotides, although primers can be longer than 50 nucleotides.

INTRODUCTION

It has been known for about 20 years that FSHD is caused by the shortening of a macrosatellite repeat array on chromosome 4, but the molecular mechanism leading to muscle pathology has been elusive and controversial. It was recently determined that the DUX4 retrogene contained in these repeats is the likely cause of FSHD, based on genetic studies that identified polymorphisms that create a DUX4 polyadenylation site as necessary for a D4Z4 contraction to cause FSHD (Lemmers et al., *Science* 329:1650-1653 (2010)). It has also been shown that a subset of individuals with clinical features of FSHD do not have contracted D4Z4 repeats on chromosome 4 but do have decreased repressive heterochromatin at the D4Z4 repeats (de Greef et al., *Hum. Mutat.* 30:1449-1459 (2009)) (FSHD2), indicating that loss of repressive chromatin at D4Z4 is the primary cause of FSHD. High sensitivity RT-PCR assays detect DUX4 mRNA specifically in FSHD muscle (Dixit et al., *PNAS* 104:18157-18162 (2007); Snider et al., *PloS Genet* 6:e1001181 (2010)). It has also been shown that DUX4 is normally expressed in germ cells and epigenetically repressed in healthy somatic tissues, but the occasional escape from epigenetic repression of FSHD muscle cells results in bursts of DUX4 in a small fraction of nuclei (Snider et al., *PloS Genet* 6:e1001181

(2010)). Still, a major problem with the hypothesis that DUX4 expression causes FSHD has been the extremely low abundance of the mRNA and inability to reliably detect the protein in FSHD biopsy samples.

Our prior work demonstrated that the low abundance of DUX4 in FSHD muscle cells represents a relatively high expression in a small subset of nuclei (Snider et al., 2010, supra). However, it remained unclear whether the low expression of DUX4 in FSHD muscle has a biological consequence that might drive the pathophysiology of FSHD.

DUX4 belongs to the double-homeobox transcription factor family, and the biological role of this large class of DNA-binding proteins is largely unknown. The coding sequence of the DUX4 retrogene has been conserved in primates (Clapp et al., *Am. J. Hum. Genet.* 81:264-279 (2007)), but whether this retrogene has a normal physiological function is unknown. Previously, we found that DUX4 is normally expressed at high levels in germ cells of human testes and is epigenetically repressed in somatic tissues (Snider et al., *PloS Genet* 6:e1001181 (2010)), whereas the epigenetic repression of the DUX4 locus in somatic tissues is less efficient in both FSHD1 and FSHD2, resulting in DUX4 expression in FSHD muscle cell nuclei. The germline-specific expression pattern of DUX4 is similar to that of other double homeodomain proteins (Booth and Holland Gene 387:7-14 (2007); Wu et al., *Duxbl Dev. Dyn.* 239:927-940 (2010)). The function of this distinct family of DNA-binding proteins is unknown, but their shared tissue expression pattern may indicate a possible role for double homeodomain transcription factors in reproductive biology.

As described in Example 1 herein, the present inventors have surprisingly discovered that FSHD results from the presence of a single nucleotide polymorphism which creates a polyadenylation site for the distal DUX4 transcript, thereby permitting stable transmission of DUX4 when there is also chromatin relaxation of the D4Z4 repeat, thereby identifying a unifying genetic mechanism for FSHD, and providing methods for screening a subject to determine whether the subject is genetically predisposed to develop, or is suffering from FSHD. As described in Example 2 herein, the inventors have further demonstrated that full-length DUX4 (DUX4-fl) mRNA is normally expressed early in development and is suppressed during cellular differentiation, whereas FSHD is associated with the failure to maintain complete suppression of full-length DUX4 expression in differentiated skeletal muscle cells. Occasional escape from repression results in the expression of relatively large amounts of DUX4 protein in a small number of skeletal muscle nuclei. As described herein in Examples 3-5, the present inventors have further discovered that DUX4 regulates the expression of genes involved in germline and early stem cell development. As described in Example 3, through the use of expression arrays and chromatin immunoprecipitation combined with high throughput sequencing, the inventors have identified DUX4 target genes that are bound and regulated by DUX4. As further described herein, DUX4 regulates germline and stem cell genes, which is consistent with its normal expression pattern and indicates a physiological role for DUX4 in germ cell and reproductive biology. As described in Example 4, the inventors identified the consensus binding site for DUX4, a double homeodomain motif, and further demonstrate that DUX4 binds to and activates transcription from endogenous retrotransposon LTRs of the MaLR family. As described in Example 5, the inventors have determined that the transcriptional targets of DUX4 are aberrantly expressed in biopsies of FSHD skeletal muscle but not in control muscle biopsies. Therefore, the low level of DUX4 expression in FSHD is sufficient to effect numerous downstream changes and activate genes of germ cell and early development in postmitotic skeletal muscle. These findings provide direct support for DUX4 as the causal factor for FSHD, and also provide valuable methods and reagents to assess the presence or risk of FSHD, a disease that has been difficult to diagnose with genetic testing.

As described in Example 6, the inventors have discovered that agents that increase chromatin mediated repression, such as agents that inhibit LSD1 activity, are useful to suppress DUX4 and therefore provide therapeutic agents for treating FSHD. Such agents are believed to also have application to other diseases, such as myotonic dystrophy or Huntington's disease, where increasing chromatin mediated suppression of the mutant allele would have therapeutic benefit. As further described in Example 6, the inventors have also discovered that an agent that modifies translation dependent nonsense mediated decay stabilizes DUX4 mRNA levels. Therefore, approaches that block translation dependent nonsense mediated decay can be used to increase DUX4 mRNA and agents that enhance nonsense mediated decay can be used to enhance the degradation of DUX4 mRNA, which provides another therapeutic approach for treating FSHD.

Methods of Screening a Mammalian Subject to Determine if the Subject has a Genetic Predisposition to Develop or is Suffering from FSHD In accordance with the foregoing, in one aspect, the invention provides a method of screening a human subject to determine if said subject has a genetic predisposition to develop, or is suffering from Facioscapulohumeral Dystrophy (FSHD). The method according to this aspect of the invention comprises: (a) providing a biological sample comprising genomic DNA from the subject; and (b) analyzing the portion of the genomic DNA in the sample corresponding to the distal D4Z4-pLAM region on chromosome 4 and determining the presence or absence of a polymorphism resulting in a functional polyadenylation sequence operationally linked to exon 3 of the DUX4 gene, wherein a determination of the absence of a functional polyadenylation sequence operationally linked to exon 3 of the DUX4 gene indicates that the subject does not have a genetic predisposition to develop, and is not suffering from FSHD, and/or wherein a determination of the presence of a functional polyadenylation sequence operationally linked to exon 3 of the DUX4 gene indicates that the subject has a genetic predisposition to develop, or is suffering from Facioscapulohumeral Dystrophy (FSHD).

As described in Examples 1 and 2 herein, the inventors have discovered that FSHD results from the presence of a single polymorphism in the pLAM region creates a canonical polyadenylation site "ATTAAA" (SEQ ID NO:26) for the distal DUX4 transcript encoding DUX4-fl (SEQ ID NO:65), comprising Exons 1-3 of DUX4, thus leading to increased DUX4-fl transcript levels. As described in Example 1 and shown in FIG. 3B, the pLAM region (pLAM refers to the plasmid subclone of lambda phage) is at the 3' end of the D4Z4 repeat region and includes exon 3 of DUX4 and the polyadenylation signal region, which in FSHD permissive (P) chromosome 4 comprises "ATTAAA" (SEQ ID NO:26). As a point of reference with respect to the nucleotide sequence provided in GenBank ref. FJ439133, set forth as SEQ ID NO:5 (see FIG. 3B), the pLAM region spans nt 7903 to 8671 of SEQ ID NO:5, wherein the polyA region (SEQ ID NO:26) is located at nt 8046-8051 of SEQ ID NO:5.

Any method of deterring the presence or absence of the polymorphism in the pLAM region located at nt 8046-8051 of SEQ ID NO:5 in genomic DNA that creates a canonical polyadenylation site "ATTAAA" (SEQ ID NO:26) is useful in the practice of the methods of this aspect of the invention. For example, the methods of this aspect of the invention may be carried out by direct sequencing, sequencing PCR-amplified DNA, single-stranded conformation analysis, allele-specific PCR and restriction length polymorphism. In the practice of this aspect of the invention, any method of obtaining reliable nucleic acid sequence data from a mammalian subject may be utilized. For example, reliable sequence data may be obtained from existing databases of sequence data, or alternatively, a reliable nucleic acid assay that will identify the presence or absence of the polymorphism leading to the sequence "ATTAAA" in the pLAM region may be utilized.

In one embodiment, the presence or absence of the polymorphism in the pLAM region is detected by amplification of a region comprising nt 8046-8051 of SEQ ID NO:5 from genomic DNA following by sequencing of the amplified DNA. For example, in some embodiments, the method comprises contacting genomic DNA isolated from a biological sample with one or more primers that specifically hybridizes to at least a portion of the region corresponding to nucleotides 7516 to 8671 of SEQ ID NO:5, which encompasses a portion of the DUX4 intron 2 and exon 3 to the end of the pLAM sequence, as shown in FIG. 4E. In another embodiment, the method comprises contacting genomic DNA isolated from a biological sample with one or more primers that specifically hybridize to at least a portion of the region corresponding to nucleotides 7903 to 8671 of SEQ ID NO:5, which encompasses the DUX4 exon 3 to the end of the pLAM sequence in FJ439133 and amplifying the region, or a portion thereof comprising nt 8046-8051 of SEQ ID NO:5. A method of amplification which is well known by those of skill in the art is the polymerase chain reaction (PCR) (see *Current Protocols in Molecular Biology*, Ausubel, et al., John Wiley and Sons, 1995).

The PCR process involves the use of pairs of primers, one for each complementary strand of the duplex DNA (wherein the coding strand is referred to as the "sense strand" and its complementary strand is referred to as the "anti-sense strand"), that will hybridize at sites located on either side of a region of interest in a gene. Chain extension polymerization is then carried out in repetitive cycles to increase the number of copies of the region of interest exponentially. Primers useful in the practice of the method of the invention comprise polynucleotides that hybridize to SEQ ID NO:5, or the complement thereof (such as in the nucleic acid region consisting of nt 7516-8671 of SEQ ID NO:5, or nt 7903-8671 of SEQ ID NO:5; or in the region consisting of 8046-8671 of SEQ ID NO:5; or in the region consisting of 8052-8671 of SEQ ID NO:5), which can serve to initiate a chain extension reaction. A "primer pair" is a pair of primers which specifically hybridize to sense (coding) and antisense (non-coding) strands of a duplex polynucleotide to permit amplification of the region lying between the primers of the pair. Primers useful in the practice of this aspect of the invention comprise a polynucleotide of any size that is capable of hybridizing to SEQ ID NO:5 under conditions suitable for PCR amplification and/or sequencing. In a preferred embodiment, primers useful in the practice of this aspect of the invention range from about 5 to 50 bp or longer of continuous sequence chosen from SEQ ID NO:5, or the complement thereof. Example 1 provides a non-limiting example of this embodiment of the method of the invention.

Consequently, the invention also deals with a method for detecting the presence of at least one polymorphism present in nucleic acid comprising a nucleotide sequence comprising nt 7516 to nt 8671 of SEQ ID NO:5, a fragment or a variant thereof and a complementary sequence thereto in a sample, said method comprising the following steps of:

a) bringing into contact a nucleic acid probe or a plurality of nucleic acid probes which can hybridize with a nucleotide sequence included in a nucleic acid comprising at least 95% identity to (or at least 96%, or at least 97%, or at least 98%, or at least 99% identity to) the sequence set forth as nt 7516 to nt 8671 of SEQ ID NO:5, a fragment or a variant thereof and a complementary sequence thereto and the sample to be assayed; and b) detecting the hybrid complex formed between the probe and a nucleic acid in the sample, to determine the presence or absence of the one or more polymorphisms indicative of the risk or presence of FSHD.

In one embodiment of the method of the invention, after amplification, the presence or absence of the polymorphism creating the canonical polyA site "ATTAAA" at the location corresponding to nt 8046-8051 of SEQ ID NO:5 is determined by sequence analysis. In some embodiments, the presence or absence of the nucleotide "T" at position 8048 of SEQ ID NO:5 is determined, wherein the presence of the nucleotide "T" forms a consensus polyA signal site and is indicative of the presence or risk of developing FSHD, and wherein the absence of a consensus polyA site at nt 8046-8051 indicates that the subject is not at risk for developing FSHD.

In some embodiments, the presence or absence of at least one additional polymorphism is determined, wherein the at least one additional polymorphism is present in intron 2 at nucleotide position 7806 ("T"), 7812 ("C"), 7820 ("G") and/or position 7827 ("T") of SEQ ID NO:5, and/or wherein the at least one additional polymorphism is present in Exon 3 at nucleotide position 7903 ("C"), 7946 ("T"), 7968 ("G"), 7987 ("C"), 8054 ("G"), 8079 ("A"), 8101 ("G") of SEQ ID NO:5, wherein the presence of the one or more polymorphisms is indicative of the presence or risk of developing FSHD, and wherein the absence of the one or more additional polymorphisms indicates that the subject is not at risk for developing FHSD, as further described in Example 1.

Methods of DNA sequence analysis are well known in the art. A well known method of sequencing is the "chain termination" method first described by Sanger et al., *PNAS (USA)* 74(12):5463-5467 (1977). Sequencing can be performed using a single primer or a primer pair. Primers are chosen for sequencing based on their proximity to the region of interest.

In accordance with this aspect of the invention, the biological sample may be obtained from a human fetus, or from a human subject suspected of having FSHD, or from a subject with a family member diagnosed with FSHD. In some embodiments, the biological sample is selected from the group consisting of a muscle biopsy, blood, plasma, serum, urine, saliva and tears.

In some embodiments, the biological sample is obtained from a fetus and comprises DNA from fetal cells obtained by amniocentesis performed at about 15 to 18 weeks gestation. In some embodiments, the biological sample is obtained from a fetus and comprises DNA from fetal cells obtained by chorionic villus sampling performed at about 10 to 12 weeks gestation. In some embodiments, the biological sample is obtained from a fetus in a pregnancy known to be at 50% risk for FSHD.

In another aspect, the invention provides a method of screening a human subject to determine if said subject is at risk for developing, or is suffering from Facioscapulohumeral Dystrophy (FSHD). The method according to this aspect of the invention comprises: (a) providing a biological sample from the subject; (b) determining, in the biological sample, the presence or amount of at least one of: (i) DUX4-fl polypeptide, set forth as SEQ ID NO:65, or a naturally occurring variant thereof, or (ii) polyadenylated mRNA encoding DUX4-fl, or nucleic acid molecules derived therefrom; and (c) comparing the presence or amount of DUX4-fl polypeptide or nucleic acid sequence encoding DUX4-fl determined in step (b) with a reference standard or control sample; wherein an increase in the presence or amount of at least one of DUX-fl polypeptide, or nucleic acid sequence encoding DUX4-fl in comparison to the reference standard or control sample is indicative of the presence of FSHD, or increased risk of developing FSHD in the mammalian subject.

In certain embodiments, the method comprises determining, in the biological sample, the presence or amount of a DUX4-fl polypeptide, set forth as SEQ ID NO:65, or a naturally occurring variant thereof. In accordance with such embodiments, a diagnosis or risk assessment of FSHD can be made by analyzing the presence or amount of DUX4-fl polypeptide in a biological sample, by a variety of methods, including methods described herein, and also generally methods comprising spectroscopy, colorimetry, electrophoresis, isoelectric focusing, immunoprecipitations, immunofluorescence, and immunoassays (e.g., David et al., U.S. Pat. No. 4,376,110) such as, for example, immunoblotting (see also *Current Protocols in Molecular Biology*, particularly Chapter 10). Both quantitative and qualitative increases of the DUX4-fl polypeptide are encompassed by the present invention. For example, in a particular embodiment, an antibody capable of binding to the DUX4-fl polypeptide, preferably an antibody with a detectable label or an antibody that can be detected by a secondary antibody, can be used. Antibodies can be polyclonal or monoclonal, and may be generated according to well known methods in the art, for example, monoclonal antibodies can be prepared, for example, using hybridoma technology (*Nature* 256:495 (1975)). An antibody for use in the present invention can be an intact immunoglobulin derived from natural sources or from recombinant sources, and can be immunoreactive portions of an intact immunoglobulin (including, for example, an antibody fragment and a single chain antibody). An antibody is typically a tetramer of immunoglobulin molecules. An antibody of the present invention can be prepared by a variety of methods (Coligan et al., *Current Protocols in Immunology* (1991). For example, cells expressing a polypeptide of the present invention are administered to an animal to induce the production of sera containing polyclonal antibodies. In particular aspects, a preparation of the secreted protein is prepared and purified to render it substantially free of natural contaminants. Such a preparation is then introduced into an animal in order to produce polyclonal antisera of greater specific activity.

In particular embodiments, an antibody for use in the present invention is a monoclonal antibody (mAb), or protein binding fragment thereof. Such monoclonal antibody can be prepared, for example, using hybridoma technology (*Nature* 256:495 (1975); *Eur. J. Immunol.* 6:511 (1976); *Eur. J. Immunol.* 6:292 (1976); Monoclonal Antibodies and T-Cell Hybridomas, Elsevier, N.Y., pp. 563-681 (1981)). In general, such methods involve immunizing an animal (e.g., a mouse) with polypeptide or with a secreted polypeptide-expressing cell. The splenocytes of, for example, such mice following the methods described above are extracted and fused with a suitable myeloma cell-line. The hybridoma cells obtained through such a selection are then assayed to identify clones that secrete antibodies capable of binding the DUX4-fl polypeptide. An intact antibody or a fragment thereof (e.g., Fab or F (ab') 2) can be used. The term "labeled" with regard to the probe or antibody is intended to encompass direct labeling of the antibody by coupling (i.e., physically linking) a detectable substance to the antibody, as well as indirect labeling of the antibody by reactivity with another reagent that is directly labeled or indirectly labeled. Examples of direct and indirect labels include, for example, a fluorescent moiety, an enzyme, a chromophoric moiety, a radioactive atom, a biotin tag, or a colorimetric tag. Some examples of a fluorescent moiety include rhodamine, fluorescein., etc. Some examples of enzymes include, horseradish peroxidase, glucose oxidase, glucose-6-phosphate dehydrogenase, alkaline phosphatase, beta-galactosidase, urease, luciferase, etc. Some examples of radioactive atoms are $^{32}$P, $^{125}$I, $^{3}$H, etc.

In some embodiments, the method comprises contacting the biological sample, or a subfraction thereof, with a cell comprising an expression cassette comprising a promoter operationally linked to a reporter gene or selectable marker, wherein the promoter contains at least one DUX-4 responsive element comprising the consensus sequence "TAAYB-BAATCA" (SEQ ID NO:89), and assaying the cell for expression of the reporter gene, or selecting for growth under conditions requiring expression of the selectable marker, wherein expression of the reporter gene, or growth under selection, is indicative of the presence of DUX4-fl protein in the biological test sample.

In some embodiments, the method comprises determining the presence or amount of polyadenylated mRNA encoding DUX4-fl, or nucleic acid molecules derived therefrom in a biological sample. In some embodiments, the method comprises isolating polyadenylated mRNA prior to analysis for the presence of DUX4-fl, or nucleic acid molecules derived therefrom. In some embodiments, the method comprises extracting RNA from the biological sample and preparing cDNA using oligo dT primers to select for polyA+ transcripts, as described in Example 2.

In some embodiments, the method comprises performing quantitative RT-PCR on the biological sample with reagents that specifically hybridize to the mRNA expressed from cDNA encoding DUX4-fl polypeptide. In some embodiments, the method comprises contacting the sample with at least one or more primers or probes that distinguish between DUX4-s and DUX4-fl. In some embodiments, the method comprises contacting the biological test sample with a nucleic acid probe or primer that specifically hybridizes to at least a portion of nucleic acid sequence comprising Exon 3.

In some embodiments, the biological test sample is obtained from a mammalian living fetus, such as a living human fetus. In some embodiments, the biological test sample is obtained from a subject suspected of having FSHD. In some embodiments, the biological test sample is obtained from a subject with a family member diagnosed with FSHD. In some embodiments, the biological test sample is obtained from a subject known to have FSHD, for example, in an embodiment in which the method is used for monitoring disease activity or progression, or response to therapy in a clinical trial or during therapeutic intervention.

In some embodiments, the biological test sample is selected from the group consisting of a muscle biopsy, blood, plasma, serum, urine, saliva, tears, In accordance with the practice of various embodiments of the invention, polynucleotide molecules are extracted from a biological sample taken from a mammalian subject. The sample may be collected in any clinically acceptable manner, but must be collected such that polynucleotides encoding DUX4-fl (i.e., RNA) are preserved and/or DUX4-fl polypeptides are preserved. In some embodiments, mRNA or nucleic acids derived therefrom (i.e., cDNA or amplified DNA) are preferably labeled distinguishably from standard or control polynucleotide molecules, and both are simultaneously or independently hybridized to a nucleic acid array, such as a microarray comprising some or all of the markers or marker sets or subsets described above. Alternatively, mRNA or nucleic acids derived therefrom may be labeled with the same label as the standard or control polynucleotide molecules, wherein the intensity of hybridization of each at a particular probe is compared. Methods for preparing total and poly(A)+RNA are well known and are described generally in Sambrook, et al., *Molecular Cloning: A Laboratory Manual* (2nd ed.), Vols. 1-3, Cold Spring Harbor Laboratory, Cold Spring Harbor, N.Y. (1989) and Ausubel, et al., *Current Protocols in Molecular Biology*, Vol. 2, Current Protocols Publishing, New York (1994).

In accordance with the methods of the invention, the presence or amount of the DUX4-fl polypeptide, polyadenylated mRNA encoding DUX4-fl, or nucleic acid molecules derived therefrom in the test biological sample is compared with a reference standard or control sample, wherein an increase in the presence or amount of the FSHD biomarker (i.e., DUX4-fl polypeptide, polyadenylated mRNA encoding DUX4-fl or nucleic acid molecules derived therefrom, such as cDNA) determined in the test sample in comparison to the reference standard or control sample is indicative of the presence of FSHD, or increased risk of developing FSHD, or predict disease onset in the mammalian subject. In some embodiments, an increase in the presence or amount of the FSHD biomarker provides a clinical diagnosis of FSHD. In some embodiments, an increase in the presence or amount of the FSHD biomarker is indicative of disease progression. In some embodiments, a decrease in the amount of the FSHD biomarker is indicative of improvement of pathology in response to a therapeutic agent.

In one embodiment, the reference standard is the level of the one or more FSHD biomarkers measured in one or more biological sample(s) obtained from healthy control subjects known not to have FSHD. One or more, including 2, 3, 4, 5, 10 or more healthy individuals can be used to generate a reference standard for use in the methods. When multiple individuals are used to generate a reference standard for a particular FSHD biomarker, the biomarker levels determined from the individuals can be averaged to create a single reference standard value. In another embodiment, the reference standard is an established threshold level. In one embodiment, the method comprises the use of a control sample which may be obtained from a healthy subject.

In some embodiments, a determination is made that the mammalian subject from which the test sample was obtained has FSHD, or has an increased risk of developing FSDH, when the FSDH biomarker is found to be expressed at an increased level of at least 2-fold or greater (i.e., at least 3-fold, at least 4-fold, at least 5-fold, at least 8-fold, at least 10-fold, at least 12-fold, at least 16-fold or greater) in the test biological sample (e.g., skeletal muscle) as compared to the control or reference standard (e.g., normal skeletal muscle).

In another aspect, the invention provides one or more isolated polynucleotide probes or primers for use in a screening assay for the presence or risk of FSHD, wherein the polynucleotide probe or primer has a length of from at least 10 nucleotides to 200 nucleotides and specifically hybridizes to a nucleic acid molecule having a sequence at least 95% identical (or at least 96%, or at least 97%, or at least 98%, or at least 99% identical) to the sequence set forth in nucleotides 7516 to 8671 of SEQ ID NO:5, or the complement thereof, which encompasses a portion of the DUX4 intron 2 and DUX4 exon 3 to the end of the pLAM sequence in FJ439133.

In some embodiments, the polynucleotide probe or primer has a length of from at least 10 nucleotides to 200 nucleotides and specifically hybridizes to a nucleic acid molecule having a sequence at least 95% identical (or at least 96%, or at least 97%, or at least 98%, or at least 99% identical) to the sequence set forth in nucleotides 7903 to 8671 of SEQ ID NO:5 or the complement thereof, which encompasses Exon 3 to the end of the pLAM sequence in FJ439133.

In some embodiments, the polynucleotide probe or primer has a length of from at least 10 nucleotides to 200 nucleotides and specifically hybridizes to a nucleic acid molecule having a sequence at least 95% identical (or at least 96%, or at least 97%, or at least 98%, or at least 99% identical) to the sequence set forth in nucleotides 8046 to 8671 of SEQ ID NO:5 or the complement thereof, which encompasses the polyA signal at the 3' end of the DUX4 exon 3 gene to the end of the pLAM sequence in FJ439133.

In some embodiments, the isolated polynucleotide probe or primer has a length of from at least 10 nucleotides to 200 nucleotides and specifically hybridizes to a nucleic acid molecule having a sequence at least 95% identical (or at least 96%, or at least 97%, or at least 98%, or at least 99% identical) to the sequence set forth in nucleotides 8052 to 8671 of SEQ ID NO:5, or the complement thereof, which encompasses the pLAM sequence 3' of the polyA signal to the end of the pLAM sequence in FJ439133.

In some embodiments, the isolated polynucleotide probe or primer is selected from the group consisting of: SEQ ID NO:7; SEQ ID NO:11; SEQ ID NO:21; and SEQ ID NO:22.

A probe or a primer according to the invention has between 10 and 200 nucleotides in length, or is specified to be at least 12, 15, 18, 20, 25, 35, 40, 50, 60, 70, 80, 100, 150 or 200 nucleotides in length. More particularly, the length of these probes and primers can range from 10, 15, 20, or 30 to 100 nucleotides, preferably from 10 to 50, more preferably from 15 to 30 nucleotides. Shorter probes and primers tend to lack specificity for a target nucleic acid sequence and generally require cooler temperatures to form sufficiently stable hybrid complexes with the template. Longer probes and primers are expensive to produce and can sometimes self-hybridize to form hairpin structures. The appropriate length for primers and probes under a particular set of assay conditions may be empirically determined by one of skill in the art.

The primers and probes can be prepared by any suitable method, including, for example, cloning and restriction of appropriate sequences and direct chemical synthesis by a method such as the phosphodiester method of Narang et al. (1979), the phosphodiester method of Brown et al. (1979), the diethylphosphoramidite method of Beaucage et al. (1981) and the solid support method described in EP 0 707 592. The disclosures of all these documents are incorporated herein by reference.

Any of the polynucleotides of the present invention can be labeled, if desired, by incorporating a label detectable by spectroscopic, photochemical, biochemical, immunochemical, or chemical means. For example, useful labels include radioactive substances (32P, 35S, 3H, 125I), fluorescent dyes (5-bromodesoxyuridin, fluorescein, acetylaminofluorene, digoxigenin) or biotin. Preferably, polynucleotides are labeled at their 3' and 5' ends. Examples of non-radioactive labeling of nucleic acid fragments are described in the French patent No FR-7810975 or by Urdea et al (1988) or Sanchez-Pescador et al (1988).

A label can also be used to capture the primer, so as to facilitate the immobilization of either the primer or a primer extension product, such as amplified DNA, on a solid support. A capture label is attached to the primers or probes and can be a specific binding member which forms a binding pair with the solid's phase reagent's specific binding member (e.g. biotin and streptavidin). Therefore depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA Labeling techniques are well known to the skilled technician.

Any of the polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes and others. The solid support is not critical and can be selected by one skilled in the art. Thus, latex particles, microparticles, magnetic or nonmagnetic beads, membranes, plastic tubes, walls of microtiter wells, glass or silicon chips, sheep (or other suitable animal's) red blood cells and duracytes are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent.

In another aspect, the invention provides a kit for determining susceptibility or presence of FSHD in a mammalian subject based on the detection of a polymorphism in the polyA signal adjacent exon 3 of DUX4 in chromosome 4, said kit comprising one or more isolated polynucleotide probe or primer molecules having a length of from at least 10 nucleotides to 200 nucleotides and capable of specifically hybridizing to a nucleic acid molecule having a sequence at least 95% identical to the sequence set forth in nucleotides 7903 to 8671 of SEQ ID NO:5, or the complement thereof, which encompasses the DUX4 exon 3 to the end of the pLAM sequence in FJ439133.

Reagents that are suited for obtaining a sample from an individual may be included in a kit of the invention, such as a syringe, collection vial, needle, or other instruments necessary to take a biopsy or other relevant sample. The kits may comprise a suitably aliquoted composition and/or additional agent compositions of the present invention, whether labeled or unlabeled, as may be used to prepare a standard curve for a detection assay. The components of the kit may be packaged in combination or alone in the same or in separate containers, depending on, for example, cross-reactivity or stability, and can also be supplied in solid, liquid, lyophilized, or other applicable form. The container means of the kits will generally include, for example, at least one vial, test tube, flask, bottle, syringe or other container means, into which a component may be placed, and preferably, suitably aliquoted. Where there is more than one component in the kit, the kit can contain a second, third or other additional container into which the additional components may be contained. However, various combinations of components may be comprised in a vial. The kits of the present invention also will typically include a means for containing the composition, additional agent and any other reagent containers in close confinement for commercial sale. Such containers may include, for example, injection or blow molded plastic containers into which the desired vials are retained.

Methods of Treating a Mammalian Subject Suffering from, or at Risk for Developing FSHD In another aspect, the invention provides a method of treating a mammalian subject suffering from, or at risk for developing FSHD. The method according to this aspect of the invention comprises administering to the mammalian subject an agent capable of inhibiting or suppressing the level of DUX4-fl expression, or an agent capable of inhibiting DUX4-fl mediated transcription activation in a population of cells in the mammalian subject.

As used herein, the term "an agent capable of inhibiting or suppressing the level of DUX4-fl mediated transcription activation" refers to any agent that binds to or interacts with DUX4-fl or competes with DUX4-fl for the DUX4 binding site and effectively inhibits DUX4—dependent transcription activation, including anti-DUX4 antibodies and DUX4 binding fragments thereof, natural and synthetic peptides, small molecules, expression inhibitors and isolated natural inhibitors. DUX4-fl inhibitory agents useful in the method of the invention may reduce DUX4-fl-dependent transcription activation by greater than 20%, such as greater than 50%, such as greater than 90%. In one embodiment, the DUX4-fl inhibitory agent reduces DUX4-fl-dependent transcription activation by greater than 90% (i.e., resulting in DUX4-fl dependent transcription activation of only 10% or less).

As used herein, the term "an agent capable of inhibiting or suppressing the level of DUX4-fl expression" refers to any agent that effectively inhibits DUX4-fl expression (mRNA or protein expression). In some embodiments, the agent inhibits DUX4 gene expression by binding to a nucleic acid sequence encoding DUX4. In some embodiments, the agent is capable of increasing chromatin mediated repression, thereby decreasing and/or completely suppressing DUX4-fl expression. In some embodiments, the agent enhances nonsense mediated decay and thereby enhances the degradation of DUX4 mRNA.

In some embodiments of this aspect of the invention, the method comprises administering a therapeutic agent that is capable of inhibiting or suppressing the level of endogenous DUX4-fl. In some embodiments, the agent is capable of increasing chromatin mediated repression, such as an agent that inhibits histone demethylase LSD1 activity (e.g., pargline). In some embodiments, the agent enhances nonsense mediated decay and thereby enhances the degradation of DUX4 mRNA.

In some embodiments, the agent is capable of inhibiting DUX4-fl mediated transcriptional activation is an agent that interferes with DUX4-fl binding to one or more DUX4-fl consensus binding site(s) "TAAYBBAATCA" that is present upstream of one or more DUX4-fl inducible genes. An exemplary agent for use in accordance with this embodiment is a DUX4-s polypeptide, or a nucleic acid encoding DUX4-s polypeptide. In some embodiments, the invention provides a pharmaceutical composition comprising a DUX4-s polypeptide or a nucleic acid encoding a DUX4-s polypeptide and a pharmaceutically acceptable carrier.

In some embodiments of this aspect of the invention, the DUX4-fl inhibitory agent comprises isolated DUX4-fl peptide inhibitors, including isolated natural peptide inhibitors and synthetic peptide inhibitors that inhibit the DUX4-fl dependent transcription activation. As used herein, the term "isolated DUX4-fl peptide inhibitors" refers to peptides that bind to or interact with DUX4-fl or that bind to or interact with the DUX4-fl binding site "TAAYBBAATCA" (SEQ ID NO:89) and inhibit DUX4-fl-dependent transcription activation that are substantially pure and are essentially free of other substances with which they may be found in nature to an extent practical and appropriate for their intended use.

In some embodiments, DUX4-fl inhibitory agents are small molecule inhibitors including natural and synthetic substances that have a low molecular weight, such as for example, peptides, peptidomimetics and nonpeptide inhibitors (including oligonucleotides and organic compounds).

In another embodiment of this aspect of the invention, the DUX4-fl inhibitory agent is a DUX4-fl expression inhibitor capable of inhibiting DUX4-fl expression (mRNA or protein). In the practice of this aspect of the invention, representative DUX4-fl expression inhibitors include DUX4-fl antisense nucleic acid molecules (such as antisense mRNA, antisense DNA or antisense oligonucleotides), DUX4-fl ribozymes and DUX4-fl RNAi molecules.

Anti-sense RNA and DNA molecules act to directly block the translation of DUX40fl mRNA by hybridizing to DUX4 mRNA and preventing translation of DUX4-fl protein. An antisense nucleic acid molecule may be constructed in a number of different ways provided that it is capable of interfering with the expression of DUX4-fl. For example, an antisense nucleic acid molecule can be constructed by inverting the coding region (or a portion thereof) of DUX4-fl cDNA (SEQ ID NO:66 or SEQ ID NO:67) relative to its normal orientation for transcription to allow for the transcription of its complement.

The antisense nucleic acid molecule is usually substantially identical to at least a portion of the target gene or genes. The nucleic acid, however, need not be perfectly identical to inhibit expression. Generally, higher homology can be used to compensate for the use of a shorter antisense nucleic acid molecule. The minimal percent identity is typically greater than about 65%, but a higher percent identity may exert a more effective repression of expression of the endogenous sequence. Substantially greater percent identity of more than about 80% typically is preferred, though about 95% to absolute identity is typically most preferred.

The antisense nucleic acid molecule need not have the same intron or exon pattern as the target gene, and non-coding segments of the target gene may be equally effective in achieving antisense suppression of target gene expression as coding segments. A DNA sequence of at least about 8 or so nucleotides may be used as the antisense nucleic acid molecule, although a longer sequence is preferable. In the present invention, a representative example of a useful inhibitory agent of DUX4-fl is an antisense DUX4-fl nucleic acid molecule which is at least ninety percent identical to the complement of the DUX4-fl cDNA consisting of the nucleic acid sequence set forth in SEQ ID NO:66 or SEQ ID NO:67.

Another alternative to antisense is the use of "RNA interference" (RNAi). Double-stranded RNAs (dsRNAs) can provoke gene silencing in mammals in vivo. The natural function of RNAi and co-suppression appears to be protection of the genome against invasion by mobile genetic elements such as retrotransposons and viruses which produce aberrant RNA or dsRNA in the host cell when they become active (see, e.g., Jensen, J., et al., Nat. Genet. 21:209-12, 1999). The double-stranded RNA molecule may be prepared by synthesizing two RNA strands capable of forming a double-stranded RNA molecule, each having a length from about 19 to 25 (e.g., 19-23 nucleotides). For example, a dsRNA molecule useful in the methods of the invention may comprise the RNA corresponding to a sequence and its complement set forth as SEQ ID NO:66 or SEQ ID NO:67. Preferably, at least one strand of RNA has a 3' overhang from 1-5 nucleotides. The synthesized RNA strands are combined under conditions that form a double-stranded molecule. The RNA sequence may comprise at least an 8 nucleotide portion of SEQ ID NO:66 or SEQ ID NO:67 with a total length of 25 nucleotides or less. The design of siRNA sequences for a given target is within the ordinary skill of one in the art. Commercial services are available that design siRNA sequence and guarantee at least 70% knockdown of expression (Qiagen, Valencia, CA).

Anti-sense RNA and DNA, ribozymes and RNAi molecules useful in the methods of the invention may be prepared by any method known in the art for the synthesis of DNA and RNA molecules. These include techniques for chemically synthesizing oligodeoxyribonucleotides and oligoribonucleotides well known in the art, such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

In general, the agents for use in the methods of the present invention are suitably contained in a pharmaceutically acceptable carrier. The carrier is non-toxic, biocompatible and is selected so as not to detrimentally affect the biological activity of the agent. The agents of the invention may be formulated into preparations for local delivery (i.e. to a specific location of the body, such as skeletal muscle or other tissue) or systemic delivery, in solid, semi-solid, gel, liquid or gaseous forms such as tablets, capsules, powders, granules, ointments, solutions, depositories, inhalants and injections allowing for oral, parenteral or surgical administration. The invention also contemplates local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose, any biocompatible oil may be employed including synthetic mono- or diglycerides. In addition, fatty acids, such as oleic acid, find use in the preparation of injectables.

The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting example, microparticles, microspheres, nanospheres or nanoparticles composed of proteins, liposomes, carbohydrates, synthetic organic compounds, inorganic compounds, polymeric or copolymeric hydrogels, and polymeric micelles.

The following examples merely illustrate the best mode now contemplated for practicing the invention, but should not be construed to limit the invention.

Example 1

This Example describes a study that identified that FSHD results from the presence of a single nucleotide polymorphism which creates a polyadenylation site for the distal DUX4 transcript thereby permitting stable transmission of DUX4 when there is also chromatin relaxation of the D4Z4 repeat, thereby identifying a unifying genetic mechanism for FSHD.

Methods and Materials

Control Individuals and Patients with FSHD

Proximal and distal region sequences from the D4Z4 repeat array were generated from control individuals and patients with FSHD that were selected from our collection of >3000 individuals and from Hapmap samples (R. J. Lemmers et al., *Am J. Hum Genet* 81:884-894 (2007); R. J. Lemmers et al., *Am J. Hum Genet* 86:364-377 (2010)). The FSHD-affected families (F1-F8) were ascertained via Neuromuscular Centers worldwide. All individuals were genotyped in detail by pulsed field gel electrophoresis (PFGE) and all markers in the D4Z4 locus that have been described previously. Blood from all individuals was collected after informed consent was obtained.

Somatic Cell Hybrids and DNA Clones

Some sequences of the D4Z4 locus were generated from monoallelic sources. FSHD chromosomes sequences were obtained from monochromosomal rodent somatic cell hybrids HHW1494 (4A161) and SU10 (4A161) (gift from S. Winokur, Irvine, CA) and phage clones λ42 (4A161), λ68 (4A161L), and λ260201 (4A161) (J. C. van Deutekom et al., *Hum Mol Genet* 2:2037-2042 (1993)). As chromosome 4qB sources, we used the monochromosomal rodent somatic cell hybrids GM11687 (4B168) (Coriell Institute for Medical Research, Camden, NJ), 4L-10 (4B163) (gift from E. Stanbridge, Irvine, CA), and HHW416 (4B163) (gift from M. Altherr, Los Alamos, NM). Chromosome 10A166 sequences were generated from cosmid C85 (J. C. van Deutekom et al., *Hum Mol Genet* 2:2037-2042 (1993)) and the monochromosomal rodent somatic cell hybrids 726-8a (U.K. Human Genome Mapping Project Resource Center) and GM11688 (Coriell Cell Repositories).

Clinical Description FSHD Families

F1

The proband presented at age 28 with right arm weakness. He was, however, aware of shoulder weakness since age 18. Examination showed mild asymmetric facial weakness, asymmetrical shoulder muscle weakness and atrophy and abdominal muscle weakness. His 62-year-old father noted shoulder muscle weakness since age 16, and pelvic girdle weakness since age 30. He was diagnosed as FSHD on clinical grounds. His parents, four brothers, two sisters and one daughter were reportedly unaffected.

Examination showed mild asymmetric shoulder girdle weakness (Shoulder abduction: Right 110°, Left 80°), severe pelvic girdle and hamstrings weakness, and Right tibialis anterior paralysis and Left paresis.

F2

The proband, a 61-year-old woman, noticed right foot dorsiflexor weakness at age 17. At age of 20, she noticed difficulty lifting her arms above shoulder level. Presently, she can walk small distances but is otherwise wheelchair dependent. Examination shows very mild orbicularis oculi weakness and moderate orbicularis oris weakness. She has bilateral scapular winging with severe biceps and triceps weakness, moderate wrist extension weakness, moderate to severe hip girdle weakness, and bilateral foot drop.

Her 32-year-old son had onset of foot dorsiflexor weakness at age 18 followed by shoulder girdle weakness at age 20. Examination showed moderate facial weakness and bilateral scapular winging. He had mild triceps and finger extension weakness in the upper extremities and normal lower extremity strength except asymmetric tibialis anterior weakness.

F3

The proband, a 47-year-old woman, developed progressive facial and shoulder girdle muscle weakness starting at age 15. At age 45, she noticed difficulty in walking and climbing stairs and was diagnosed clinically with FSHD. Her 26-year-old older daughter had asymmetric facial and shoulder girdle involvement (R. arm abduction 80°, L. arm 70°) and right foot dorsiflexor weakness highly evocative of FSHD.

F4

The proband was noted to have dysarthria and facial weakness at age two. Examination at age 5 showed severe facial weakness, scapular winging, as well as abdominal, quadriceps and hamstring weakness.

His father, aged 37, has had right facial weakness since childhood. Examination showed facial weakness as well as right scapular winging with shoulder girdle weakness, asymmetric pectoralis major atrophy, and abdominal muscle weakness.

F5

This family is an example of a FSHD family in which the deletion of D4Z4 extends proximally and was described in Lemmers et al., *Hum Mol Genet* 7:1207-1214 (1998).

F6

Family F6 consists of a deceased affected father who has six children, of whom four sons are affected and have been examined. Two children and fourteen grandchildren have not been examined. The proband (66 years old) reported a drop-foot at the age of 18 and was noted to have facial and shoulder muscle weakness on clinical examination. He became aware of significant upper-arm weakness at the age of 45 and pelvic girdle weakness at 50 years, and noticed a weak handgrip at 62 years when he started wearing foot-ankle orthoses. Although the four brothers differed in age by 8 years, they all had a comparable clinical condition on a recent physical examination.

F7

Family F7 has been reported before as Rf207 in Lemmers et al., *Am J. Hum Genet* 75:1124-1130 (2004). The proband had mild facial weakness, moderate shoulder girdle weakness, and mild foot-extensor weakness when he was examined for the first time at the age of 49. Her eldest daughter had mild facial, shoulder, and foot-extensor weakness in addition to Klippel-Trenaunay-Weber syndrome. Her sister had mild facial and shoulder girdle weakness. The proband's brother (55 years) complained of inability to run, what he related to low back pain. His oldest son (29 years) had mild shoulder weakness, another son (321; 20 years) had asymmetrical facial weakness, and one daughter (324; 18 years) had mild facial and shoulder-girdle weakness.

F8

The proband, aged 64, had symptom onset at age 25 with proximal leg weakness. Exam shows facial weakness, scapular winging, mild biceps and hip flexion weakness, and asymmetric tibialis anterior weakness. Her twin daughters have FSHD. In one, symptom onset was at age 30 with difficulty raising her right arm. Examination at age 45 shows facial weakness, scapular winging, severe biceps weakness and asymmetric wrist extension weakness, and mild quadriceps tibialis anterior weakness as well as abdominal muscle weakness. Her twin sister dates her symptoms to age 18 with difficulty lifting her arm. Exam at age 45 shows facial weakness, scapular winging, severe biceps weakness, mild triceps weakness, mild hip girdle, tibialis anterior and abdominal weakness.

Detailed Genotyping D4Z4 Locus

For the genotyping, high quality DNA was isolated from peripheral blood lymphocytes. The genotyping (haplotype differentiation) was based on the chromosomal location (chromosome 4q or 10q), the SSLP variation, the array size and composition (sensitivity to restriction enzymes BlnI and XapI) of the D4Z4 repeat array and on the distal variation A and B, as described in Lemmers et al., *Am J Hum Genet* 81:884-894 (2007)). Briefly described, restriction enzyme digested genomic DNA was separated by PFGE and after Southern blotting analyzed with different radioactive labeled DNA probes. The SSLP size variation was determined by PCR. This genotyping method has been described previously and can by found on the Fields Center Website (www.fieldscenter.org).

Sequence Analysis of the Proximal D4Z4 Sequence (D4F104S1-D4Z4 Region) and Distal D4Z4 Sequence (D4Z4 and pLAM or D4Z4 and 4qB)

For PCR analysis, high-quality plug DNA was prepared as described for PFGE analysis in Lemmers et al., *Am. J. Hum Genet* 81:884-894 (2007), incorporated herein by reference. After the DNA was prepared, prior to PCR analysis, it was equilibrated in TE$^{-4}$, dissolved in TE$^{-4}$ to a final DNA concentration of 25 ng/µl.

All primers for proximal and distal D4Z4 PCR were designed using Primer3 software. The sequence of the D4F104S1-D4Z4 region (FIG. 1B; A, A-L and B chromosomes, nucleotides 4309-7854 of the sequence set forth as GenBank accession number AF117653 (SEQ ID NO:1) of different chromosomes was determined with either forward primer 5'-CTG GGA GTT GGG CAT TTT CTc ATT AGC-3' (SEQ ID NO:2) or forward primer 5'-CTG GGA GTT GGG CAT TTT CTg ATT AGC-3' (SEQ ID NO:3) in combination with reverse primer 5'-GGC GGT CTG GGA TCC GGT GA-3' (SEQ ID NO:4).

To enable a PCR reaction that was specifically amplifying a single chromosome 4q, we selected individuals that carry the chromosome of interest in combination with a hybrid chromosome 4. Hybrid chromosomes 4 (with normal-sized D4Z4 array) can be found in about 10% of the population. In these individuals, all undesirable chromosomes (homologous 4q and 10q) can be eliminated from PCR amplification by a preceding BlnI digestion in which the BlnI restriction site is exclusively absent from the chromosome of interest.

In addition, some D4F104S1-D4Z4 sequences were determined in the somatic cell hybrids and DNA clones described above.

The PCR reaction was performed on 100 ng of genomic DNA with 1.5 µl GC-dNTPs (0.5 mM dATP, 0.5 mM dCTP, 0.5 mM dTTP, 0.3 mM dGTP and 0.2 mM 7-deaza-dGTP), 0.4 U of Phusion F530-L DNA polymerase and supplemented GC buffer, in a total volume of 25 µl. The PCR conditions consisted of an initial denaturation step at 98° C. for 3 min., followed by 39 cycles of denaturation at 98° C. for 25 s, annealing at 68° C. for 20 s, and extension at 72° C. for 3 min. The final extension time was 6 min. at 72° C. To determine the sequence consensus for haplotypes 4A161, 4A161L, 4B163, 4B168 and 10A166, at least 3 independent chromosomes of each haplotype were sequenced.

To obtain D4Z4-pLAM sequences for different 4q and 10q haplotypes, we analyzed individuals that carry different combinations of A and B chromosomes. For example, we selected an individual with one 4qA, one 4qB and two BlnI sensitive 10q chromosomes and used A-specific reverse primers in combination a BlnI digestion prior to the PCR amplification to specifically amplify the 4qA chromosome. The same primers were used to amplify different chromosome 10 haplotypes in individuals with two 4qB chromosomes.

To amplify the D4Z4-pLAM sequence of 4qA and 10q chromosomes (FIG. 1B, nucleotides 4580-8195 in GenBank accession number FJ439133, set forth as SEQ ID NO:5), we used forward primer 5'-AGC GTT CCA GGC GGG AGG GAA G-3' (SEQ ID NO:6) and either reverse primer 5'-CAG GGG ATA TTG TGA CAT ATC TCT GCA CTC ATC-3' (SEQ ID NO:7) (for 4qA and 10A176 chromosomes), or reverse primer 5'-TGG AGT TCT GAA ACA CAT CTG CAC TGA-3' (SEQ ID NO:8) (for 10A166 chromosomes).

Figure 1B:
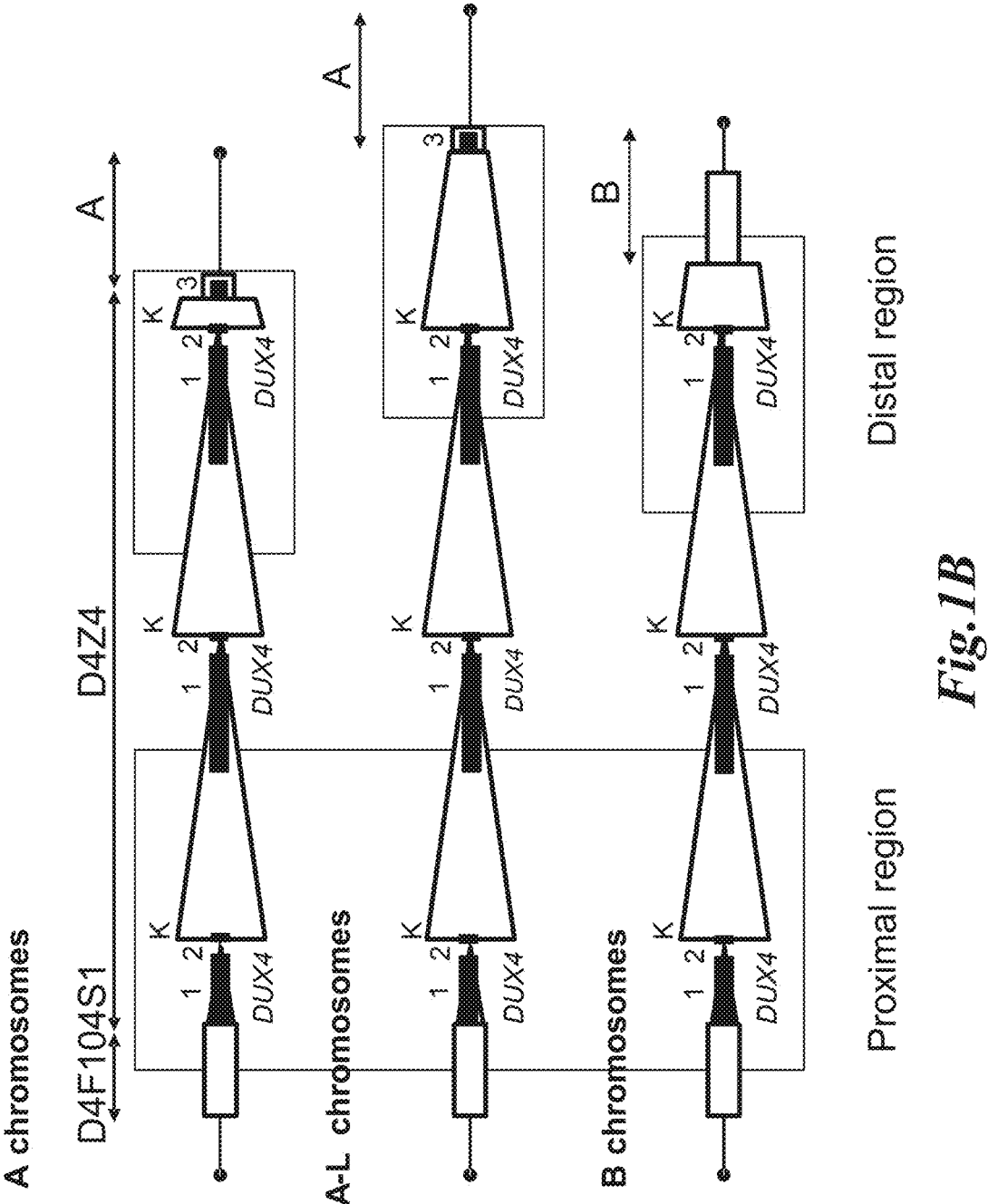
FIG. 1B is a schematic diagram of the D4Z4 repeat and flanking sequences on A chromosomes, A-L chromosomes (with an extended distal D4Z4 repeat unit), and B chromosomes, wherein each D4Z4 unit is defined by the KpnI restriction site (K). The proximal and distal regions that were sequenced are indicated, and the exons of DUX4 are indicated as grey boxes numbered 1-3, as described in Example 1.

For the amplification of 4qB chromosomes (FIG. 1B, nucleotides 4988-7695 in GenBank accession number FJ439133 (SEQ ID NO:5), combined with nucleotides 0-1047 in AF017466, set forth as SEQ ID NO:9), we used forward primer 5'-CGC GGT TCA CAG ACC GCA CAT C-3' (SEQ ID NO: 10) and a 4qB specific reverse primer 5'-GCC CGG CAC ACA TGT TTG TCT CCT T-3' (SEQ ID NO: 11).

Finally, the D4Z4-pLAM sequences from 4A161L chromosomes and from the complex F4 chromosome (FIG. 1B, nucleotides 6188-7506 in Genbank accession number FJ439133, (SEQ ID NO:5) combined with nucleotides 0-2221 in U74497, set forth as SEQ ID NO:12), were determined with forward primer 5'-AGC CCA GGG TCC AGA TTT GGT TTC AG-3' (SEQ ID NO:13) and reverse primer 5'-CAG GGG ATA TTG TGA CAT ATC TCT GCA CTC ATC-3' (SEQ ID NO:7).

All PCR reactions were performed on 100 ng of genomic DNA, in a solution containing 1.5 µl GC-dNTPs (0.5 mM dATP, 0.5 mM dCTP, 0.5 mM dTTP, 0.3 mM dGTP and 0.2 mM 7-deaza-dGTP, 2.5 U of LA-Taq DNA polymerase and supplemented with 2×GC buffer (TAKARA), with a total volume of 25 µl. The PCR conditions consisted of an initial denaturation step at 94° C. for 1 min., followed by 34 cycles of denaturation at 94° C. for 30 s, annealing at 68° C. for 30 s, and extension at 72° C. for 3 min. The final extension time was 10 min. at 72° C. To determine the sequence consensus for haplotypes 4A161, 4A161L, 4B163, 4B168, 10A166 and 10A176T, at least 3 independent chromosomes of each haplotype were sequenced.

Site Directed Mutagenesis poly(A) Signals

Site directed mutagenesis of the poly(A) signals (PAS) were performed using PCR and mismatched primers. For the construction of the 10A166 mutated PAS on the 4A161 construct (generation 4A161b[10mPAS]), PCR products were created with forward primer 5'-GCT GGA AGC ACC CCT CAG CGA GGA A-3' (SEQ ID NO:14) and PAS[10] reverse primer 5'-GGA TCC ACA GGG AGG GGG AAT TTT GAT ATA TCT CTG AAC TAA TC-3' (SEQ ID NO:15) (fragment 1) and with PAS[10] forward primer 5'-GAT TAG TTC AGA GAT ATA TCA AAA TTC CCC CTC CCT GTG GAT CC-3' (SEQ ID NO:16) and M13-Reverse Primer (fragment 2). Similarly, for the construction of the 4A161 PAS on the 10A166 and 10A176T construct (generation 10A166b[4PAS] and 10A176T[4PAS]), PCR products were created with forward primer 5'-GCT GGA AGC ACC CCT CAG CGA GGA A-3' (SEQ ID NO:14) and with PAS[4] reverse primer 5'-GGA TCC ACA GGG AGG GGG CAT TTT AAT ATA TCT CTG AAC TAA TC-3' (SEQ ID NO:17) (fragment 1) and with PAS[4] forward primer 5'-GAT TAG TTC AGA GAT ATA TTA AAA TGC CCC CTC CCT GTG GAT CC-3' (SEQ ID NO:18) and M13-Reverse Primer (fragment 2).

After gel purification, PCR fragments 1 and 2 were mixed and amplified with forward primer 5'-GCT GGA AGC ACC CCT CAG CGA GGA A-3' (SEQ ID NO:14) and M13-Reverse primer, thereby creating a 1 kb D4Z4-pLAM-pCR2.1 fragment. The PCR reaction was performed on 100 ng of plasmid DNA with 3 μl dNTPs (2 mM), 0.4 U of Phusion F530-L DNA polymerase and supplemented GC buffer (fragment 1) or HF buffer (fragment 2), in a total volume of 30 μl. The PCR conditions consisted of an initial denaturation step at 98° C. for 3 min., followed by 20 cycles of denaturation at 98° C. for 25 s, annealing at 55° C. for 30 s, and extension at 72° C. for 45 s (fragment 1 and 1 kb D4Z4-pLAM-pCR2.1 fragment) or 15 s (fragment 2). The final extension time was 10 min. at 72° C. Finally, with a KpnI digestion, the original Poly(A) signals were replaced by the mutated ones. All constructs were sequence-verified.
Cloning of Proximal and Distal D4Z4 Sequences.

Proximal and distal D4Z4 fragments were cloned in either the TOPO blunt-II (for Phusion amplified fragments) or in the TOPO TA pCR2.1 (for LA-Taq amplified fragments) vector and subsequently these vectors were transfected into NEB 5-alpha F'I[q] Competent *E. coli* cells (New England Biolabs).
Transfection of Distal D4Z4 Constructs into C2C12 Cells C2C12 mouse muscle cells were cultured in DMEM supplemented with 20% fetal bovine serum, 4 mM L-glutamine, 4.5 g/L glucose and 1% penicillin-streptomycin in an incubator with 10% CO2 atmosphere at 37° C. For transfection, $8 \times 10^4$ cells were seeded in each well of a 6-well cell culture plate (Nunc) and grown for 24 hours prior to transfection. To monitor the transfection efficiency, D4Z4 plasmids were co-transfected with pEGFP-C1 plasmids. For each construct, 2 μg of D4Z4 plasmid DNA was mixed with 2 μg of pEGFP-C1 plasmid DNA after which 365 μl sera-free DMEM was added and 9 μl Plus reagent (Invitrogen). The DNA-Plus Reagent mixture was incubated for 15 minutes at room temperature. Meanwhile, 365 μl sera-free DMEM was prepared with 9 μl Lipofectamine reagent (Invitrogen). Then, DNA-Plus reagent mixture and Lipofectamine reagent were combined and incubated for 15 minutes at room temperature to subsequently replace the C2C12 medium for 1 hour in an incubator at 37° C. Afterwards, transfection medium was replaced by 2 mL fresh C2C12 medium and after 24 hour incubation, cells were harvested.

Quantification of DUX4 mRNA Levels Using Real-Time RT-PCR

Total RNA was extracted using the Macherey Nagel total RNA isolation kit with DnaseI treatment. The RNA concentration was determined on a ND-1000 spectrophotometer (Thermo Scientific, Wilmington, DE, USA) and the quality was analyzed with a RNA 6000 nanochip on an Agilent 2100 BioAnalyzer (Agilent Technologies Netherlands BV, Amstelveen, The Netherlands). cDNA was synthesized from 0.5 μg of total RNA using random hexamer primers (Fermentas, St Leon-Rot, Germany) and the RevertAid H Minus M-MuLV First Strand Kit (Fermentas Life Sciences, Burlington, ON, Canada) according to the manufacturer's instructions. After the cDNA reaction, 30 μL of water was added to an end volume of 50 μL. The mRNA levels were measured by real-time PCR using a SYBR Green QPCR master mix kit (Stratagene) on a MyiQ (Biorad Laboratories, Veenendaal, The Netherlands) running an initial denaturation step at 95° C. for 3 min, followed by 40 cycles of 10 s at 95° C. and 45 s at 62° C. The ratio between PAS and DAS primer set were determined by forward primer 5'-CCC AGG TAC CAG CAG ACC-3' (SEQ ID NO:19) and reverse primers 5'-TCC AGG AGA TGT AAC TCT AAT CCA-3' (PAS) (SEQ ID NO:20) or 5'-TGA TCA CAC AAA AGA TGC AAA TC-3' (DAS) (SEQ ID NO:21). All the primers used for real-time PCR were designed using Primer 3 software. To ensure that residual genomic DNA was not being amplified, control experiments were performed in which reverse transcriptase was omitted during cDNA synthesis. Amplification efficiencies were determined from standard curves generated by serial dilution of plasmid DNA.
Northern Blot Analysis For the Northern blot analysis of the D4Z4 transcript, the previously described C2C12 transfection was scaled up to two 10-cm-diameter Petri dishes per D4Z4 construct. Total RNA was extracted using the Macherey Nagel total RNA isolation kit with DnaseI treatment. For each lane, 10 μg total RNA was separated on a 0.8% agarose gel containing 10% formaldehyde and blotted onto Hybond XL (GE Healthcare Life Science). Hybridizations were performed in a formamide hybridization mix (as described in J. Sambrook et al., *"Molecular Cloning,"* 2nd ed., New York, NY: Cold Spring Harbor Laboratory Press (1989)) for 16 h at 50° C. using a 32p labeled a D4Z4 probe that covers the 300 bp homeobox region of D4Z4 (D4Z4-HD). As a control, the transfection efficiency for the different conditions was analyzed by hybridization with a GFP probe. Probe labeling was performed using the Megaprime labeling kit (GE Healthcare Life Science) according to the manufacturer's protocol. The blots were washed at 65° C. and to a stringency of 2×SSC and 0.1% SDS. The radioactivity on the membranes was visualized by phosphor imaging on a Storm 840 Phosphor Imaging System (Molecular Dynamics).
DUX4 Expression Analysis in Primary Myotubes Myoblasts were isolated from a needle muscle biopsy sample of the Vastus Lateralismuscle as described in R. Klooster et al., *Eur. J. Hum Genet* 17:1615-1624 (2009). After pre-plating, myoblasts were cultured in F-10 Nutrient medium (Gibco Invitrogen, Carlsbad, USA), 20% FCS, 100 U/ml penicillin and 100 g/ml streptomycin, 4 μg/ml bFGF and 1 μM hexamethazone, in a humidified atmosphere containing 5% $CO_2$ at 37° C.

Myotubes were obtained by growing the myoblasts at 70% confluency on differentiation media (DMEM (+glucose, +L-glutamin, +pyruvate), 2% horse serum) for 6 days. Total RNA isolation, cDNA preparation and real-time PCR were performed as described in the previous sections. All samples were run in duplicate. All PCR products were analyzed for specificity by melting curve analysis and on a 2% agarose gel. The results of the quantitative RT-PCR were analyzed and quantified using iQ5 optical system software version 2.0 (Biorad Laboratories, Veenendaal, The Netherlands). All expression levels were calculated using GAPDH (primers hGAPDHFw 5'-AGC ACA TCG CTC AGA CAC-3' (SEQ ID NO:22) and hGAPDHRev 5'-GCC CAA TAC GAC CAA ATC C-3' (SEQ ID NO:23) as constitutively expressed standard for cDNA input, and the relative steady-state RNA levels of the DUX4 gene (forward primer 5'-CCC AGG TAC CAG CAG ACC-3' (SEQ ID NO: 19) and reverse primers 5'-TCC AGG AGA TGT AAC TCT AAT CCA-3' (SEQ ID NO:20) (PAS)) were calculated by the method of Pfaffl (Pfaffl, *Nucleic Acids Res* 29:e45 (2001)).

3' RACE

The polyadenylation site was identified by 3' RACE using the GeneRacer kit (Invitrogen) according to manufacturer's instructions. Total RNA (1 μg) from C2C12 transfected cells was treated with amplification grade DNase I followed by clean-up on RNeasy column (Invitrogen). Reverse transcription was performed using the GeneRaceroligodT primer and Superscript III, followed by treatment with RNase H. DUX4 transcripts were amplified by nested PCR using forward primers LS 182 5'-CAC TCC CCT GCG GCC TGC TGC TGG ATG A-3' (SEQ ID NO:24) then 1A 5'-GAG CTC CTG GCG AGC CCG GAG TTT CTG-3' (SEQ ID NO:25) combined with the GeneRacer 3' primer and then GeneRacer 3' nested primer. PCR conditions were 95° C. denaturation for 30 seconds, 62° C. annealing for 30 seconds and 68° C. extension for 1 minute. Primary and nested reactions were each 35 cycles.

In Silico Prediction of Poly(A) Signals

For the in silico prediction of poly(A) signals, we used the online available tools DNAFSminer (http://dnafsminer.bic-.nus.edu.sg/) and PolyApred (http://www.imtech.res.in/rag-hava/polyapred/). We used accession numbers FJ439133 (4A161) and AL732375 (10A166).

Results

Facioscapulohumeral muscular dystrophy (FSHD) affects 1:20,000 people and is caused by contraction of the D4Z4 repeat array on a specific genetic background of chromosome 4q. Repeat contractions on other 4q backgrounds and of its homologue on chromosome 10q are non-pathogenic. In this Example, we show that FSHD is associated with the interplay of specific sequence variants in the last D4Z4 repeat unit with the adjacent distal sequence, even when this configuration is located on chromosome 10. The FSHD-predisposing configuration increases the polyadenylation efficiency of the DUX4 gene copy straddling this last repeat unit and adjacent sequence and encoding for a double homeobox transcription factor. These findings explain previous genetic observations and suggest a toxic gain of function due to the presence of a stable distal DUX4 transcript.

Autosomal dominant FSHD, which presents with progressive and often asymmetric weakness and wasting of facial, shoulder girdle, and upper arm muscles (R. Tawil et al., *Muscle Nerve* 34:1-15 (2006)), is most often caused by contraction of the D4Z4 repeat array in the subtelomere of chromosome 4q (FSHD1; OMIM 158900) (C. Wijmenga et al., *Nat Genet* 2:26-30 (1992)). This polymorphic macrosatellite repeat normally consists of 11-100 D4Z4 units, each 3.3 kb in size and ordered head-to-tail. Patients with FSHD1 have one repeat array of 1-10 units (FIG. 1A). At least one unit of D4Z4 is required to develop FSHD (R. Tupler et al., *J Med Genet* 33:366-370 (1996)).

A schematic overview of the minimal genetic requirement for FSHD is provided in FIG. 1. FIG. 1A is a schematic diagram of the minimal genetic requirement for FSHD illustrating the D4Z4 repeat array on chromosome 4 (open triangles) and its homologue on chromosome 10 (closed, filled-in triangles), showing the localization of the simple sequence length polymorphism ("SSLP") and 4qA/4qB polymorphisms that define the genetic background of the D4Z4 repeat, wherein patients with FSHD1 have a D4Z4 repeat array size of 1-10 units on 4qA but not on 4qB or 10q chromosomes. FIG. 1B is a schematic diagram of the D4Z4 repeat and flanking sequences on A chromosomes, A-L chromosomes (with an extended distal D4Z4 repeat unit) and B chromosomes, wherein each D4Z4 unit is defined by the KpnI restriction site (K). The proximal and distal regions that were sequenced are indicated, and the exons of DUX4 are indicated as grey boxes numbered 1-3.

D4Z4 contraction needs to occur on a specific chromosomal background to cause FSHD. The chromosome 10q subtelomere contains an almost identical repeat but contractions here are non-pathogenic (shown in FIG. 1A). Based on differential restriction enzyme sensitivity of the repeat unit on chromosome 4 and 10, translocated copies of both units can be frequently encountered on either chromosome end (J. C. de Greef et al., *Mutat Res* 647:94-102 (2008)). This complex genetic situation in which genetically almost identical repeat units can be exchanged between both chromosomes with apparently discordant pathological consequences has long hampered the identification of the disease mechanism.

Disease models were postulated in which D4Z4 repeat contractions cause chromatin remodeling and transcriptional deregulation of genes close to D4Z4. Indeed, contracted D4Z4 repeat arrays show partial loss of DNA methylation and of heterochromatic histone 3 lysine 9 trimethylation and heterochromatin protein 17 markers consistent with a more open chromatin structure (P. G. van Overveld et al., *Nat Genet* 35:315-317 (2003); W. Zeng et al., *PloS Genet* 5:e1000559 (2009)). Transcriptional upregulation of genes proximal to D4Z4 was reported in FSHD patients (D. Gabellini et al., *Cell* 110:339-348 (2002)), but could not be confirmed (R. Klooster et al., *Eur J. Hum Genet* 17:1615-1624 (2009); P. S. Masny et al., *Eur J. Hum Genet* 18:448-456 (2010)).

Recent studies showed that exchanges between repeat units of chromosomes 4 and 10 occur much less frequently than previously anticipated (Lemmers et al., *Am J. Hum Genet* 86:364-377 (2010)). Of the two distal chromosome 4q configurations, 4qA and 4qB, only contractions of the 4qA form led to FSHD (Lemmers et al., *Nat Genet* 32:235-236 (2002)). Genetic follow-up studies unveiled consistent polymorphisms in the FSHD locus resulting in the recognition of at least 17 variants of distal 4q (Lemmers et al., *Am J. Hum Genet* 86:364-377 (2010)). Contractions in the common variant 4A161 cause FSHD, while contractions in many other variants such as the common 4B163 are not causing FSHD (FIG. 1A) (Lemmers et al., *Am J Hum Genet* 81:884-894 (2007)). Thus, it appears that 4A161 haplotype-specific sequence variants are causally related to FSHD.

As at least one D4Z4 unit is necessary to cause disease, we reasoned that the minimal pathogenic region might reside in the first or the last unit. The distal unit of the D4Z4 repeat was recently shown to have a transcriptional profile that differs from internal units (M. Dixit et al., *PNAS* 104:18157-18162 (2007); L. Snider et al., *Hum Mol Genet*

18:2414-2430 (2009)). While the major transcript in each unit is the DUX4 gene encoding a toxic double homeobox protein, none of these transcripts seem to be stable, probably due to the absence of a polyadenylation signal in internal D4Z4 units. The DUX4 gene in the last unit, however, is spliced to a unique last exon in the pLAM region (J. C. van Deutkom et al., *Hum Mol Genet* 2:2037-2042 (1993) immediately distal to this last unit (shown in FIG. 1B) containing a poly(A) signal which presumably stabilizes this distal transcript (M. Dixit et al., *PNAS* 104:18157-18162 (2007); L. Snider et al., *Hum Mol Genet* 18:2414-2430 (2009)).

When expressed in C2C12 muscle cells, DUX4 causes a phenotype compatible with molecular observations in FSHD (D. Bosnakovski et al., *EMBO J.* 27:2766-2779 (2008)).

Figure 2:
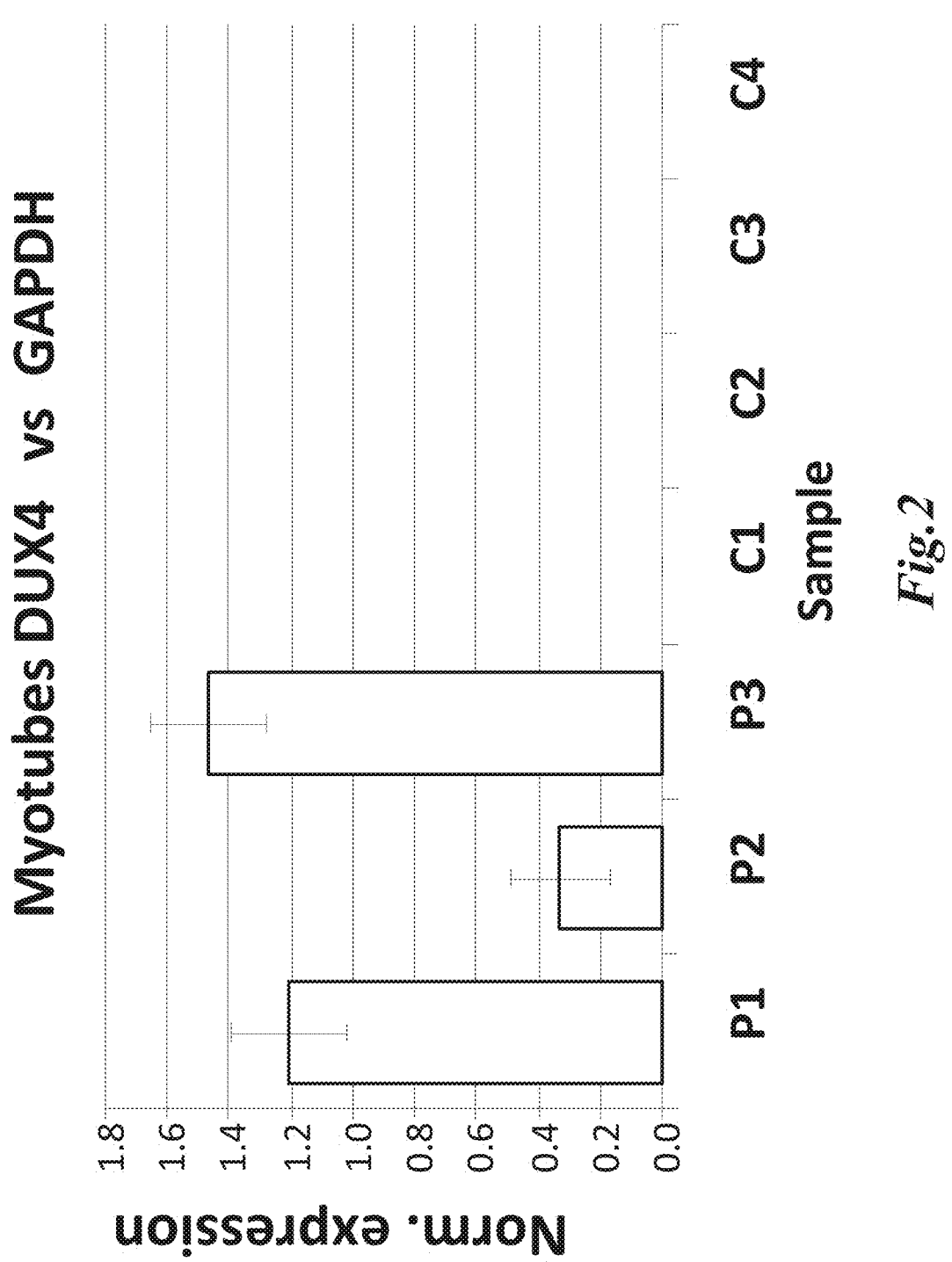
FIG. 2 graphically illustrates expression analysis of the distal DUX4 transcript in primary myoblast cultures of FSHD1 patients (P1-P3) and controls (C1-C4), as described in TABLE 1, where the DUX4 expression level is shown relative to GAPDH control, as described in Example 1.

FIG. 2 graphically illustrates expression analysis of the distal DUX4 transcript in primary myoblast cultures of FSHD1 patients (P1-P3) and controls (C1-C4), (described below in TABLE 1) where the DUX4 expression level is shown relative to GAPDH control. The primary myoblast cultures were allowed to differentiate for 6 days and RNA was tested for the expression of the distal DUX4 transcript by quantitative PCR. As shown in FIG. 2, the distal DUX4 transcript can be observed in FSHD myotubes but not in control myotubes.

TABLE 1

| characterization of samples shown in FIG. 2: | | |
| --- | --- | --- |
| FIG. 2 Legend | Chromosome Analysis | Number of D4Z4 units |
| Patient 1 (P1) (from patient 201, family F8) | 4A168 | 5.5 |
| Patient 2 (P2) | 4A161 | 7.5 |
| Patient 3 (P3) | 4A161 | 4.5 |
| Control 1 (C1) | 4A161 | >10 |
| Control 2 (C2) | 4A161 | >10 |
| Control 3 (C3 | 4A161 | >10 |
| Control 4 (C4) | 4A161 | >10 |

Figure 3A:
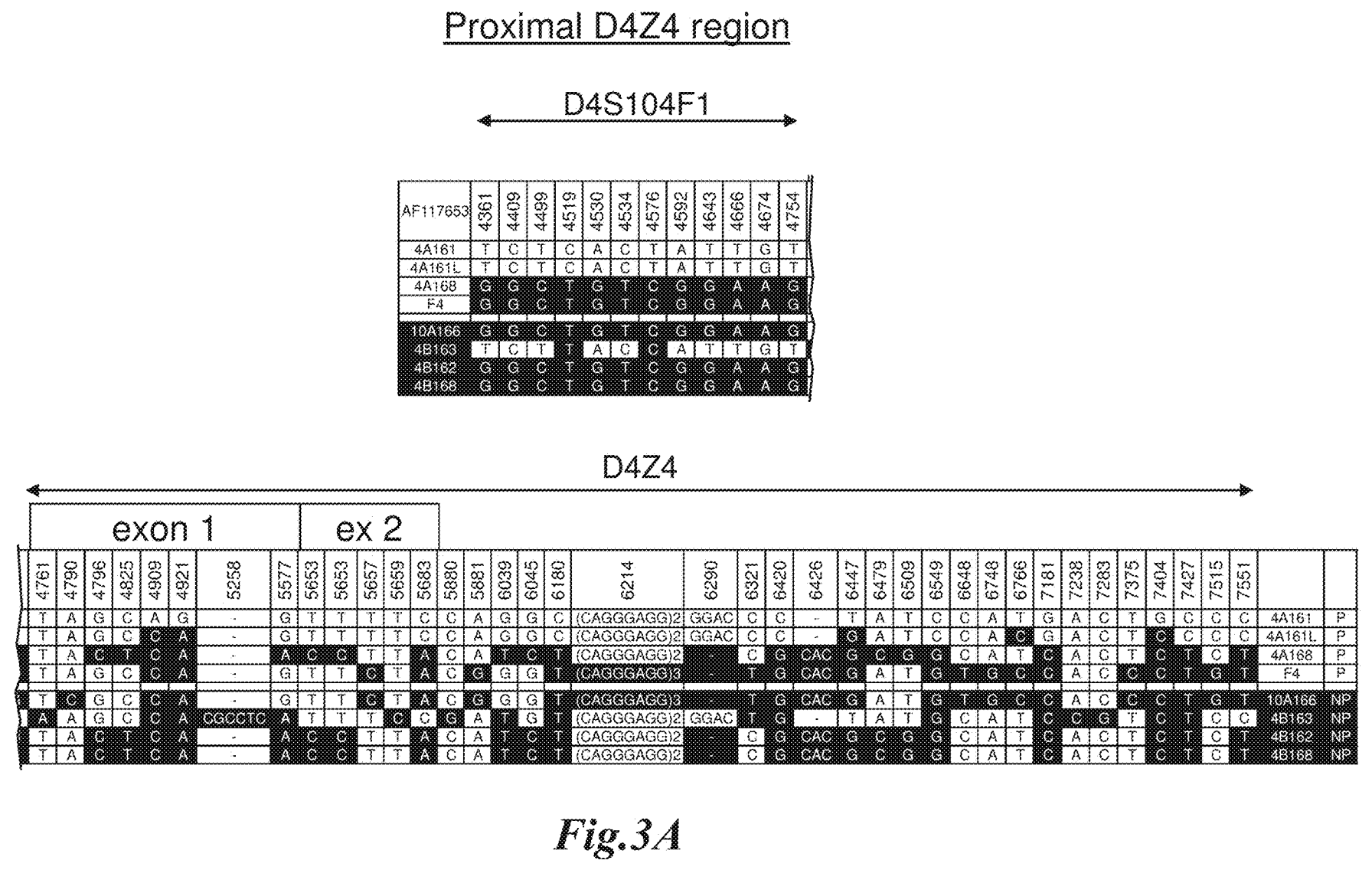

To find an explanation for the permissiveness of 4A161, we compared the sequence of the 4A161 haplotype with that of common, non-permissive 4B163 and 10A166 chromosomes. FIG. 3 shows a comparison of sequence variants of the D4Z4 repeat on permissive and non-permissive haplotypes. FIG. 3A shows a comparison of the sequence variants identified at the proximal end of the D4Z4 repeat on permissive and non-permissive haplotypes, wherein the sequence shown is with reference to nucleotides 4361-7551 of the sequence of GenBank Ref. AF117653, set forth as SEQ ID NO:1. FIG. 3B shows a comparison of the sequence variants identified at the distal end of the D4Z4 repeat on permissive and non-permissive haplotypes, wherein the sequence shown is with reference to nucleotides 4650-8079 of the sequence of GenBank Ref. FJ439133, set forth as SEQ ID NO:5. The black nucleotides in white boxes indicate the 4A161 sequence. The white nucleotides in black boxes indicate sequence variation with respect to 4A161. White haplotypes are permissive to FSHD (P). Black haplotypes are non-permissive to FSHD (NP). The exons (ex1, ex2 and ex3) of DUX4 are indicated as well as the position of the poly(A) signal (PAS) and the open reading frame (ORF). All sequences shown have been deposited under the following GenBank under accession numbers HM101229, HM101230, HM101232, HM101233, HM101234, HM101235, HM101240, HM101241, HM101242, HM101243, HM101244, HM101245, HM101246, HM101247, HM101248, HM101249, HM101250, HM101251 and HM190160, HM190161, HM190162, HM190163, HM190164, HM190165, HM190166, HM190167, HM190168, HM190169, HM190170, HM190171, HM190172, HM190173, HM190174, HM190175, HM190176, HM190177, HM190178, HM190179, HM190180, HM190181, HM190182, HM190183, HM190186, HM190187, HM190188, HM190189, HM190190, HM190191, each of which is hereby incorporated herein by reference.

As shown in FIG. 3A, in the proximal unit of the repeat array we could not identify a sequence signature that could explain the permissiveness of the 4A161 haplotype. However, as shown in FIG. 3B, immediately distal to the 4A161 repeat, in the adjacent pLAM sequence, we found a polymorphism potentially affecting polyadenylation of the distal DUX4 transcript. The DUX4 poly(A) signal ATTAAA (SEQ ID NO:26), which is the canonical polyA signal sequence commonly used in humans (E. Beaudoing et al., *Genome Res* 10:1001-1010 (2000), is present on the permissive 4A161 haplotype, while the corresponding ATCAAA (SEQ ID NO:27) sequence on chromosome 10q (as shown in FIG. 3B in the NP haplotype) is not known as a poly(A) signal. Non-permissive 4qB haplotypes, like 4B163, lack pLAM altogether, including this poly(A) site (see FIG. 1B). As further shown in FIG. 3B, another non-permissive 10qA haplotype (10A176T) carries ATTTAA (SEQ ID NO:28) at this position, which is also not known as a poly(A) signal. In silico poly(A) signal prediction programs (F. Ahmed et al., *In Silico Biol* 9:135-148 (2009); H. Liu et al., *Bioinformatics* 21:671-673 (2005)) also recognized the DUX4 poly(A) signal in 4A161 but failed to identify potential poly(A) signals in non-permissive 10A haplotypes 10A166, and 10A176T.

To test whether these polymorphisms might affect the distal DUX4 transcript, we transfected the last D4Z4 unit and flanking pLAM sequence of permissive and non-permissive chromosomes in C2C12 cells and analyzed the distal DUX4 transcript stability on Northern blot, as summarized below in TABLE 2.

TABLE 2

| Summary of Northern blot results from DUX4 expression analysis after transfection of the distal D4Z4 unit and flanking pLAM sequence into C2C12 cells | | | |
| --- | --- | --- | --- |
| Sample | construct | derived from permissive or non-permissive chromosomes | DUX4 expression (2.4 kb band) | GFP expression (co-transfected construct) |
| 1 | F1 | P | + | + |
| 2 | F3 | P | + | + |
| 3 | 4A161a | P | + | + |
| 4 | 4A161b | P | + | + |
| 5 | 4A161b(10 mPAS) | P, but polyA replaced by 10 mPAS (NP) | – | + |
| 6 | 10A166a | NP | – | + |
| 7 | 10A166b | NP | – | + |
| 8 | 10A166b(4PAS) | NP, but polyA replaced by 4PAS (P) | + | + |
| 9 | 10A176T | NP | – | + |
| 10 | 10A176T(4PAS) | NP, but polyA replaced by 4PAS (P) | + | + |

Figure 4A:
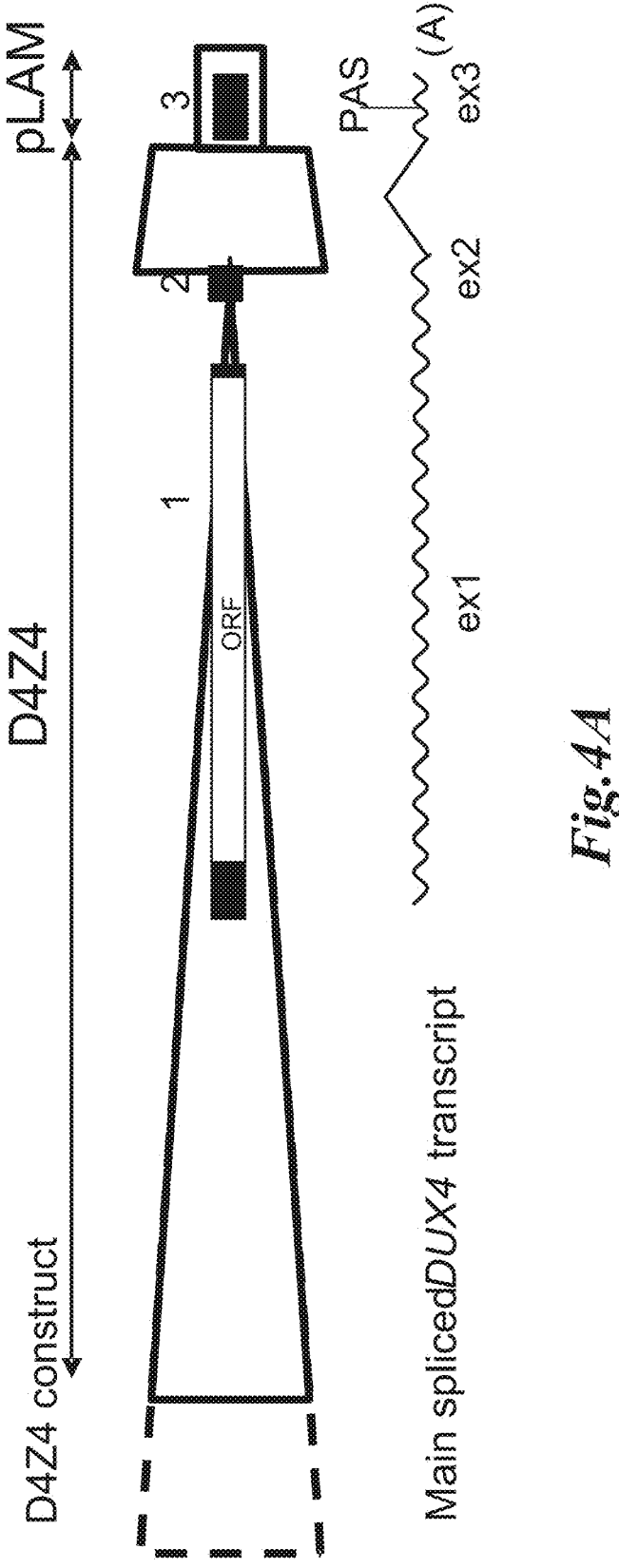
FIG. 4A is a schematic of the transfected sequences used to generated the data in TABLE 2, including the distal D4Z4 unit and flanking pLAM sequence, wherein the DUX4 gene and the poly(A) signal were part of the transfected sequence, and wherein the major DUX4 transcript and its open reading frame (ORF) are indicated, as described in Example 1.

TABLE 2 summarizes the results of Northern blot analysis to measure DUX4 expression analysis after transfection into C2C12 cells of genomic constructs (see FIG. 4A)

derived from the distal D4Z4 unit and flanking pLAM sequence from permissive (lanes 1-4) or non-permissive chromosomes (lanes 6, 7 and 9) or constructs in which the poly (A) signals from non-permissive chromosomes are replaced by those from permissive chromosomes (4PAS; lanes 8 and 10) and vice versa (10 mPAS; lane 5). As shown in TABLE 2, only constructs with canonical poly (A) signals showed a DUX4 transcript. Co-transfected GFP was used as a control.

FIG. 4A is a schematic of the transfected sequences used to generated the data in TABLE 2, including the distal D4Z4 unit and flanking pLAM sequence, wherein the DUX4 gene and the poly(A) signal were part of the transfected sequence. The major DUX4 transcript and its open reading frame (ORF) are indicated.

Figure 4B:
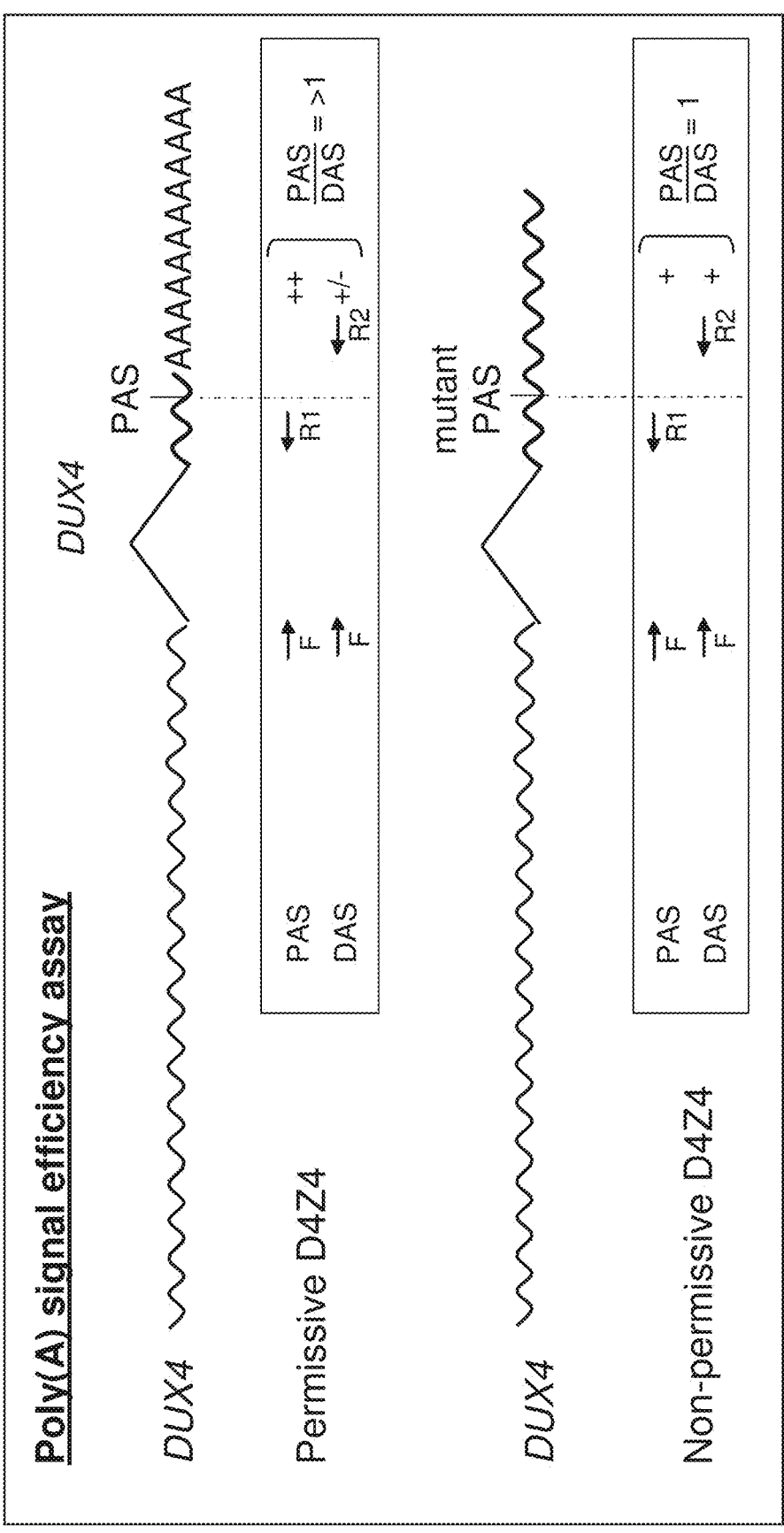
FIG. 4B illustrates the design of the assay used to quantify the polyadenylation efficiency of the DUX4 poly(A) signal, wherein a primer set Proximal to the poly(A) Signal (PAS) and a primer set using the same forward primer but a reverse primer Distal to the poly(A) Signal (DAS) are indicated, as well as the expected PAS/DAS ratios, wherein the primer "F"=SEQ ID NO:19, primer "R1"=SEQ ID NO:20 and primer "R2"=SEQ ID NO:21; as described in Example 1.

Polyadenylation efficiency of the DUX4 poly(A) signals was assayed by a qRT-PCR assay that compared DUX4 transcript levels proximal and distal of the poly(A) site, as shown in FIGS. 4B and C.

FIG. 4B illustrates the location of the primers used to quantify polyadenylation efficiency. The boxed area shows the design of the assay to quantify the polyadenylation efficiency of the DUX4 poly(A) signal. The primer set Proximal to the poly(A) Signal (PAS) and a primer set using the same forward primer but a reverse primer Distal to the poly(A) Signal (DAS) are indicated as well as the expected PAS/DAS ratios, wherein the primers shown in FIG. 4B are as follows: primer "F"=SEQ ID NO:19, primer "R1"=SEQ ID NO:20 (PAS) and primer "R2"=SEQ ID NO:21 (DAS).

Figure 4C:
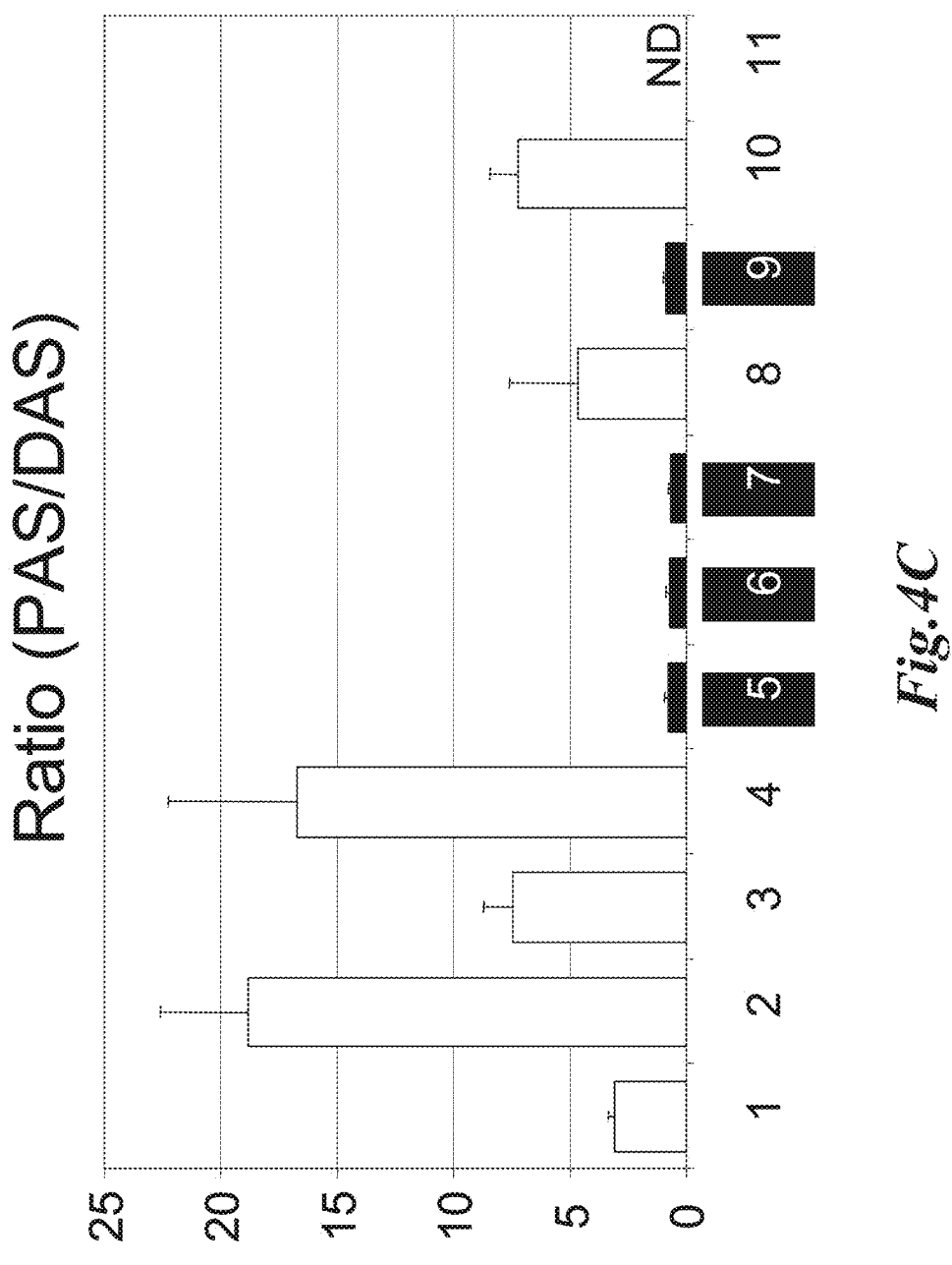
FIG. 4C is a bar diagram showing the observed PAS/DAS ratios (with reference to TABLE 2) of permissive chromosomes (samples 3 and 4), non-permissive chromosomes (samples 6, 7 and 9), and permissive chromosomes in which the poly(A) signal is replaced for a sequence derived from a non-permissive chromosome (10 mPAS; sample 5) or vice versa (4PAS; samples 8 and 10), or of pathogenic chromosomes derived from families F1 and F3 (samples 1 and 2). Sample 11 is negative control. ND=not detected Bars represent values of quadruple experiments with standard errors of the mean, as described in Example 1.

FIG. 4C is a bar diagram showing the observed PAS/DAS ratios (with reference to TABLE 2) of permissive chromosomes (samples 3 and 4), non-permissive chromosomes (samples 6, 7 and 9), and permissive chromosomes in which the poly(A) signal is replaced for a sequence derived from a non-permissive chromosome (10 mPAS; sample 5) or vice versa (4PAS; samples 8 and 10), or of pathogenic chromosomes derived from families F1 and F3 (samples 1 and 2). Sample 11 is negative control. ND=not detected Bars represent values of quadruple experiments with standard errors of the mean.

FIG. 4D shows an alignment between nt 7802 to nt 8101 of SEQ ID NO:5 (pLAM region of Chromosome 4qA161) and the corresponding region from chromosome 10, set forth as SEQ ID NO:99, wherein the consensus polyA site is shown in the boxed region (corresponding to nt 8046-8051 of SEQ ID NO:5), and the poly-A addition sites are underlined, and the SNPs are shown in red (greyscale in black and white). The sequence shown in FIG. 4D includes a portion of intron 2 (nt 7802 to nt 7878 of SEQ ID NO:5), exon 3 (nt 7879 to nt 8079 of SEQ ID NO:5), and a region in pLAM adjacent to Exon 3 (nt 8080 to nt 8101 of SEQ ID NO:5).

As shown in FIG. 4D, a polymorphism of nucleotide "T" at nucleotide position 8048 of SEQ ID NO:5 is present in the 4qA161 chromosome in the boxed poly A region, resulting in a consensus polyA site. In contrast, chromosome 10 contains a "C" at the corresponding position, which does not result in a polyA consensus site.

As further shown in FIG. 4D, three additional polymorphisms were identified in the region 3' to the polyA consensus site as follows:

at position 8054 of SEQ ID NO:5, nucleotide "G" is present, as compared to nucleotide "T" in chromosome 10;

at position 8079 of SEQ ID NO:5, nucleotide "A" is present, as compared to nucleotide "G" in chromosome 10;

at position 8101 of SEQ ID NO:5, nucleotide "G" is present, as compared to nucleotide "C" in chromosome 10; As further shown in FIG. 4D, four additional polymorphisms were identified in the region of exon 3 (nt 7879 to nt 8045 of SEQ ID NO:5) that is 5' to the polyA site as follows:

at position 7903 of SEQ ID NO:5, nucleotide "C" is present, as compared to nucleotide "G" in chromosome 10;

at position 7946 of SEQ ID NO:5, nucleotide "T" is present, as compared to nucleotide "G" in chromosome 10;

at position 7968 of SEQ ID NO:5, nucleotide G" is present, as compared to nucleotide "C" in chromosome 10;

at position 7987 of SEQ ID NO:5, nucleotide "C" is present, as compared to nucleotide "G" in chromosome 10.

As further shown in FIG. 4D, four additional polymorphisms were identified in intron 2 as follows:

at position 7806 of SEQ ID NO:5, nucleotide "T" is present, as compared to nucleotide "G" in chromosome 10;

at position 7812 of SEQ ID NO:5, nucleotide "C" is present, as compared to nucleotide "G" in chromosome 10;

at position 7820 of SEQ ID NO:5, nucleotide "G" is present, as compared to nucleotide "A" in chromosome 10;

at position 7827 of SEQ ID NO:5, nucleotide "T" is present, as compared to nucleotide "G" in chromosome 10.

FIG. 4E shows the sequence of intron 2 of 4qa161 (corresponding to nt 7516 to nt 7878 of SEQ ID NO:5) and the sequence of exon 3 of 4qa161 and adjacent pLAM region (corresponding to nt 7879 to nt 8671 of SEQ ID NO:5), wherein the SNP locations are shown in red (greyscale in black and white), which are the same as those described in connection with FIG. 4D.

Figure 4F:
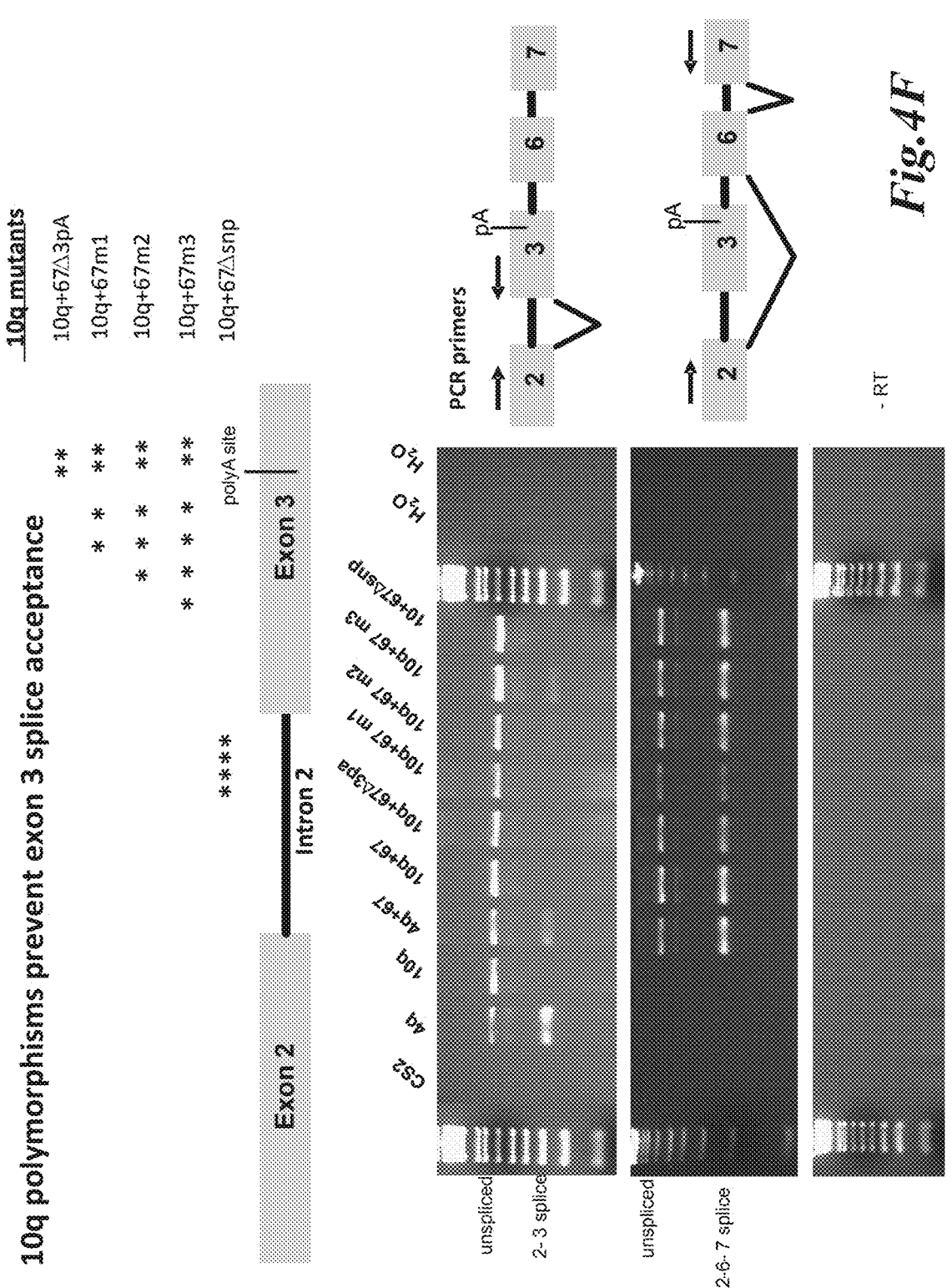
FIG. 4F shows the results of an experiment demonstrating that the polymorphic nucleotides identified in 4qa161 that characterize the permissive allele for FSHD regulate splice acceptor usage of exon 3 as well as polyadenylation, as described in Example 1.

FIG. 4F shows the results of an experiment demonstrating that the polymorphic nucleotides identified in 4qa161 that characterize the permissive allele for FSHD regulate splice acceptor usage of exon 3 as well as polyadenylation. The top panel shows the approximate location of the mutations such that: 10q+67delta3 pA represents the exon 3 sequence of 10q with the two nucleotides at and 3-prime adjacent to the DUX4 polyA site have been back-mutated to represent the two polymorphism present in the 4qA161 permissive allele that reconstitute the active polyadenylation site; 10q+67 ml represents same with the additional 5-prime polymorphisms of 4qA161; 10q+67m2 represents same with the additional three polymorphisms of 4qA161; 10q+67m3 represents same with the additional 4 5-prime polymorphisms of 4qA161; 10q+67deltasnp represents 10q sequence in exon 3 but has introduced the intron 2 polymorphisms from the 4qA161 permissive allele. These sequences were contained in a DUX4 genomic construct driven by the CMV promoter and transfected into C2C12 cells, RNA harvested, oligo-dT primed to make cDNA and PCR amplified using primers located in positions shown adjacent to the respective gel images to detect exon 2-3 splicing and exon 2-6-7 splicing. Construct 4q+67 (containing the entire genomic structure of eons 2, 3, 6, 7 and respective introns 2, partial 3/5, and 6) shows use of both the exon 3 splice acceptor site (2-3 spice in upper panel) and the 2-6-7 spice acceptor sites (2-6-7 splice in lower panel). Construct 10q+67 (same as 4q+67 but with the 10q polymorphisms in intron 2 and exon 3) shows that the 2-3 splice acceptor is not used, whereas the 2-6-7 splice acceptors are used. The back-mutations introducing the 4qA166 polymorphisms back into the 10q exon 3 demonstrate that addition of the six polymorphisms from the 5-prime end of exon 3 through the pA site reconstitutes usage of the exon 3 splice acceptor. The intron 2 polymorphisms do not have any discernible affect on the use of the splice acceptors. Therefore, in addition to regulating polyadenylation of the DUX4 mRNA the 4qA161 polymorphisms of the allele permissive for FSHD also facilitate usage of the exon 3 splice acceptor site.

We also transfected constructs in which the poly(A) signal of permissive chromosomes was replaced by those of nonpermissive chromosomes, and vice versa. DUX4 transcripts were stable (TABLE 2) and efficiently polyadenylated (FIG. 4C) when using constructs from permissive chromosomes or when the poly(A) signal of a permissive haplotype was introduced on constructs derived from non-permissive chromosomes. Consistently, when constructs derived from nonpermissive chromosomes were transfected, no DUX transcripts could be detected on Northern blot (TABLE 2) and polyadenylation was inefficient (FIG. 4C). DUX4 stability and polyadenylation efficiency decreased when the poly(A) signal of permissive constructs was replaced by non-permissive sequences. Altogether, constructs with a bona fide poly(A) signal produced stable transcripts and showed 4-16 fold higher polyadenylation efficiency than constructs with a mutation in the poly(A) signal. This suggests that increased polyadenylation, and hence stability, of the distal DUX4 transcript may be centrally involved in FSHD pathogenesis. The use of this poly(A) signal was also verified by 3'RACE (data not shown).

TABLE 3 summary of results of 4 quantitative PCR assays with primer set PAS and DAS to determine the ratio of (PAS/DAS)

| Sample | permissive or non-permissive | Average value (ratio of PAS/DAS) | STD | N | Standard error of the mean |
|---|---|---|---|---|---|
| F1 | P | 3.1 | 0.6 | 4 | 0.28 |
| F3 | P | 18.8 | 7.6 | 4 | 3.79 |
| 4A161a | P | 7.4 | 2.6 | 4 | 1.31 |
| 4A161b | P | 16.7 | 11.0 | 4 | 5.51 |
| 4A161b10PAS | NP | 0.8 | 0.4 | 4 | 0.19 |
| 10A166a | NP | 0.7 | 0.3 | 4 | 0.15 |
| 10A166b | NP | 0.6 | 0.3 | 4 | 0.13 |
| 10A166b4PAS | P | 4.7 | 5.9 | 4 | 2.96 |
| 10A176T | NP | 0.9 | 0.2 | 4 | 0.09 |
| 10A176T4PAS | P | 7.2 | 2.4 | 4 | 1.21 |
| H2O | control | 0.0 | 0.0 | 4 | 0.00 |

To find further support for this model, we studied FSHD patients with unusual hybrid D4Z4 repeat array structures that contain mixtures of 4-type and 10-type units. We identified four families (F1-F4) with one or more individuals with FSHD, carrying a contracted D4Z4 repeat array that commences with 10-type units, and ends with 4-type units, as summarized in FIG. 5A.

Figure 5A:
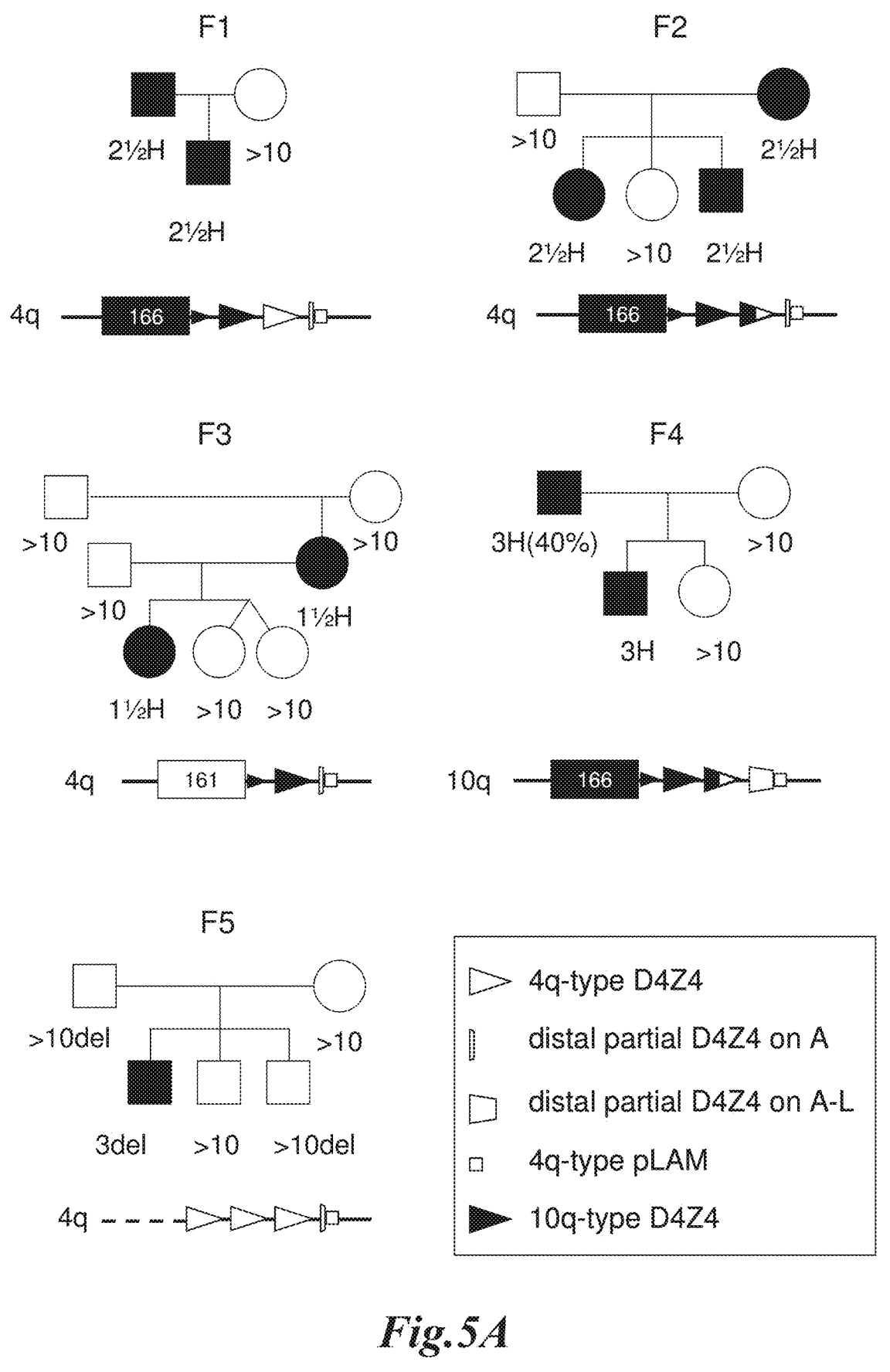

FIG. 5A illustrates the pedigrees of five FSHD families with complex pathogenic chromosomes. Families F1-F4 all carry a hybrid D4Z4 repeat that commences with chromosome 10-type repeat units (closed triangles), but end with 4-type repeat units (open triangles). In family F3, a meiotic rearrangement between chromosomes 4 and 10 generated a short hybrid repeat structure on 4A161. In family F4, this pathogenic repeat is located on chromosome 10 and originates from a mitotic D4Z4 contraction in the mildly affected father which is transmitted to his affected son. Family F5 represents a disease chromosome in which in addition to partial deletion of the D4Z4 repeat, the region proximal to the D4Z4 repeat is also deleted.

In family F3, we identified a patient with a de novo meiotic rearrangement between chromosomes 4q and 10q leaving one and a half 10-type repeat unit on a permissive 4A161 chromosome. In family F4, the mildly affected father is a mosaic FSHD patient (S. M. van der Maarel et al., *Am J Hum Genet* 66:26-35 (2000)) due to a mitotic contraction of such hybrid repeat array. The mosaic pathogenic repeat starts with two and a half 10-type D4Z4 unit and ends with one and a half 4-type repeat unit. This repeat array is transmitted to his affected son demonstrating its pathogenicity and, surprisingly, was found to reside on chromosome 10.

PFGE Southern blot and FISH studies were carried out on family F4. FIG. 5B shows the results of the PFGE Southern blot of genomic DNA digested with EcoRI (E), EcoRI and BlnI (B) or with XapI (X) and hybridized with p13E-11. The chromosomal origin of the different D4Z4 repeat arrays as well as the percentage mosaicism is indicated. The pathogenic allele is marked with an arrow. The cross-hybridizing Y fragment is labeled with Y. Marker lane on the left. Segregation analysis of chromosomes 4 and 10 in family F4 indicated that the pathogenic mosaic 16 kb (3 units) large D4Z4 repeat array in the father was located on chromosome 10. This chromosome was transmitted to the affected son, but not to the unaffected daughter. FISH analysis to metaphase chromosomes of patient 201 using digoxigenin-labeled chromosome 4 paint and fluorescently labeled probes recognized a region (cY313, green signal) 80kb proximal to the D4Z4 repeat on chromosome 4, showing that sequences proximal to the D4Z4 repeat were not transferred to chromosome 10 (data not shown). In addition, we hybridized a 4.1 kb KpnI-NaeI fragment (red signal) (data not shown) on which p13E-11 resides and 500 bp of the proximal D4Z4 sequence for which we previously showed that the signal intensity of this probe correlates with the D4Z4 repeat array size (R. J. Lemmers et al., *Hum. Mol. Genet.* 7:1207-1214 (1998)). Indeed, it was determined that patient 201 showed equally intense D4Z4 signals on both chromosomes 4 (both 80 kb D4Z4), while one of the chromosomes 10 showed a stronger signal (160 kb D4Z4) and the other showed the weakest D4Z4 signal corresponding to the 16 kb hybrid FSHD repeat array.

Only the distal end of the D4Z4 repeat array was transferred to chromosome 10q so that none of the FSHD candidate genes located proximal to the D4Z4 repeat array were co-transferred to chromosome 10 (FIG. 5A). This report of a FSHD family linked to chromosome 10 apparently precludes a key role for proximal 4q genes in the pathogenesis of FSHD. Altogether, all unusual FSHD-causing repeat arrays reported here, thus share the commonality of a terminal 4qA repeat unit with a directly adjacent pLAM sequence.

We also analyzed other disease permissive chromosome 4 variants, as shown in FIG. 6. FIG. 6 illustrates the pedigrees of three FSHD families F6, F7 and F8 with D4Z4 repeat contractions on rare permissive haplotypes 4A161L, 4A159 and 4A168. In all families the contracted D4Z4 repeat cosegregated with the disease. The composition of the disease repeat is shown below each pedigree. 4A161L was previously described (Lemmers et al., *Am J. Hum Genet* 86:364-377 (2010); J. C. van Deutekom et al., *Hum Mol Genet* 2:2037-2042 (1993)), while 4A159 and 4A168 are newly discovered uncommon permissive variants from a survey of >300 independent patients with FSHD. In addition, we studied >2,000 control individuals and identified additional non-permissive chromosome variants: 4B168, 10A164 (data not shown). Thus, D4Z4 contractions on 4A161, 4A161L, 4A159 and 4A168 chromosomes are pathogenic, while D4Z4 contractions on 4B163, 4B168, 4A166, 10A166, 10A164 and 10A176T chromosomes are non-pathogenic.

We sequenced the first and last D4Z4 units and flanking sequences in these newly identified permissive and non-permissive chromosomes. (FIGS. 1B, 3A, and 3B). In support of our earlier data, there is no common sequence in the proximal D4Z4 region that unifies FSHD permissive chromosomes.

At the distal end all permissive haplotypes differed very little in sequence and all contained a canonical DUX4 poly(A) signal, while non-permissive haplotypes showed much more sequence variation relative to the permissive haplotypes. The only exception, 4qB163, has a highly identical D4Z4 sequence but, importantly, lacks the pLAM sequence (FIG. 1). The permissive 4A161L chromosome is identical to 4A161 but carries an extended D4Z4 sequence preceding an identical pLAM sequence (FIG. 1B and FIG. 3B). Sequence analysis of the distal D4Z4-pLAM region of the pathogenic chromosome in our four families with complex repeat array structures showed a sequence identical to the permissive 4A161 sequence. Transfection experiments with D4Z4-pLAM sequences derived from the disease chromosomes of families F1 and F3 showed transcript stabilities and polyadenylation efficiencies of the distal DUX4 transcript comparable to those found in standard FSHD chromosomes. This demonstrates that DUX4 can also be efficiently produced from these chromosomes.

Altogether, our study demonstrates that all patients with FSHD have an identical sequence in the last D4Z4 unit and immediately flanking pLAM sequence and shows that specific sequence variants unique to the permissive haplotypes confer pathogenicity to the repeat irrespective of the chromosomal localization, as illustrated in FIG. 7.

FIG. 7 illustrates the structure of chromosomes that are permissive or non-permissive for FSHD. As shown in FIG. 7, all permissive chromosomes, including those with unusual disease associated repeat structures (complex pathogenic chromosomes that have been identified in FSHD families F1-F5), share the distal end of the D4Z4 repeat and flanking pLAM sequences indicated by the open grey box. This region is absent in the non-permissive chromosomes in the right panel.

Finally, this distal pLAM region is also preserved in individuals with FSHD in whom the deleted region extends proximally to the D4Z4 repeat array (F5 in FIG. 5) as well as in FSHD2 patients, who have a classical FSHD phenotype but show a similar local chromatin relaxation on a 4qA161 chromosome independent of D4Z4 repeat array contraction (W. Zeng et al., *PloS Genet* 5:e10000559 (2009); J. C. de Greef et al., *Hum Mutat* 30:1449-1459 (2009)).

Our study puts forward a plausible, genetic model for FSHD. In this model, a single polymorphism creating a polyadenylation site for the distal DUX4 transcript, located in the pLAM sequence, in combination with the chromatin relaxation of the repeat, leads to increased DUX4 transcript levels, suggesting a toxic gain-of-function of this transcript as the model for FSHD pathogenesis. Our study thus not only explains the striking haplotype-specificity of the disorder, but also provides a genetic mechanism that unifies all genetic observations in all patients with FSHD.

Example 2

This example demonstrates that full-length DUX4 (DUX4-fl) mRNA is normally expressed early in development and is suppressed during cellular differentiation, whereas FSHD is associated with the failure to maintain complete suppression of full-length DUX4 expression in differentiated skeletal muscle cells. Occasional escape from repression results in the expression of relatively large amounts of DUX4 protein in a small number of skeletal muscle nuclei.

Rationale:

As described herein, Facioscapulohumeral dystrophy (FSHD) is an autonomic dominant muscular dystrophy caused by the deletion of a subset of D4Z4 macrosatellite repeat units in the subtelomeric region of 4q on the 4A161 haplotype (FSHD1; OMIM 158900) (Lemmers et al., *Am J Hum Genet* 81:884-894 (2007)). The unaffected population has 11-100 D4Z4 repeat units, whereas FSHD1 is associated with 1-10 units (Tawil, R., et al., *Muscle Nerve* 34:1-15 (2006)). The retention of at least a portion of the D4Z4 macrosatellite in FSHD1 and the demonstration that the smaller repeat arrays have diminished markings of heterochromatin (Zeng, W., et al, *PloS Genet* 5:e1000559 (2009)) support the hypothesis that repeat contraction results in diminished heterochromatin-mediated repression of a D4Z4 transcript, or a transcript from the adjacent subtelomeric region. The hypothesis that derepression of a regional transcript causes FSHD is further supported by individuals with the same clinical phenotype and decreased D4Z4 heterochromatin markings but without a contraction of the D4Z4 macrosatellite in the pathogenic range (FSHD2) (van Overveld et al., *Nat Genet* 35:315-317 (2003); de Greef et al., *Hum Mutat* 30:1449-1459 (2009)).

The D4Z4 repeat unit contains a conserved open reading frame for the DUX4 retrogene, which Clapp et al. suggest originated from the retrotransposition of the DUXC mRNA (Clapp et al., *Am J Hum Genet* 81:264-279 (2007)), a gene present in many mammals but lost in the primate lineage. Dixit et al. demonstrated that DUX4 transcripts were present in cultured FSHD muscle cells and mapped a polyadenylation site to the region telomeric to the last repeat, a region referred to as pLAM (Dixit et al., *PNAS* 104:18157-18162 (2007)).

As described in Example 1, the present inventors demonstrated that the region necessary for a contracted D4Z4 array to be pathogenic maps to this polyadenylation site, which is intact on the permissive 4A chromosome but not on the non-permissive chromosomes 4B or 10, indicating that stabilization of the DUX4 mRNA is necessary to develop FSHD on a contracted allele (see also Lemmers et al., *Science vol.* 329 (5999):1650-3 (2010). Our prior study demonstrated bidirectional transcription of the D4Z4 region associated with the generation of small RNAs, and we suggested that these D4Z4-associated small RNAs might contribute to the epigenetic silencing of D4Z4 (Snider et al., *Hum Mol Genet* 18:2414-2430 (2009)). We also identified alternatively spliced transcripts from the DUX4 retrogene that terminate at the previously described (Dixit et al., *PNAS* 104:18157-18162 (2007)) polyadenylation site in the pLAM region. However, we identified DUX4 mRNA transcripts in both FSHD and wild-type muscle cells, as well as similar amounts of D4Z4-generated small RNAs.

Together these studies implicate a stabilized DUX4 mRNA transcript from the contracted D4Z4 array as the cause of FSHD. However, several important questions remain to be addressed:

(1) Our prior study identified two alternative splice forms of the DUX4 mRNA, which in this report we call DUX4-fl and DUX4-s, and showed that both control and FSHD muscle with a 4A chromosome contained polyadenylated DUX4 mRNA. Therefore, it is important to determine whether the overall abundance of the DUX4 mRNA or the relative abundance of the alternative splice forms is associated with FSHD.

(2) All studies reporting DUX4 mRNA associated with FSHD have used high cycle PCR to detect mRNA that are present at extremely low abundance. It remains to be determined whether the amount of DUX4 mRNA detected in FSHD cells makes sufficient DUX4 protein to have a biological consequence.

(3) DUX4 has been referred to as a pseudogene and the D4Z4 region has been referred to as "junk" DNA. The conclusion that DUX4 is not a functional gene is supported only by the absence of evidence that the DUX4 mRNA and protein is normally expressed in any human tissue. Yet, the open reading frame (ORF) of DUX4 is conserved, raising the possibility that it might have an as-yet undetected role in human biology.

In this Example, we have addressed each of these important questions. Together, our data substantiate a developmental model for FSHD: full-length DUX4 mRNA is normally expressed early in development and is suppressed during cellular differentiation, whereas FSHD is associated with the failure to maintain complete suppression of full-length DUX4 expression in differentiated skeletal muscle cells. Occasional escape from repression results in the expression of relatively large amounts of DUX4 protein in a small number of skeletal muscle nuclei.

Methods and Materials

Muscle Biopsies, Cultures, and Human RNA and Protein:

Muscle biopsy samples were collected from the vastus lateralis muscle of clinically affected and control individuals using standardized needle muscle biopsy protocol and cell cultures were derived from biopsies as described on the Fields Center website: http://www.urmc.rochester.edu/field-scenter/protocols/documents/PreparingPrimaryMyo-blastCultures.pdf., hereby incorporated herein by reference.

The sex, age, and severity score for the FSHD muscle biopsies were:

F1998 (M, 43, 2); F0519 (M, 43, 4); F0515 (F, 48, 2); F0509 (M, 47, 2); F0531 (F, 47, 2); F2306 (F, 46, ND); F2331 (F, 56, 4); F2316 (F, 34, 5); F2319 (M, 52, ND); F2315 (F, 40, 3). The pathologic grading scale is from 0-12 (from normal to severe) based on a score of 0-3 for each of four parameters: muscle fiber size/shape; degree of central nucleation; presence of necrotic/regenerating fibers or inflammation; and degree of fibrosis. Controls were selected in the same age range and sex representation. Muscle cell culture MB216 and muscle biopsy F2316 are from the same individual, otherwise the muscle cultures were derived from other individuals. RNA and protein lysates from human tissues were purchased from BioChain (Hayward, CA) and Origene (Rockville, MD).

RT-PCR for DUX4-fl, DUX4-s, and DUX4-fl3'.

Total RNA was isolated from muscle biopsies and cultured cells using Trizol (Invitrogen) and then treated with DNase I for 15 minutes using conditions recommended by Invitrogen with the addition of RNaseOUT (Invitrogen) to the reaction. DNase reaction components were removed using the RNeasy (Qiagen) system and RNA eluted by two sequential applications of 30 μl of RNase-free water. Volume was reduced by speed vac and 1.5-2 μg of RNA used for first strand cDNA synthesis. RNA from adult human tissues was purchased from Biochain and had been DNase-treated by the supplier. First strand synthesis was performed using Invitrogen SuperScript III reverse transcriptase and Oligo dT primers according to manufacturer's instructions at 550 for 1 hour followed by digestion with RNase H for 20 minutes at 37° C. Finally, the reactions were cleaned using the Qiaquick (Qiagen) PCR purification system and eluted with 50 μl of water. Primary PCR reactions were performed with 10% Invitrogen PCRx enhancer solution and Platinum Taq polymerase using 10-20% of the first strand reaction as template in a total reaction volume of 20 μl. Nested pcr reactions used 1 μl of the primary reaction as template. Primers for Dux4-fl and -s detection in biopsy and cultured cell samples were 14A forward and 174 reverse, nested with 15A (or 16A) forward and 175 reverse. Primers for 3' detection were 182 forward and 183 reverse nested with 1A forward and 184 reverse (shown below).

Dux4-fl and -s in adult human tissues were detected using 14A forward and 183 reverse, then nested with 15A forward and 184 reverse primers. PCR cycling conditions were as follows for both primary and nested PCR: 94° C. 5 minutes denaturation, 35 cycles of 94° C. for 30", 62° C. for 30" and 68° C. for 2.5 minutes or 1 minute depending on expected length of product. A single final extension of 7 minutes at 68° C. was included. PCR products were examined on 2% NuSieve GTG (Lonza) agarose gels in TBE.

```
Primers for DUX4-fl and DUX4-s:
                                     (SEQ ID NO: 29)
    14A     5' CCCCGAGCCAAAGCGAGGCCCTGCGAGCCT 3'
            forward (SEQ ID NO: 30)
    174     5' GTAACTCTAATCCAGGTTTGCCTAGA 3'
            reverse (SEQ ID NO: 31)
    15A     5' CGGCCCTGGCCCGGGAGACGCGGCCCGC 3'
            forward (SEQ ID NO: 32)
    16A.    5' GGATTCAGATCTGGTTTCAGAATCGAAGG 3'
            forward (SEQ ID NO: 33)
    175     5' TCTAATCCAGGTTTGCCTAGACAGC 3'
            reverse Primers for DUX4-fl3':
                                     (SEQ ID NO: 24)
    182     5' CACTCCCCTGCGGCCTGCTGCTGGATGA 3'
            forward (SEQ ID NO: 34)
    183     5'CCAGGAGATGTAACTCTAATCCAGGTTTGC 3'
            reverse (SEQ ID NO: 25)
    1A      5' GAGCTCCTGGCGAGCCCGGAGTTTCTG 3'
            forward (SEQ ID NO: 35)
    184     5' GTAACTCTAATCCAGGTTTGCCTAGACAGC 3'
            reverse
```

Pooled PCR for DUX4.

To assess for stochastic expression of DUX4 in affected muscle cells, FSHD primary myoblasts were trypsinized and collected at confluence or after differentiation for 96 hr. Cells were counted and split into pools of 100-cell, 600-cell, or 10,000-cell aliquots. RNA was extracted from individual aliquots using Dynabeads mRNA DTRECT Kit (Invitrogen) following manufacturer's instructions. Bound polyadenylated mRNA was used directly for reverse transcription reaction with SuperScript III using on-bead oligo dT as primer. Synthesis was carried out at 52° C. for 1 hr, terminated at 70° C. for 15 min, followed by 15 min of RNase H treatment. 2 μL of cDNA product was used for nested DUX4-fl3' PCR as described above.

RT-PCR for Transcripts from Chromosomes 10 and 4.

PCR reactions were performed on RT reactions generated as described above and using nested primer sets to sequences in exons 1 and 2 that are common to alleles on chromosomes 4 as well as 10. Transcripts were detected using primers 1A and LS 187 followed by nesting with LS 138 and LS 188. Diagnostic polymorphisms (underlined) in the 5' end of exon 2 were used to assign allele origins of transcripts:

```
    4A161, 159, 168
                                (SEQ ID NO: 36)
    5' GTCTAGGCCCGGTGAGAGACTCCACACCGCG 3'

4A166
                                (SEQ ID NO: 37)
    5' GTCTAGGCCCGGTGAGAGACTCCACACAGCG 3'

10A 166
                                (SEQ ID NO: 38)
    5' GCCTAGGCCCGGTGAGAGACTCCACACAGCG 3'

4B163
                                (SEQ ID NO: 39)
    5' GTCCAGGCCCGGTGAGAGACTCCACACCGCG 3'

Primers
    138
                                (SEQ ID NO:   40)
    5' CGGAGTTTCTGCAGCAGGCGCAACCTCTCCT 3'
    forward 187
                                (SEQ ID NO: 41)
    5' CTGCTGGTACCTGGGCCGGCTCTGGGATCCC 3'
    reverse 188
                                (SEQ ID NO: 42)
    5' GTACCTGGGCCGGCTCTGGGATCCCCGGGAT 3'
    reverse
```

Quantitative RT-PCR for DUX4-fl3'.

For quantitative PCR, 1 μg of DNase'd RNA was used for first strand cDNA synthesis. Reverse transcription was performed as above, except at 52° C. for the synthesis reaction followed by 15 minutes of RNase H treatment and the Qiaquick purification eluted in 30 μl of water. One round of PCR reactions were performed using the same reagents as above and 2 μL of purified cDNA template. Primers for full length detection were 92 forward and 116 reverse. PCR cycling conditions were as follows: 95° C. 5 min denaturation, 36 cycles of 95° C. for 30", 62° C. for 30" and 68° C. for 1 min, and final extension of 5 min at 68° C. Sequence of the product matched DUX4. A standard curve for DUX4 template copies was generated from PCR reactions using the same primers and cycling conditions but with known dilutions of a plasmid containing full length DUX4 cDNA in water. Test sample PCR reactions and standard PCR reactions were run in triplicate and examined on the same 1% agarose/TBE gels stained with SYBR Gold (Invitrogen) for 40 min per manufacturer instructions. Fluorescence was detected with Typhoon Trio Multi-mode Imager (GE Healthcare): excitation laser 488 nm; emission filter 520DP 40, PMT 500 V, 100 m resolution. Histogram analysis was performed to ensure no signals were saturated. Gel band intensities were quantitated with ImageQuant TL v2005 (GE Healthcare) software. Estimates for the copies of DUX4 full length template in the test samples were interpolated from the line of best fit of the dilutional standards, with the lowest visible dilutional signal setting the detection limit. The interpolated number was doubled to adjust for the single-stranded cDNA input in contrast to the double-stranded plasmid standard input. This resulted in an estimated copy number of DUX4 full-length per ug of total RNA. Final copy number estimates per cell were calculated based on assumptions of 100% efficient reverse transcription and 3.3 μg of total RNA per cell.

```
    Primers for qPCR or DUX4-fl3'
                                (SEQ ID NO: 43)
      92  5' CAAGGGGTGCTTGCGCCACCCACGT 3'
          forward (SEQ ID NO:  44)
     116  5' GGGGTGCGCACTGCGCGCAGGT 3'
          reverse
```

Open Reading Frame PCR for DUX4-fl. To assess for the full coding region of DUX4, three rounds of PCR were performed on cDNA, totaling 36 cycles. Conditions for each round were as follows: 95° C. for 5', 3 cycles of 95° C. for 30" and 68° C. for 1'33", 3 cycles of 95° C. for 30" and 65° C. for 30" and 68° C. for 1'33", 6 cycles of 95° C. for 30" and 62° C. for 30" and 68° C. for 1'33". 3 μL of primary PCR was used in the secondary PCR, and 3 μL of secondary PCR were used in the tertiary PCR.

```
Primers for ORF PCR for DUX4-fl
                                (SEQ ID NO: 45)
     133   5' ATGGCCCTCCCGACACCCTCGGACAGCACC 3'
           forward (SEQ ID NO: 46)
     134   5' CTCGGACAGCACCCTCCCCGCGGAAGCCCG 3'
           forward (SEQ ID NO: 47)
     135   5' GGAAGCCCGGGGACGAGGACGGCGACGGAG 3'
           forward (SEQ ID NO: 48)
     136   5' CTAAAGCTCCTCCAGCAGAGCCCGGTATTCTTCCTC 3'
           reverse (SEQ ID NO: 49)
     137   5' CCCGGTATTCTTCCTCGCTGAGGGGTGCTTCCAG 3'
           reverse (SEQ ID NO:  50)
     138   5' GGGGTGCTTCCAGCGAGGCGGCCTCTTCCG 3'
           reverse
```

3' RACE for Dux4 in Human Testes.

3' RACE was performed on total RNA using Invitrogen Gene Racer kit essentially as described. Prior to PCR with gene specific primers and the GeneRacer 3' primers, the RT reaction was cleaned using Qiaquick (Qiagen) spin columns as described above. Gene specific forward primers were 182 and 1A (nesting). PCR products were gel purified, cloned into TOPO 4.0 (Invitrogen), and sequenced.

Generation of Induced Pluripotent Stem (IPS) Cells.

IPS cells were generated by forced expression of human OCT4, SOX2, and KLF4 using the retroviral vectors essentially as previously described in Lemmer et al, *Am J Hum Genet* 81:884-894 (2007)). MLV vectors (pMXs-hOCT4, pMXs-hSOX2, and pMXs-hKLF4) were purchased from Addgene (Cambridge, MA) and vector preparations were generated by transient transfection of Phoenix-GP cells (Tawil, R., et al., *Muscle Nerve* 34:1-15 (2006)) with pCI-VSV-G and vector plasmids (1:1 ratio), replacing the culture medium 16 and 48 hours later, harvesting and filtering (0.45 mm pore size) conditioned medium after a 16 hour exposure to cells, and concentrating 50 to 100-fold by centrifugation (Zeng et al., *PloS Genet* 5:e1000559 (2009). Transduction with MLV vectors was performed with polybrene (4 mg/ml concentration) (Sigma-Aldrich Corp., St. Louis, MO) added to the medium. IPS cell colonies were identified by their characteristic morphology, cloned by microdissection, and expanded on irradiated mouse embryo fibroblasts (6000 rads) for further characterization. Typically, 5×10$^4$ fibroblasts cultured in DMEM+10% FBS were seeded to a 9.4 cm$^2$ well on day −1, the medium was replaced with medium containing vectors and polybrene on day 0, and changed again to medium with DMEM +10% FBS on day 1. Cells were detached with trypsin and seeded to five 55 cm$^2$ dishes on day 2 and medium changed on day 4. On day 6, cells were again detached with trypsin and 5×10$^5$ cells seeded to 55 cm$^2$ dishes containing 7×10$^5$ irradiated mouse embryo fibroblasts (6000 rads) in human ES cell culture medium (see below). Medium was replaced every other day and colonies with typical morphology of IPS cells appear between day 20 and day 30 post infection. Colonies are mechanically dissected using drawn Pasteur pipettes and seeded to mouse embryo fibroblast feeder layers for culture and passaged every 2-3 days using 2 u/ml dispase.

Stem Cell Culture.

IPS cells and Human ES cells were grown in a solution of DMEM:F12 (1:1) with 3.151 g/L glucose, supplemented with L-Glutamine (Invitrogen), non-essential amino acids (10 mM (100×) liquid, Invitrogen, #11140-076), sodium pyruvate (100 mM (100×), liquid, #11360-070), 20% knockout serum replacer (#10828010) (Invitrogen, Carlsbad, CA), 1mM☐b-mercapto Ethanol (Sigma, St. Louis MO), and 5 ng/ml basic fibroblast growth factor (Peprotech, #AF-100-18B). Cells were generally cultured in 0.1% gelatin coated dishes containing irradiated mouse embryo fibroblasts at a density of 1.3×10$^4$ cells/cm$^2$. When cells were used as a source of RNA, DNA, or protein, they were cultured on matrigel (1:60 dilution, BD Biosciences, #356234) coated dishes in medium conditioned by exposure to confluent layers of mouse embryo fibroblasts over a 3-day period. Cells were passaged a minimum of 4 times under these conditions before DNA, RNA, or protein was harvested.

Detection of Embryonic Antigens in IPS Cells.

IPS cells were evaluated for the presence of tissue non-specific alkaline phosphatase activity by fixing colonies in phosphate buffered saline solution containing 0.5% gluteraldehyde, and washing ×3 in PBS. A staining buffer containing 100 mM Tris pH 8.5, 100 mM NaCL, 50 mM MgCl$_2$, 0.1 mg/ml 5-Bromo-4-chloro-3-indolyl phosphate (xphos) and 1 mg/ml p-Nitro-Blue tetrazolium chloride (NBT) (Sigma-Aldrich, St. Louis, MO, USA) was used to detect tissue non-specific alkaline phosphatase activity. Stage Specific embryonic antigen 4 (SSEA4) was detected using mouse monoclonal MC-813-70 and goat anti-mouse FITC conjugated secondary. TRA-1-60 was detected using mouse monoclonal TRA-1-60 (Millipore, Billerica, MA), and goat anti-mouse FITC conjugated secondary (Millipore, Billerica, MA). Human NANOG was detected with a goat polyclonal flurophore (Northern Lights™) conjugated antibody (NL493, R & D systems, Minneapolis, MN). Human OCT4 was detected with a rabbit polyclonal (Abcam, Cambridge, MA) and goat anti-rabbit secondary conjugated with the Alexa 488 flurophore (Invitrogen, Carlsbad, CA). Cell karyotypes were determined by the University of Washington Cytogenetics laboratory.

Teratoma Formation and Staining.

Induced pluripotent stem cells were detached from culture dishes with dispase (2 units/ml working concentration), 2×10$^6$ cells resuspended in F12:DMEM (1:1 mixture) medium without supplements, and injected into the femoral muscle of SCID-Beige mice (CB17.B6-Prkdc$^{scid}$Lyst$^{bg}$/Crl Charles River, Stock #250). Mice were maintained under biosafety containment level 2 conditions and palpable tumor masses developed approximately 6 weeks later. When a tumor mass was palpable, the mice were sacrificed and tumor tissue fixed for several days in phosphate buffered saline solution containing 4% formaldehyde, and imbedded in paraffin. Sections of the tumor (5 mM thickness) were placed on slides and stained with hematoxylin and eosin using standard protocols.

Embryoid Body Formation.

Human IPS were prepared for embryoid body formation by expanding cell numbers on mouse irradiated feeder layers detaching colonies with dispase, triturating with a Pasteur pipette, and seeding colony fragments to dense layers of mouse embryo fibroblast feeders (5×10$^4$ irradiated mef/cm$^2$) prior to EB formation. Four days later, densely grown colonies from a 55 cm$^2$ dish were treated with dispase and gently detached by pipetting or scraping. Colony fragments were washed several times and seeded (1:1) to Ultra Low Attachment 55 cm$^2$ culture dishes (Corning, Corning, NY) in DMEM supplemented with 20% Fetal Bovine Serum. Every three days, EB's were allowed to gravity settle and the medium was gently removed and replaced. RNA and chromatin was harvested three weeks later for analysis.

Analysis of Gene Expression in IPS Cells.

IPS cells were grown without MEF feeders for preparation of RNA to be used in gene expression analysis. Cells were seeded to matrigel coated dishes and filtered conditioned medium from mouse embryo fibroblasts was used for culture. RNA was purified from cells using standard techniques and treated with DNAse to remove residual genomic DNA from the cells. cDNA synthesis was primed with oligo dT and reverse transcriptase. In all cases a tube was processed in parallel without the addition of reverse transcriptase to serve as a control for possible DNA contamination. The presence of RNA transcripts were detected using 28 thermal cycles with the following primer pairs. RNA was replaced with water as a negative control for the reaction.

TABLE 4

| Primer Pairs for Gene Expression Analysis in IPS Cells | | |
|---|---|---|
| Gene | Forward primer | Reverse primer |
| OCT | 5'-gacaggggcaggggaggagctagg-3' (SEQ ID NO: 51) | 5'-cttccctccaaccagttgccccaaac 3' (SEQ ID NO: 52) |

TABLE 4-continued

| Primer Pairs for Gene Expression Analysis in IPS Cells | | |
| --- | --- | --- |
| Gene | Forward primer | Reverse primer |
| SOX2 | 5'-gctagtctccaagcgacgaa-3 (SEQ ID NO: 53) | 5'-gcaagaagcctctccttgaa-3' (SEQ ID NO: 54) |
| hTERT | 5'-cctgctcaagctgactcgacaccgtg-3 (SEQ ID NO: 55) | 5'-ggaaaagctggccctggggtggagc-3' (SEQ ID NO: 56) |
| NANOG | 5'-cagtctggacactggctgaa-3 (SEQ ID NO: 57) | 5'-ctcgctgattaggctccaac-3' (SEQ ID NO: 58) |
| KLF4 | 5'-tatgacccacactgccagaa-3' (SEQ ID NO: 59) | 5'-tgggaacttgaccatgattg-3 (SEQ ID NO: 60) |
| cMYC | 5'-cggaactcttgtgcgtaagg-3' (SEQ ID NO: 61) | 5'-ctcagccaaggttgtgaggt-3' (SEQ ID NO: 62) |
| GAPDH | 5'-tgttgccatcaatgacccctt-3 (SEQ ID NO: 63) | 5'-ctccacgacgtactcagcg-3' (SEQ ID NO: 64) |

Chromatin Immunoprecipitation

The Chromatin Immunoprecipitation (ChIP) analysis of repressive histone modifications at the 5'-region of DUX4 was performed on primary fibroblasts, induced pluripotent stem (iPS) cells and corresponding embryoid bodies (EB) derived from unaffected individuals and FSHD patients, following a previously described protocol (Nelson et al., *Nat Protoc* 1:179-185 (2006)). Briefly described, cells were cross-linked with formaldehyde at 1.42% final concentration for 15 min at room temperature, quenched, and sonicated to generate 500-100 bp DNA fragments. g aliquots (representing approximately 500,000 cells) of chromatin were used for each immunoprecipitation with anti-Histone H3K9me3 antibodies (Abcam) and nonimmune IgG fraction used as a mock control. After reverse cross-linking and DNA purification, the IP products were analyzed by real time PCR. The 5'-region of the DUX4 gene was analyzed using the 4q-specific D4Z4 primers, 4qHox or Q-PCR, that detect internal D4Z4 units including the last repeat unit (Zeng et al., *PloS Genet* 5:e1000559 (2009)). The real-time PCR signals obtained for IP antibodies were normalized to mock control IgG and to input to account for the number of D4Z4 repeats. Data are presented as mean±stdev and represent the results of at least three independent immunoprecipitations followed by real-time PCR analysis done in triplicates.

Generation of Antibodies to DUX4

We generated monoclonal antibodies to the amino- and carboxy-terminus of DUX4 for this study. Briefly described, the N-terminal 159 amino acids and the C-terminal 76 amino acids of DUX4 were fused to glutathione-s-transferase tags, respectively, and injected into the animals as immunogens. Mouse monoclonals were produced at the Antibody Development core facility at the Fred Hutchinson Cancer Research Center and will be commercially available. Rabbit monoclonals were produced in collaboration with and will be available through Epitomics (Burlingame, CA). Hybridoma clones were screened for specificity by ELISA, western blot and immunofluorescence in C2C12 myoblasts transfected with DUX4. The C-terminal antibodies P4H2, P2B1 and E5-5 are specific to DUX4 and do not recognize DUX4c, whereas the N-terminal antibodies P2G4 and E14-3 recognize both DUX4 and DUX4c.

Protein Analysis

For western blotting, protein lysates were prepared by resuspension in standard Laemmli buffer and sonicated briefly. Equivalent amounts of test samples were loaded onto 4-12% gradient gel and transferred to nitrocellulose membrane, which were then blocked with 5% non-fat dry milk in PBS 0.1% Tween-20. Custom monoclonal antibodies (Epitomics) raised against DUX4 were used to probe the blots and detected by ECL reagent (Pierce). Membranes were stripped and reprobed with anti-α-tubulin antibody (Sigma-Aldrich) for loading control. Immunoprecipitation was performed on samples resuspended in PBS with protease inhibitor cocktail (Roche) by incubating overnight at 4° C. with pooled anti-DUX4 rabbit monoclonal antibodies bound to protein A- and G-coupled Dynabeads (Invitrogen). Samples were eluted directly into Laemmli buffer and analyzed on western blot as described. For immunofluorescence, cells were fixed in 2% paraformaldehyde for 7 min and permeabilized in 1% Triton X-100 in PBS for 10 min at room temperature. Cells were probed with pairs of rabbit and mouse primary antibodies raised against N- or C-terminus of DUX4 diluted in PBS overnight at 4° C. Double labeling was detected with Alexa Fluor 488 goat anti-mouse IgG and Alexa Fluor 568 goat anti-rabbit IgG (Invitrogen) at 1:500 in PBS for 1 hr and counterstained with DAPI.

Dux4 IHC on Frozen Tissue

Immunohistochemistry was performed by the FHCRC Experimental Histopathology Shared Resource. Six-micron sections of OCT embedded frozen de-identified human testes tissue were sectioned and fixed for 10 minutes in 10% neutral buffer formalin. The slides were rehydrated in TBS-T wash buffer, permeablized with 0.1% triton X-100 for 10 minutes, and then endogenous peroxidase activity was blocked with 0.3% hydrogen peroxide (Dako, Carpinteria, CA) for 8 minutes. Five minute incubation in 50% acetone and 50% methanol was used for antigen retrieval on a subset of slides. Protein block containing 0.25% casein and 0.1% Tween 20 was applied for 10 minutes. Slides were incubated over night at 4° C. with a 1:5 dilution of either clone E5-5 or P2B1 in a 0.3 M NaCl antibody diluent containing 1% BSA. Staining was developed using Mach2 HRP-labeled polymers (Biocore Medical, Concord, CA). The staining was visualized with 3,3'-diaminobenzidine (DAB, Dako) for 8 minutes, and the sections were counterstained with hematoxylin (Dako) for 2 minutes. Concentration matched isotype control slides were run for each tissue sample (Jackson ImmunoResearch).

49

Results

Alternative DUX4 mRNA Splicing Distinguishes Control and FSHD Muscle

Figures 8A, 8B:
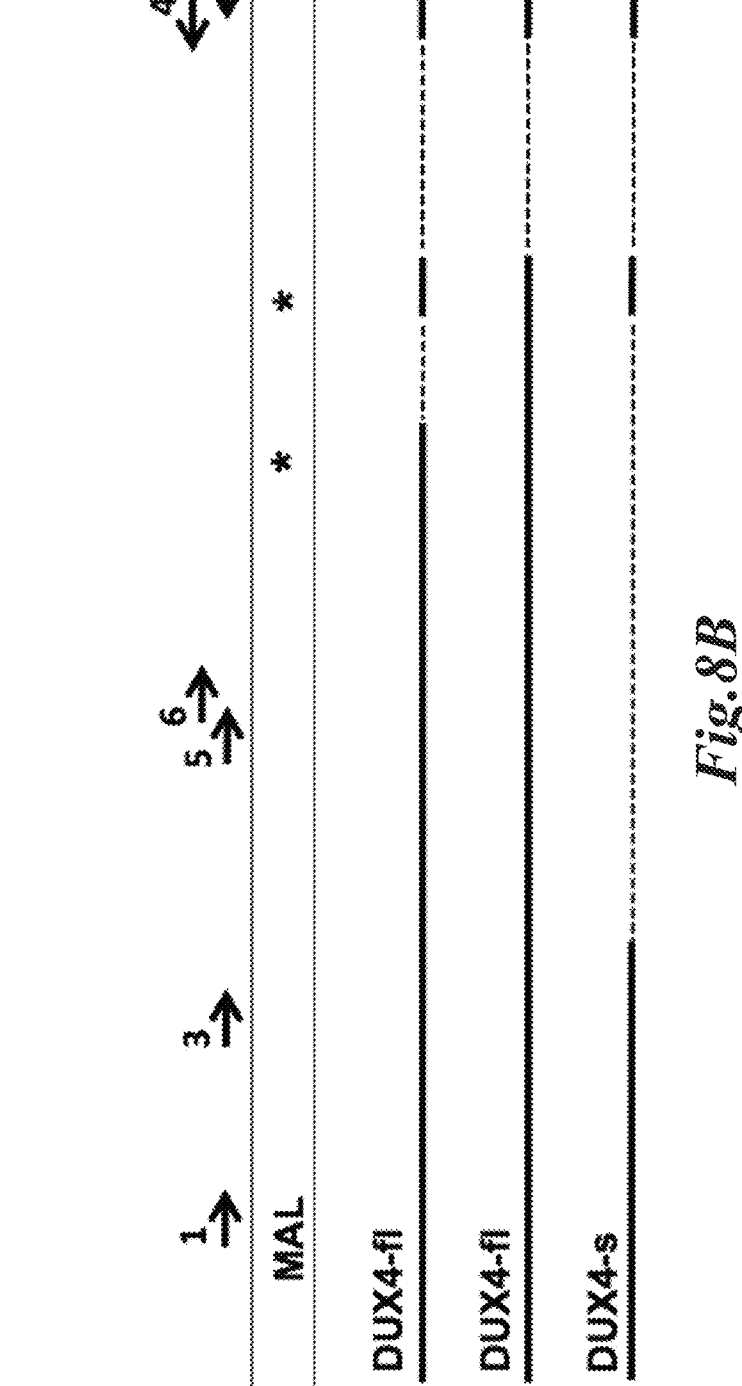
FIG. 8A is a schematic diagram of the D4Z4 repeat array with two most telomeric full units (large triangles), the last partial repeat, and the adjacent pLAM sequence that contains exon 3. Exons are shown as shaded rectangles, with exon 1 and 2 in the D4Z4 units and exon 3 in the pLAM region, as described in Example 2.
FIG. 8B is a diagram of the DUX4 coding region, wherein the open rectangle represents the region of D4Z4 and pLAM containing the DUX4 retrogene and the solid and dashed lines represent the regions of exons and introns, respectively, in the short splice form (DUX4-s) and the transcript with the full-length DUX4 ORF (DUX4-fl), which has two isoforms with alternative splicing in the 3-prime untranslated region. First round PCR for DUX4-fl and DUX4-s was performed with primer sets 1 and 2 and second round PCR with nested primers 3 and 4. Nesting was used to ensure specificity and because of the very low abundance of DUX4 transcripts, both DUX4-fl and DUX4-s. MAL represents location of initial amino-acid codons; *, Stop codons; P, polyadenylation site, as described in Example 2.

As described in Example 1, we have demonstrated that the sequence polymorphisms of the 4A161 haplotype necessary for FSHD include the region of the poly-adenylation signal for the DUX4 mRNA, and we further showed that this correlated with the detection of DUX4 mRNA in three FSHD muscle cultures compared to controls. Our previous study of RNA transcripts from D4Z4 repeat units identified a full-length mRNA transcript that contains the entire DUX4 open reading frame and has one or two introns spliced in the 3-prime UTR, and a second mRNA transcript utilizing a cryptic splice donor in the DUX4 ORF that maintains the amino-terminal double-homeobox domains and removes the carboxyterminal end of DUX4, as illustrated in FIGS. 8A and B. We will refer to these two transcripts as DUX4-fl (full length) and DUX4-s (shorter ORF), respectively (see Snider et al., *Hum Mol Genet* 18:2414-2430 (2009) for splice junction sequences).

FIG. 8A is a schematic diagram of the D4Z4 repeat array with two most telomeric full units (large triangles), the last partial repeat, and the adjacent pLAM sequence that contains exon 3. Exons are shown as shaded rectangles, with exon 1 and 2 in the D4Z4 units and exon 3 in the pLAM region.

FIG. 8B is a diagram of the DUX4 coding region, wherein the open rectangle represents the region of D4Z4 and pLAM containing the DUX4 retrogene and the solid and dashed lines represent the regions of exons and introns, respectively, in the short splice form (DUX4-s) and the transcript with the full-length DUX4 ORF (DUX4-fl), which has two isoforms with alternative splicing in the 3-prime untranslated region. First round PCR for DUX4-fl and DUX4-s was performed with primer sets 1 and 2 and second round PCR with nested primers 3 and 4. Nesting was used to ensure specificity and because of the very low abundance of DUX4 transcripts, both DUX4-fl and DUX4-s. MAL, represents location of initial amino-acid codons; *, Stop codons; P, polyadentylation site.

Figure 8C:
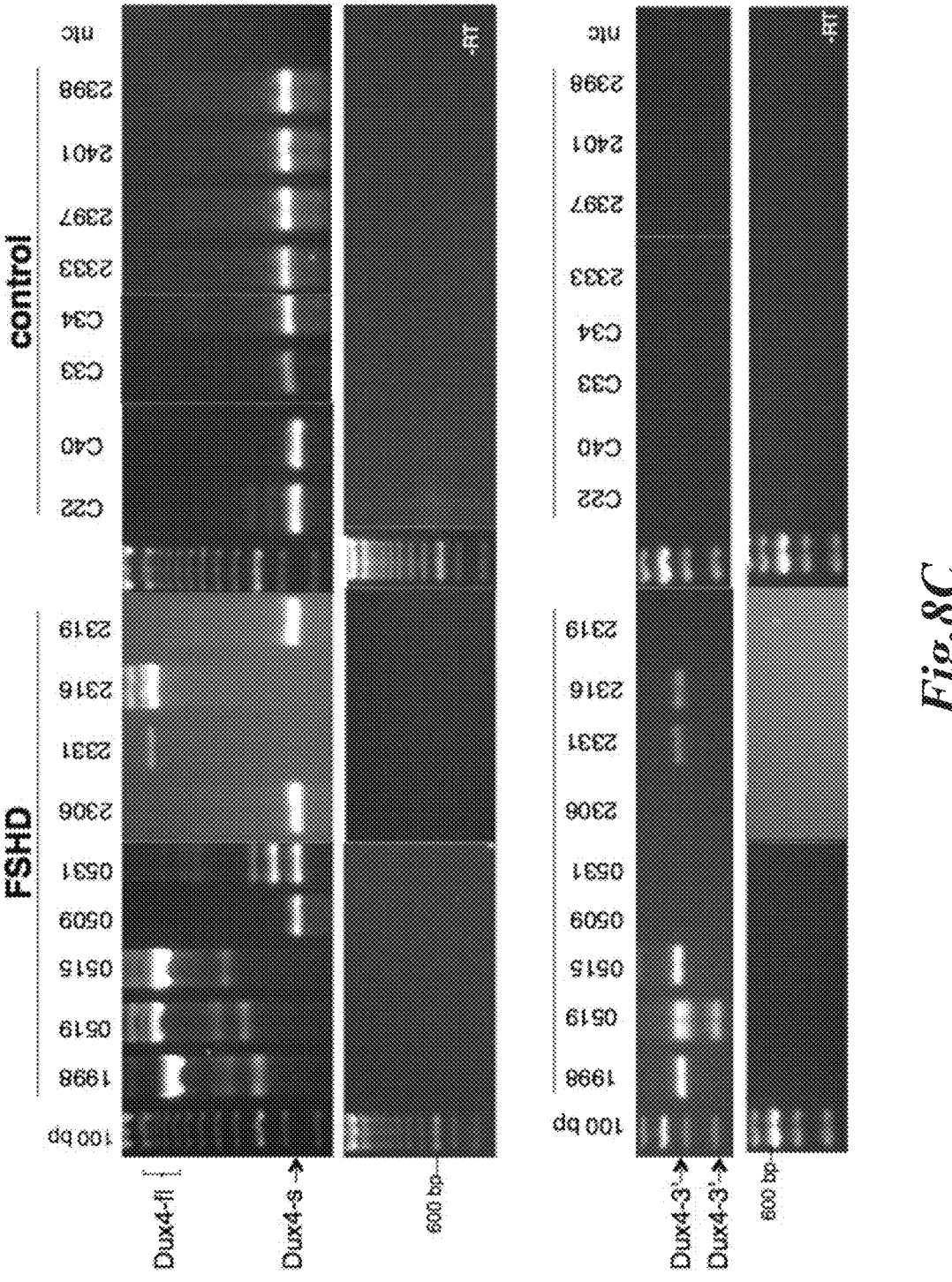
FIG. 8C shows the results of a representative PCR assay from FSHD and control muscle biopsies for DUX-fl, DUX4-s and DUX4-fl3', as described in Example 2.

FIG. 8C shows the results of a representative PCR assay from FSHD and control muscle biopsies for DUX-fl, DUX4-s and DUX4-fl3'. FIG. 8C is a composite image of representative PCR products from FSHD and control muscle biopsies for DUX4-fl, DUX4-s, and DUX4-fl3'. DUX4-fl and DUX4-s are indicated. Variation in size reflects alternative intron usage and the faint intermediate bands represent background non-DUX4 PCR amplicons frequently associated with repetitive sequence.

The PCR approach in the Lemmers et al study (Science 2010, supra) would not have detected the DUX4-s mRNA because it relied on amplification solely of the 3-prime region of the polyadenylated mRNA with the reverse primer in the exon 1 region that is not present in the DUX4-s mRNA.

We used oligo-dT primed cDNA and a PCR strategy that would detect both DUX4-fl and DUX4-s (see FIG. 8B) to determine the presence of polyadenylated DUX4 mRNAs in quadriceps muscle needle biopsies from ten FSHD and fifteen control individuals, as shown in FIG. 8C, and summarized in TABLE 5.

In general, we used two cycles of PCR with nested primers to increase specificity and to detect low abundance transcripts. DUX4-fl was detected in five of the ten FSHD samples, based on primers amplifying DUX4-fl and primers amplifying the 3-prime region of DUX4-fl (DUX4-fl3') that is contained in DUX4-fl but not in DUX4-s (see FIG. 8B). The sequenced products matched the FSHD-permissive 4A161 haplotype polymorphisms and the variation in size of the PCR product reflected alternative splicing of only the second intron in the UTR or both the first and second UTR introns (see FIG. 8B). In contrast, none of the fifteen control samples expressed mRNA that amplified with primers to DUX4-fl or DUX4-fl3', including seven biopsies from individuals with at least one 4A161 chromosome. Instead, DUX4-s was detected in all control samples with 4A161 and in some of the FSHD samples. We did not detect DUX4 transcripts using these primers in six control biopsies that do not contain the 4A chromosome. These data indicate that the 4A D4Z4 region is actively transcribed and produces alternatively spliced and polyadenylated DUX4 mRNA in both FSHD and unaffected individuals. However, the full-length DUX4 mRNA was only detected in the FSHD muscle biopsies, whereas DUX4-s was detected in muscle from controls and some FSHD individuals.

TABLE 5

DUX4 mRNA Expression in FSHD and Control Biopsies

| Biopsy Code | Status | Haplotypes[A] | Dux4-fl | Dux4-s | 3-prime |
|---|---|---|---|---|---|
| F 1998 | FSHD | A161(10)/n.d. | XS | O | XS |
| F 0519 | FSHD | A161(8)/A161 | XS | O | XS |
| F-0515 | FSHD | A161(5)/A161 | XS | O | XS |
| F-0509 | FSHD | A161(5)/A166H | O | XS | O |
| F-0531 | FSHD | A161(7)/A161 | O | XS | O |
| F-2306 | FSHD | A161(4)/B163 | O | X | O |
| F-2331 | FSHD | A161(3)/B163 | X | O | XS |
| F-2316 | FSHD | A161(6)/A168 | X | O | XS |
| F-2319 | FSHD | A161(5)/B168 | O | X | O |
| F-2315 | FSHD | A161(5)/B168 | O | O | O |
| C22 | contr | A161/B163 | O | X | O |
| C34 | contr | A161/B163 | O | XS | O |
| C40 | contr | A161/B168 | O | X | O |
| 2333 | contr | A161/A161 | O | X | O |
| 2397 | contr | A161/B168 | O | X | O |
| 2401 | contr | A161/B168 | O | X | O |
| 2398 | contr | A161/B163 | O | X | O |
| C33 | contr | A166/B170 | O | X | O |
| C39 | contr | A166/B168 | O | O | O |
| C10 | contr | B168/B168 | O | O | O |
| C11 | contr | B168/B163 | O | O | O |
| C31 | contr | B163/B163 | O | O | O |
| 2318* | contr | B169/B166 | O | O | O |
| C20 | contr | B168/B168 | O | O | O |
| C38 | contr | B162/B163 | O | O | O |

[A]Chromosome 4 haplotype. For FSHD the number in parentheses indicates the number of D4Z4 units on the contracted allele;
n.d., indicates that the haplotype of the second allele was not determined.
X, product present;
XS, product sequenced;
O, product absent
*has contracted 10qA allele with 9 repeats The expression of DUX4-fl mRNA in FSHD muscle biopsies could be a primary consequence of the D4Z4 contraction or a secondary response to the inflammation associated with muscle degeneration and/or regeneration. Therefore, we extended our analysis to myoblast cultures derived from four control and six FSHD individuals, including one individual with FSHD2. As seen in the muscle biopsies, the control muscle cells contained no detectable amounts of DUX4-fl mRNA, whereas muscle cells derived from both FSHD1 and FSHD2 samples expressed DUX4-fl transcripts as well as the DUX4fl-3' (TABLE 6). All control and a subset of the FSHD samples expressed DUX4-s.

51

TABLE 6

DUX4 mRNA Expression in FSHD and Control Cell Lines

| Cell Code | Status | Haplotypes | Cell type[A] | Dux4-fl | Dux4-s | 3-prime |
|---|---|---|---|---|---|---|
| MB73 | FSHD | A161(8)[B]/161[C] | MB | X | X | X |
| MB183 | FSHD | A161(5)/B163 | MB | X | O | X |
| MB148 | FSHD | A161(3)/A161 | MB | X | O | X |
| MB200 | FSHD2 | A161(14)/B168 | MB | X | XS | X |
| MB216 | FSHD | A161(6)/A168 | MB | O | O | O |
| MB219 | FSHD | A161(5)/B168 | MB | O | O | O |
| MB230 | contr | A161/163[A] | MB | O | X | O |
| MB196 | contr | A161/163[A] | MB | O | X | O |
| MB226 | contr | A161/A161 | MB | O | X | O |
| MB135 | contr | A161/B163 | MB | O | XS | O |
| MB73 | FSHD | A161/161 | MT | X | X | XS |
| MB183 | FSHD | A161/B163 | MT | X | O | X |
| MB148 | FSHD | A161/A161 | MT | X | O | XS |
| MB200 | FSHD2 | A161/B168 | MT | XS | O | XS |
| MB216 | FSHD | A161/A168 | MT | X | O | XS |
| MB219 | FSHD | A161/B168 | MT | X | O | X |
| MB230 | contr | A161/163[A] | MT | O | X | O |
| MB196 | contr | A161/163[A] | MT | O | X | O |
| MB226 | contr | A161/A161 | MT | O | X | O |
| MB135 | contr | A161/B163 | MT | O | X | O |
| M83-9 | contr | A161/168[A] | fibro | O | XS | O |
| M83-9 | contr | | IPS | XS | O | X |
| M83-9 | contr | | EB | O | X | O |
| 43-1 | FSHD | A161(5)/A161 | fibro | XS | O | O |
| 43-1 | FSHD | | IPS | XS | O | X |
| 43-1 | FSHD | | EB | X | O | XS |
| 83-6 | FSHD | A161(7)/B168 | fibro | XS | XS | X |
| 83-6 | FSHD | | IPS | X | O | X |
| 83-6 | FSHD | | EB | X | O | XS |

[A]MB, myoblasts; MT, myotubes; fibro, fibroblasts; IPS, induced pleuripotent stem cells, EB, embryoid bodies
[B]Number of repeats on contracted allele, if known
[C]Assignment of the second 4q allele variant is incomplete
n.d., not tested; X, product present; XS, product sequenced; O, product absent These data are consistent with observations made in the muscle biopsies and indicate that both FSHD and control muscle cells actively transcribe DUX4. Unaffected cells produce DUX4-s from a splice donor site in the DUX4 ORF, whereas FSHD cells produce DUX4-fl with an alternative splice donor site after the translation termination codon of the DUX4 ORF.

a Small Fraction of FSHD Muscle Cells Produce a Relatively Large Amount of DUX4

In both control and FSHD cells, the DUX4 mRNA transcripts, either DUX4-fl or DUX4-s, were only detected after nested PCR amplifications, indicating very low abundance of DUX4 mRNA in the FSHD and control biopsies and cells. We used the 9A12 mouse monoclonal anti-DUX4 antibody (Dixit et al., PNAS 104:18157-18162 (2007) and also produced mouse and rabbit monoclonal antibodies to the amino-terminal and carboxyterminal portion of the DUX4 protein (Geng et al., Hybridoma (Larchmt), vol 30(2):125-30 (2011), but were unable to detect DUX4 protein in western analysis of FSHD muscle cultures, consistent with the very low amounts of DUX4 mRNA.

Low transcript abundance could reflect a small number of transcripts in every cell or a large number of transcripts in a small subset of cells in the population. We assessed the presence of DUX4-fl mRNA in samplings of 100, 600, and 10,000 FSHD cultured muscle cells by RT-PCR analysis, in which RT-PCR for full length DUX4 (DUX4-3') was performed in duplicate on polyadenylated RNA isolated from ten pools of 600 cultured FSHD muscle cells and a single pool of 10,000 cells. DUX4-fl mRNA was present in five-out-of-ten pools of 600 cells and three-out-of-20 pools of 100 cells, as well as in the single pool of 10,000 cells (data not shown). This frequency of positive pools indicates that approximately one-out-of-1000 cells is expressing a relatively abundant amount of DUX4-fl mRNA at any given time.

Immunostaining of cultured FSHD muscle cells and control cultured muscle cells with four independent anti-DUX4 monoclonal antibodies showed that approximately one-out-of-1000 nuclei co-stained with an antibody to the amino-terminus and an antibody to the carboxy-terminus of DUX4, whereas no nuclei in the control cultures showed staining (data not shown). Approximately 1 cell per 1000 showed nuclear staining and the co-localization of both the n-terminal and c-terminal regions indicates that these cells are expressing the full-length DUX4 protein. No positive nuclei were apparent in the control muscle cultures (data not shown).

Both the mRNA analysis and the immunodetection indicate that approximately 0.1% of FSHD muscle nuclei express DUX4 mRNA and protein. This could represent transient bursts of expression or stochastic activation of expression that leads to cell death, or both. Forced expression of DUX4 has been shown to induce apoptosis in muscle cells (Snider et al., Hum Mol Genet 18:2414-2430 (2009); Bosnakovski D. et al., PloS One 4:e7003 (2009)). When DUX4 is expressed in control human muscle cells by lenti-viral delivery, the DUX4 protein is distributed relatively homogeneously during the first 24 hrs and then aggregates in nuclear foci at 48 hrs when the cells are undergoing apoptosis (data not shown). These DUX4 nuclear foci associated with apoptosis are present in the nuclei of FSHD muscle cultures. Expression of DUX4-s in control human muscle cells does not induce apoptosis and does not accumulate in nuclear foci at 48 hrs (data not shown).

Therefore, the data from these experiments indicates that a small number of FSHD muscle cells express a relatively large amount of DUX4, and that FSHD muscle cells that express endogenous full-length DUX4 also exhibit the nuclear foci that are characteristic of DUX4-induced apoptosis.

DUX4 mRNA and Protein are Expressed in Human Testis

Although there is no known function of DUX4 in human biology, the open reading frame has been conserved (Clapp et al., Am J Hum Genet 81:264-279 (2007)). DUX4 is a retrogene thought to be derived from DUXC (Clapp et al., Am J Hum Genet 81:264-279 (2007)), or a DUXC-related gene, but also similar to the DUXA family mouse Duxbl gene (Wu et al., Duxbl Dev Dyn 239:927-940)). Therefore, if DUX4 has a biological function it is likely to be similar to DUXC or Duxbl. Duxbl is expressed in mouse germ-line cells and we reasoned that because retrotranspositions entering the primate lineage must have occurred in the germ-line, then DUXC must be expressed in the germ-line. Indeed, we detect the canine DUXC mRNA in canine testis but not in canine skeletal muscle (data not shown). Therefore, if DUX4 has a biological function similar to DUXC, we would anticipate DUX4 expression in the human germ-line.

Figure 9A:
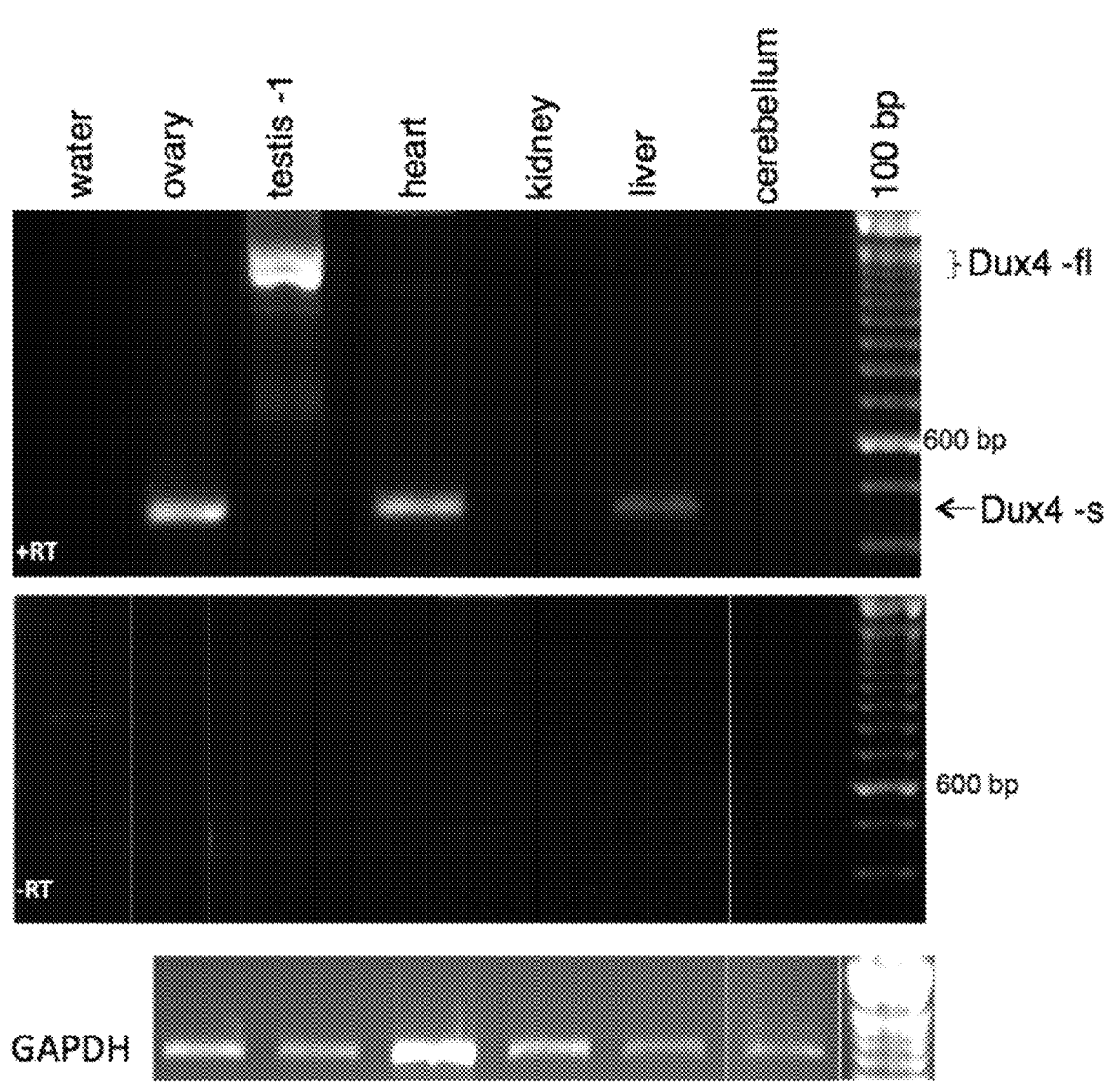
FIG. 9A shows the results of RT-PCR analysis of RNA from human tissues showing DUX4-fl in the testis sample (Testis-1) and DUX4-s in ovary, heart, and liver, as described in Example 2.
Figure 9B:
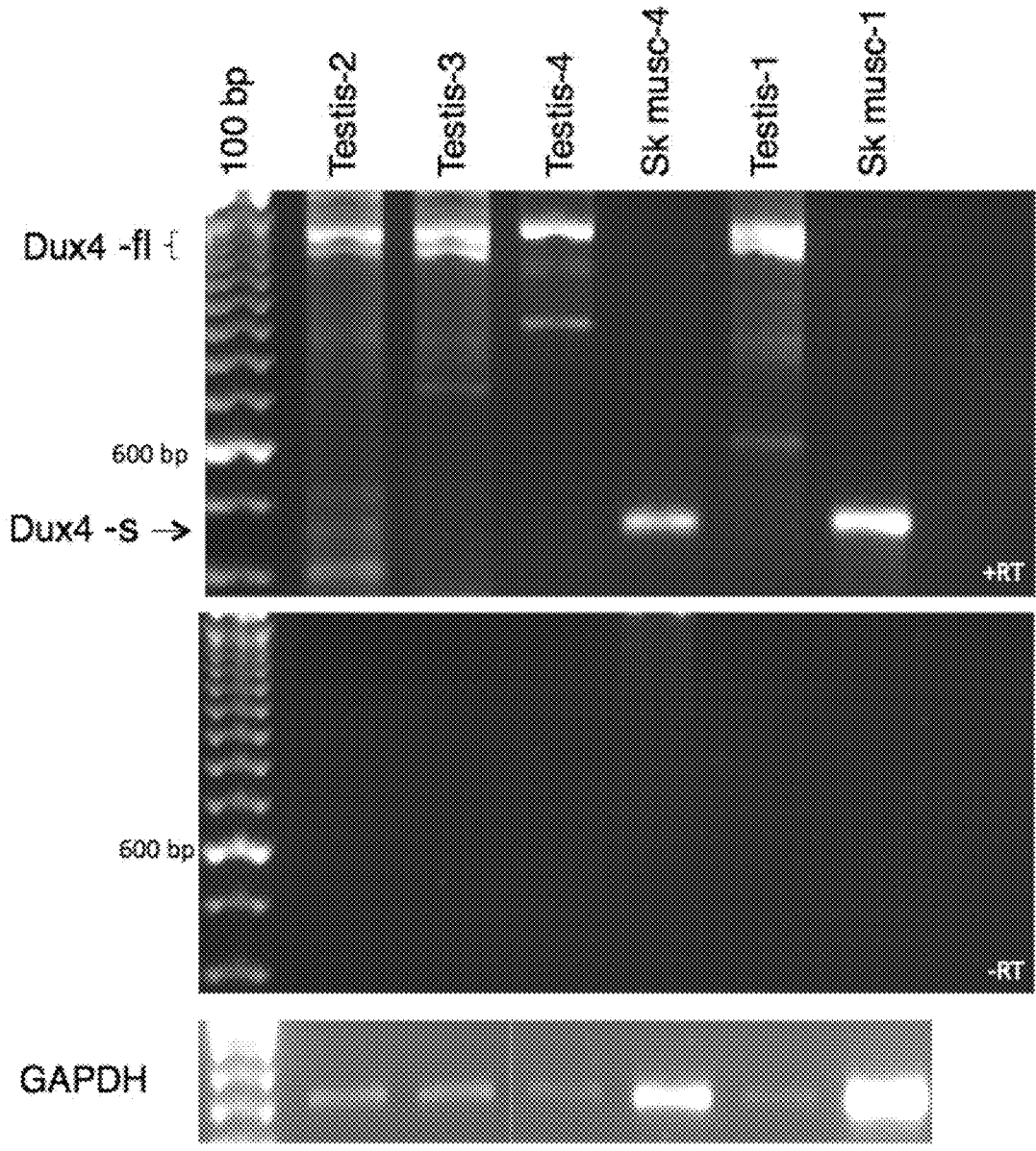
FIG. 9B shows the results of RT-PCR analysis of three additional testis samples and matched skeletal muscle RNA from the Testis-1 and Testis-4 donors, as described in Example 2.

We obtained RNA from different adult human tissues and identified DUX4-fl in testis (FIG. 9A), whereas DUX4-s was present in a subset of differentiated tissues. DUX4-fl was detected in six additional testis samples, whereas only DUX4-s was detected in donor-matched skeletal muscle (FIGS. 9B and C). Quantitative PCR (qPCR) showed that human testis samples expressed almost 100-fold higher amounts of DUX4 mRNA compared to FSHD muscle biopsies, and almost 15-fold higher amounts compared to cultured FSHD muscle cells (FIG. 9D). Western analysis using three different DUX4 antibodies identified a protein of the correct mobility in protein lysates from testes but not in other cells or tissues that do not express DUX4-fl mRNA, including control muscle cells (FIG. 9E and data not shown). Furthermore, immunoprecipitation of testis proteins with rabbit anti-DUX4 antibodies followed by western with a mouse monoclonal antibody to DUX4 detected the same protein (FIG. 9F).

FIG. 9A shows the results of RT-PCR analysis of RNA from human tissues showing DUX4-fl in the testis sample (Testis-1) and DUX4-s in ovary heart and liver. Note that each sample is from an unknown individual and their genotype is not known.

FIG. 9B shows the results of RT-PCR analysis of three additional testis samples and matched skeletal muscle RNA from the Testis-1 and Testis-4 donors.

Figure 9C:
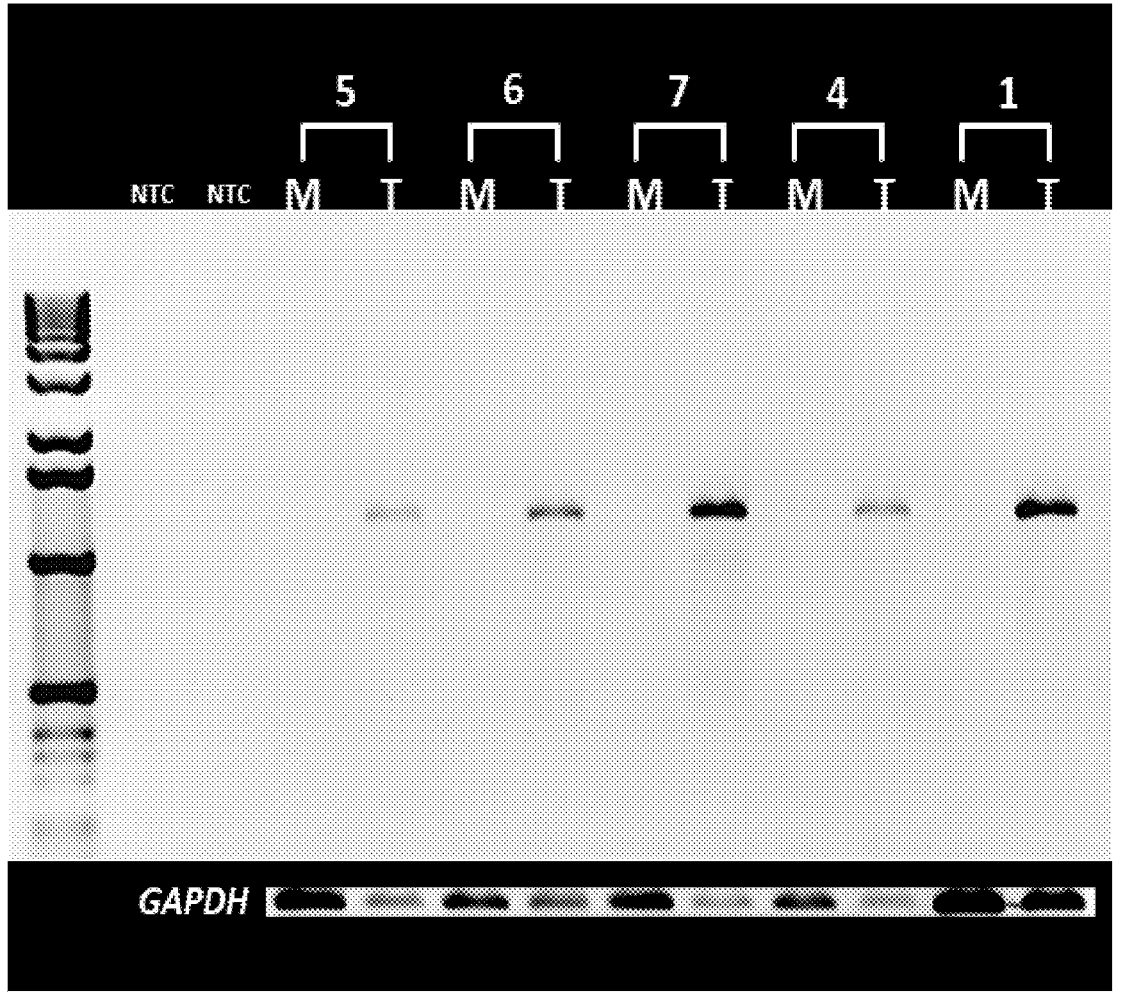
FIG. 9C shows the results of RT-PCR analysis of the full-length DUX4 ORF (nested with 36 total cycles) in muscle (M) and testes (T) RNA from the same individuals, showing expression in testes and not in muscle, as described in Example 2.
Figure 9D:
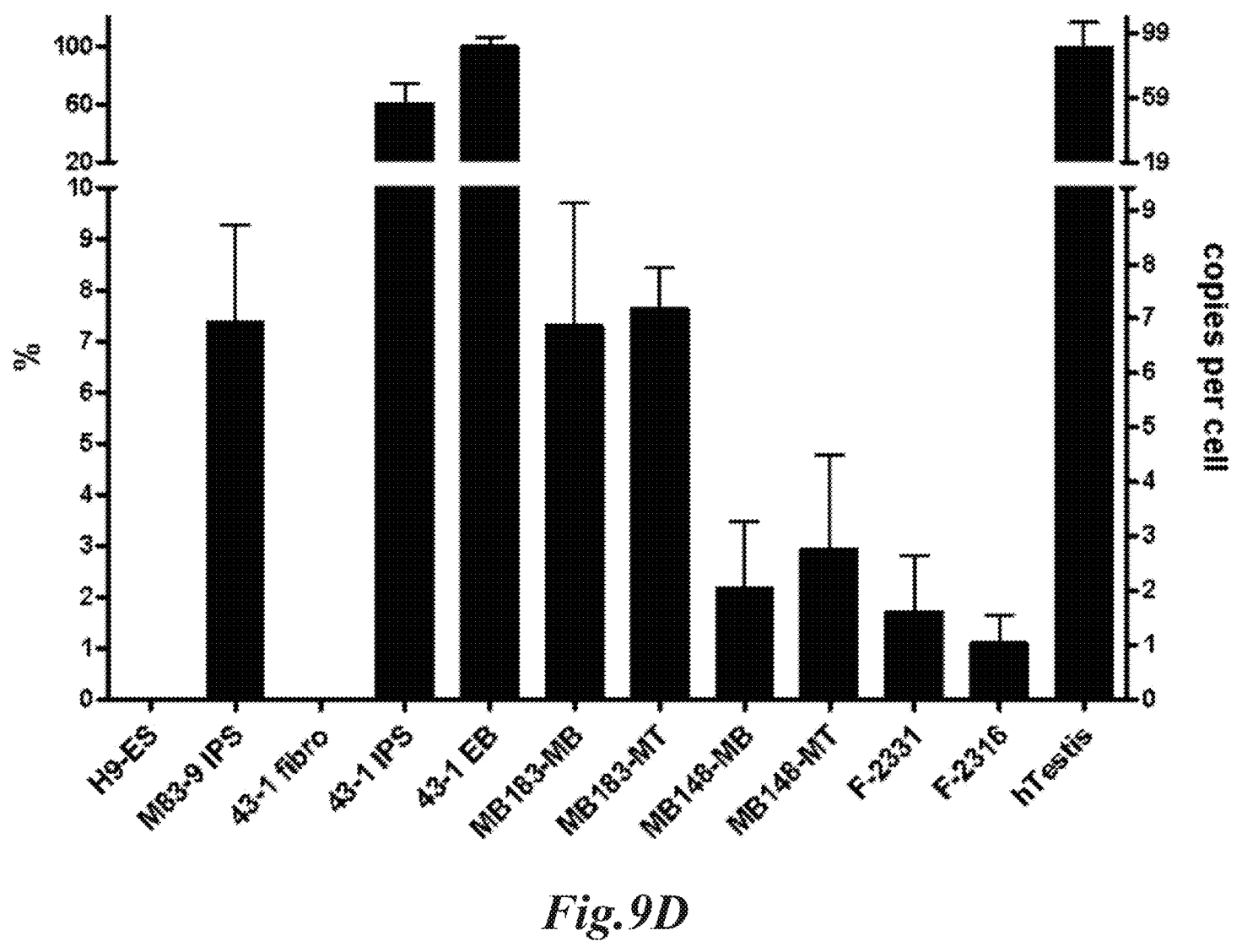
Figure 9E:
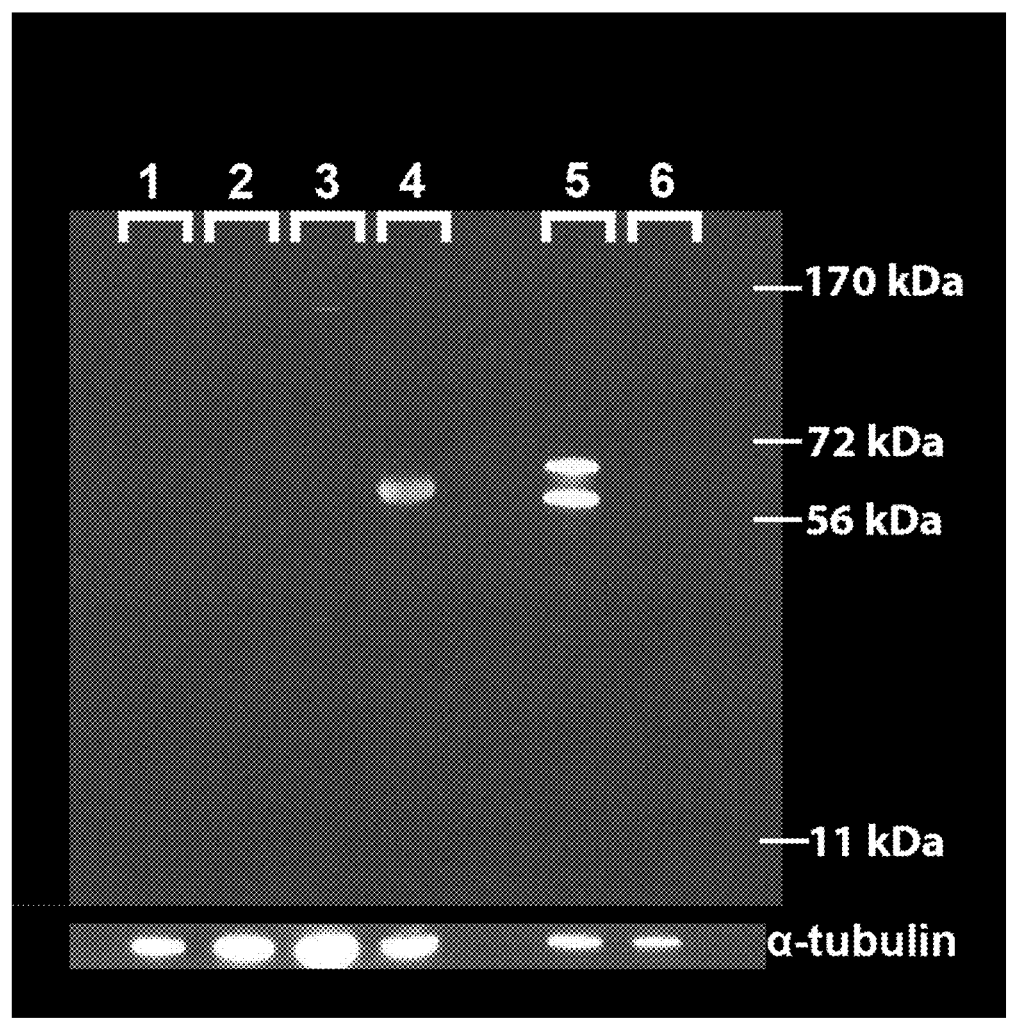
FIG. 9E shows the results of Western blot detection of DUX4 protein in whole cell extracts from tissues and cell lines using a rabbit monoclonal antibody (E14-3) raised to the amino terminus of the human DUX4 protein. Lanes: 1-control muscle culture; 2-HCT116 cell line; 3-mouse testis; 4-human testis; 5-C2C12 cells transfected with human DUX4 expression vector; 6-C2C12 cells, as described in Example 2.
Figure 9F:
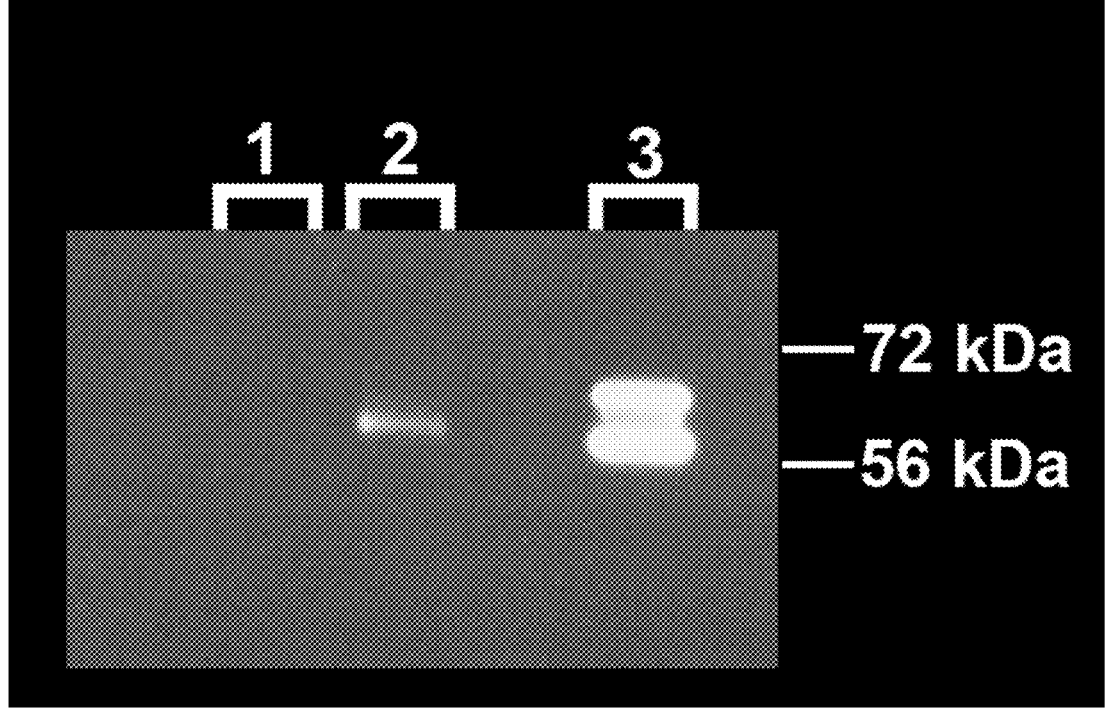
FIG. 9F shows the results of an Immunoprecipitation of indicated protein extracts with the E14-3 rabbit monoclonal to the N-terminal region of DUX4 followed by western with the P4H2 mouse monoclonal to the C-terminal region of DUX4 demonstrating that the protein recognized by the rabbit anti-DUX4 is also recognized by an independent mouse monoclonal to DUX4. Lanes: 1-HCT116 cell line lysate; 2-Testis protein lysate; 3-C2C12 cells transfected with DUX4 expression vector, as described in Example 2.

FIG. 9C shows the results of RT-PCR analysis of the full-length DUX4 ORF (nested with 36 total cycles) in muscle (M) and testes (T) RNA from the same individuals, showing expression in testes and not in muscle. Numbers indicate Testis-1, 4, 7, 6, 5.

FIG. 9D graphically illustrates the results of quantitative RT-PCR analysis of DUX4-fl3' showing relative abundance in muscle cells, muscle biopsies, human testis and other indicated cells. The sample with the highest expression was set at 100% and the number of copies per cell roughly estimated based on titration of input DNA. H9-ES, human embryonic cell line H9; M83-9 IPS, iPS line made from control fibroblasts; 43-1 series are the fibroblast, IPS, and EB cells from an FSHD fibroblast line; MB183 and MB148, FSHD muscle cultures under growth (MB) and differentiation (MT) conditions; F-2331 and F-2316, FSHD muscle biopsy samples; hTestis, human testis.

FIG. 9E shows the results of Western blot detection of DUX4 protein in whole cell extracts from tissues and cell lines using a rabbit monoclonal antibody (E14-3) raised to the aminoterminus of the human DUX4 protein. Lanes: 1-control muscle culture; 2-HCT116 cell line; 3-mouse testis; 4-human testis; 5-C2C12 cells transfected with human DUX4 expression vector; 6-C2C12 cells. Specificity of the antibody is indicated by selective detection of DUX4 protein in C2C12 cells transfected with a DUX4 expression vector, pCS2-DUX4 (note that this vector contains two ATG codons resulting in the standard DUX4 protein and an in-frame slightly larger protein accounting for the two bands on the western), compared to untransfected C2C12. Human testis has a single reactive band that migrates marginally slower than the transfected standard DUX4 species in C2C12 cells. This DUX4-reactive band is not present in mouse testis extract (note that mice do not have a highly conserved DUX4), HCT 116 human colon cancer cells, nor unaffected myotubes (MB196-36 hr). Similar results were obtained with an additional DUX4 antibody (E5-5) raised to the carboxyterminal region of DUX4 (data not shown) and on protein extracts from two additional testis samples (data not shown).

FIG. 9F shows the results of an Immunoprecipitation of indicated protein extracts with the E14-3 rabbit monoclonal to the N-terminal region of DUX4 followed by western with the P4H2 mouse monoclonal to the C-terminal region of DUX4 demonstrating that the protein recognized by the rabbit anti-DUX4 is also recognized by an independent mouse monoclonal to DUX4. Lanes: 1-HCT116 cell line lysate; 2-Testis protein lysate; 3-C2C12 cells transfected with DUX4 expression vector. Western analysis of protein extracts from three additional human testis samples identified a similar band (data not shown).

Immunostaining identified DUX4-expressing cells near the periphery of the seminiferous tubule that have the large round nucleus characteristic of spermatogonia or primary spermatocytes, and additional more differentiated appearing cells in the seminiferous tubules were also stained following antigen retrieval. The large numbers and nuclear morphology of the cells staining with DUX4 in the seminiferous tubules, together with expression of DUX4 in the human germ-cell cell lines SuSa and 833K (data not shown), leads us to conclude that DUX4 is expressed in the germ-line lineage.

Chromosomes 4 and 10 Produce DUX4 mRNA in Human Testes

The relatively high abundance of DUX4 mRNA and protein in human testes suggests a possible role for this protein in normal development. However, we have previously demonstrated that the alleles of chromosome 4 and 10 that are non-permissive for FSHD contain polymorphisms that inhibit polyadenylation of the DUX4 transcript and, therefore, only the 4A allele would be predicted to make a DUX4 mRNA. We do not have haplotype information on the testis donors and it is possible that some might lack the 4A haplotype entirely. To determine whether only the 4A haplotype produced stable DUX4 mRNA in human testes, we sequenced mRNAs from the seven testis samples in a region with informative polymorphisms regarding transcripts from 4A, 4B, and 10. All testis mRNA had transcripts from both chromosomes 4 and 10 in approximately equal amounts (Table 7). Some samples had 4A and 4B haplotypes.

TABLE 7

| Haplotype identification of Dux4 mRNA in Human Testis | | | |
|---|---|---|---|
| Sample Code | % 10A[A] | % 4A | % 4B | Total Number[B] |
| T1 | 22 | 78 | 0 | 9 |
| T2 | 60 | 40 | 0 | 10 |
| T3: 8606 | 22 | 67 | 11 | 9 |
| T4: H12817 | 56 | 0 | 44 | 9 |
| T7: N30 | 56 | 22 | 22 | 9 |
| T6: N21 | 20 | 80 | 0 | 10 |
| T5: N11 | 22 | 78 | 0 | 9 |
| Total | 38 | 53 | 9 | 64 |

Figure 10:
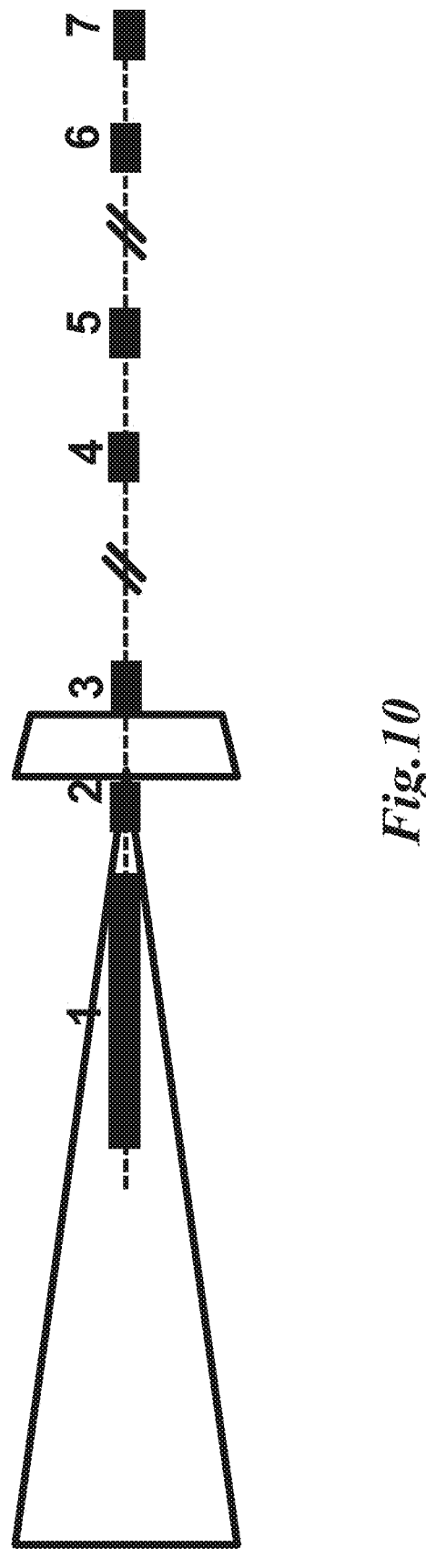
FIG. 10 is a schematic diagram illustrating alternative exon and polyadenylation site usage in germ-line and somatic tissues, showing the last D4Z4 unit, last partial repeat, and distal exons, wherein Exon 7 is approximately 6.5 kb from the polyadenylation site in exon 3. DUX4-fl from FSHD muscle contains exons 1-2-3. DUX4-s uses a non-consensus splice donor in the middle of exon 1 to create a short exon 1: 1s-2-3, as described in Example 2.

[A]Percentage of the sequences containing SNPs of each haplotype
[B]Number of sequenced cDNA 3-prime RACE analysis on testis mRNA demonstrated that the chromosome 10 transcripts used alternative 3-prime exons with a polyadenylation signal in exon 7 that is approximately 6.5 kb further telomeric than the previously identified 4A polyadenylation site in the pLAM region (FIG. 10). Some 4A transcripts also use the exon 7 polyadenylation site, but the exon 3 polyadenylation site associated with the permissive allele is preferred (data not shown). The 4B transcripts do not use either the exon 3 or exon 7 polyadenylation sites since the 4B haplotype lacks these regions, however, we have not yet identified the full 3-prime sequence of the DUX4 mRNA from the 4B chromosome. Re-analysis of the muscle cell line, muscle biopsy, and somatic tissue transcripts did not identify any DUX4 mRNA utilizing the exon 7 polyadenylation site from either chromosome 10 or 4, including a control sample with a contraction to 9 copies of D4Z4 on chromosome 10 (biopsy 2318).

We conclude that chromosome 10 DUX4 transcripts in the testes use a distal exon 7 polyadenylation signal, whereas this region is not used in somatic tissues, even when the chromosome 10 D4Z4 array has contracted to ten repeats.

Therefore, polyadenylated DUX4 mRNA from chromosomes 4 and 10 are present in the testis, but only chromosome 4A produces polyadenylated transcripts in somatic tissues.

FIG. 10 is a schematic diagram illustrating alternative exon and polyadenylation site usage in germ-line and somatic tissues, showing the last D4Z4 unit, last partial repeat, and distal exons. Exon 7 is approximately 6.5 kb from the polyadenylation site in exon 3. DUX4-fl from FSHD muscle contains exons 1-2-3. DUX4-s uses a non-consensus splice donor in the middle of exon 1 to create a short exon 1: 1s-2-3. Both are derived exclusively from chromosome 4A in muscle and other sampled somatic tissues. Germ line tissue expresses the 4A transcript with exons 1-2-3 but also expresses both 4A and 10A transcripts with exons 1-2-6-7. We have also identified a transcript in testis that shows a 1-2-4-5-6-7 splice usage.

As used herein, the term "DUX4-fl" encompasses naturally occurring DUX4-fl protein that is isolated from a human subject (i.e., SEQ ID NO:65, or a naturally occurring variant thereof, encoded by at least one of SEQ ID NO:66 or SEQ ID NO:67, or a naturally occurring variant thereof. As used herein, the term "DUX-s" encompasses naturally occurring DUX4-s protein that is isolated from a human subject (i.e., SEQ ID NO:68, or a naturally occurring variant thereof, encoded by DUX4-s cDNA (GenBank No. HQ266762) (SEQ ID NO:69).

The nucleotide sequences of Exons 1-7 of DUX4 are provided as follows: Exon 1 is set forth as SEQ ID NO:70; Exon 2 is set forth as SEQ ID NO:71; Exon 3 is set forth as SEQ ID NO:72; Exon 4 is set forth as SEQ ID NO:73; Exon 5 is set forth as SEQ ID NO:74; Exon 6 is set forth as SEQ ID NO:75 and Exon 7 is set forth as SEQ ID NO:76.

Exon 6 and 7 sequences are from a cDNA assigned to chromosome 10, exon 4 and 5 sequences are from a cDNA assigned to 4A161.

Developmental Regulation of Alternative Splicing Suppresses DUX4-Fl from Chromosome 4

The expression of DUX4-fl mRNA in unaffected human testes and the expression of DUX4-s in some unaffected somatic tissues, including skeletal muscle, suggested a developmental regulation of splice site usage in the DUX4 transcript. To directly determine whether the transition between DUX4-fl and DUX4-s expression is developmentally regulated, we generated induced pluripotent stem (IPS) cells from FSHD and control fibroblasts by expression of SOX2, OCT4, and KLF4 transcription factors from Moloney murine leukemia virus vectors (Takahashi et al., *Cell* 131:861-872 (2007)). Stem-cell clones had normal karyotypes, exhibited the expected cellular and colony morphology, contained tissue non-specific alkaline phosphatase activity, and expressed embryonic antigens (data not shown) RT-PCR demonstrated expression of stem cell markers NANOG, HTERT, cMYC, and endogenous transcripts from OCT4, SOX2, and KLF4 (data not shown). Pluripotency was demonstrated by the ability to form teratomas containing tissues derived from ectoderm, endoderm, and mesoderm. We used these characterized IPS cells to determine the expression of DUX4-fl and DUX4-s in the parental fibroblasts, undifferentiated IPS cells, and in the IPS cells after differentiation into embryoid bodies.

The induced Pluripotent Stem (IPS) cells from unaffected and FSHD-affected individuals, generated from skin fibroblasts cultured from an unaffected (M83-9) and two FSHD-affected individuals (FSHD83-6 and FSHD43-1), and human ES cells (HESC) were analyzed. Each IPS cell line was generated by transduction of fibroblasts with murine retrovirus vectors encoding Human SOX2, OCT4, and KLF4. Colonies developed approximately 20 days after infection and had the characteristic growth morphology of an IPS cell with flat, well organized colonies, sharply defined colony and cell boarders, high nuclear to cytoplasmic ratio, and prominent single nucleoli. Cells contained tissue non-specific alkaline phosphatase activity (AP), had normal karyotypes, and were immunoreactive (green) for Stage Specific Embryonic Antigen 4 (SSEA4), NANOG, OCT4, and TRA-1-60. 4,6-Diamidino-2-phenylindole (DAPI) staining (blue) indicated total cell content per image (data not shown).

Hematoxylin and eosin stained tissue sections of teratomas from Teratomas that developed in SCID-Beige mice after intramuscular injection of IPS cells generated from skin fibroblasts of a normal individual (M83-9) or two different FSHD-affected individuals (FHSD83-6 and FSHD43-1) were analyzed. Endoderm-derived tissue was identified by a gut-like structure surrounded by smooth muscle, parenchymal tissue, and lined with a columnar endothelium. Mesoderm-derived tissue is identified by bone (M83-9) or by the presence of cartilage containing chondrocytes (FSHD83-6 and FSHD43-1), and ectoderm-derived tissue was identified by the presence of pigmented neural epithelium (M83-9 and FSHD43-1) or neural rosettes (FSHD83-6) (data not shown).

A Northern blot analysis was carried out in which total cellular RNA was purified from human dermal fibroblasts (HDF), IPS cells used in this study (M83-9, FSHD83-6, FSHD43-1), and Human ES cells (HESC). The presence of RNA transcripts from the genes indicated was detected by priming reverse transcription reactions with oligo dT and PCR amplification of cDNA with oligonucleotides complementary to the sequence of the genes listed (28 cycles). Priming oligonucleotides used for OCT4, SOX2, and KLF4 amplification were specific for non-vector encoded transcripts. As a positive control, RNA from Human embryonic stem cells (HESC) was processed in parallel. Water instead of RNA was used as a negative control, and reverse transcriptase was left out of the cDNA synthesis step (-RT) to demonstrate RNA purity, and RNA transcripts from glyceraldehyde phosphate dehydrogenase (GAPDH) were amplified to demonstrate RNA integrity (data not shown).

Figure 11A:
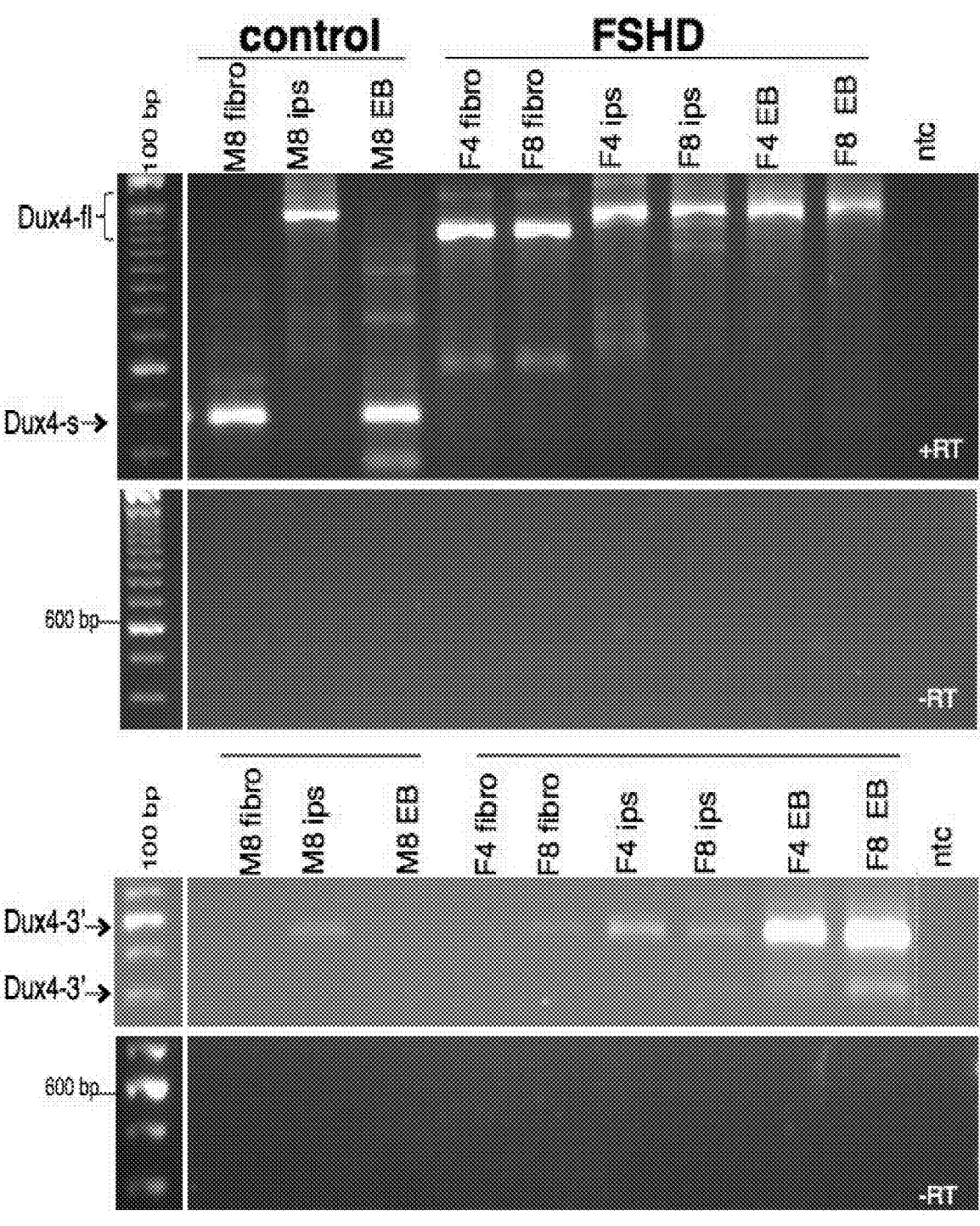
FIG. 11A shows the results of RT-PCR analysis of DUX4 mRNA in iPS cells derived from control or FSHD fibroblasts. M8, control fibroblast line; F4 and F8, FSHD fibroblast line, as described in Example 2.

FIG. 11A shows the results of RT-PCR analysis of DUX4 mRNA in iPS cells derived from control or FSHD fibroblasts. M8, control fibroblast line; F4 and F8, FSHD fibroblast line.

Figure 11B:
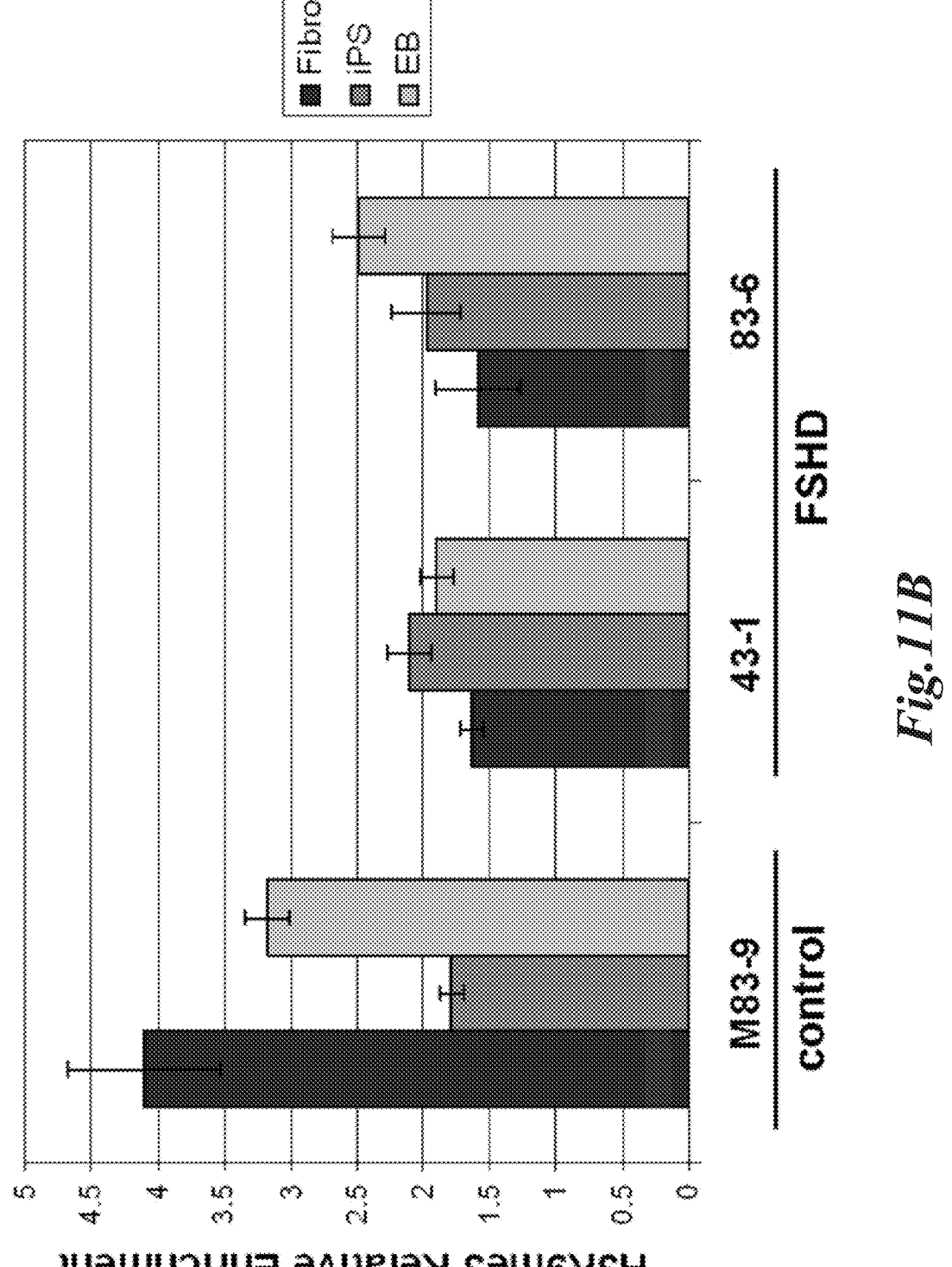
FIG. 11B shows the results of Chromatin immunoprecipitation (ChIP) analysis of H3K9me3 at the 5'-region of DUX4 in control and FSHD fibroblasts, induced pluripotent stem (iPS) cells, and embryoid bodies (EB) differentiated from the iPS. Bars represent relative enrichment by real-time PCR with primers previously described and confirmed as specific to D4Z4. The H3K9me3 IP signals were normalized to control IgG IP and to input, presented as mean±stdev, as described in Example 2.

FIG. 11B shows the results of Chromatin immunoprecipitation (ChIP) analysis of H3K9me3 at the 5'-region of DUX4 in control and FSHD fibroblasts, induced pluripotent stem (iPS) cells, and embryoid bodies (EB) differentiated from the iPS. Bars represent relative enrichment by real-time PCR with primers previously described and confirmed as specific to D4Z4. The H3K9me3 IP signals were normalized to control IgG IP and to input, presented as mean±stdev.

DUX4-s, but not DUX4-fl, was detected in control fibroblasts. In contrast, IPS cells derived from the control fibroblasts expressed DUX4-fl, whereas differentiation of these cells to embryoid bodies resulted in a switch to the expression of DUX4-s and loss of DUX4-fl transcripts (Table 6 and FIG. 11A). In contrast, DUX4-fl was detected in FSHD fibroblasts and the IPS cells and embryoid bodies derived from FSHD fibroblasts. As expected, DUX4-fl3' was detected in samples expressing DUX4-fl. (The relative amounts of DUX4-fl in a subset of iPS cells is shown in FIG. 11A and a band migrating at the size of DUX4 was detected on a western with an anti-DUX4 antibody (data not shown)).

DUX4-fl was detected in some human ES cell lines, but at much lower levels compared to the iPS cells (data not shown).

All of the splice donor and acceptor sites in the multiple alternative splicing events in the 3-prime UTR have consensus splice donor and acceptor sequences. In contrast, the splice donor in the ORF that produces DUX4-s is a non-canonical donor sequence and would normally not be favored for splicing. Recent studies have indicated that repressive chromatin modifications can favor splice donor usage (Luco et al., *Science* vol 327 (5968):996-1000 (2010)), and we tested whether the degree of H3K9me3 correlated with the usage of the DUX4-s splice site. Chromatin immunoprecipitation showed that the control fibroblasts and embryoid bodies with DUX4-s expression had relatively higher levels of trimethylation of lysine 9 in histone H3 (H3K9me3), a repressive chromatin modification, compared to the control IPS cells, which express DUX4-fl (FIG. 11B). The FSHD cells maintained relatively low levels of H3K9me3 in both IPS and differentiated cells. These findings are consistent with previous studies showing decreased H3K9me3 at the D4Z4 region in FSHD1 and FSHD2 (Zeng et al., *PloS Genet* 5:e1000559 (2009) and suggest a correlation between the relatively higher levels of repressive chromatin modifications and the use of the cryptic splice donor to produce DUX4-s.

Discussion

We note that prior studies reported the presence of poly-adenylated DUX4 transcripts in a small number of samples of cultured FSHD muscle cells but not in control muscle cells (Dixit et al., *PNAS* 104:18157-18162 (2007); Lemmers et al., *Science,* 2010 supra). The results in this Example both confirms and significantly extends these studies by (a) including a larger number of FSHD muscle cell cultures, (b) assaying controls that have a permissive 4A chromosome and non-permissive 4B chromosomes, (c) extending the analysis to mRNA from primary muscle biopsies of FSHD and haplotype-matched controls, (d) identifying the DUX4-s splice form of the DUX4 mRNA in control cells and showing that the qualitative difference between control and affected muscle is splice-site usage and not production of DUX4 mRNA; (e) demonstrating that the very low abundance of DUX4 mRNA in FSHD muscle represents a small percentage of nuclei with relatively high abundance mRNA and protein; (f) demonstrating that relatively high amounts of the DUX4 mRNA are expressed in the human testes and pluripotent cells and that developmental regulation is achieved by a combination of chromatin-associated splice-site usage and polyadenylation site usage.

Together, our data provide the basis for a specific model of FSHD pathophysiology: (1) full-length DUX4 is produced from the last D4Z4 unit in early stem cells; (2) in differentiated tissues, the D4Z4 array is associated with increased repressive H3K9me3 and DUX4 expression is repressed; (3) in the residual transcripts that escape repression, an alternative first-intron splice donor is utilized to produce DUX4-s instead of DUX4-fl; (4) contraction of the D4Z4 arrays impedes the conversion to repressive chromatin and the transition from DUX4-fl to DUX4-s, resulting in expression of the full-length DUX4 in skeletal muscle and possibly other tissues; and (5) the very low levels of full-length DUX4 expression in FSHD muscle reflects relatively high amounts of expression in a small sub-population of cells. Several groups have shown that expression of full-length DUX4 in muscle cells can induce pathologic features of apoptosis and expression of PITX1 (Dixit et al., *PNAS* 104:18157-18162 (2007); Bosnakovski et al., *PloS One* 4:e7003 (2009); Kowaljow et al., *Neuromuscul Disord* 17:611-623 (2007); Bosnakovski et al., *Exp Neurol vol* 214(1):87-96 (2008). In contrast, expression of DUX4c, a DUX4-like protein that lacks the carboxyterminal portion of DUX4, does not induce apoptosis (Bosnakovski et al., *Exp Neurol* (2008), supra). Therefore, it is reasonable to believe that expression of DUX4-fl might induce muscle cell damage in FSHD, whereas DUX4-s expression would not be harmful to the cells. Indeed, FSHD muscle cells expressing the endogenous DUX4 have nuclear foci of DUX4 characteristic of the foci that appear during early stages of apoptosis when DUX4 is exogenously expressed in human skeletal muscle cells (see FIG. 9), suggesting that these DUX4 expressing cells might be initiating a process of nuclear death.

The observed association of decreased H3K9me3 of D4Z4 with detectable levels of DUX4-fl mRNA suggests a specific mechanism of regulating DUX4 splicing. Previously (Snider et al., *Hum Mol Genet* 18:2414-2430 (2009)), we demonstrated bidirectional transcription of the D4Z4 repeats with the generation of small si/mi/pi-like RNA fragments and suggested that the small RNAs generated from D4Z4 might function to suppress DUX4 expression in a developmental context, a suppression mechanism observed for other retrogenes (Tam et al., *Nature* 453:543-538 (2008); Watanabe et al., *Nature* 453:539-543 (2008); Booth et al., *Gene* 387:7-14 (2007)). A recent publication demonstrated that the small RNAs mediating heterochromatin formation also regulate splice-donor usage, either by targeting the nascent transcripts or by altering the rate of polymerase progression through condensed chromatin (Luco et al., *Science*; Allo et al., *Nat Struct Mol Biol* 16:717-724 (2009)). Therefore, the repressive chromatin associated with D4Z4 in differentiated cells might facilitate the usage of the non-canonical splice donor to generate DUX4s, either through siRNAs from the region or through the impediment of polymerase progression, whereas the more permissive chromatin in FSHD and pluripotent cells might favor polymerase progression through to the consensus splice donor and generate DUX4-fl.

The results shown in Example 1 identified sequence variants on 4A necessary to produce polyadenylated DUX4 mRNA transcripts in somatic tissues. The results described in this Example are consistent with these findings since we have not been able to identify polyadenylated transcripts from non-permissive alleles in somatic tissues. In contrast, we do find alternative distal polyadenylation usage for DUX4 mRNA from non-permissive alleles in the testis. Developmentally regulated polyadenylation site usage has been described for other genes (Ji Z et al., *PloS One* 4:e8419 (2009)) and appears to be one additional mechanism of silencing expression of the DUX4 retrogene in somatic cells.

Our finding that the wild-type chromosomes 4 and 10 express a full-length DUX4 mRNA in human testes, most likely in the germ-line, and that the protein is relatively abundant suggests that DUX4 might have a normal role in development. This is supported by the expression of canine DUXC in germ-line tissue (data not shown). In addition, a DUX4-like gene in the mouse, Duxbl, is expressed in mouse germ-line cells in both spermatogenesis and oogenesis, as well as in early phases of skeletal muscle development (Wu S. L. et al., *Duxbl Dev Dyn* 239:927-940 (2010)). Similar to DUX4, Duxbl has developmentally regulated splicing to produce a full-length protein and a protein truncated after the double homoeodomains and studying the roles of Duxbl in germ-line and muscle development in mouse will likely inform our understanding of DUX4. We should note that our study describes the expression of human DUX4 in testes, but we believe it is likely to be expressed in oogenesis as well. Limited access to appropriate tissue has limited our ability to carefully examine expression in cells of the ovary.

Generating new genes through retrotransposition is a common mechanism of mammalian evolution (Kaessmann H. et al., *Nat Rev Genet* 10:19-31 (2009)), particularly for genes with a role in germ cell development. Recently, an FGF4 retrogene was identified as causing the short-legged phenotype in many dog breeds (Parker H et al., *Science* 325:995-998 (2009)), indicating that retrogenes can direct dramatic phenotypic evolution in a population. Our study demonstrates that the expression of the DUX4 retrogene is developmentally regulated and might have a role in germ-line development, and, if similar to Duxbl, possibly in aspects of early embryonic muscle development. Maintaining the DUX4 retrogene in the primate lineage suggests some selective advantage compared to maintaining the parental gene itself. Based on current knowledge, this could be due to a function in germ-line development, or to a modulation of muscle mass in primate face and upper extremity. In this regard, it is interesting to speculate that a normal function of the DUX4 retrogene might be to a regulate the development of facial and upper-extremity muscle mass in the primates, and that FSHD represents a hypermorphic phenotype secondary to inefficient developmental suppression. Alternatively, the persistent expression of full-length DUX4 might induce a neomorphic phenotype unrelated to an evolutionarily selected role of DUX4. In either case, our findings substantiate a comprehensive developmental model of FSHD and demonstrate that FSHD represents the first human disease to be associated with the incomplete developmental silencing of a retrogene array that is expressed in pluripotent stem cells and in normal development.

Example 3

This Example demonstrates that DUX4-fl activates the expression of germline genes and binds uniformly throughout the genome.

Background/Rationale:

Previously, we identified two different DUX4 mRNA transcripts in human skeletal muscle, both at extremely low abundance: a full-length open reading frame mRNA (DUX4-fl) only detected in FSHD muscle and an internally spliced form of DUX4 mRNA (DUX4-s) that maintains the N-terminal double-homeobox domains but deletes the C-terminal domain and is detected in both control and FSHD muscle (Snider et al., *PloS Genet* 6:e1001181 (2010)).

Forced over-expression of DUX4-fl is toxic to cells, inducing apoptotic cell death (Kowaljow et al., *Neuromuscul. Discord* 17:611-623 (2007); Wallace et al., *Ann Rev. Neurol.* 69(3):540-52 (2011)), whereas forced over-expression of DUX4-s is not toxic to cultured human skeletal muscle cells (Geng et al., *Larchmt* 30:125-130 (2011)).

To determine whether gene expression is regulated by DUX4-fl and/or DUX4-s in human muscle cells, as described in this Example, we transduced primary myoblasts from a control individual (unaffected by muscle disease) with a lentiviral vector expressing either DUX4-fl or DUX4-s and performed expression microarrays.

Methods and Materials

Transduction of Primary Control Myoblasts with Lentiviral Vectors Expressing DUX4-Fl or DUX4-s Lentiviral vectors expressing either DUX4-fl or DUX4-s were constructed as follows:

The DUX4-fl and DUX4-s lentiviral constructs were generated by replacing the GFP gene in the lentiviral vector backbone "pRRLSIN.cPPT.PGK-GPF.WPRE", as described in http://www.addgene.org/12252/" incorporated herein by reference, with the cDNA encoding DUX-4fl (SEQ ID NO:66 or SEQ ID NO:67), or with the cDNA encoding DUX4-s (SEQ ID NO:69).

Primary myoblasts from a control individual unaffected by muscle disease were transduced with the Lentiviral vectors expressing either DUX4-fl or DUX4-s. Primary human myoblasts were collected and cultured as previously described (Snider et al., *PloS Genet* 6:e1001181 (2010)). Primary myoblasts were maintained at or below 70% confluency for proliferation. For differentiation, cells were allowed to reach 95-100% confluency in growth medium. Once confluency was reached, the cells were changed to differentiation medium (F10 media supplemented with 1% horse serum, 10 g/mL insulin, and 10 g/mL transferrin, penicillin/streptomycin) and maintained for 4 days. Human RD cells were grown in DMEM in 10% bovine calf serum (Hyclone) and penicillin/streptomycin. The primary myoblasts were transduced with lentivirus carrying DUX-fl, DUX4- or GFP (MOI=15).

Expression Analysis

Expression microarrays were performed on the transduced cells at 24 hours after transduction as follows. Quadruplicate total RNA samples were collected from control human primary myoblasts transduced with lentivirus carrying DUX4-fl, DUX4-s or GFP (MOI=15) for 24 h. Samples were analyzed by Illumina Human Whole Genome microarrays. Probe intensities were corrected, normalized, and summarized by the Lumi package of Bioconductor (Du et al., *Bioinformatics* 24:1547-1548 (2008)). Differentially expressed genes were identified by the LIMMA package of Bioconductor (Wettenhall and Smyth, *Bioinformatics* 20:3705-3706 (2004)). Gene set enrichment analysis (GSEA) was performed using the Bioconductor GOstats package (Falcon and Gentleman, *Bioinformatics* 23:257-258 (2007)).

Microarray Gene Target Validation by RT-PCR

RNA was collected from cultured control skeletal muscle either transduced with a DUX4-fl expressing lentivirus (+) or not transduced (−). RPL13A was used as an internal standard. Total RNA was treated with DNase using TURBO DNA-free kit (Ambion) according to manufacturer's protocol. One μg of DNase-treated RNA was reverse transcribed to first strand cDNA with SuperScript III and anchored oligo dT (Invitrogen) at 52° C. for 1 h. Residual RNA was digested with RNase H at 37° C. for 20 min. cDNA was used in various PCR and real-time PCR reactions with primers listed below.

cDNA from DUX4-fl transduced or untransduced primary myoblasts was diluted 1:5 and used in PCR reactions with Platinum Taq polymerase (Invitrogen) with conditions of 55° C. annealing temperature and 35 cycles using primers designed to span exon-exon junctions where possible from select genes. Primers from select genes were also used in real-time PCR reactions to examine endogenous expression of targets in FSHD versus control samples.

Results:

Identification of Genes Regulated by DUX4 in Human Primary Myoblasts

At 24 hours after transduction, DUX4-fl increased the expression of 1071 genes and decreased the expression of 837 genes compared to a control myoblast population similarly infected with a GFP expressing lentivirus (2-fold change and FDR<0.01); whereas DUX4-s increased the expression of 159 genes and decreased expression of 45 genes.

Using a more stringent 3-fold criteria (>1.584 log 2-fold change and FDR<0.01), 466 genes were increased and 244 decreased by DUX4-fl; and 37 were increased and one decreased by DUX4-s. Only two annotated genes were increased 3-fold or more by both (CCNA1, MAP2), and none were decreased 3-fold or more by both.

A representative sample of genes activated by DUX4-fl is shown in Table 8.

TABLE 8

Representative genes induced by DUX4-fl

| Category | Log$_2$ DUX4-fl Fc* | Log$_2$ DUX4-s Fc* | Comments |
|---|---|---|---|
| Germline and Stem Cells | | | |
| ZSCAN4 | 8.3 | 0.0 | Genome stability, telomere length |
| PRAMEF1 | 8.1 | 0.1 | Melanoma antigen family |
| SPRYD5 | 8.0 | −0.1 | Expressed in oocyte |
| KHDC1L | 8.0 | −0.1 | KH RNA binding domain |
| MBD3L2 | 7.6 | 0.0 | Methyl-CpG-binding protein |
| ZNF705A | 6.8 | −0.1 | Zinc finger protein |
| TRIM43 | 5.8 | 0.0 | Preimplantation embryo |
| TPRX1 | 4.5 | −0.1 | Homeobox protein |
| ZNF217 | 4.1 | −0.3 | Expressed in cancer stem cells |
| HSPA2 | 3.7 | −0.3 | Chaperone, heat shock 70 kd |
| JUP | 3.2 | −0.1 | expressed in germline and testicular cancers |
| FGFR3 | 3.1 | 0.0 | Expressed in spermatogonia |
| CD24 | 2.6 | −0.4 | Stem cell marker |
| SLC2A14 | 2.4 | 0.2 | Spermatogenesis |
| ID2 | 2.3 | 0.3 | Negative regulator of cell differentiation |
| PVRL3 | 2.2 | 0.4 | Spermatid-sertoli junction |
| HOXB2 | 2.2 | 0.0 | Anterior-posterior axis development |
| ZSCAN2 | 2.2 | −0.2 | Spermatogenesis and embryonic development |
| RNA Processing | | | |
| SFRS2B | 4.2 | −0.3 | Splicing |
| THOC4 | 4.0 | −0.2 | Splicing, RNA transport |
| ZNHIT6 | 3.5 | 0.3 | sno-RNA processing |
| DBR1 | 3.4 | 0.2 | RNA lariat debranching enzyme |
| TFIP11 | 3.2 | 0.1 | Spliceosome assembly |
| CWC15 | 2.6 | 0.1 | Spliceosome-associated |
| ARS2 | 2.6 | −0.2 | miRNA processing |
| PABPN1 | 2.6 | −0.3 | PolyA binding |
| SFRS17A | 2.5 | 0.2 | Spliceosome-associated |
| RMRP | 2.3 | 0.1 | Mitochondrial RNA processing |
| SNIP 1 | 2.1 | −0.2 | miRNA biogenesis |
| RPPH1 | 2.0 | 0.2 | tRNA processing |
| RNGTT | 2.0 | −0.6 | mRNA processing |
| Ubiquitin Pathway | | | |
| SIAH1 | 3.7 | −0.1 | Targets TRF2 telomere maintenance |
| FBXO33 | 3.2 | 0.2 | E3 ubiquitin-protein ligase complex |
| PELI1 | 2.9 | 0.1 | E3 ligases involved in innate immunity |

TABLE 8-continued

Representative genes induced by DUX4-fl

| Category | Log$_2$ DUX4-fl Fc* | Log$_2$ DUX4-s Fc* | Comments |
|---|---|---|---|
| USP29 | 2.6 | −0.1 | Ubiquitin-specific peptidase |
| ARIH1 | 2.2 | 0.8 | Ubiquitin-conjugating enzyme E2 binding protein |
| TRIM23 | 2.2 | 0.6 | E3 ubiquitin ligase involved in immunity |
| Immunity and Innate Defense | | | |
| DEFB103B | 6.4 | 0.1 | Innate defense |
| IFRD1 | 3.0 | −0.2 | Interferon-related developmental regulator |
| CXADR | 2.5 | −0.1 | Leukocyte migration |
| CBARA1 | 2.1 | −0.2 | T-helper 1-mediated autoreactivity |
| SON | 2.1 | −0.3 | Viral response |
| CXCR4 | 2.0 | −0.1 | Chemotaxis |
| General Transcription | | | |
| GTF2F1 | 3.2 | 0.3 | General transcription factor IIF |
| MED26 | 2.1 | 0.1 | RNA Pol II mediator complex |
| RRN3 | 2.1 | 0.1 | RNA Pol I preinitiation complex |
| Cancer Expressed | | | |
| CSAG3 | 5.9 | 0.1 | Chondrosarcoma-associated gene |
| SLC34A2 | 5.5 | 0.0 | Breast cancer biomarker |
| PNMA6B | 3.6 | −0.2 | Paraneoplastic antigen |
| CSE1L | 2.9 | 0.1 | Cellular apoptosis susceptibility protein |
| AMACR | 2.7 | 0.1 | Prostate cancer biomarker |
| Other | | | |
| FLJ45337 | 3.7 | −0.2 | Endogenous retrovirus |
| HNRNPCL1 | 3.5 | −0.1 | Nucleosome assembly |
| SPTY2D1 | 3.3 | −0.3 | Suppressor of ty retrotransposons in yeast |
| MGC10997 | 2.4 | −0.3 | Endogenous retrotransposon |

The up-regulation of a large number of transcription-related and RNA processing factors suggests that DUX4-fl might be a central component of a complex gene regulatory network, and the large number of germline associated genes suggests a possible role in reproductive biology.

Figure 12:
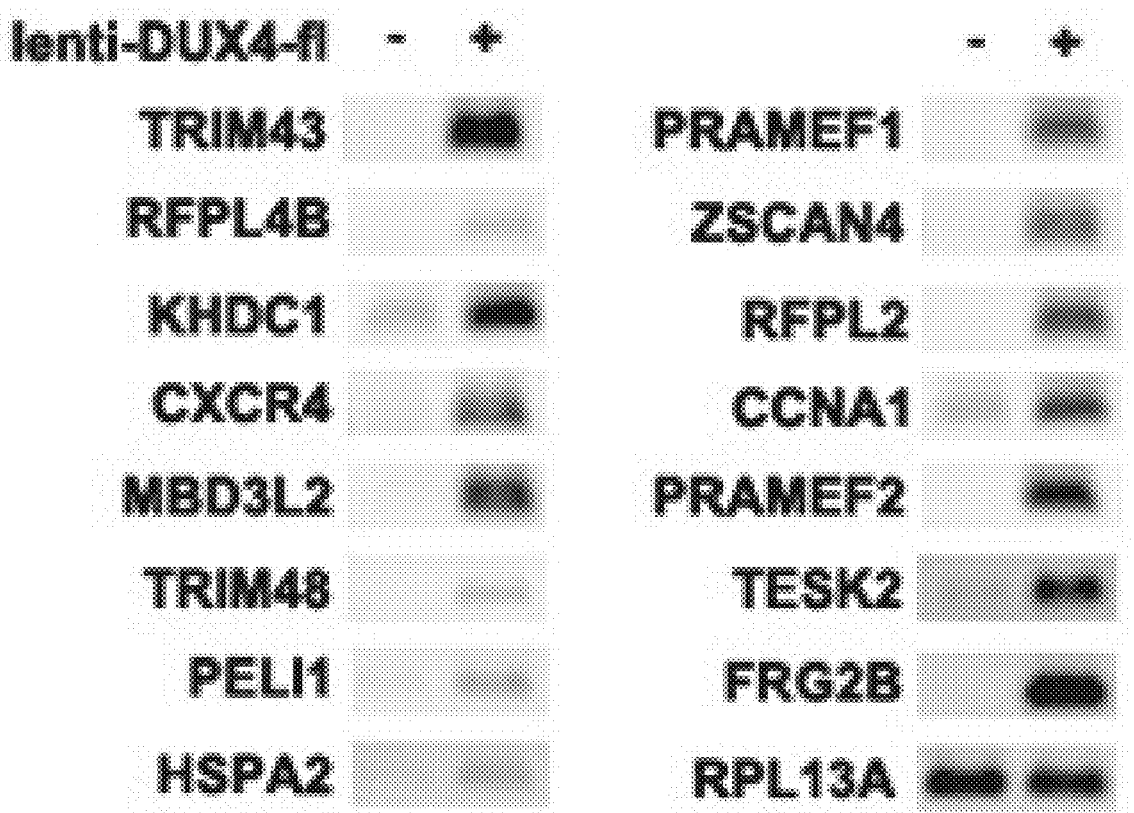
FIG. 12 shows the results of RT-PCR validation of DUX-fl target genes shown to be upregulated in the expression microarray, as described in Example 3.

We validated the differential expression of 15 of the DUX4-fl regulated genes by RT-PCR, as shown in FIG. 12. FIG. 12 shows the results of RT-PCR validation of DUX-fi target genes shown to be upregulated in the expression microarray.

Discussion

Prior genetic and molecular studies identified DUX4 as the most likely candidate gene for FSTID, however, the abundance of DUX4-fl mRNA was extremely low in FSTID muscle and the protein was not reliably detected. Therefore, it was unclear whether DUX4-fl was expressed at levels sufficient to have a biological consequence in FSHD. In our current study, we identify genes regulated by DUX4-fl and show that they are expressed at readily detectable levels in FSHD skeletal muscle, both cell lines and muscle biopsies, but not in control tissues, providing direct support for the model that misexpression of DUX4-fl is a causal factor for FSTID. Furthermore, the genes regulated by DUX4-fl suggest several specific mechanisms for FSHD pathophysiology.

Many of the genes highly upregulated by DUX4-fl normally function in the germline and/or early stem cells and are not present in healthy adult skeletal muscle. This supports a biological role for DUX4-fl in germ cell development and suggests potential disease mechanisms for FSHD. Activation of the gametogenic program might be incompatible with post-mitotic skeletal muscle, leading to apoptosis or cellular dysfunction. Also, the testis is an immune-privileged site and testis proteins misexpressed in cancers can induce an immune response (Simpson et al., *Nat. Rev. Cancer* 5:615-625 (2005)). In fact, some of the genes regulated by DUX4-fl, such as the PRAME family (Chang et al., *PloS One* 6:e16867 (2011)), are known cancer testis antigens, so it is reasonable to suggest that expression of these genes in skeletal muscle might also induce an immune response. An immune-mediated mechanism for FSHD is consistent with the focal inflammation and CD8+ T cell infiltrates that characterize FSHD muscle biopsies (Frisullo et al., *J. Clin. Immunol.* 31:155-166 (2011); Molnar et al., *Eur. Arch. Psychiatry Clin. Neuroscie.* 241:105-108 (1991)).

DUX4-fl regulated targets also include genes involved in RNA processing, developmentally regulated components of the PolII transcription complex, ubiquitin-mediated protein degradation pathways and the innate immune response pathways, all of which may have pathophysiological consequences. For example, abnormal splicing has been reported in FSHD, although this was attributed to potential misexpression of another candidate gene for FSHD, FRG1 (Gabellini et al., *Nature* 439:973-977 (2006)). In addition, reactivation of retroelements can result in genomic instability (Belancio et al., *Semin. Cancer Biol.* 20:200-210 (2010)) and transcriptional deregulation (Schulz et al., *J. Biomed. Biotechnol.* 83672 (2006)), so DUX4's activation of MaLR transcripts might contribute to the apoptosis or modulation of the innate immune response seen in muscle cells expressing DUX4.

Example 4

This Example describes the identification of DUX4-fl binding sites and a consensus binding sequence motif and demonstrates that DUX4-fl activates the expression of germline genes by binding to a double homeodomain motif.
Background/Rationale:

Double homeodomain proteins comprise a distinct group of DNA-binding proteins (Holland et al., BMC Biol. 5:47 (2007)), but their consensus recognition sites and genomic targets are unknown. Therefore, we performed chromatin immunoprecipitation combined with high throughput sequencing (ChIP-Seq) to identify DUX4-binding sites in human muscle cells, as described in this Example.
Methods:
Antibody Development and Characterization Custom anti-DUX4 polyclonal antibodies were developed through Covance. Rabbits were immunogenized with GST-DUX4 C-terminus fusion protein as antigen (Geng et al., *Hybridoma (Larchmt)* 30:125-130 (2011)). C2C12 myoblasts were transfected with pCS2-DUX4-fl and used for testing the antibodies on western blot and immunofluorescence as previously described in Geng et al., 2011, supra. Briefly described, for western blot, 5 μg of lysate from transfected or untransfected cells were run on 4-12% gradient bis-tris polyacrylamide gel and transferred to 0.45 μm nitrocellulose membranes. Membranes were probed with antibodies at a 1:500 dilution. α-tubulin was used as a loading control. Briefly described, for immunofluorescence, cells were fixed in 2% paraformaldehyde and incubated overnight with antibodies at a 1:500 dilution. Cells were counterstained with 4',6-diamidino-2-phenylindole (DAPI) for nuclei. The results are shown in FIG. 13.

Figure 13B:
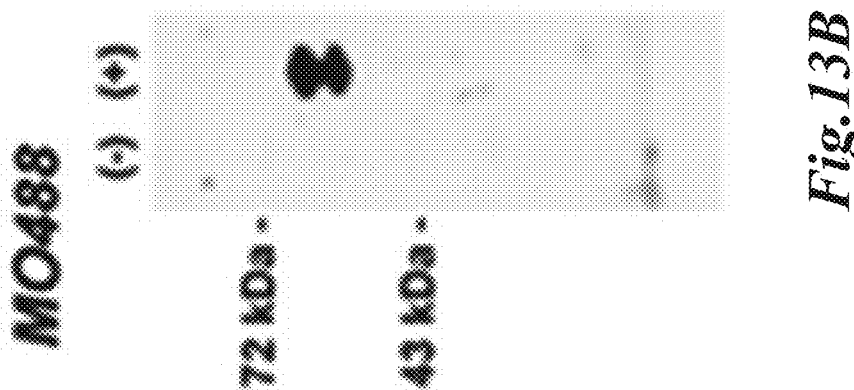
FIG. 13B shows the results of a Western blot on C2C12 myoblasts transfected with CXS2-DUX4-fl using polyclonal antibody MO488. Each are raised against the DUX4 C-terminus, (−) untransfected lysates; (+) transfected lysates (arrows indicate DUX4-fl protein bands, doublet band is due to expression construct containing additional upstream translation start site), as described in Example 3.
Figure 13A:
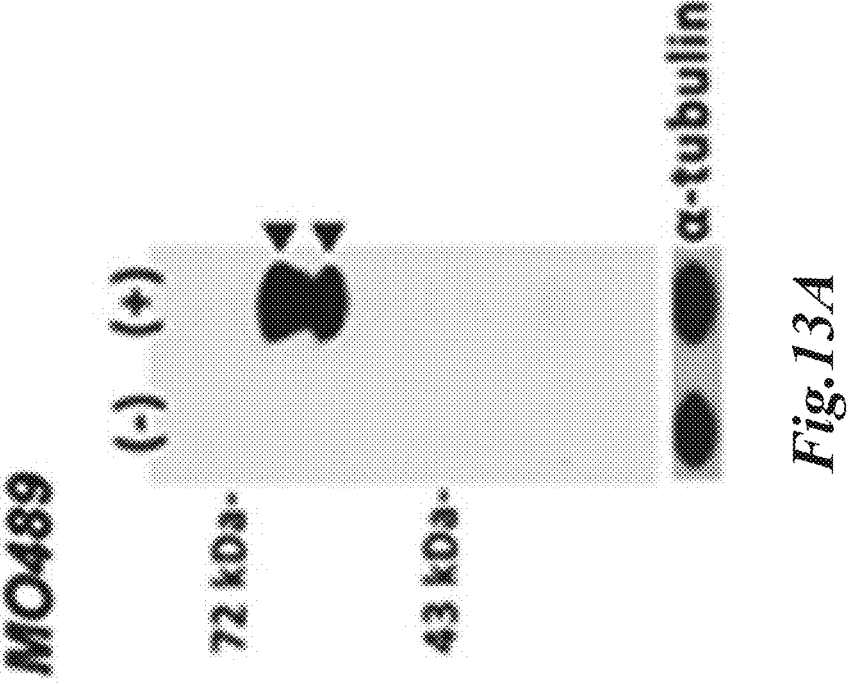
FIG. 13A shows the results of a Western blot on C2C12 myoblasts transfected with CXS2-DUX4-fl using polyclonal antibody MO489.

FIG. 13 shows the results of a Western blot on C2C12 myoblasts transfected with CXS2-DUX4-fl using polyclonal antibody MO489 (FIG. 13A), or polyclonal antibody MO488 (FIG. 13B), each raised against the DUX4 C-terminus, (−) untransfected lysates; (+) transfected lysates (arrows indicate DUX4-fl protein bands, doublet band is due to expression construct containing additional upstream translation start site). C2C12 myoblasts were transfected with pCS2-DUX4-fl for immunofluorescence and western blots and fixed or collected for lysate 24 hr post-transfection, respectively. For immunofluorescence, nuclei were counterstained with DAPI, and positive signal was detected (data not shown). For western blots, HRP-conjugated anti-rabbit secondary antibodies were used.
Immunoprecipitation Analysis We used two polyclonal rabbit antisera against DUX4 (shown in FIG. 13) to immunoprecipitate DUX4-fl from human primary myoblasts 24 hours after transduction with lentiviral expressed DUX4-fl or control non-transduced primary myoblasts. Non-redundant reads unambiguously mapped to the human genome were computationally extended to a total length of 200 nucleotides and "peaks" were defined as regions where the number of reads was higher than a statistical threshold compared to the background, as described below. Reads mapping to the X and Y chromosomes were excluded from our analysis.

Chromatin Immunoprecipitation and Ultra-High-Throughput Sequencing ChIP was performed and ChIP DNA samples were prepared as previously described in Cao et al., *Dev. Cell* 18:662-674 (2010), hereby incorporated herein by reference. Anti-DUX4 C-terminus rabbit polyclonal antibodies MO488 and MO489 were combined to immunoprecipitate DUX4-fl. Anti-DUX4 N-terminus polyclonal antibodies FH106 and FH107 were combined to immunoprecipitate DUX4-s. The samples were sequenced with Illumina Genome Analyzer II.
Defining Peaks Sequences were extracted by Illumina package GApipeline and reads were aligned using BWA to the human genome (hg18). We only kept one of the duplicated sequences to minimize the artifacts of PCR amplification. Each read was extended in the sequencing orientation to a total of 200 bases to infer the coverage at each genomic position. We performed Peak calling by a house developed R package "peakSig" (pending submission to Bioconductor), which model background reads by a negative binomial distribution. The negative binomial distribution can be viewed as a continuous mixture of Poisson distribution where the mixing distribution of the Poisson rate is modeled as a Gamma prior. This prior distribution is used to capture the variation of background reads density across the genome. Model parameters were estimated by fitting the truncated distribution on the number of bases with low coverage (one to three), to avoid the problem of inferring effective genome size excluding the non-mappable regions, and to eliminate contamination of any foreground signals in the high coverage regions. We also fit a GC dependent mixture model so that the significance of the peaks is determined not only by peak height, but also by the GC content of the neighboring genomic regions.
Motif Analysis Discriminative motif discovery was carried out as described in Palii et al., *EMBO J.* 30:494-509 (2011), in which motifs were identified that distinguish a positive and a negative sequence dataset, which in this study, the positive sequences correspond to Dux4 binding sites and negative sequences correspond to the randomly sampled flanking regions of Dux4 binding sites. To generate more accurate presentation of the Dux4 binding sites from the consensus pattern returned by this analysis, we tried to learn a positional weight matrix (PWM) model, using the matches of the consensus pattern as the seed to initialize the iterative expectation-maximization (EM) refinement process similar to MEME. If appropriate, the motifs are extended iteratively as long as there is sequence preference in the flanking region, and refined in the same EM process.

Electromobility Shift Assay

EMSA was performed with $^{32}$P-labeled 31-bp oligonucleotides from endogenous genomic sequences containing the putative DUX4 binding site as probes (sequences below; only forward shown). Radiolabeled probes were incubated with in vitro translated protein generated from pCS2-DUX4-fl or pCS2-DUX4-s$^2$ vectors using the TNT SP6 Coupled Wheat Germ Extract System (Promega) according to manufacturer's instructions. To obtain supershift of protein-DNA complexes, 0.1 µg of E14-3 anti-DUX4 rabbit monoclonal antibody was added to the mixtures. For competition experiments, excess unlabeled probes of either wild-type or mutant sequences were included in the binding reaction. The gels were prepared and run as previously described (Knoepfler et al., *Nucleic Acids Res* 27:3752-3761 (1999)).

| Probe | Forward oligo sequence | SEQ ID NO: |
|---|---|---|
| TRIM48 | AGGAGTGATGATAATTTAATCAGCCGTGCAA | 77 |
| TRIM48mut | AGGAGTGATGATACTTTTATGAGCCGTGCAA | 78 |
| THED1 | CCTGTGGGAGGTAATCCAATCATGGAGGCAG | 79 |
| THE1Dmut | CCTGTGGGAGGTACTCCTATGATGGAGGCAG | 80 |
| CSF1R | CCAGGTGGAGATAATTGAATCATGGGGGCAG | 81 |
| CSF1Rmut | CCAGGTGGAGATACTTGTATGATGGGGGCAG | 82 |

Association of Binding and Expression

We associated a peak to its closest TSS within the region flanked by CTCF binding sites, which were identified in a ChIP-seq experiment on human CD4+ T cells (GEO accession number GSE12889/GSM325895).

MaLR Expression Analysis

Real-time PCR was performed as described in main methods. Water and minus RT controls were checked to ensure there was no amplification of these repetitive elements from residual or contaminating genomic DNA. Primer sequences were:

THE1 forward, 5'-ACCCCTCATGGAGAACCTCT-3' (SEQ ID NO:83) and
THE1 reverse, 5'-ACCCTCTTCTCACAGCTCCA-3' (SEQ ID NO: 84).

Luciferase Assay

Transient DNA transfections of RD cells were performed using SuperFect (Qiagen) according to manufacturer specifications. Briefly, 3×10$^5$ cells were seeded per 35 mm plate the day prior to transfection. Cells were co-transfected with pCS2 expression vectors (2 ug/plate) carrying either 0-galactosidase, DUX4-fl or DUX4-s and with pGL3-promoter luciferase reporter vectors (1 µg/plate) carrying various putative DUX4 binding sites or mutant sites upstream of the SV40 promoter or pGL3-basic reporter vector (1 µg/plate) carrying test promoter fragment upstream of the firefly luciferase gene. Cells were lysed 24 h post-transfection in Passive Lysis Buffer (Promega). Luciferase activities were quantified using reagents from the Dual-Luciferase Reporter Assay System (Promega) following manufacturer's instructions. Light emission was measured using BioTek Synergy2 luminometer. Luciferase data are given as the averages ±SD of at least triplicates.

Real-Time PCR of Targets in Matched Testis and Skeletal Muscle

Real-time PCR was performed as described above. Primer sequences for muscle markers are listed below.

| Gene name | Forward primer sequence | Reverse primer sequence |
|---|---|---|
| MYH2 | TTCTCAGGCTTCAAGATTTGG (SEQ ID NO: 85) | CTGGAGCTTGCGGAATTTAG (SEQ ID NO: 86) |
| CKM | CACCCCAAGTTCGAGGAGAT (SEQ ID NO: 87) | AGCGTTGGACACGTCAAATA (SEQ ID NO: 88) |

DUX4-fl PCR

Nested DUX4-fl3' PCR on primary myoblast and muscle biopsies were performed as described herein. Primers used were:

182 forward (5'-CACTCCCCTGCGGCCTGCTGCTG-GATGA-3') (SEQ ID NO:24) and
183 reverse (5'-CCAG-GAGATGTAACTCTAATCCAGGTTTGC-3') (SEQ ID NO:34)

nested with 1A forward (5'-GAG CTC CTG GCG AGC CCG GAG TTT CTG-3') (SEQ ID NO:25) and
184 reverse (5'-GTAACTCTAATCCAGGTTTGCCTA-GACAGC-3') (SEQ ID NO:35).

Knockdown of DUX4-fl Targets

FSHD cultured myoblasts were grown to confluence and switched to differentiation media as described in main methods. Simultaneously, cells were transduced by lentivirus carrying DUX4-s or GFP along with 8 µg/mL polybrene. Cells were washed and changed to plain differentiation media after 24 hours. Cells were harvested for RNA after 48 hours of differentiation. Untransduced cells were used to assess baseline expression of DUX4-fl target genes.

Results:

A total of 62,028 and 39,737 peaks were identified at P-value thresholds of 10$^{10}$ and 10$^{15}$, respectively, after subtracting background peaks in the control samples. DUX4-fl peaks were widely distributed both upstream and downstream of gene transcription start sites (TSSs) with higher numbers in introns and intergenic regions, but showing a relatively constant peak density in all genomic regions when normalized for the size of the genomic compartment. This pattern differs from that reported for many other transcription factors, such as MYOD (Cao et al., *Dev. Cell* 18:662-674 (2010)), that show higher average peak density in regions near TSSs.

Figures 14A, 14B:
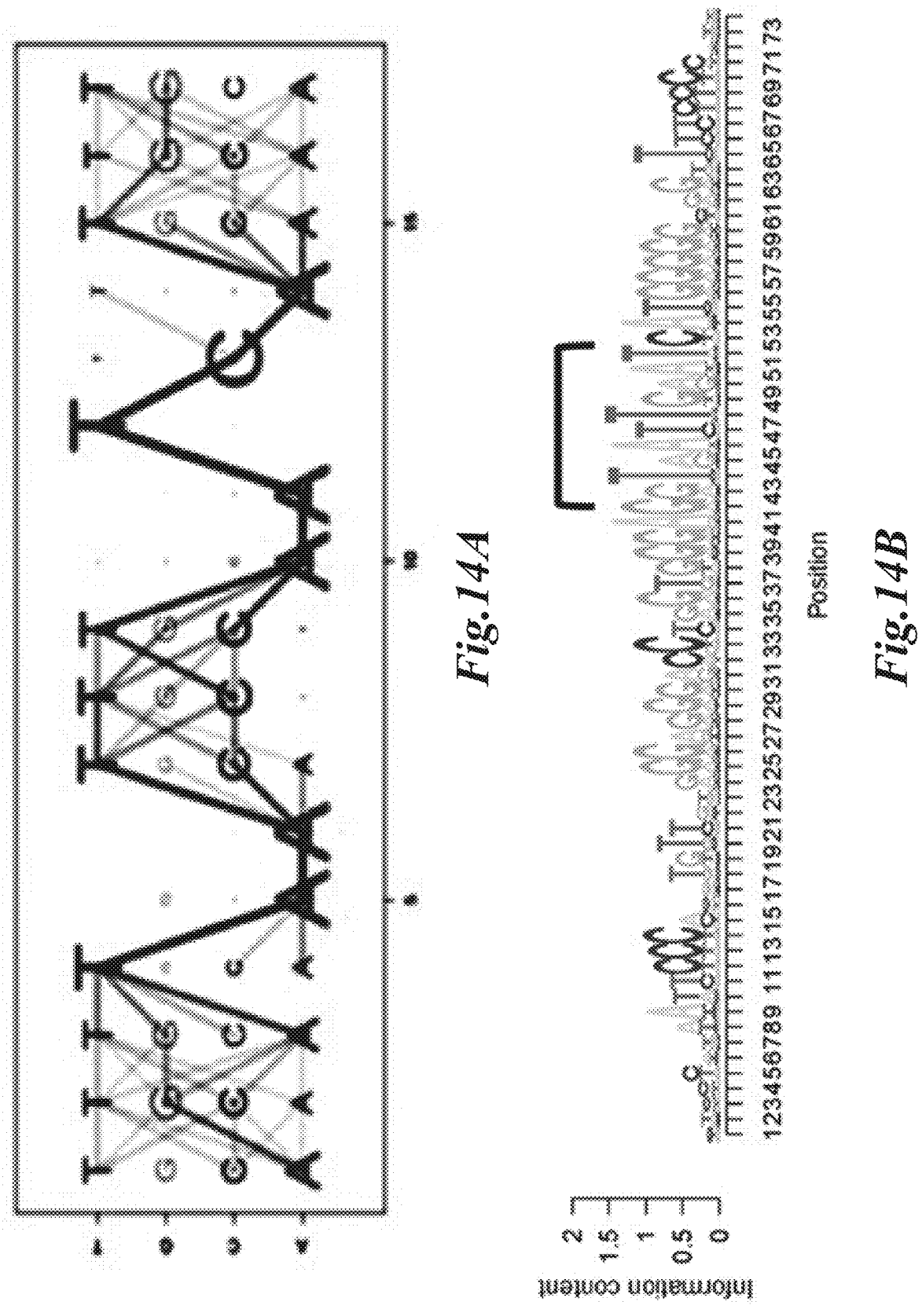
FIG. 14A illustrates a DUX4-fl motif Logo in which the size of each nucleotide at a given position is proportional to the frequency of the nucleotide at that position, and the darkness of the line connecting two adjacent nucleotides represents corresponding dinucleotide frequency, as described in Example 4.
FIG. 14B illustrates that the DUX4 binding motif matches MaLR repeat consensus sequence. We identified the best DUX4 binding sites (bracket) within the MaLR repeats annotated in the RepeatMasker track provided by the UCSC genome browser (hg18) and extended the motif in the flanking regions to reflect general MaLR repeat consensus, as described in Example 4.

FIG. 14 shows that DUX4-fl binds a double homeodomain motif present in the MaLR family of retrotransposons and in non-repetitive genomic regions. FIG. 14A illustrates a DUX4-fl motif Logo in which the size of each nucleotide at a given position is proportional to the frequency of the nucleotide at that position, and the darkness of the line connecting two adjacent nucleotides represents corresponding dinucleotide frequency.

FIG. 14B illustrates that the DUX4 binding motif matches MaLR repeat consensus sequence. We identified the best DUX4 binding sites (bracket) within the MaLR repeats annotated in the RepeatMasker track provided by the UCSC genome browser (hg18) and extended the motif in the flanking regions to reflect general MaLR repeat consensus.

As shown in FIG. 14A, a de novo motif analysis identified the sequence "TAAYBBAATCA" (SEQ ID NO:89) (IUPAC nomenclature: wherein: T=Thymine; A=Adenine; Y=Pyrimidine (Cytosine (C), Thymine (T), or Uracil (U)); B=Cytosine (C), Thymine (T), Uracil (U) or Guanine (G) (not Adenine (A)); C=cytosine), near the center of greater than 90% of peaks.

To our knowledge, this motif has not been described for any other transcription factor, but does contain two canonical homeodomain binding motifs (TAAT) arranged in tandem and separated by one nucleotide. Approximately 30% of sequences under the DUX4-fl peaks also contained a second larger motif that encompasses the primary DUX4-fl binding motif. This longer motif matches the long terminal repeat (LTR) of retrotransposons (FIG. 14B).

FIG. 15 shows the results of EMSA validation of DUX4 binding to ChIP-seq determined motifs. (a) in vitro translated DUX4-fl binds to radiolabeled oligos containing the TAATTAATCA (SEQ ID NO:90) core sequence found near the TRIM48 gene. Competition with cold TRIM48 oligos reduces binding whereas competition with cold TRIM48mut oligos, containing the mutated core sequence TACTTTTATGA (SEQ ID NO:91), does not. Supershift with DUX4 antibody E14-3 confirmed the specificity of binding. (b,c) In vitro translated DUX4-fl binds to radiolabeled oligos containing the TAATTGAATCA (SEQ ID NO:92) core sequence found within the LTR of a THE1B retroelement near the CSF1R gene (b) or to oligos containing the TAATCCAATCA (SEQ ID NO:93) core sequence found within the LTR of the THE1D retroelement (c). Competition with the cold CSF1R and THE1D probes to their respective radioactive oligos inhibited binding, whereas competition with cold mutant CSF1Rmut and THE1Dmut oligos, containing sites TACTTCTATG (SEQ ID NO:94) and TACTCCTATGA (SEQ ID NO:95), respectively, do not. (d) DUX4-s also binds the same core motifs; left, CSF1R; right, TRIM48. Supershift with anti-DUX4 N-terminus antibody E14-3 confirmed specificity of binding.

Figure 15A:
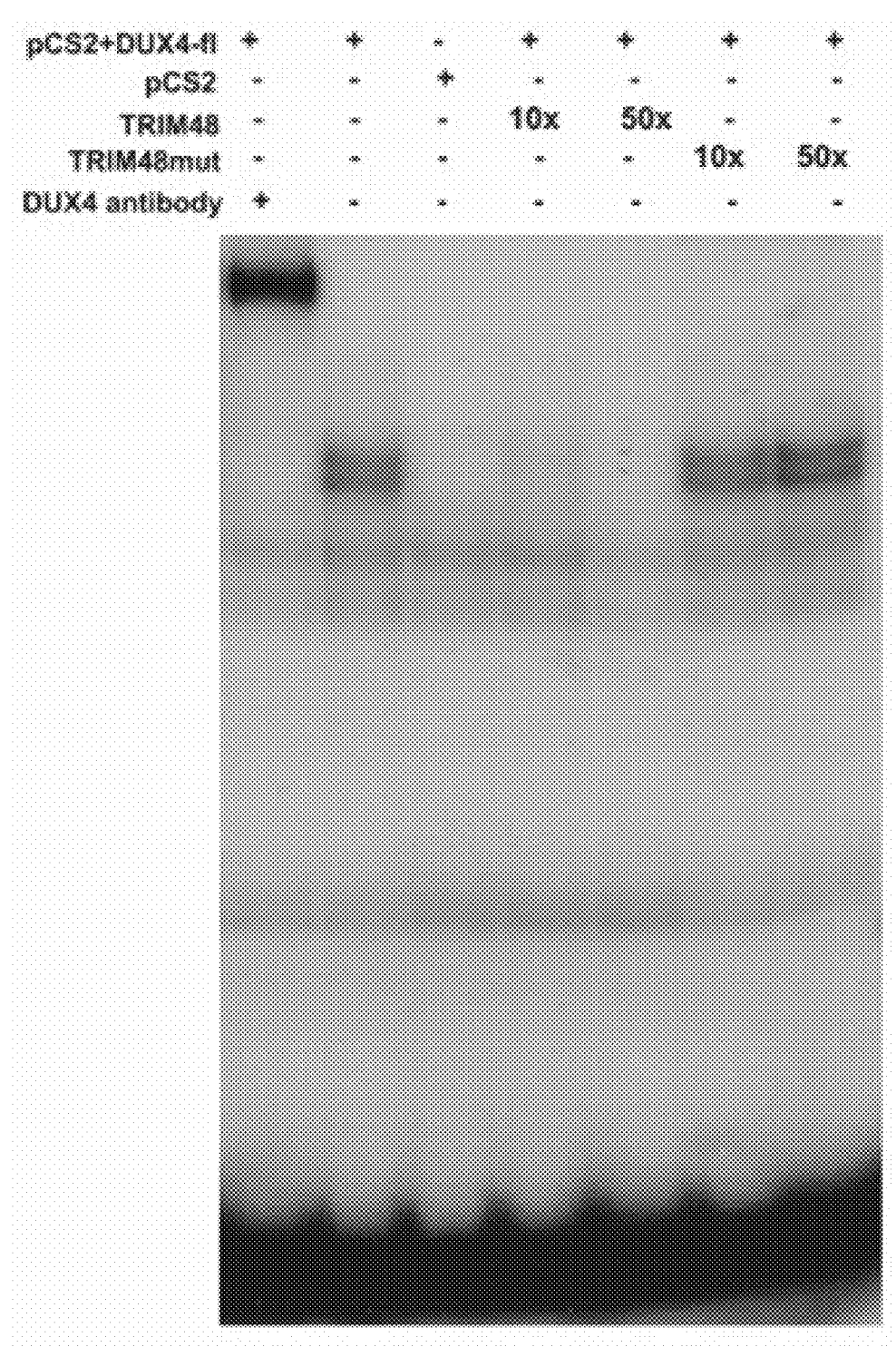
FIG. 15A-FIG. 15D shows the results of EMSA validation of DUX4 binding to ChIP-seq determined motifs.
Figure 15B:
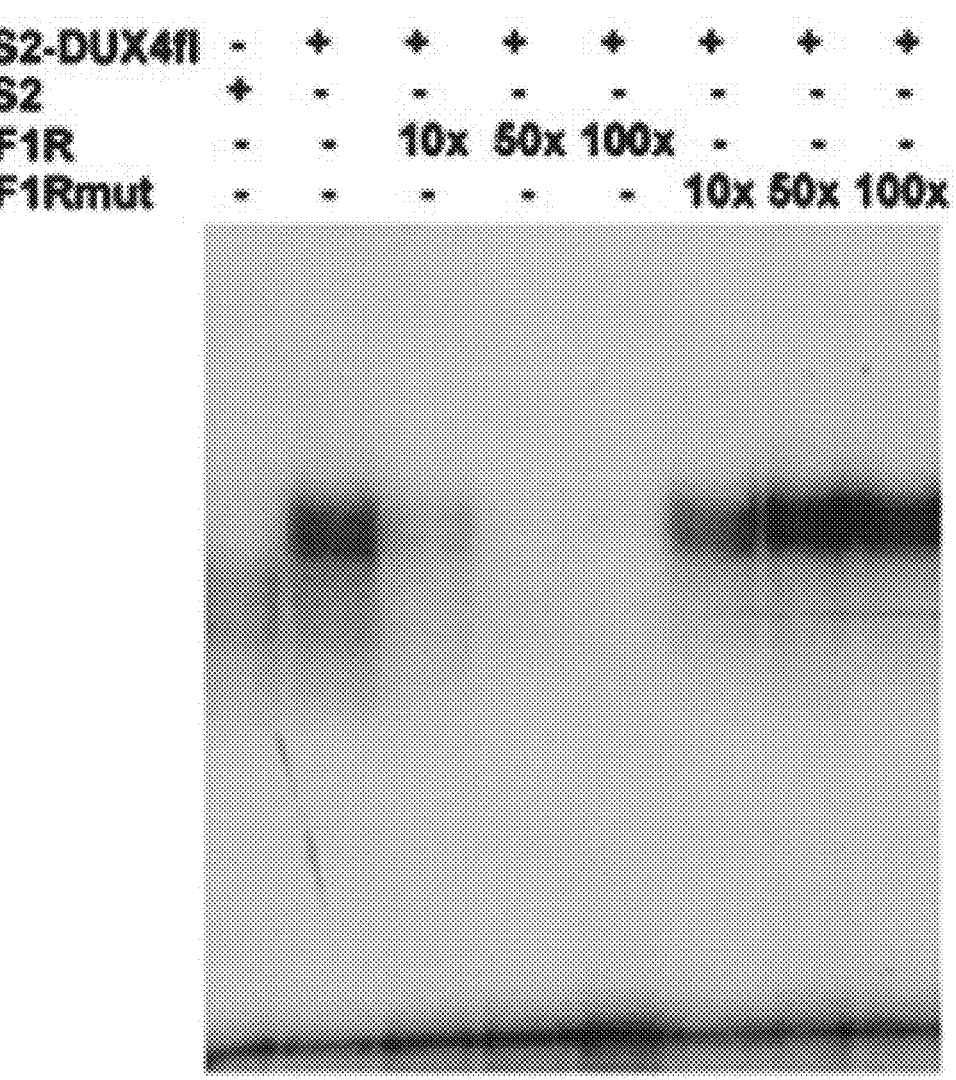
Figure 15C:
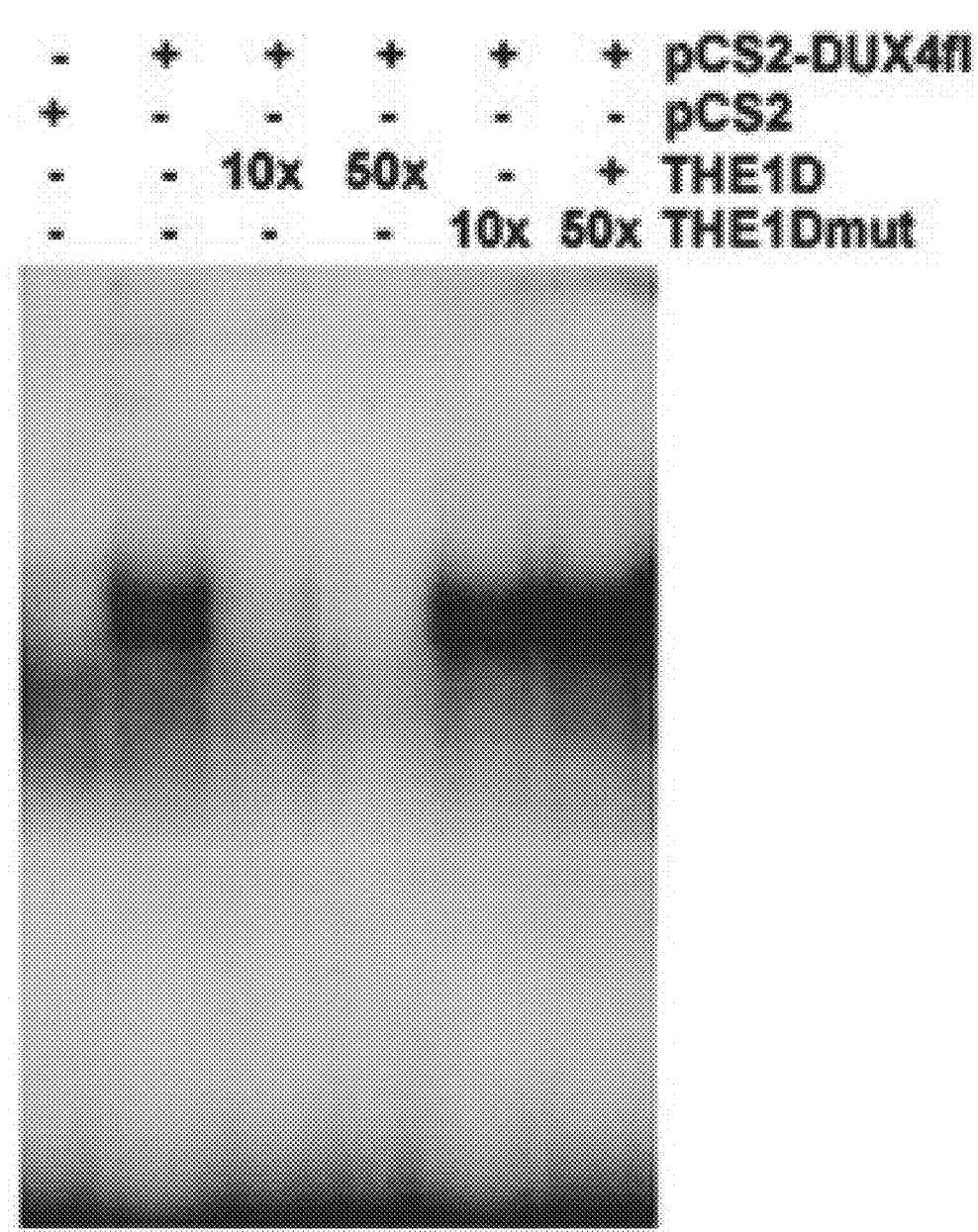
Figure 15D:
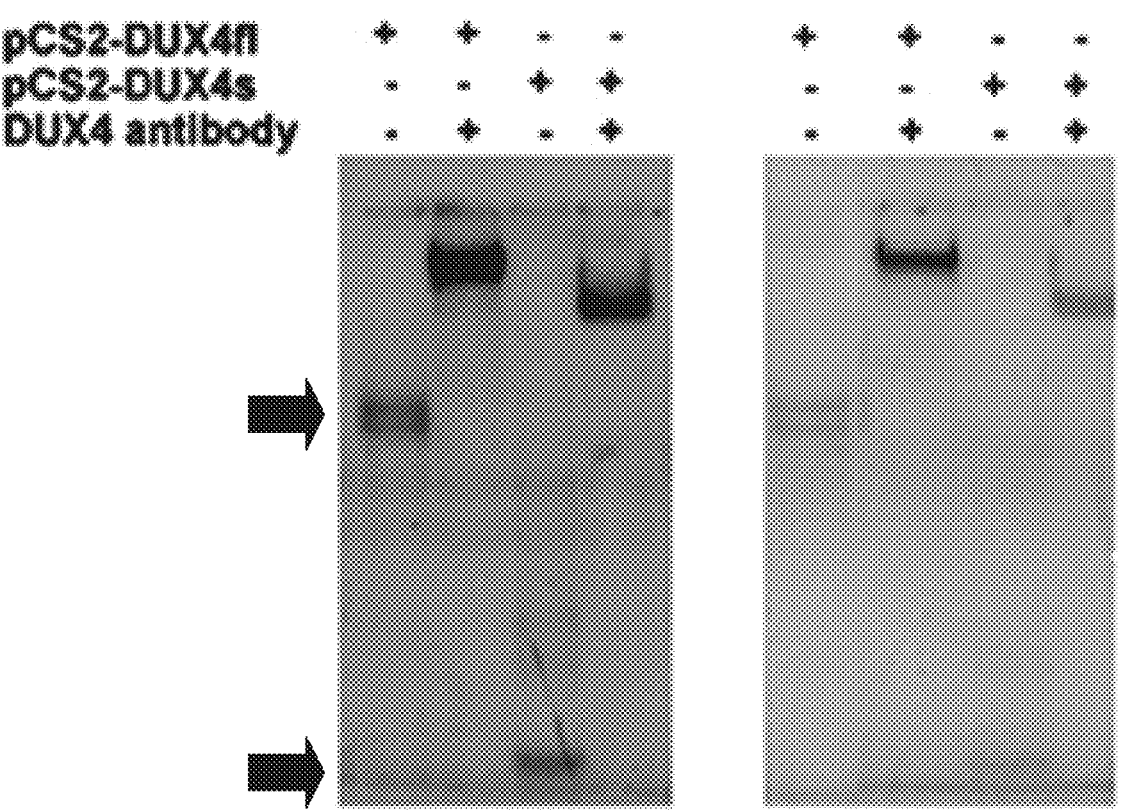

As shown in FIG. 15A-C, Electrophoretic mobility shift assay (EMSA) confirmed that DUX4-fl binds the core motif present in both MaLR-associated and non-repeat associated sites and that mutation of the core nucleotides abolishes binding, including sites from both repeat and non-repeat regions. Because the DUX4-s alternative splice form retains the N-terminal DNA-binding homeodomains, we hypothesized that it would bind to the same sites as DUX4-fl. EMSA confirmed that DUX4-s specifically binds the same core binding site as DUX4-fl in vitro (FIG. 15D).

Thus, these results demonstrate that DUX4-s can bind the same sequences as DUX4-fl but does not activate transcription of the same genes, which supports the prior determination that the C-terminus contains a transactivation domain (Kawamura-Saito et al., *Hum. Mol. Genet.* 15:2125-2137 (2006)).

DUX4-fl is a Transcriptional Activator

To determine whether DUX4-fl binding might function as a transcriptional activator at some of the identified binding sites, DUX4 binding sites from selected genes were cloned upstream of the SV40 promoter in the pGL3-promoter luciferase construct as follows (DUX4 binding sites are underlined)

```
DUX4 binding site from TRIM48:
                                  (SEQ ID NO: 96)
     5' AGGAGTGATGATAATTTAATCAGCCGTGCAA 3'

DUX4 binging site from ZSCAN4:
                                  (SEQ ID NO:  97)
     5' AATCACGTCTTTAAATCAATCACTGACATGG 3'
```

Figure 16A:
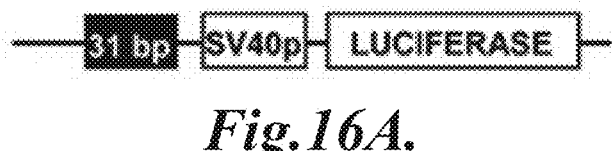
FIG. 16A-FIG. 16C illustrates that DUX4-fl activates transcription in vivo and DUX4-s can interfere with its activity.

The 31 bp DUX4 binding site from TRIM48 (SEQ ID NO:96) or ZSCAN4 (SEQ ID NO:97) were inserted into the luciferase reporter construct upstream of the SV40 promoter, as shown in FIG. 16A.

Figure 16B:
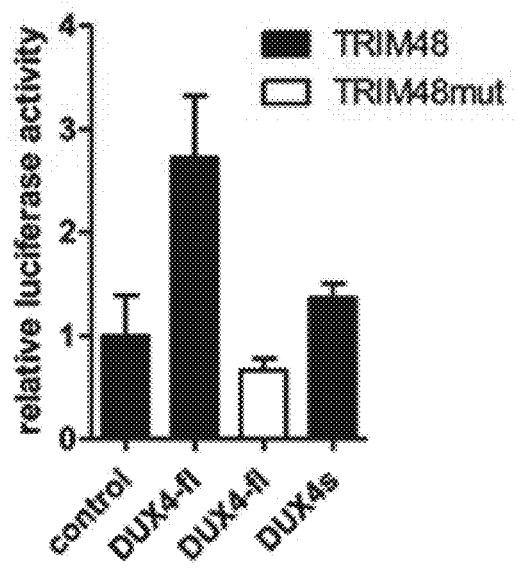
Figure 16C:
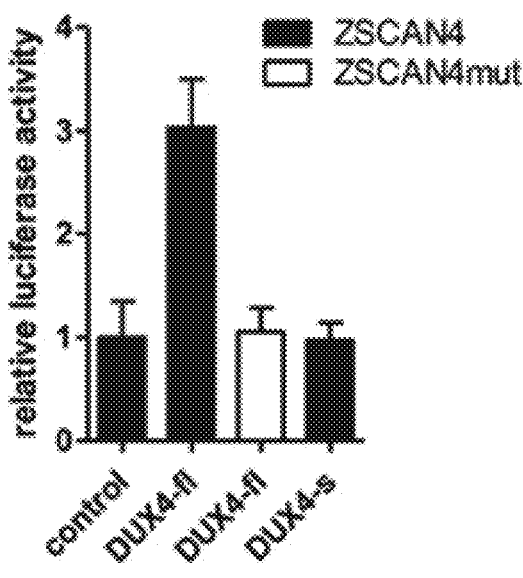

FIG. 16 illustrates that DUX4-fl activates transcription in vivo and DUX4-s can interfere with its activity. (A) reporter construct structure; Genomic fragments near the TRIM48 (B) and ZSCAN4 genes (C) containing DUX4 binding sites were cloned into pGL3-promoter reporter vector (schematic, top) and transfected into human rhabdomyoscaroma cell line RD. Cells were co-transfected with DUX4-fl or DUX4-s. pCS2-P galactosidase (beta gal) was used to balance DNA amount in control condition. TRIM48mut and ZSCAN4mut, mutated binding sites. Luciferase activity was set relative to control.

As shown in FIG. 16 co-transfection with DUX4-fl in human rhabdomyosarcoma cell line RD significantly induced luciferase expression, and mutation of the DUX4 binding motif eliminated the induction. In contrast to DUX4-fl, DUX4-s did not activate expression despite demonstrating in vitro binding to this site.

To determine whether DUX4 binding might directly regulate transcription of select genes, we cloned the 1.9 kb enhancer and promoter region of the ZSCAN4 gene that includes four DUX4 binding sites as follows: (DUX4 binding sites are underlined.)

```
                                  (SEQ ID NO:  98)
5'AGTAATTCAATCAACAGACAAGTGTTATCCAATCACGTCTTTAAATCA

ATCACTGACATGGAGCTGGGGCTGGATGAAGATTCCATCAGTAATTCAAT

CAACAGACAAGTGTTATCCAATCACGTCTTTAAATCAATCACT3'
```

Figure 17A:
FIG. 17A-FIG. 17E, as described in Example 4: The 1.9kb enhancer and promoter region of the ZCAN4 gene that includes the four DUX4 binding sites from ZCAN4 (SEQ ID NO:98) were inserted upstream of the luciferase reporter construct (pGL3 basic luciferase vector) as shown in FIG. 17A.
Figure 17B:
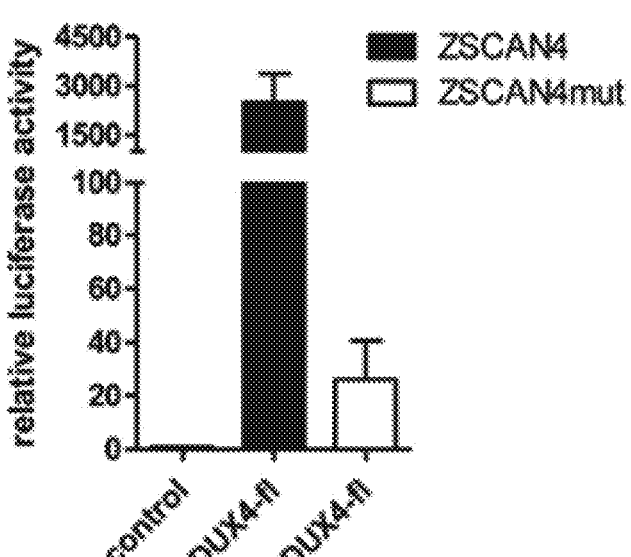
Figure 17C:
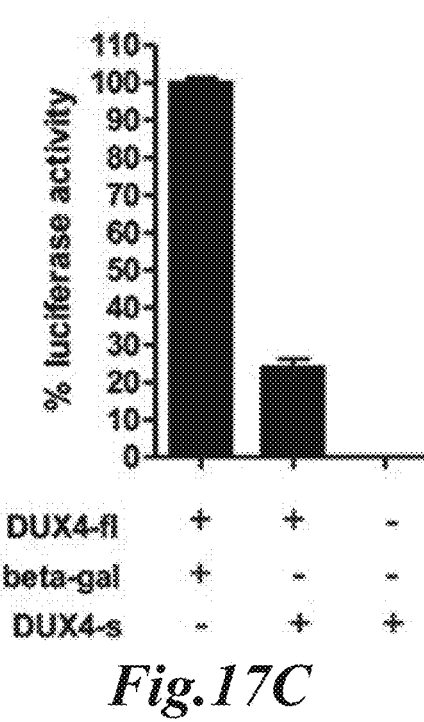
Figure 17D:
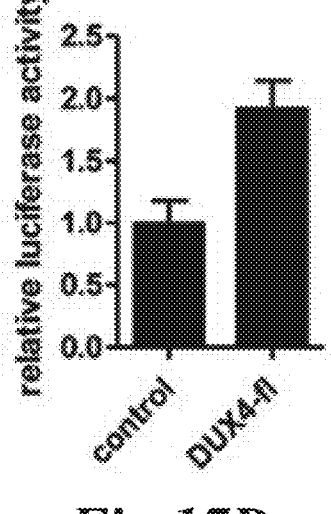
Figure 17E:
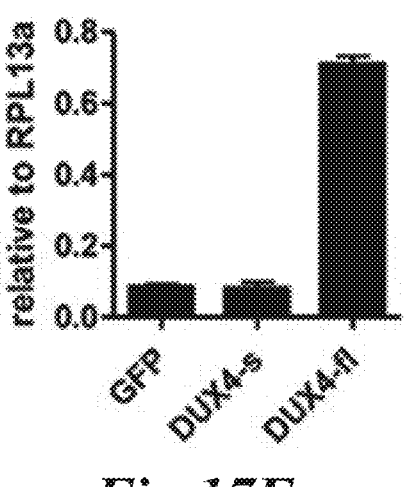
Figures 18A, 18B, 18C:
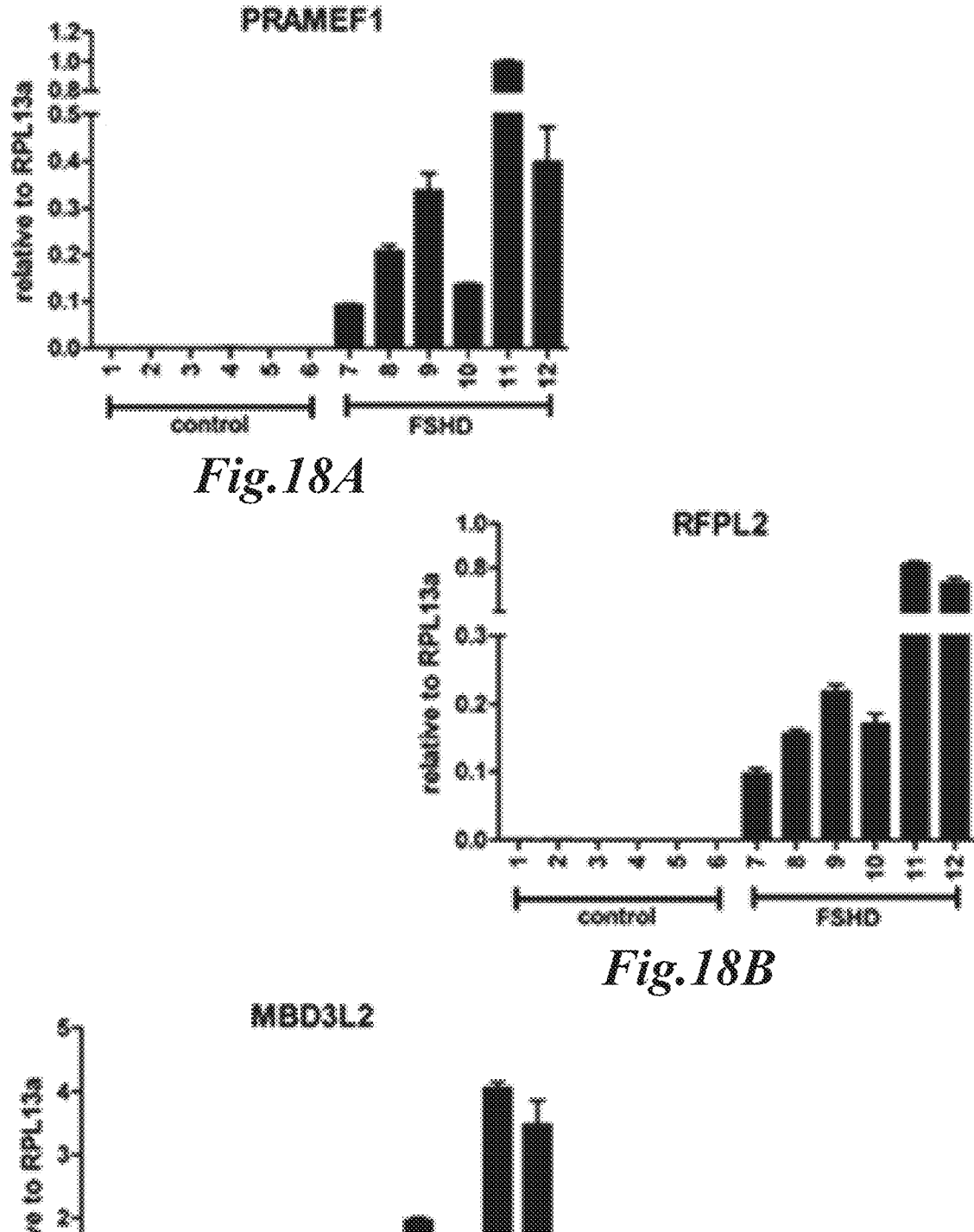
FIG. 18 graphically illustrates the results of real-time RT-PCR analysis of expression of DUX4-fl target genes in cultured control and FSHD muscle cells from 11 individuals for the following target genes: (A) PRAMEF1; (B) RFPL2; (C) MBD3L2; (D) TRIM43; (E) KHDC1; and (F) ZSCAN4, values are expressed as relative to internal standard RPL13a and represent mean+/−SD from triplicates, as described in Example 5.
Figures 18D, 18E, 18F:
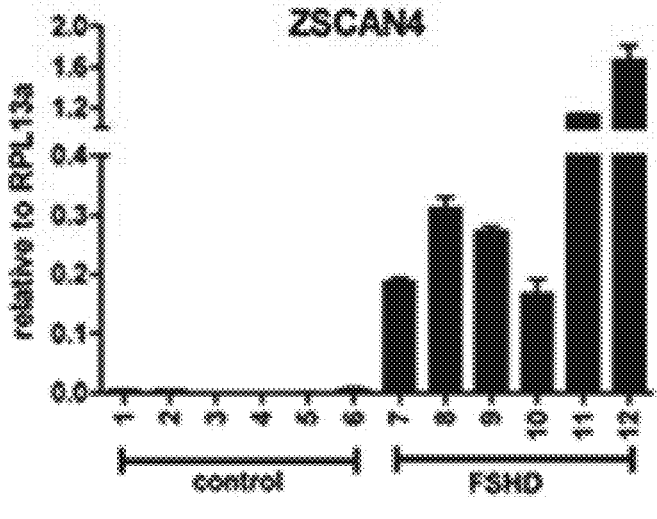
Figure 19A:
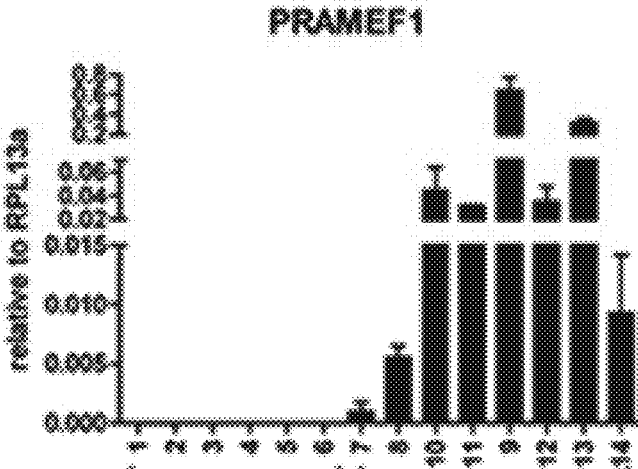
FIG. 19A-FIG. 19F graphically illustrates the results of real-time RT-PCR analysis of expression of DUX4-fl target genes in Control and FSHD muscle biopsies from 15 individuals for the following target genes.
Figure 19B:
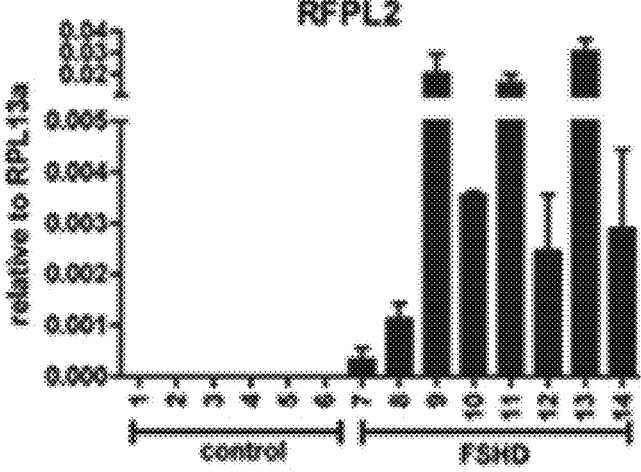
Figure 19C:
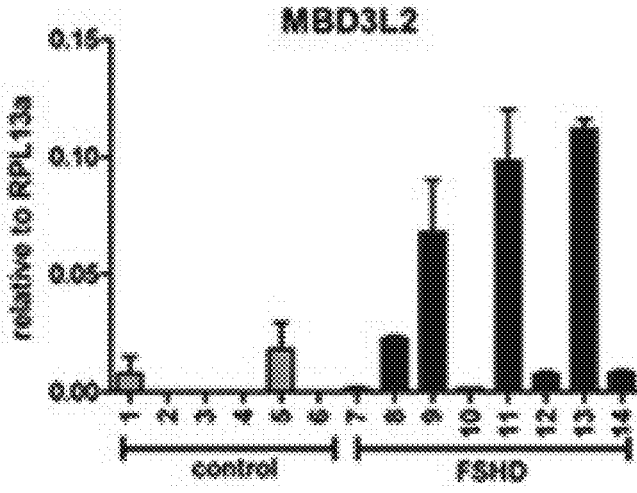
Figure 19D:
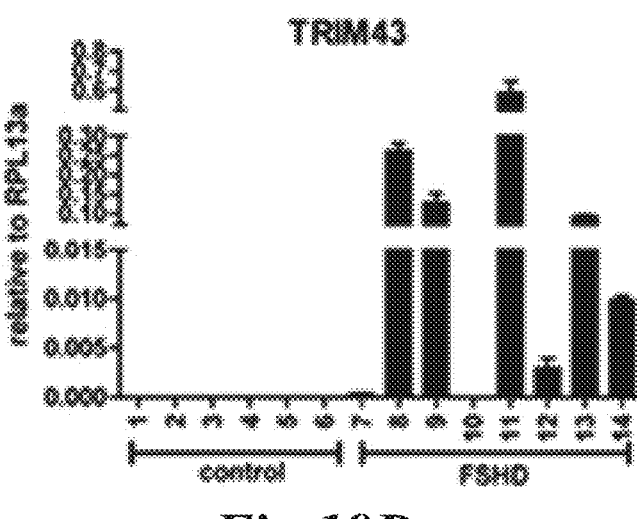
Figure 19E:
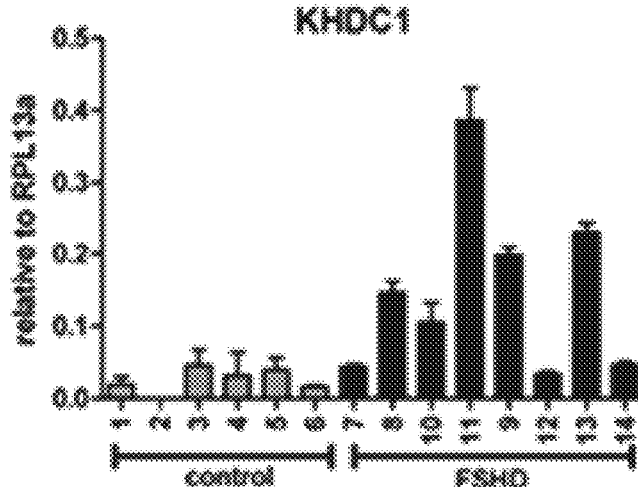
Figure 19F:
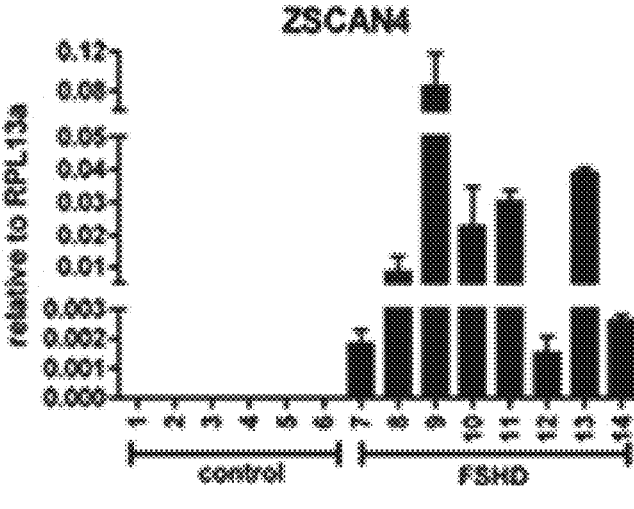

The 1.9kb enhancer and promoter region of the ZCAN4 gene that includes the four DUX4 binding sites from ZCAN4 (SEQ ID NO:100) were inserted upstream of the luciferase reporter construct (pGL3 basic luciferase vector) as shown in FIG. 17A. FIG. 17B shows that DUX4-fl highly activates the luciferase expression, whereas mutation of the binding sites (ZSCAN4mut) drastically reduces this induction. FIG. 17C: Co-transfection of equal amounts of DUX4-fl and DUX4-s diminishes luciferase activity. Luciferase activity from DUX4-fl co-transfected with equal amount of beta gal is set at 100%. FIG. 17D: Genomic fragment from the LTR of THE1D MaLR element containing the DUX4 binding site were cloned into pGL3-promoter vector and tested for response to DUX4-fl as in (b). FIG. 17E: Transcripts from endogenous retroelement MaLRs are upregulated by lentiviral transduction of DUX4-fl into primary human myoblasts. No upregulation is seen with lentiviral transduction of GFP or DUX4-s. Real-time RT-PCR quantitation is reported relative to internal standard RPL13a. All data represent mean+/–SD from at least triplicates.

As shown in FIG. 17, co-transfection with DUX4-fl significantly induced expression of this reporter and mutation of three of the four DUX4 binding sites nearly abolished the induction (FIG. 17B). DUX4-s interfered with the activity of DUX4-fl when the two were co-expressed (FIG. 17C), suggesting that DUX4-s acts as a dominant negative for DUX4-fl activity. DUX4-fl also activated transcription through DUX4 sites in repetitive elements: DUX4-fl activated transcription of a luciferase reporter containing DUX4 binding sites cloned from LTRs at a MaLR THE1D element (FIG. 17D) and RT-PCR showed induction of endogenous MaLR transcripts in muscle cells transduced with DUX4-fl (FIG. 17E).

Discussion

The results in this Example demonstrate that DUX4 binds to and activates transcription from endogenous retrotransposon LTRs of the MaLR family. To the inventor's knowledge, this is the first identification of a transcription factor that can regulate the expression of these repetitive elements in the human genome. The induction of DUX4 expression may be used to induce expression to create placental like invasion and tolerance in allogeneic organ transplants, or to induced mobilization of retrotransposed elements for insertional mutagenesis.

Example 5

This Example demonstrates that DUX4 targets are normally expressed in human testis but not in healthy skeletal muscle, and that DUX4 regulated genes normally expressed in the testis are aberrantly expressed in FSHD muscle.

Methods and Materials

Real Time PCR

One microgram of total RNA was reverse transcribed into first strand cDNA in a 20 uL reaction using SuperScript III (Invitrogen) and digested with 1 U of RNase H (Invitrogen) for 20 min at 37° C. cDNA was diluted and used for quantitative PCR with iTaq SYBR Green supermix with ROX (Bio-Rad). The relative expression levels of target genes were normalized to those of ribosomal protein L13A (RPL13A) by $2^{\Delta Ct}$. Undetermined values were equated to zero. Standard deviations from the mean of the $\Delta Ct$ values were calculated from triplicates. PCR primers used for detecting the transcripts of the selected genes are listed in Supplementary methods.

Muscle Biopsies and Human RNA

Muscle biopsy samples were collected from the vastus lateralis muscle of clinically affected and control individuals as previously described (Snider et al., *PloS Genet* 6:e1001181 (2010)). RNA from matched tissues from healthy donors was purchased from BioChain (Hayward, CA).

Statistical Analyses

Statistical significance between two means was determined by unpaired one-tailed t tests with P-value <0.05. Statistics for the microarray and ChIP-Seq experiments are described separately.

Results:

DUX4-Fl-Regulated Gene Targets are Expressed in FSHD Muscle

To determine whether the low levels of endogenous DUX4-fl mRNA detected in FSHD skeletal muscle is sufficient to activate DUX4 target genes, we assessed the expression of these genes in a set of control and FSHD muscle. Cultured muscle cells from control biopsies showed low or absent expression of the six DUX4-fl regulated genes, whereas these genes were expressed at significantly higher levels in the FSHD muscle cultures (FIG. 18A-F), including those from both FSHD1 and FSHD2 individuals.

FIG. 18 graphically illustrates the results of real-time RT-PCR analysis of expression of DUX4-fl target genes in cultured control and FSHD muscle cells from 11 individuals for the following target genes: (A) PRAMEF1; (B) RFPL2; (C) MBD3L2; (D) TRIM43; (E) KHDC1; and (F) ZSCAN4, Values are expressed as relative to internal standard RPL13a and represent mean+/–SD from triplicates.

The sample names used in FIG. 18 and the endogenous DUX4-fl expression status is provided in TABLE 9.

TABLE 9

| | | | |
|---|---|---|---|
| DUX4-fl expression in FSHD and control muscle | | | |
| Sample # | Formal Identifier | DUX4-fl expression | Disease Status |
| Primary Human Myoblasts | | | |
| 1 | MB135 | not detected | control |
| 2 | MB196 | not detected | control |
| 3 | MB201 | not detected | control |
| 4 | MB209 | not detected | control |
| 5 | MB230 | not detected | control |
| 6 | MB54-1* | not detected | control* |
| 7 | MB073 | detected | FSHD1 |
| 8 | MB183 | detected | FSHD1 |
| 9 | MB197 | detected | FSHD1 |
| 10 | MB216 | detected | FSHD1 |
| 11 | MB200 | detected | FSHD2 |
| 12 | MB54-2* | detected | FSHD1* |
| Muscle Biopsies | | | |
| 1 | C-20 | not detected | control |
| 2 | C-22 | not detected | control |
| 3 | C-33 | not detected | control |
| 4 | C-38 | not detected | control |
| 5 | C-40 | not detected | control |
| 6 | C-2333/C-2397 | not detected | control |
| 7 | F-2315 | not detected | FSHD1 |
| 8 | F-2316 | detected | FSHD1 |
| 9 | F-2319 | not detected | FSHD1 |
| 10 | F-2326 | not detected | FSHD1 |
| 11 | F-2331 | detected | FSHD1 |
| 12 | F-2367 | detected | FSHD1 |
| 13 | F-2369 | detected | FSHD1 |
| 14 | F-2377 | detected | FSHD1 |

*Myoblasts cultured from the same mosaic individual that either do not have (MB54-1) or have (MB54-2) a contracted 4q allele The results shown in FIG. 18 demonstrate that DUX4 regulated genes normally expressed in the testis are aberrantly expressed in FSHD muscle. Similar to the expression of DUX4-fl regulated targets in cultured FSTID muscle (as shown in FIG. 18), muscle biopsies from FSHD individuals had readily detectable mRNA of DUX4-fl regulated genes, although at varying levels in different biopsies.

FIG. 19 graphically illustrates the results of real-time RT-PCR analysis of expression of DUX4-fl target genes in Control and FSHD muscle biopsies from 15 individuals for the following target genes: (A) PRAMEF1; (B) RFPL2; (C) MBD3L2; (D) TRIM43; (E) KHDC1; and (F) ZSCAN4. It is noted that the DUX4-fl mRNA is at extremely low abundance in FSHD muscle and it is notable that some biopsy samples in which the DUX4-fl mRNA was not detected showed elevation of DUX4 regulated targets (Table 9), indicating that the target mRNA is of significantly higher abundance and perhaps more stable than the DUX4 mRNA.

Figure 20:
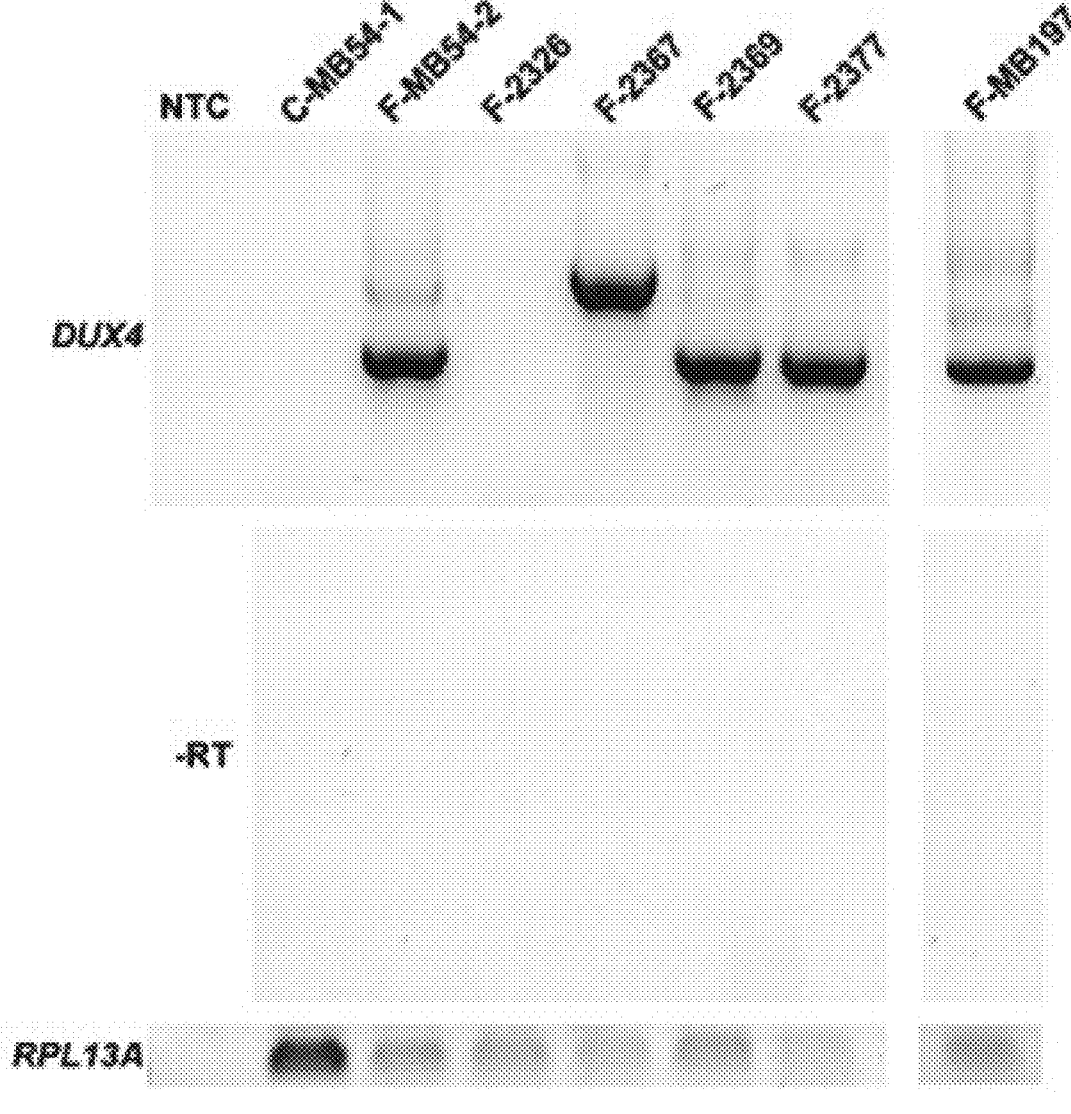
FIG. 20 shows the DUX4 expression status in the muscle samples analyzed in FIG. 12, as determined by nested DUX4 PCR on cDNA from cultured muscle cells or biopsies. RPL13A PCR was used for an internal standard. The coded sample names and complete status information for the biopsy samples analyzed in FIG. 18 and FIG. 19 are provided in TABLE 9, as described in Example 5.

FIG. 20 shows the DUX4 expression status in the muscle samples analyzed in FIG. 12, as determined by nested DUX4 PCR on cDNA from cultured muscle cells or biopsies. RPL13A PCR was used for an internal standard. The coded sample names and complete status information for the biopsy samples analyzed in FIGS. 18 and 19 are provided in TABLE 9.

Figure 21:
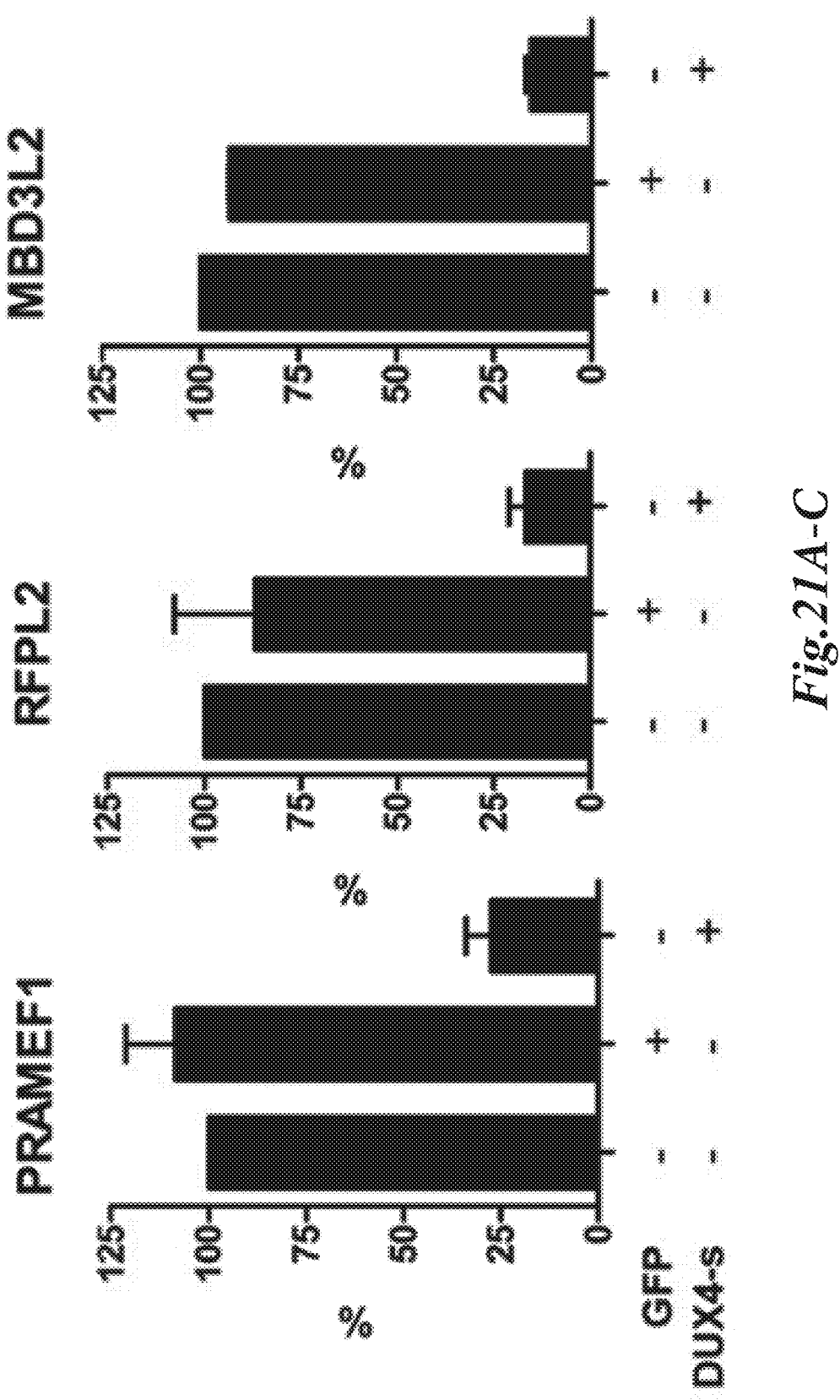
FIG. 21A-FIG. 21C shows that DUX4-s blocks expression of DUX4-fl target genes in FSHD muscle cells. DUX4-s maintains the DNA binding domain of DUX4 but lacks the transcriptional activation domain and therefore acts as a dominant negative to DUX4-fl by binding to the DUX4 motif (see FIG. 16, FIG. 17, and FIG. 15). Real-time RT-PCR quantitation of three DUX4 target genes, (A) PRAMEF1, (B) RFPL2 and (C) MBD3L2 in FSHD cultured muscle cells transduced with lenti-GFP or lenti-DUX4-s or untransduced. Abundance of targets was calculated relative to internal standard RPL13a and then set as percentages relative to the untransduced condition. Values represent mean+/−SEM from three independent experiments, as described in Example 5.

To determine whether the expression of the DUX4 target genes in FSHD muscle was due to binding of the DUX4 protein to its consensus DNA motif, we used DUX4-s to interfere with DUX4-fl activity. As shown above, DUX4-s binds the same consensus motif as DUX4-fl but does not activate gene expression and co-transfection of DUX4-s with DUX4-fl interferes with the ability of DUX4-fl to activate a reporter construct (see FIG. 17). Lentiviral expression of DUX4-s in FSHD muscle cells inhibited the endogenous expression of the target genes as well (FIG. 21), indicating that the DUX4 target genes in FSHD muscle require an activating factor that binds at the DUX4 motif, which is most likely the DUX4-fl protein.

FIG. 21A-C shows that DUX4-s blocks expression of DUX4-fl target genes in FSHD muscle cells. DUX4-s maintains the DNA binding domain of DUX4 but lacks the transcriptional activation domain and therefore acts as a dominant negative to DUX4-fl by binding to the DUX4 motif (see FIGS. 16, 17 and FIG. 15). Real-time RT-PCR quantitation of three DUX4 target genes, (A) PRAMEF1, (B) RFPL2 and (C) MBD3L2 in FSHD cultured muscle cells transduced with lenti-GFP or lenti-DUX4-s or untransduced. Abundance of targets was calculated relative to internal standard RPL13a and then set as percentages relative to the untransduced condition. Values represent mean+/−SEM from three independent experiments.

In summary, our data support the model that inappropriate expression of DUX4 plays a causal role in FSHD skeletal muscle pathophysiology by activating germline gene expression and endogenous retrotransposons in postmitotic skeletal muscle. The DUX4 targets identified in Example 3 point to specific mechanisms of disease and may help guide the development of therapies for FSHD.

Example 6

This Example demonstrates that an agent known to inhibit the histone demethylase LSD1 suppresses DUX4 mRNA levels, and an agent that modifies translation dependent nonsense mediated decay stabilizes DUX4 mRNA levels.
Methods and Results:
An Agent Previously Shown to Inhibit the Histone Demethylase LSD1 can Suppress DUX4 mRNA Levels Our previous work demonstrated that DUX4 expression is epigenetically repressed and the inefficient repression of DUX4 that causes FSHD is correlated with decreased repressive histone methylation at lysine nine of histone 3 (H3K9 methylation). The monamine oxidase inhibitor pargyline has been reported to inhibit the activity of the LSD1 histone demethylase that demethylates H3K9. Treatment of FSHD muscle cultures with pargyline suppresses the expression of DUX4 mRNA expression, whereas another MAO inhibitor that has a different spectrum of demethylase inhibition activity does not alter DUX4 mRNA levels, as shown in FIGS. 22 and 23.

Figure 22:
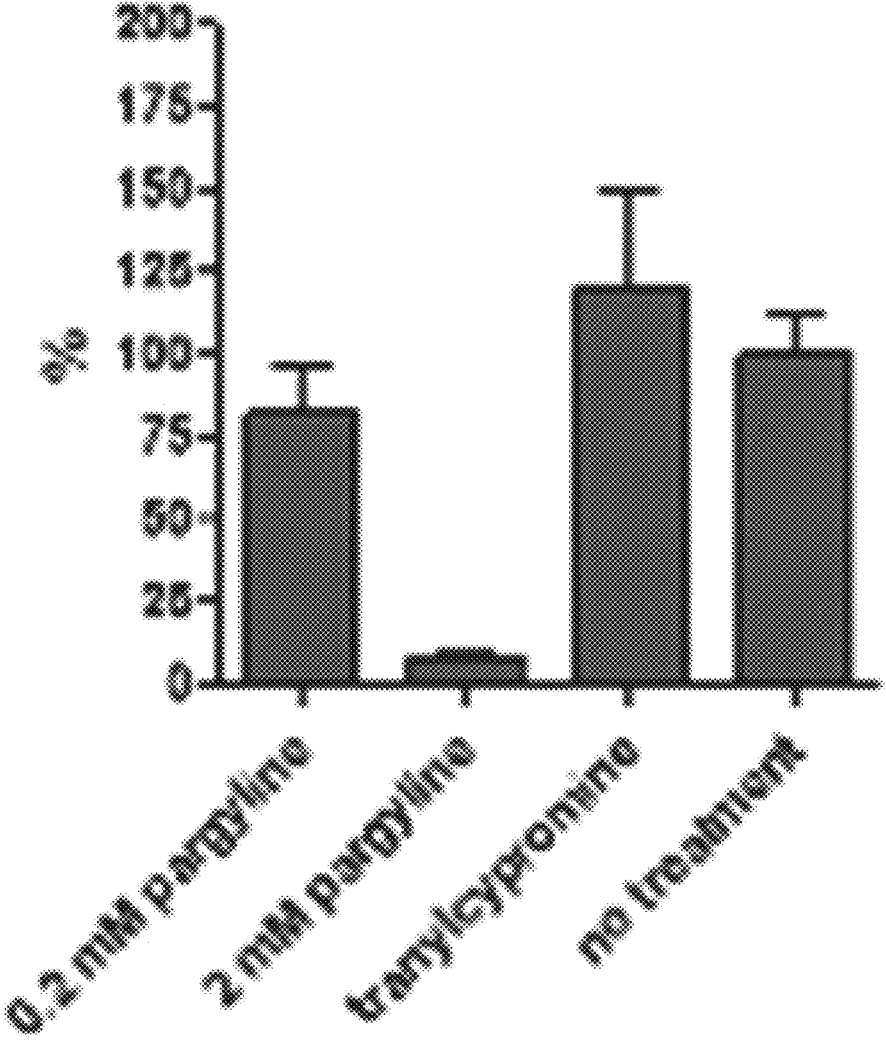
FIG. 22 graphically illustrates that pargyline decreases the amount of DUX4 mRNA in FSHD muscle cells. FSHD muscle cells that express endogenous DUX4-fl mRNA were treated with the MAO inhibitor pargyline that has been reported to inhibit the histone demethylase LSD1, or with another MAO inhibitor tranylcypromine that has a different spectrum of demethylase inhibition activity. The pargyline decreases the abundance of DUX4-fl mRNA in a dose-dependent manner as measured by quantitative RT-PCR, as described in Example 6.

FIG. 22 graphically illustrates that pargyline decreases the amount of DUX4 mRNA in FSHD muscle cells. FSHD muscle cells that express endogenous DUX4-fl mRNA were treated with the MAO inhibitor pargyline that has been reported to inhibit the histone demethylase LSD1, or with another MAO inhibitor tranylcypromine that has a different spectrum of demethylase inhibition activity. The pargyline decreases the abundance of DUX4-fl mRNA in a dose-dependent manner as measured by quantitative RT-PCR.

Figure 23:
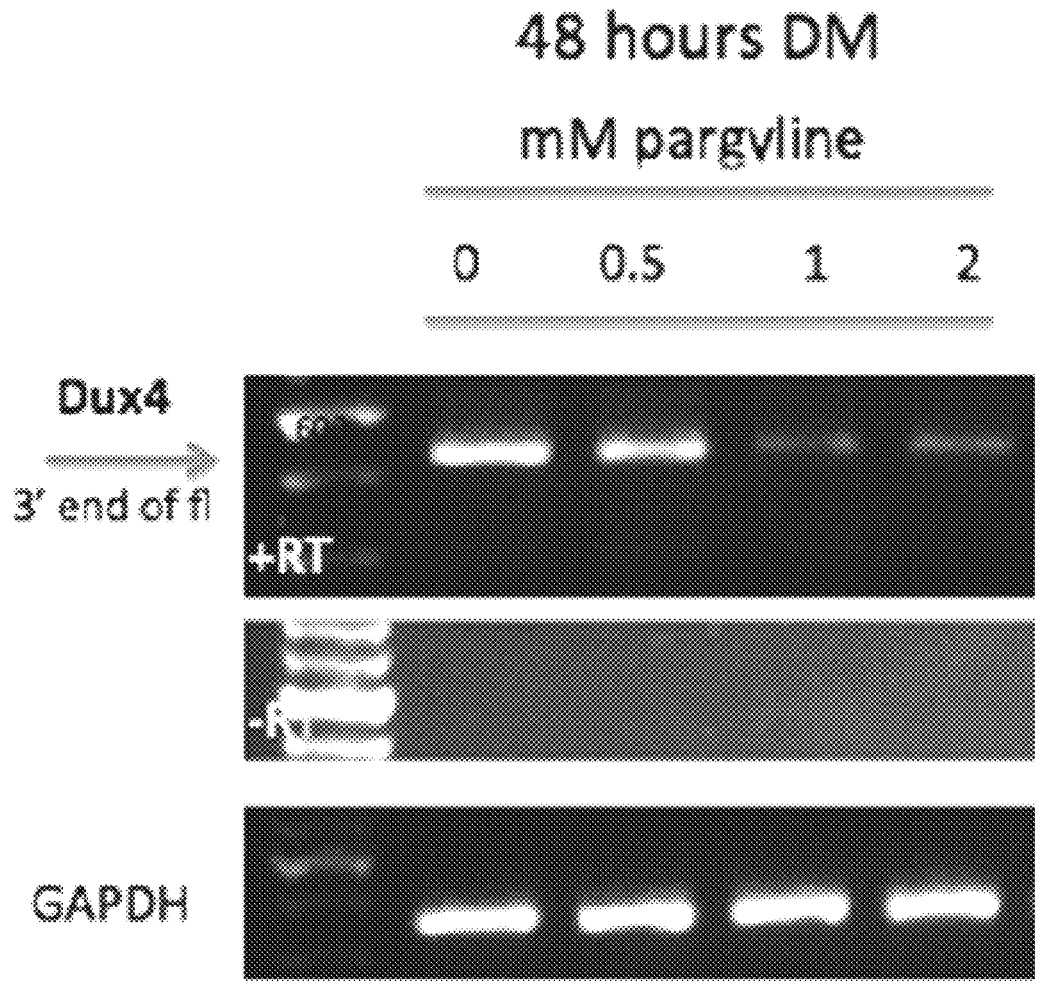
FIG. 23 graphically illustrates that pargyline has a dose-dependent inhibition of DUX4 mRNA expression in FSHD muscle cells. Cultured FSHD muscle cells were differentiated for 48 hours in differentiation medium (DM) with varying amounts of pargyline and the amount of DUX4-fl mRNA was measured by RT-PCR. There was a dose-dependent inhibition of DUX4 expression (top panel). Middle panel is a no RT control and bottom panel is a GAPDH loading control, as described in Example 6.

FIG. 23 graphically illustrates that pargyline has a dose-dependent inhibition of DUX4 mRNA expression in FSHD muscle cells. Cultured FSHD muscle cells were differentiated for 48 hours in differentiation medium (DM) with varying amounts of pargyline and the amount of DUX4-fl mRNA was measured by RT-PCR. There was a dose-dependent inhibition of DUX4 expression (top panel). Middle panel is a no RT control and bottom panel is a GAPDH loading control.

We conclude that agents that increase chromatin mediated repression, such as agents that inhibit LSD1 activity, will be useful to suppress DUX4 and are candidate therapeutic agents for FSHD. Such agents are believed to also have application to other diseases, such as myotonic dystrophy or Huntington's disease, where increasing chromatin mediated suppression of the mutant allele would have therapeutic benefit.
An Agent that Modifies Translation Dependent Nonsense Mediated Decay Will Stabilize DUX4 mRNA Levels The 3-prime untranslated region (UTR) of the DUX4 mRNA has an unusual exon-intron structure. The translational stop codon is in the first exon, whereas the polyadenylation sequence is in the third exon. The separation of the translational stop codon from the polyadenylation site by two exon-intron junctions would be predicted to make this mRNA subject to translation dependent nonsense mediated decay. We can demonstrate that blocking translation with cycloheximide results in the accumulation of the DUX4 mRNA, whereas washing out the cycloheximide and permitting translation of the accumulated DUX4 mRNA (as evidenced by the activation of DUX4 target genes) results in the rapid degradation of the DUX4 mRNA, as shown in FIG. 24.

Figure 24:
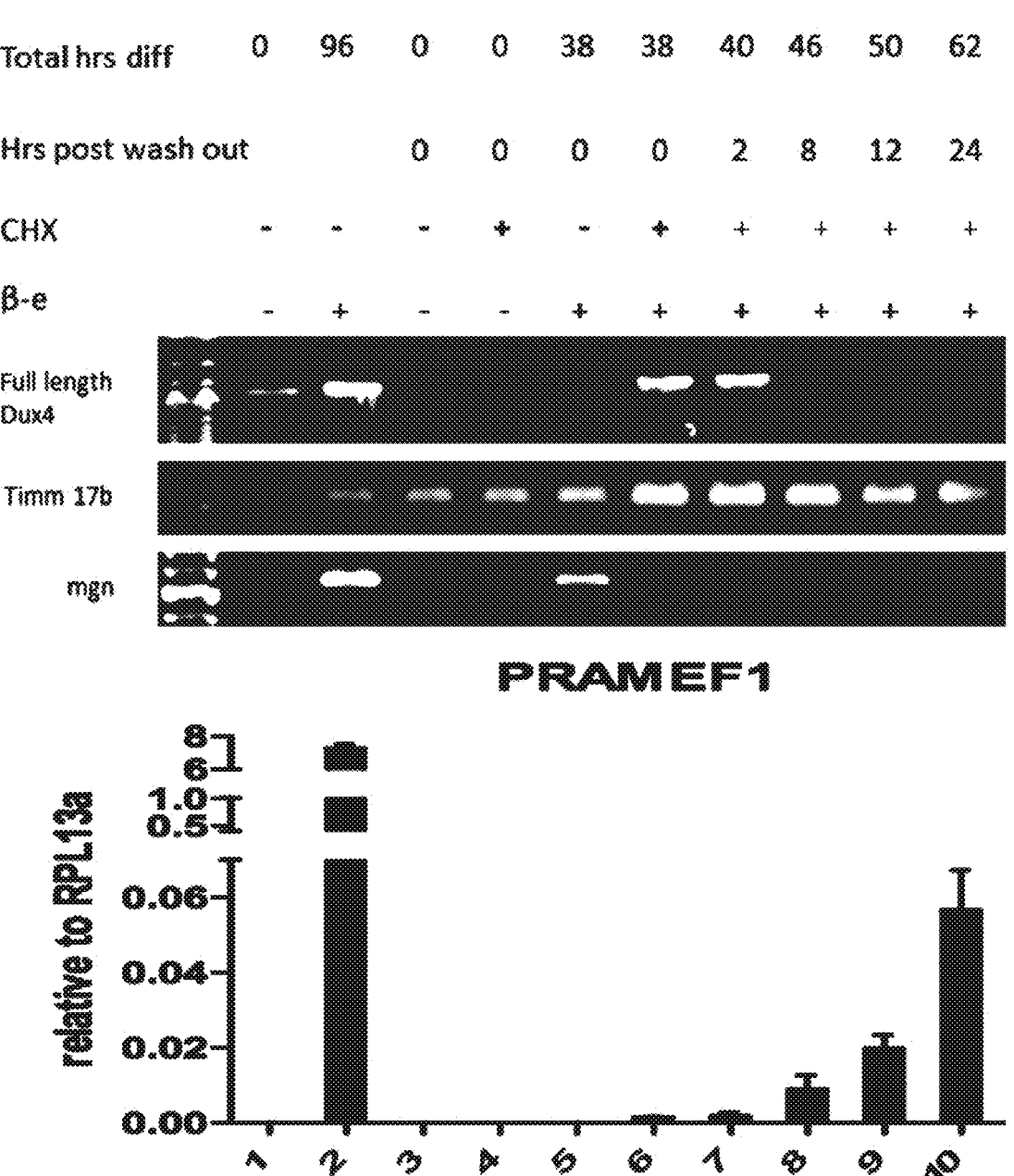
FIG. 24 demonstrates that the protein synthesis inhibitor cycloheximide (chx) prevents decay of the DUX4 mRNA. FSHD fibroblasts expressing low amounts of DUX4 mRNA were stably transduced with a beta-estradiol inducible MyoD so that addition of beta-estradiol will convert them to skeletal muscle, which after 96 hours of induction increases the steady-state levels of the DUX4 mRNA and activates expression of the MyoD target Mgn (compare lanes 1 and 2). At 38 hours in differentiation conditions, there is very low abundance of DUX4 mRNA with MyoD induction alone (Beta-e, lane 6), whereas the addition of chx results in a significant increase in DUX4 mRNA (lane 7). Washout of the chx results in the rapid loss of the DUX4 mRNA, disappearing between 2 and 8 hrs of washout. The loss of DUX4 mRNA is associated with its translation since the DUX4 target PRAME 1 is induced as the DUX4 mRNA disappears, as described in Example 6.

FIG. 24 demonstrates that the protein synthesis inhibitor cycloheximide (chx) prevents decay of the DUX4 mRNA. FSHD fibroblasts expressing low amounts of DUX4 mRNA were stably transduced with a beta-estradiol inducible MyoD so that addition of beta-estradiol will convert them to skeletal muscle, which after 96 hours of induction increases the steady-state levels of the DUX4 mRNA and activates expression of the MyoD target Mgn (compare lanes 1 and 2). At 38 hours in differentiation conditions, there is very low abundance of DUX4 mRNA with MyoD induction alone (Beta-e, lane 6), whereas the addition of chx results in a significant increase in DUX4 mRNA (lane 7). Washout of the chx results in the rapid loss of the DUX4 mRNA, disappearing between 2 and 8 hrs of washout. The loss of DUX4 mRNA is associated with its translation since the DUX4 target PRAME 1 is induced as the DUX4 mRNA disappears.

Therefore, approaches that block translation dependent nonsense mediated decay can be used to increase DUX4 mRNA and agents that enhance nonsense mediated decay can be used to enhance the degradation of DUX4 mRNA. The latter would be candidate therapies for FSHD.
Summary of Results:

These results demonstrate that an agent known to inhibit the histone demethylase LSD1 suppresses DUX4 mRNA levels. Therefore, agents that increase chromatin mediated repression, such as agents that inhibit LSD1 activity, will be useful to suppress DUX4 and are candidate therapeutic agents for FSHD. Such agents are believed to also have application to other diseases, such as myotonic dystrophy or Huntington's disease, where increasing chromatin mediated suppression of the mutant allele would have therapeutic benefit.

These results also demonstrate that an agent that modifies translation dependent nonsense mediated decay stabilizes DUX4 mRNA levels. Therefore, approaches that block translation dependent nonsense mediated decay can be used to increase DUX4 mRNA and agents that enhance nonsense mediated decay can be used to enhance the degradation of DUX4 mRNA, which provides a candidate therapy for FSHD.

It is further noted, as described above in Example 2, DUX4-s can bind the same sequences as DUX4-fl but does not activate transcription of the same genes. Therefore, DUX4-s functions as an inhibitor of DUX4-fl and can also be used as an inhibitor for FSHD.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for alleviating Facioscapulohumeral Dystrophy (FSHD) in a subject having FSHD, the method comprising administering to the subject a Double homeobox, 4 full length (DUX4-fl) inhibitor agent, wherein the DUX4-fl inhibitor agent comprises a Double homeobox, 4 (DUX4) antisense nucleic acid molecule that is identical to a portion of the DUX4 gene and hybridizes to DUX4 mRNA, and wherein the DUX4 antisense nucleic acid molecule inhibits production of DUX4.

2. The method of claim 1, wherein the subject has a functional polyadenylation sequence operationally linked to exon 3 of the DUX4 gene at the distal D4Z4-pLAM region of their genome.

3. The method of claim 2, wherein the polyadenylation sequence is present at the pLAM region located at nucleotides 8046-8051 of SEQ ID NO:5.

4. The method of claim 1, wherein the antisense nucleic acid molecule is an antisense oligonucleotide.

5. The method of claim 1, wherein the antisense nucleic acid molecule is identical to non-coding segments of the DUX4 gene.

6. The method of claim 1, wherein the antisense nucleic acid molecule is identical to at least 8 nucleotides of the DUX4 gene.

7. The method of claim 1, wherein the antisense nucleic acid molecule is administered systemically.

8. The method of claim 1, wherein the subject is a human subject.

9. The method of claim 7, wherein the subject is administered a DUX4 antisense oligonucleotide in a composition and wherein the composition comprises a fatty acid, and wherein the composition is administered parenterally.

10. A method for alleviating Facioscapulohumeral Dystrophy (FSHD) in a subject having FSHD, the method comprising administering to the subject a composition comprising Double homeobox, 4 full length (DUX4-fl) inhibitor agent and a fatty acid, wherein the DUX4-fl inhibitor agent comprises a Double homeobox, 4 (DUX4) antisense nucleic acid molecule that is identical to a portion of the DUX4 gene and hybridizes to DUX4 m RNA, and wherein the DUX4 antisense nucleic acid molecule inhibits production of DUX4; and wherein the composition is administered parenterally.

11. The method of claim 10, wherein the subject has a functional polyadenylation sequence operationally linked to exon 3 of the DUX4 gene at the distal D4Z4-pLAM region of their genome.

12. The method of claim 11, wherein the polyadenylation sequence is present at the pLAM region located at nucleotides 8046-8051 of SEQ ID NO:5.

13. The method of claim 10, wherein the antisense nucleic acid molecule is an antisense oligonucleotide.

14. The method of claim 10, wherein the antisense nucleic acid molecule is identical to non-coding segments of the DUX4 gene.

15. The method of claim 10, wherein the antisense nucleic acid molecule is identical to at least 8 nucleotides of the DUX4 gene.

16. The method of claim 10, wherein the subject is a human subject.

* * * * *